United States Patent
Shirai et al.

(10) Patent No.: US 8,247,403 B2
(45) Date of Patent: Aug. 21, 2012

(54) BENZOXAZEPINE DERIVATIVES AND USE THEREOF

(75) Inventors: Junya Shirai, Osaka (JP); Takahiro Matsumoto, Osaka (JP); Izumi Kamo, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 346 days.

(21) Appl. No.: 12/449,975

(22) PCT Filed: Mar. 6, 2008

(86) PCT No.: PCT/JP2008/054093
§ 371 (c)(1),
(2), (4) Date: Sep. 4, 2009

(87) PCT Pub. No.: WO2008/108445
PCT Pub. Date: Sep. 12, 2008

(65) Prior Publication Data
US 2010/0087418 A1     Apr. 8, 2010

(30) Foreign Application Priority Data
Mar. 7, 2007   (JP) ................................. 2007-057857

(51) Int. Cl.
| | |
|---|---|
| *A61P 1/00* | (2006.01) |
| *A61P 3/04* | (2006.01) |
| *A61P 13/02* | (2006.01) |
| *A61P 15/02* | (2006.01) |
| *A61P 43/00* | (2006.01) |
| *A61K 31/553* | (2006.01) |
| *C07D 267/14* | (2006.01) |
| *C07D 413/04* | (2006.01) |
| *C07D 417/04* | (2006.01) |

(52) U.S. Cl. .............. 514/211.05; 514/211.09; 540/490; 540/552

(58) Field of Classification Search ............. 514/211.09, 514/211.05; 540/552, 490
See application file for complete search history.

(56) References Cited

U.S. PATENT DOCUMENTS

| | | | |
|---|---|---|---|
| 3,493,585 | A | 2/1970 | Schenker et al. |
| 3,542,807 | A | 11/1970 | Lunsford et al. |
| 3,676,460 | A | 7/1972 | Hirohashi et al. |
| 3,686,217 | A | 8/1972 | Schenker et al. |
| 4,125,538 | A | 11/1978 | Standridge |
| 6,319,916 | B1 | 11/2001 | Goto et al. |
| 6,809,092 | B2 | 10/2004 | Ohmoto et al. |
| 2005/0038032 | A1 | 2/2005 | Allison et al. |
| 2006/0069087 | A1 | 3/2006 | Wager |
| 2007/0274913 | A1 | 11/2007 | Kamo et al. |
| 2009/0131402 | A1 | 5/2009 | Shirai et al. |

FOREIGN PATENT DOCUMENTS

| | | |
|---|---|---|
| BE | 669838 | 3/1966 |
| DE | 2014 223 | 3/1970 |
| DE | 2116222 | 3/1971 |
| EP | 0 376 633 | 7/1990 |
| EP | 0 567 090 | 7/2000 |
| EP | 1 792 629 | 6/2007 |
| FR | 1 463 402 | 1/1966 |
| SU | 245787 | 6/1968 |
| WO | 97/17344 | 5/1997 |
| WO | 98/46590 | 10/1998 |
| WO | 98/47876 | 10/1998 |
| WO | 98/50382 | 11/1998 |
| WO | 01/00185 | 1/2001 |
| WO | 01/55118 | 8/2001 |
| WO | 02/18377 | 3/2002 |
| WO | 02/36555 | 5/2002 |
| WO | 02/051232 | 7/2002 |
| WO | 02/051838 | 7/2002 |
| WO | 03/013545 | 2/2003 |
| WO | 2004/014851 | 2/2004 |
| WO | 2004/069244 | 8/2004 |
| WO | 2004/094371 | 11/2004 |
| WO | 2004/096196 | 11/2004 |
| WO | 2005/115145 | 12/2005 |
| WO | 2006/022420 | 3/2006 |
| WO | 2006/136454 | 12/2006 |
| WO | 2007/004959 | 1/2007 |
| WO | 2007/004960 | 1/2007 |

(Continued)

OTHER PUBLICATIONS

Supplementary European Search Report issued May 26, 2011 in European Application No. 08721512.5.
European Search Opinion in European Application No. 08721512.5, Chemical Abstracts Service, 2004.
Database Registry RN 795260-10-5, 2004.
L. Simchowitz et al., "Cell Volume Regulation in Human Neutrophils: 2-(aminomethyl)phenols as Cl⁻ Channel Inhibitors", American Journal of Physiology, vol. 265, pp. C143-C155, 1993.

(Continued)

*Primary Examiner* — Brenda Coleman
(74) *Attorney, Agent, or Firm* — Wenderoth, Lind & Ponack, L.L.P.

(57) ABSTRACT

Compounds represented by the general formula (I):

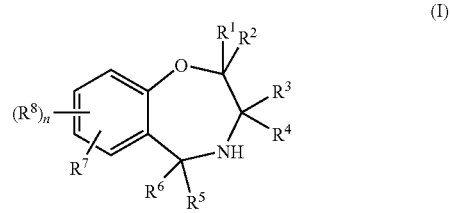

wherein each symbol is as defined in the description [with the proviso that 9-chloro-7-(1,1-dimethylethyl)-2,3,4,5-tetrahydro-1,4-benz-oxazepine and N-[[(5S)-2-oxo-3-(2,3,4,5-tetrahydro-1,4-benz-oxazepin-7-yl)-5-oxazolidinyl]methyl]acetamide are excluded], salts of the same, and prodrugs thereof have selective activation effect on serotonin 5-HT$_{2C}$ receptor and are useful as preventive and therapeutic agents for lower urinary tract diseases, obesity, and/or pelvic organ prolapse.

11 Claims, 1 Drawing Sheet

FOREIGN PATENT DOCUMENTS

| WO | 2007/049123 | 5/2007 |
|---|---|---|
| WO | 2007/132841 | 11/2007 |
| WO | 2007/135527 | 11/2007 |
| WO | 2009/063992 | 5/2009 |

OTHER PUBLICATIONS

J. R. Martin et al., "5-HT$_{2C}$ Receptor Agonists: Pharmacological Characteristics and Therapeutic Potential", The Journal of Pharmacology and Experimental Therapeutics, vol. 286, No. 2, pp. 913-924, 1998.

D. Hoyer et al., "Molecular, Pharmacological and Functional Diversity of 5-HT Receptors", Pharmacology Biochemistry and Behavior, vol. 71, pp. 533-554, 2002.

M. Bancila et al., "5-Hydroxytryptamine$_{2C}$ Receptors on Spinal Neurons Controlling Penile Erection in the Rat", Neuroscience, vol. 92, No. 4, pp. 1523-1537, 1999.

Y. Kimura et al., "Pharmacological Profile of YM348, a Novel, Potent and Orally Active 5-HT$_{2C}$ Receptor Agonist", European Journal of Pharmacology, vol. 483, pp. 37-43, 2004.

Izvestiya Vysshikh Uchcebnykh Zavedenii, Khimiya i Khimicheskaya Tekhnologiya, vol. 48, No. 4, pp. 142-147, 2005 (with partial English translation of page 142).

Y. Ishichi et al., "Novel Acetylcholinesterase Inhibitor as Increasing Agent on Rhythmic Bladder Contractions: SAR of 8-{3-[1-(3-fluorobenzyl)piperidin-4-yl]propanoyl}-1,2,5,6-tetrahydro-4H-pyrrolo[3,2,1-ij]quinolin-4-one (TAK-802) and related compounds", Bioorganic & Medicinal Chemistry, vol. 13, pp. 1901-1911, 2005.

M. H. Bolli et al., "Novel Benzo[1,4]diazepin-2-one Derivatives as Endothelin Receptor Antagonists", Journal of Medicinal Chemistry, vol. 47, No. 11, pp. 2776-2795, 2004.

U. R. Mach et al., "Development of Novel 1,2,3,4-Tetrahydroisoquinoline Derivatives and Closely Related Compounds as Potent and Selective Dopamine D$_3$ Receptor Ligands", ChemBioChem, vol. 5, pp. 508-518, 2004.

F. Heaney et al., "Isoxazolo[2,3-d][1,4]benzoxazepine rings from 1,3-dipolar cycloaddition of [1,4]benzoxazepine N-oxides with Acetylenic and Olefinic Dipolarophiles", ARKIVOC, vol. 7, pp. 161-179, 2003.

H. Kwiecien et al., "Synthesis and Properties of New 2-Alkyl-2,3,4,5-tetrahydro-1,4-benzoxazepine Derivatives. Part IV. Reduction of 2-Alkyl-2,3,4,5-tetrahydro-1,4-benzoxazepin-3,5-diones", Polish Journal of Chemistry, vol. 74, pp. 141-145, 2000.

G. L. Grunewald et al., "Comparative Molecular Field Analysis (COMFA) Models of Phenylethanolamine N-Methyltransferase (PNMT) and the α$_2$-Adrenoceptor: The Development of New, Highly Selective Inhibitors of PNMT", Bioorganic & Medicinal Chemistry Letters, vol. 9, pp. 481-486, 1999.

G. L. Grunewald et al., "Effect of Ring Size or an Additional Heteroatom on the Potency and Selectivity of Bicyclic Benzylamine-Type Inhibitors of Phenylethanolamine N-Methyltransferase", Journal of Medicinal Chemistry, vol. 39, No. 18, pp. 3539-3546, 1996.

Y. Ishihara et al., "Regioselective Friedel-Crafts Acylation of 2,3,4,5-Tetrahydro-1H-2-benzazepine and Related Nitrogen Heterocycles", Journal of the Chemical Society, Perkin Transactions 1, vol. 20, pp. 2993-2999, 1994.

B. S. Orlek et al., "Steric Acceleration of Intramolecular Azide Cycloadditions", Journal of the Chemical Society. Chemical Communications, vol. 7, pp. 607-608, 1993.

I. Sharma et al., "A Convenient Synthesis of N-substituted Benzoxazepines and Benzoxazines", Indian Journal of Chemistry. Section B, vol. 28B, pp. 592-594, Jul. 1989.

P. A. Duckworth et al., "Synthesis and Structural Studies of Nickel(II) Complexes of 14-Membered trans-N$_2$O$_2$ and trans-N$_2$S$_2$ Quadridentate Macrocylces", Inorganic Chemistry, vol. 28, No. 25, pp. 4531-4535, 1989.

J. W. L. Martin et al., "Synthesis of 2,3-Dihydro- and 2,3,4,5-Tetrahydro-1,4-benzothia- and -benzoxazepines and their 14-Membered Macrocylic Dimers with Chelating Trans N$_2$S$_2$ and N$_2$O$_2$ Donor Atom Arrangements: Crystal Structure of cis-[NiCl$_2$(C$_{18}$H$_{18}$N$_2$S$_2$)]", Inorganic Chimica Acta, vol. 99. pp. L5-L7, 1985.

G. E. Stokker et al., "2-(Aminomethyl)phenols, a New Class of Saluretic Agents. 4. Effects of Oxygen and/or Nitrogen Substitution", Journal of Medicinal Chemistry, vol. 25, No. 6, pp. 735-742, 1982.

J. P. Waefelaer et al., "Synthese de Derives De Benzoxazepines. II. 5-Aryl-2,3,4,5-Tetrahydrobenzo[f]1,4-oxazepines", Bulletin des Societes Chimiques Belegs, vol. 85, No. 11, pp. 898-903, 1976 (with English abstract).

D. Misiti et al., "Reazione de Schmidt sui flavanoni. Sintesi de 2.3-diidro-2-fenil-1.4-benzossazepin-5-(4H)-oni", Annali dell'Istituto superior di sanita, vol. 9, pp. 150-159, 1973 (with English abstract).

M. L. Fielden et al., "Synthesis and Central Nervous System Depressant Activity of Some 5-(2-Substituted Alkyl)-2-oxazolidinones", Journal of Medicinal Chemistry, vol. 16, No. 10, pp. 1124-1128, 1973.

A. N. Kost et al., "Reductive Cyclization of o-Cyanocinnamic Acids and Their Analogs", Khimiya Geterotsiklicheskikh Soedinenii, vol. 7, pp. 1288-1292, 1971, (with English translation thereof).

Gazzetta Chimica Italiana, vol. 101, pp. 167-172, 1971.

D. Misiti et al., "2,3-Dihydro-2-Phenyl-1,4-Benzoxazepin-5(4H)-One From the Reaction of the Flavanone with Hydrazoic Acid", Tetrahedron Letters, vol. 12, pp. 947-950, 1970.

H. A. Luts, "Two New Bicyclic Ring Systems, 1,4,5-Benzodioxazocine and 1,4-Benzoxazepine", Journal of Pharmaceutical Sciences, vol. 58, No. 12, pp. 1460-1463, Dec. 1969.

V. K. Schenker et al., "2,3,4,5-Tetrahydro-1,4-benzoxazepine", Helvetica Chemica Acta, vol. 46, pp. 1696-1704, 1963 (with English summary).

L. M. Marson, "Benzossazepine A Presumibile Azione Sul Sistema Neurovegetativo", Farmaco, Edizione Scientifica, vol. 14, No. 3, pp. 159-175, Mar. 1959.

J. E. Jelovsek et al., "Pelvic Organ Prolapse", Lancet, vol. 369, pp. 1027-1038, Mar. 24, 2007.

R. Bartoletti et al., "Pelvic Organ Prolapse: A Challenge for the Urologist", European Urology, vol. 51, pp. 884-886, 2007.

I. Kamo et al., "The Role of Bladder-to-Urethral Reflexes in Urinary Continence Mechanisms in Rats", American Journal of Physiology, Renal Physiology, vol. 287, pp. F434-F441, 2004.

J. Paterson et al., "Pelvic Floor Exercises as a Treatment for Post-Micturition Dribble", British Journal of Urology, vol. 79, pp. 892-897, 1997.

G. Dorey et al., "Pelvic Floor Exercises for Treating Post-Micturition Dribble in Men with Erectile Dysfunction: A Randomized Controlled Trial", Urologic Nursing, vol. 24, No. 6, pp. 490-497 and 512, Dec. 2004.

G. Dorey, "Restoring Pelvic Floor Function in Men: Review of RCTs", British Journal of Nursing; vol. 14, No. 19, pp. 1014-1018, 1020-1021, 2005.

M. M. Cavalluzzi et al., "Synthesis of (R)-, (S)-, and (RS)-Hydroxymethylmexiletine, one of the Major Metabolites of Mexiletine", Tetrahedron, Asymmetry, vol. 18, pp. 2409-2417, 2007.

J. Mishra et al., "Diversity-Oriented Synthetic Approach to Naturally Abundant S-Amino Acid Based Benzannulated Enantiomerically Pure Medium Ring Heterocyclic Scaffolds Employing Inter- and Intramolecular Mitsunobu Reactions", Journal of Combinatorial Chemistry, vol. 9, No. 2, pp. 321-338, 2007.

L. Simchowitz et al., "Cell Volume Regulation in Human Neutrophils: 2-(aminomethyl)phenols and Cl$^-$ Channel Inhibitors", Journal of Medicinal Chemistry, vol. 25, No. 6, pp. C143-C155, Jun. 1982.

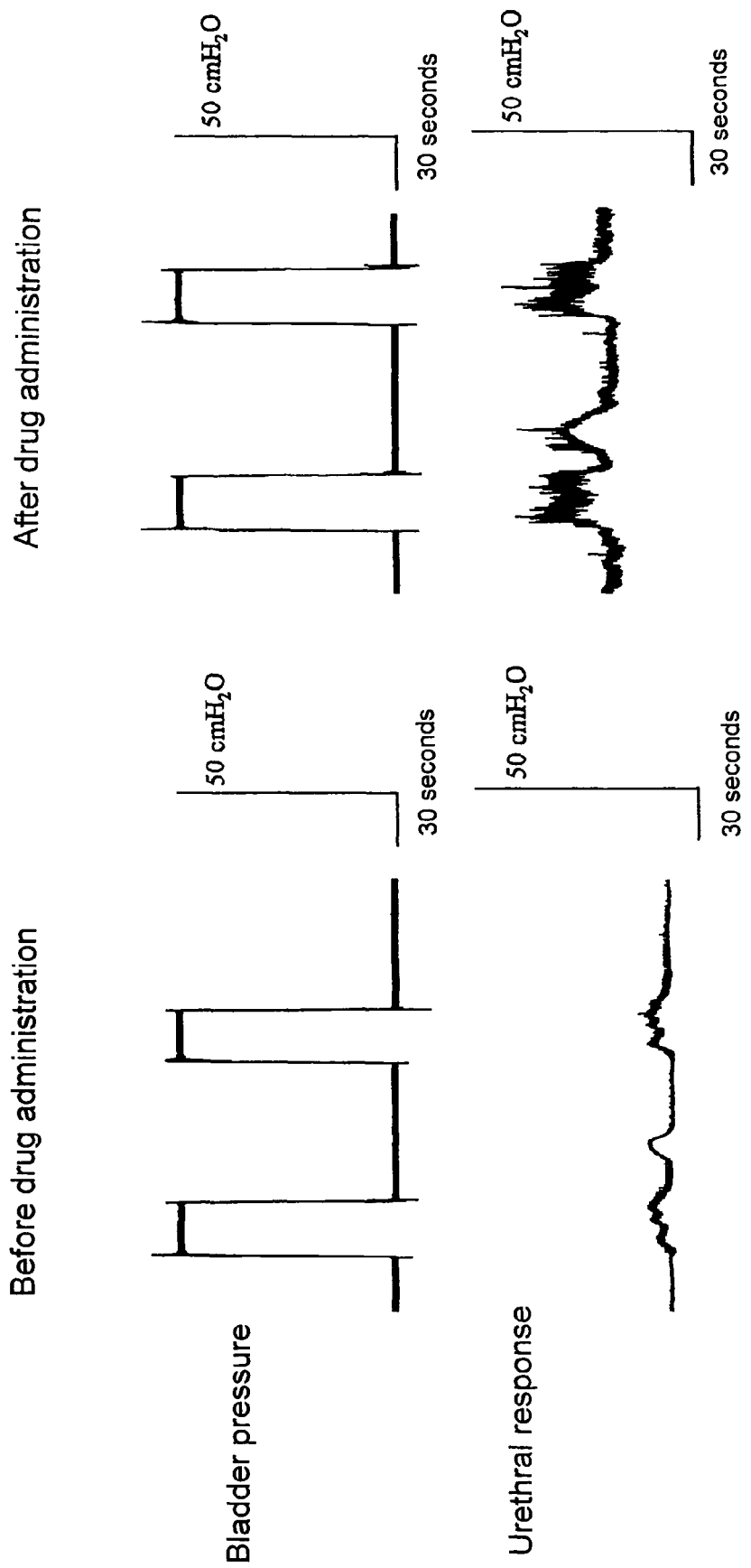

BENZOXAZEPINE DERIVATIVES AND USE THEREOF

This application is a U.S. national stage of International Application No. PCT/JP2008/054093 filed Mar. 6, 2008.

TECHNICAL FIELD

The present invention relates to a benzoxazepine derivative having a superior serotonin 5-$HT_{2C}$ receptor activation action and useful as a drug for the treatment or prophylaxis of lower urinary tract symptom (including stress urinary incontinence, mixed urinary incontinence, post-micturition dribble), obesity or pelvic organ prolapse (anterior vaginal wall prolapse, posterior vaginal wall prolapse, uterine prolapse, prolapse of the apical segment of the vagina, rectal prolapse [rectocele], enterocele, cystocele, urethral prolapse etc.), and the like.

BACKGROUND OF THE INVENTION

Serotonin 5-$HT_{2C}$ receptor is one of the receptors of the biological transmitter serotonin, which is distributed mainly in the central nervous system and controls many physiological functions in vivo. A representative example is the control of appetite. It has been demonstrated in a study using rodents that stimulation of the central serotonin 5-$HT_{2C}$ receptor decreases eating behavior, resulting in decreased body weight. It has also been reported that, in human as well, administration of a serotonin 5-$HT_{2C}$ receptor activator suppresses appetite and decreases body weight (see non-patent document 1). In addition, it has been demonstrated in a rat test using a serotonin 5-$HT_{2C}$ receptor activator that stimulation of the central serotonin 5-$HT_{2C}$ receptor suppresses depression-related behaviors (see non-patent document 2), and has also been reported to be effective for many central nervous diseases such as anxiety etc. (see non-patent document 3). The serotonin 5-$HT_{2C}$ receptor is also highly expressed in the parasympathetic nucleus and motorial nerve cell bodies in the sacral spinal cord, and is considered to control the peripheral nervous functions (see non-patent document 4). It has been reported that when a serotonin 5-$HT_{2C}$ receptor activator is administered to rats, penile erection is induced (see non-patent document 5), and urethral resistance is increased (see patent document 1); all these actions are attributed to stimulation of the serotonin 5-$HT_{2C}$ receptor in the sacral spinal cord. For serotonin 5-$HT_{2C}$ receptor activators, many clinical applications are likely, with particular expectations for anti-obesity drugs, anti-depressants, anti-anxiety drugs, therapeutic drugs for male erectile dysfunction, and therapeutic drugs for stress urinary incontinence and the like.

"Pelvic organ prolapse" is a disease wherein a pelvic organ descends and protrudes from the vaginal orifice, and is known to include prolapse of anterior vaginal wall, posterior vaginal wall, uterus, the vaginal cuff scar after hysterectomy, rectum, small intestine, bladder or urethra, which are called anterior vaginal wall prolapse, posterior vaginal wall prolapse, uterine prolapse, prolapse of the apical segment of the vagina, rectal prolapse [rectocele], enterocele, cystocele and urethral prolapse, respectively (see, for example, non-patent documents 30-32). The pelvic organ prolapse becomes conspicuous when abdominal pressure rises transiently as a result of straining or bearing a heavy load and the like. Childbirth, aging, and obesity are known risk factors of pelvic organ prolapse and one of suggested causes thereof is the weakening of the pelvic floor muscles and perivisceral connective tissue that support the vagina, the uterus and the like. The pelvic floor muscles are skeletal muscles that unite with the pelvis in a hammock-like way, serving constantly to maintain some contraction and support the organs in the pelvis from below. In pelvic organ prolapse, these pelvic floor muscles are weakened to be unable to support the pelvic organs against their weights, resulting in the descent of the organs (see, for example, non-patent documents 30-32). Particularly, when abdominal pressure rises, the prolapse becomes more conspicuous because of insufficient opposing force to the increased abdominal pressure. On the other hand, it has been reported that when abdominal pressure rises, the urinary bladder is compressed, reflex via the urinary bladder—spinal cord—pelvic floor muscles and the urethra causes the contraction of the pelvic floor muscles and the urethral sphincter to increase urethral internal pressure, whereby urinary incontinence is prevented (see, for example, non-patent document 33). For this reason, it is considered that upon a rise in abdominal pressure, the pelvic floor muscles contract reflexly to prevent not only urinary incontinence, but also the descent of the pelvic organs. If there is a failure in this reflex pathway or the pelvic floor muscles, sufficient contraction of the pelvic floor muscles cannot be obtained and support for the organs becomes inadequate. Therefore, a therapeutic drug for pelvic organ prolapse can be screened by the evaluation of contractile responses of the pelvic floor muscles.

The lower urinary tract symptoms consist of storage symptoms, voiding symptoms and post micturition symptoms, and one of the main post micturition symptoms is post-micturition dribble. Post-micturition dribble is a complaint of involuntary loss of urine immediately after one has finished passing urine, which generally takes place after leaving toilet in men and after rising from the toilet in women. Pelvic floor muscle exercise is reported to be effective for the post-micturition dribble (see non-patent documents 34-36), and such dribble is considered to be related to weakened pelvic floor muscles. Therefore, a therapeutic drug for post-micturition dribble can also be screened by the evaluation of the contractile responses of the pelvic floor muscles.

In the meantime, compounds having structures similar to the benzoxazepine derivative described in the specification of this application have been reported in non-patent document 6-non-patent document 29, and patent documents 2-25.

non-patent document 1: Expert Opinion on Investigational Drugs, 2006, vol. 15, p. 257-266 non-patent document 2: J. Pharmacol. Exp. Ther., 1998, vol. 286, p. 913-924 non-patent document 3: Pharmacology Biochemistry Behavior, 2002, vol. 71, p. 533-554 non-patent document 4: Neuroscience, 1999, vol. 92, p. 1523-1537 non-patent document 5: Eur. J. Pharmacol., 2004, vol. 483, p. 37-43 non-patent document 6: Izvestiya Vysshikh Uchebnykh Zavedenii, Khimiya i Khimicheskaya Tekhnologiya (2005), 48(4), 142-147 non-patent document 7: Bioorganic&Medicinal Chemistry (2005), 13(6), 1901-1911 non-patent document 8: Journal of Medicinal Chemistry (2004), 47(11), 2776-2795 non-patent document 9: Chem. Bio. Chem. (2004), 5(4), 508-518 non-patent document 10: ARKIVOC (Gainesville, Fla., United States) (2003), (7), 161-179 non-patent document 11: Polish Journal of Chemistry (2000), 74(1), 141-145 non-patent document 12: Bioorganic&Medicinal Chemistry Letters (1999), 9(3), 481-486 non-patent document 13: Journal of Medicinal Chemistry (1996), 39(18), 3539-3546 non-patent document 14: Journal of the Chemical Society, Perkin Transactions 1: Organic and Bio-Organic Chemistry (1994), (20), 2993-9
non-patent document 15: American Journal of Physiology (1993), 265 (1, Pt. 1), C143-C155
non-patent document 16: Journal of the Chemical Society, Chemical Communications (1993), (7), 607-8
non-patent document 17: Indian Journal of Chemistry, Section B: Organic Chemistry Including Medicinal Chemistry (1989), 28B(7), 592-4
non-patent document 18: Inorganic Chemistry (1989), 28(25), 4531-5
non-patent document 19: Inorganica Chimica Acta (1985), 99(1), L5-L7
non-patent document 20: Journal of Medicinal Chemistry (1982), 25(6), 735-42
non-patent document 21: Bulletin des Societes Chimiques-Belges (1976), 85(11), 898-903
non-patent document 22: Annali dell'Istituto Superioredi Sanita (1973), 9, Pt 2-3, 150-9
non-patent document 23: Journal of Medicinal Chemistry (1973), 16(10), 1124-8
non-patent document 24: Khimiya Geterotsiklicheskikh Soedinenii (1971), 7(9), 1288-92
non-patent document 25: Gazzetta Chimica Italiana (1971), 101(2), 167-72
non-patent document 26: Tetrahedron Letters (1970), (12), 947-50
non-patent document 27: Journal of Pharmaceutical Sciences (1969), 58(12), 1460-3
non-patent document 28: Helvetica Chimica Acta (1963), 46, 1696-704
non-patent document 29: Farmaco, Edizione Scientifica (1959), 14, 159-75
non-patent document 30: Journal of The Japan Neurogenic Bladder Society 2003, vol. 14, p. 278-289
non-patent document 31: Lancet 2007, vol. 369, p. 1027-38
non-patent document 32: Europian Urology 2007, vol. 51, p. 884-886
non-patent document 33: American Journal of Physiology Renal Physiology 2004, vol. 287, p. F434-441
non-patent document 34: British Journal of Urology 1997, vol. 79, p. 892-7
non-patent document 35: Urologic Nursing 2004, vol. 24, p. 490-7, 512
non-patent document 36: British Journal of Nursing 2005, vol. 14, p. 1014-8, 1020-1
patent document 1: WO2004/096196
patent document 2: US2006/0069087
patent document 3: WO2005/115145
patent document 4: US2005/0038032
patent document 5: WO2004/094371
patent document 6: WO2004/069244
patent document 7: WO2004/014851
patent document 8: WO2003/013545
patent document 9: WO2002/051838
patent document 10: WO2002/051232
patent document 11: WO2002/036555
patent document 12: WO2002/018377
patent document 13: WO2001/055118
patent document 14: WO98/50382
patent document 15: WO98/47876
patent document 16: WO98/46590
patent document 17: WO97/17344
patent document 18: EP567090
patent document 19: U.S. Pat. No. 4,125,538
patent document 20: DE2116222
patent document 21: DE2014223
patent document 22: SU245787
patent document 23: U.S. Pat. No. 3,542,807
patent document 24: FR1463402
patent document 25: BE669838

DISCLOSURE OF THE INVENTION

Problems to be Solved by the Invention

There is a demand on the development of a compound having a serotonin 5-$HT_{2C}$ receptor activation action, which is useful as a drug for the treatment or prophylaxis of lower urinary tract symptom such as stress urinary incontinence and the like, obesity and pelvic organ prolapse and the like, and has superior properties in terms of receptor selectivity, efficacy, duration of action, specificity, lower toxicity and the like.

Currently, a superior agent for the prophylaxis or treatment of pelvic organ prolapse and post-micturition dribble does not exist. If a drug that potentiates reflective contractile force of the pelvic floor muscles can be found, a superior therapeutic drug for pelvic organ prolapse and post-micturition dribble can be provided.

The present invention aims to provide a novel benzoxazepine derivative having a serotonin 5-$HT_{2C}$ receptor activation action and the like, which has a chemical structure different from those of known compounds including the aforementioned compounds, and an agent for the prophylaxis or treatment of diseases such as stress urinary incontinence and the like, which comprises the compound.

Means of Solving the Problems

The present inventors have conducted intensive studies and succeeded for the first time in the creation of a serotonin 5-$HT_{2C}$ receptor activator comprising a compound represented by the formula (I):

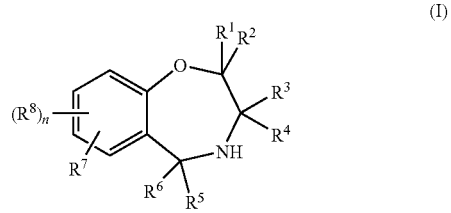

wherein
$R^1$, $R^2$, $R^3$, $R^4$, $R^5$ and $R^6$ are the same or different and each is
(1) a hydrogen atom,
(2) a halogen atom,
(3) a group via a carbon atom,
(4) a group via a nitrogen atom,
(5) a group via an oxygen atom, or
(6) a group via a sulfur atom;
$R^7$ is
(1) a mono-alkylamino group,
(2) a di-alkylamino group optionally having substituent(s),
(3) a non-aromatic heterocyclic group optionally having substituent(s),
(4) an aryl group optionally having substituent(s),
(5) a cycloalkyl group optionally having substituent(s),
(6) a cycloalkenyl group optionally having substituent(s), (7) an aromatic heterocyclic group optionally having substituent(s),
(8) a $C_{2-6}$ alkyl group,
(9) an alkoxy-alkyl group,
(10) a halo-$C_{2-6}$ alkyl group,
(11) an alkenyl group,
(12) an aryl-alkenyl group,
(13) an alkoxy-alkenyl group, or
(14) a non-aromatic heterocyclyl-carbonyl group;
$R^8$ is
(1) a halogen atom,
(2) a group via a carbon atom,
(3) a group via a nitrogen atom,
(4) a group via an oxygen atom, or
(5) a group via a sulfur atom; and
n is an integer of 0 to 3,
excluding 9-chloro-7-(1,1-dimethylethyl)-2,3,4,5-tetrahydro-1,4-benzoxazepine and N-[[(5S)-2-oxo-3-(2,3,4,5-tetrahydro-1,4-benzoxazepin-7-yl)-5-oxazolidinyl]methyl]acetamide,
or a salt thereof (hereinafter sometimes to be abbreviated as compound (I)) or a prodrug thereof. They have further found that compound (I) unexpectedly has superior properties as a serotonin 5-$HT_{2C}$ receptor activator, and is sufficiently satisfactory as a pharmaceutical composition, which resulted in the completion of the present invention.

In addition, the present inventors raised, under anesthesia, the bladder pressure of female rat whose spinal code is cut at the thoracic cord and the hypogastric nerve and the nerus pudendus are bilaterally cut. They have found that the urethral closure response observed at this time is caused by the iliococcygeus muscle and the pubococcygeus muscle, which are pelvic floor muscles, since the reaction markedly decreases when the nerves to the iliococcygeus muscle and the pubococcygeus muscle are bilaterally cut. In other words, they have found that, by bilaterally cutting the hypogastric nerve and pudendal nerves, raising the bladder pressure and observing the urethral closure response, the contractile responses of the pelvic floor muscles can be evaluated in vivo and a superior therapeutic drug for pelvic organ prolapse and post-micturition dribble can be searched for. Using this in vivo efficacy evaluation method, the present inventors have found that a substance that activates a serotonin 5-$HT_{2C}$ receptor, which is the compound of the present invention, can prevent or treat pelvic organ prolapse or post-micturition dribble by enhancing the contractile responses of the reflective pelvic floor muscles.

Accordingly, the present invention relates to
[1] a compound represented by the formula (I):

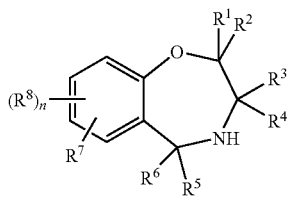

(I)

wherein
$R^1$, $R^2$, $R^3$, $R^4$, $R^5$ and $R^6$ are the same or different and each is
(1) a hydrogen atom,
(2) a halogen atom,
(3) a group via a carbon atom,
(4) a group via a nitrogen atom,
(5) a group via an oxygen atom, or
(6) a group via a sulfur atom;
$R^7$ is
(1) a mono-alkylamino group,
(2) a di-alkylamino group optionally having substituent(s),
(3) a non-aromatic heterocyclic group optionally having substituent(s),
(4) an aryl group optionally having substituent(s),
(5) a cycloalkyl group optionally having substituent(s),
(6) a cycloalkenyl group optionally having substituent(s),
(7) an aromatic heterocyclic group optionally having substituent(s),
(8) a $C_{2-6}$ alkyl group,
(9) an alkoxy-alkyl group,
(10) a halo-$C_{2-6}$ alkyl group,
(11) an alkenyl group,
(12) an aryl-alkenyl group,
(13) an alkoxy-alkenyl group, or
(14) a non-aromatic heterocyclyl-carbonyl group;
$R^8$ is
(1) a halogen atom,
(2) a group via a carbon atom,
(3) a group via a nitrogen atom,
(4) a group via an oxygen atom, or
(5) a group via a sulfur atom; and
n is an integer of 0 to 3,
or a salt thereof;

[2] the compound of the above-mentioned [1], which is represented by the formula (Ia):

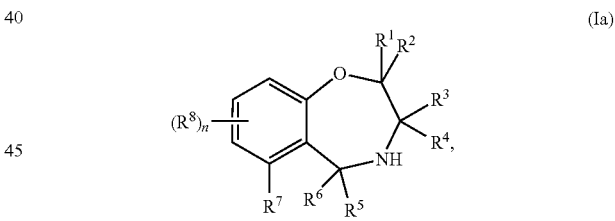

(Ia)

wherein each symbol is as defined in the above-mentioned [1] (hereinafter sometimes to be abbreviated as compound (Ia));

[3] the compound of the above-mentioned [1], which is represented by the formula (Ib):

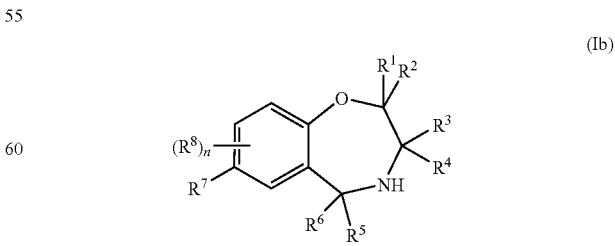

(Ib)

wherein each symbol is as defined in the above-mentioned [1] (hereinafter sometimes to be abbreviated as compound (Ib));

[4] the compound of the above-mentioned [1], which is represented by the formula (Ic):

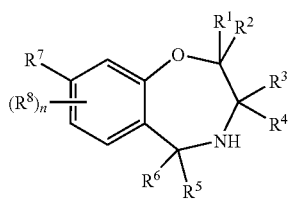

wherein each symbol is as defined in the above-mentioned [1] (hereinafter sometimes to be abbreviated as compound (Ic));

[5] the compound of the above-mentioned [1], which is represented by the formula (Id):

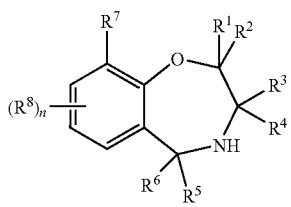

wherein each symbol is as defined in the above-mentioned [1] (hereinafter sometimes to be abbreviated as compound (Id));

[6] the compound of the above-mentioned [1], wherein $R^7$ is (1) a mono-alkylamino group, (2) a di-alkylamino group optionally having substituent(s), (3) a non-aromatic heterocyclic group, (4) an aryl group optionally having substituent(s), (5) a cycloalkyl group optionally having substituent(s), (6) a cycloalkenyl group optionally having substituent(s), or (7) an aromatic heterocyclic group optionally having substituent(s);

[7] the compound of the above-mentioned [1], wherein $R^7$ is (1) a non-aromatic heterocyclic group optionally having substituent(s), (2) a cycloalkyl group optionally having substituent(s), (3) a $C_{2-6}$ alkyl group, or (4) a halo-$C_{2-6}$ alkyl group;

[8] the compound of the above-mentioned [1], wherein n is 0 or 1;

[9] 9-(1-methylethyl)-2,3,4,5-tetrahydro-1,4-benzoxazepine, 9-(tetrahydrofuran-3-yl)-2,3,4,5-tetrahydro-1,4-benzoxazepine, 9-(2,2,2-trifluoro-1-methylethyl)-2,3,4,5-tetrahydro-1,4-benzoxazepine, 9-cyclobutyl-2,3,4,5-tetrahydro-1,4-benzoxazepine, or 9-cyclopropyl-2,3,4,5-tetrahydro-1,4-benzoxazepine or a salt thereof;

[10] a prodrug of compound (I);

[11] a pharmaceutical composition comprising a compound represented by the formula (I'):

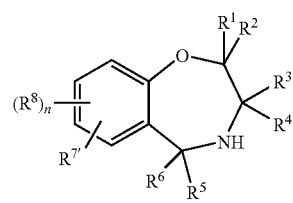

wherein $R^1, R^2, R^3, R^4, R^5$ and $R^6$ are the same or different and each is (1) a hydrogen atom, (2) a halogen atom, (3) a group via a carbon atom, (4) a group via a nitrogen atom, (5) a group via an oxygen atom, or (6) a group via a sulfur atom;

$R^{7'}$ is (1) a mono-alkylamino group, (2) a di-alkylamino group optionally having substituent(s), (3) a non-aromatic heterocyclic group optionally having substituent(s), (4) an aryl group optionally having substituent(s), (5) a cycloalkyl group optionally having substituent(s), (6) a cycloalkenyl group optionally having substituent(s), (7) an aromatic heterocyclic group optionally having substituent(s), (8) a $C_{2-6}$ alkyl group, (9) an alkoxy-alkyl group,

(10) a halo-$C_{2-6}$ alkyl group,

(11) an alkenyl group,

(12) an aryl-alkenyl group,

(13) an alkoxy-alkenyl group,

(14) a non-aromatic heterocyclyl-carbonyl group, or

(15) a carboxyl group;

$R^8$ is (1) a halogen atom, (2) a group via a carbon atom, (3) a group via a nitrogen atom, (4) a group via an oxygen atom, or (5) a group via a sulfur atom; and n is an integer of 0 to 3, provided that 9-chloro-7-(1,1-dimethylethyl)-2,3,4,5-tetrahydro-1,4-benzoxazepine and N-[[(5S)-2-oxo-3-(2,3,4,5-tetrahydro-1,4-benzoxazepin-7-yl)-5-oxazolidinyl]methyl]acetamide are excluded, and provided that when the 2,3,4,5-tetrahydro-1,4-benzoxazepine has $R^7$ or $R^8$ at the 9-position, then the substituent at the 7-position is not (i) a group represented by —$B_1$—$SO_2$-$Q_1$ wherein $B_1$ is an oxygen atom or an amino group optionally having substituent(s), and $Q_1$ is a hydrocarbon group optionally having substituent(s) or a heterocyclic group optionally having substituent(s), or $B_1$ combined with $Q_1$ is a nitrogen-containing aromatic heterocyclic group optionally having substituent(s), nor (ii) a group represented by —$SO_2$—$B_2$-$Q_2$ wherein $B_2$ is an oxygen atom or an amino group optionally having substituent(s), and Q₂ is a hydrocarbon group optionally having substituent(s) or a heterocyclic group optionally having substituent(s), or —B₂-Q₂ is a nitrogen-containing aromatic heterocyclic group optionally having substituent(s), (hereinafter sometimes to be abbreviated as compound (I')) or a salt thereof or a prodrug thereof;

[12] the pharmaceutical composition of the above-mentioned [11], which is a serotonin 5-HT$_{2c}$ receptor activator;

[13] the pharmaceutical composition of the above-mentioned [11], which is an agent for the prophylaxis or treatment of lower urinary tract symptom, obesity and/or pelvic organ prolapse;

[14] the pharmaceutical composition of the above-mentioned [11], which is an agent for the prophylaxis or treatment of anterior vaginal wall prolapse, posterior vaginal wall prolapse, uterine prolapse, prolapse of the apical segment of the vagina, rectal prolapse, enterocele, cystocele, urethral prolapse or post-micturition dribble;

[15] a method for the prophylaxis or treatment of lower urinary tract symptom, obesity and/or pelvic organ prolapse in a mammal, which comprises administering an effective amount of a compound represented by the formula (I'):

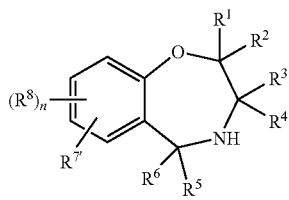

(I')

wherein
$R^2, R^3, R^4, R^5$ and $R^6$ are the same or different and each is
(1) a hydrogen atom,
(2) a halogen atom,
(3) a group via a carbon atom,
(4) a group via a nitrogen atom,
(5) a group via an oxygen atom, or
(6) a group via a sulfur atom;
$R^{7'}$ is
(1) a mono-alkylamino group,
(2) a di-alkylamino group optionally having substituent(s),
(3) a non-aromatic heterocyclic group optionally having substituent(s),
(4) an aryl group optionally having substituent(s), (5) a cycloalkyl group optionally having substituent(s),
(6) a cycloalkenyl group optionally having substituent(s),
(7) an aromatic heterocyclic group optionally having substituent(s),
(8) a $C_{2-6}$ alkyl group,
(9) an alkoxy-alkyl group,
(10) a halo-$C_{2-6}$ alkyl group,
(11) an alkenyl group,
(12) an aryl-alkenyl group,
(13) an alkoxy-alkenyl group,
(14) a non-aromatic heterocyclyl-carbonyl group, or
(15) a carboxyl group;
$R^8$ is
(1) a halogen atom,
(2) a group via a carbon atom,
(3) a group via a nitrogen atom,
(4) a group via an oxygen atom, or
(5) a group via a sulfur atom; and
n is an integer of 0 to 3, provided that 9-chloro-7-(1,1-dimethylethyl)-2,3,4,5-tetrahydro-1,4-benzoxazepine and N-[[(5S)-2-oxo-3-(2,3,4,5-tetrahydro-1,4-benzoxazepin-7-yl)-5-oxazolidinyl]methyl] acetamide are excluded, and provided that when the 2,3,4,5-tetrahydro-1,4-benzoxazepine has $R^7$ or $R^8$ at the 9-position, then the substituent at the 7-position is not
(i) a group represented by —B₁—SO₂-Q₁
wherein
B₁ is an oxygen atom or an amino group optionally having substituent(s), and
Q₁ is a hydrocarbon group optionally having substituent(s) or a heterocyclic group optionally having substituent(s), or B₁ combined with Q₁ is a nitrogen-containing aromatic heterocyclic group optionally having substituent(s), nor
(ii) a group represented by —SO₂—B₂-Q₂
wherein
B₂ is an oxygen atom or an amino group optionally having substituent(s), and
Q₂ is a hydrocarbon group optionally having substituent(s) or a heterocyclic group optionally having substituent(s), or —B₂-Q₂ is a nitrogen-containing aromatic heterocyclic group optionally having substituent(s),
or a salt thereof or a prodrug thereof to the mammal;

[16] use of a compound represented by the formula (I'):

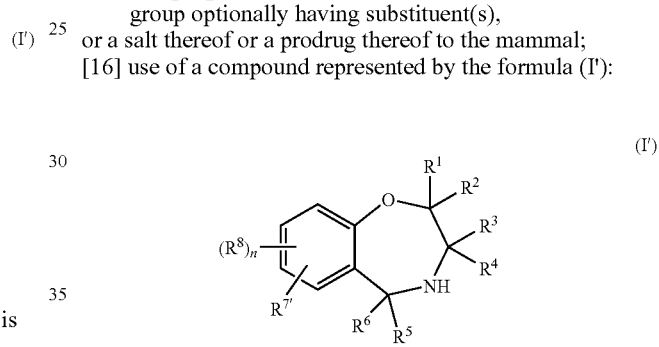

(I')

wherein
$R^1, R^2, R^3, R^4, R^5$ and $R^6$ are the same or different and each is
(1) a hydrogen atom,
(2) a halogen atom,
(3) a group via a carbon atom,
(4) a group via a nitrogen atom,
(5) a group via an oxygen atom, or
(6) a group via a sulfur atom;
$R^{7'}$ is
(1) a mono-alkylamino group,
(2) a di-alkylamino group optionally having substituent(s),
(3) a non-aromatic heterocyclic group optionally having substituent(s),
(4) an aryl group optionally having substituent(s),
(5) a cycloalkyl group optionally having substituent(s),
(6) a cycloalkenyl group optionally having substituent(s),
(7) an aromatic heterocyclic group optionally having substituent(s),
(8) a $C_{2-6}$ alkyl group,
(9) an alkoxy-alkyl group,
(10) a halo-$C_{2-6}$ alkyl group,
(11) an alkenyl group,
(12) an aryl-alkenyl group,
(13) an alkoxy-alkenyl group,
(14) a non-aromatic heterocyclyl-carbonyl group, or
(15) a carboxyl group;
$R^8$ is
(1) a halogen atom,
(2) a group via a carbon atom, (3) a group via a nitrogen atom,
(4) a group via an oxygen atom, or
(5) a group via a sulfur atom; and
n is an integer of 0 to 3,
provided that 9-chloro-7-(1,1-dimethylethyl)-2,3,4,5-tetrahydro-1,4-benzoxazepine and N-[[(5S)-2-oxo-3-(2,3,4,5-tetrahydro-1,4-benzoxazepin-7-yl)-5-oxazolidinyl]methyl]acetamide are excluded, and
provided that when the 2,3,4,5-tetrahydro-1,4-benzoxazepine has $R^7$ or $R^8$ at the 9-position, then the substituent at the 7-position is not
(i) a group represented by —$B_1$—$SO_2$-$Q_1$
  wherein
    $B_1$ is an oxygen atom or an amino group optionally having substituent(s), and
    $Q_1$ is a hydrocarbon group optionally having substituent(s) or a heterocyclic group optionally having substituent(s), or $B_1$ combined with $Q_1$ is a nitrogen-containing aromatic heterocyclic group optionally having substituent(s), nor
(ii) a group represented by —$SO_2$—$B_2$-$Q_2$
  wherein
    $B_2$ is an oxygen atom or an amino group optionally having substituent(s), and
    $Q_2$ is a hydrocarbon group optionally having substituent(s) or a heterocyclic group optionally having substituent(s), or —$B_2$-$Q_2$ is a nitrogen-containing aromatic heterocyclic group optionally having substituent(s),
or a salt thereof or a prodrug thereof, for the production of an agent for the prophylaxis or treatment of lower urinary tract symptom, obesity and/or pelvic organ prolapse;
[17] an agent for the prophylaxis or treatment of pelvic organ prolapse or post-micturition dribble, which comprises a serotonin 5-$HT_{2C}$ receptor activator;
[18] a method for the prophylaxis or treatment of pelvic organ prolapse or post-micturition dribble in a mammal, which comprises administering an effective amount of a serotonin 5-$HT_{2C}$ receptor activator;
[19] a serotonin 5-$HT_{2C}$ receptor activator for the prophylaxis or treatment of pelvic organ prolapse or post-micturition dribble;
and the like.

Effect of the Invention

Compound (I) of the present invention (or compound (I')) or a prodrug thereof is useful as a drug for the prophylaxis or treatment of all serotonin 5-$HT_{2C}$ associated diseases, since it has superior serotonin 5-$HT_{2C}$ receptor activation action, for example, lower urinary tract symptom (including stress urinary incontinence, mixed urinary incontinence, post-micturition dribble), obesity, pelvic organ prolapse and the like, which has safety and lower toxicity.

BRIEF DESCRIPTION OF THE DRAWINGS

FIG. 1 shows a typical example, in the condition of bilaterally cutting hypogastric nerve and pudendal nerves in urethane-anesthetized female rat, in the action of the compound in the present invention to the urethral closure response induced by increasing bladder pressure (Experimental Example 3).

BEST MODE FOR CARRYING OUT THE INVENTION

The present invention is explained in detail in the following.
In the present specification, the "halogen atom" is a fluorine atom, a chlorine atom, a bromine atom or an iodine atom.

In the present specification, the "group via a carbon atom" is, for example, cyano, a hydrocarbon group optionally having substituent(s), a heterocyclic group bonded via a carbon atom, which optionally has substituent(s), or the like.

Examples of the "hydrocarbon group optionally having substituent(s)" include an alkyl group optionally having substituent(s), an alkenyl group optionally having substituent(s), an alkynyl group optionally having substituent(s), a cycloalkyl group optionally having substituent(s), a cycloalkenyl group optionally having substituent(s), an aryl group optionally having substituent(s), a cycloalkylalkyl group optionally having substituent(s), a cycloalkenylalkyl group optionally having substituent(s), an aralkyl group optionally having substituent(s), a cycloalkanedienyl group optionally having substituent(s) and the like.

Examples of the "alkyl group optionally having substituent(s)" include a $C_{1-6}$ alkyl (e.g., methyl, ethyl, propyl, isopropyl, butyl, isobutyl, sec-butyl, tert-butyl, pentyl, hexyl etc.) optionally having 1 to 3 substituents selected from the following substituent group (hereinafter to be abbreviated as Substituent Group A), and the like.

Substituent. Group A:
(1) a halogen atom;
(2) cyano;
(3) nitro;
(4) hydroxy;
(5) $C_{1-6}$ alkoxy (e.g., methoxy, ethoxy, propoxy, isopropoxy, butoxy, isobutoxy, tert-butoxy, trifluoromethoxy etc.) optionally having 1 to 3 halogen atoms;
(6) $C_{2-6}$ alkenyloxy (e.g., ethenyloxy, propenyloxy, butenyloxy, pentenyloxy, hexenyloxy etc.) optionally having 1 to 3 halogen atoms;
(7) $C_{2-6}$ alkynyloxy (e.g., ethynyloxy, propynyloxy, butynyloxy, pentynyloxy, hexynyloxy etc.) optionally having 1 to 3 halogen atoms;
(8) $C_{3-6}$ cycloalkyloxy (e.g., cyclopropyloxy, cyclobutyloxy, cyclopentyloxy, cyclohexyloxy etc.) optionally having 1 to 3 halogen atoms;
(9) $C_{3-6}$ cycloalkenyloxy (e.g., cyclopropenyloxy, cyclobutenyloxy, cyclopentenyloxy, cyclohexenyloxy etc.) optionally having 1 to 3 halogen atoms;
(10) $C_{6-10}$ aryloxy (e.g., phenoxy, 1-naphthyloxy, 2-naphthyloxy etc.) optionally having 1 to 3 halogen atoms;
(11) $C_{3-6}$ cycloalkyl-$C_{1-6}$ alkoxy (e.g., cyclopropylmethyloxy, cyclopropylethyloxy, cyclobutylmethyloxy, cyclopentylmethyloxy, cyclohexylmethyloxy, cyclohexylethyloxy etc.) optionally having 1 to 3 halogen atoms;
(12) $C_{3-6}$ cycloalkenyl-$C_{1-6}$ alkoxy (e.g., cyclopentenylmethyloxy, cyclohexenylmethyloxy, cyclohexenylethyloxy, cyclohexenylpropyloxy etc.) optionally having 1 to 3 halogen atoms;
(13) $C_{6-10}$ aryl-$C_{1-6}$ alkoxy (e.g., benzyloxy, phenylethyloxy etc.) optionally having 1 to 3 halogen atoms;
(14) $C_{1-6}$ alkylaminosulfonyl (e.g., methylaminosulfonyl, ethylaminosulfonyl, propylaminosulfonyl etc.);
(15) di-$C_{1-6}$ alkylaminosulfonyl (e.g., dimethylaminosulfonyl, diethylaminosulfonyl, dipropylaminosulfonyl etc.);
(16) $C_{1-6}$ alkylamino-carbonyl (e.g., methylaminocarbonyl, ethylaminocarbonyl, propylaminocarbonyl etc.);
(17) di-$C_{1-6}$ alkylamino-carbonyl (e.g., dimethylaminocarbonyl, diethylaminocarbonyl, dipropylaminocarbonyl etc.);
(18) formyl;
(19) $C_{1-6}$ alkyl-carbonyl (e.g., acetyl, ethylcarbonyl, propylcarbonyl, isopropylcarbonyl etc.);
(20) $C_{2-6}$ alkenyl-carbonyl (e.g., ethenylcarbonyl, propenylcarbonyl, butenylcarbonyl, pentenylcarbonyl, hexenylcarbonyl etc.);

(21) $C_{2-6}$ alkynyl-carbonyl (e.g., ethynylcarbonyl, propynylcarbonyl, butynylcarbonyl, pentynylcarbonyl, hexynylcarbonyl etc.);
(22) $C_{3-6}$ cycloalkyl-carbonyl (e.g., cyclopropylcarbonyl, cyclobutylcarbonyl, cyclopentylcarbonyl, cyclohexylcarbonyl etc.);
(23) $C_{3-6}$ cycloalkenyl-carbonyl (e.g., cyclopropenylcarbonyl, cyclobutenylcarbonyl, cyclopentenylcarbonyl, cyclohexenylcarbonyl etc.);
(24) $C_{6-10}$ aryl-carbonyl (e.g., benzoyl, 1-naphthylcarbonyl, 2-naphthylcarbonyl etc.);
(25) $C_{3-6}$ cycloalkyl-$C_{1-6}$ alkyl-carbonyl (e.g., cyclopropylmethylcarbonyl, cyclopropylethylcarbonyl, cyclobutylmethylcarbonyl, cyclopentylmethylcarbonyl, cyclohexylmethylcarbonyl, cyclohexylethylcarbonyl etc.);
(26) $C_{3-6}$ cycloalkenyl-$C_{1-6}$ alkyl-carbonyl (e.g., cyclopentenylmethylcarbonyl, cyclohexenylmethylcarbonyl, cyclohexenylethylcarbonyl, cyclohexenylpropylcarbonyl etc.);
(27) $C_{6-10}$ aryl-$C_{1-6}$ alkyl-carbonyl (e.g., benzylcarbonyl, phenylethylcarbonyl etc.);
(28) 5- or 6-membered monocyclic aromatic heterocyclyl-carbonyl (e.g., furylcarbonyl, thienylcarbonyl, pyrrolylcarbonyl, oxazolylcarbonyl, isooxazolylcarbonyl, thiazolylcarbonyl, isothiazolylcarbonyl, imidazolylcarbonyl, pyridylcarbonyl, pyrazolylcarbonyl etc.);
(29) 8- to 12-membered fused aromatic heterocyclyl-carbonyl (e.g., benzofurylcarbonyl, isobenzofurylcarbonyl, benzothienylcarbonyl, isobenzothienylcarbonyl, indolylcarbonyl, isoindolylcarbonyl, 1H-indazolylcarbonyl, benzimidazolylcarbonyl, benzoxazolylcarbonyl etc.);
(30) 3- to 6-membered non-aromatic heterocyclyl-carbonyl (e.g., oxiranylcarbonyl, azetidinylcarbonyl, oxetanylcarbonyl, thietanylcarbonyl, pyrrolidinylcarbonyl, tetrahydrofurylcarbonyl, thioranylcarbonyl, piperidinylcarbonyl, morpholinylcarbonyl etc.);
(31) $C_{1-6}$ alkylsulfonyl (e.g., methylsulfonyl, ethylsulfonyl etc.);
(32) $C_{2-6}$ alkenylsulfonyl (e.g., ethenylsulfonyl, propenylsulfonyl etc.);
(33) $C_{2-6}$ alkynylsulfonyl (e.g., ethynylsulfonyl, propynylsulfonyl, butynylsulfonyl, pentynylsulfonyl, hexynylsulfonyl etc.);
(34) $C_{3-6}$ cycloalkylsulfonyl (e.g., cyclopropylsulfonyl, cyclobutylsulfonyl etc.);
(35) $C_{3-6}$ cycloalkenylsulfonyl (e.g., cyclopropenylsulfonyl, cyclobutenylsulfonyl etc.);
(36) $C_{6-10}$ arylsulfonyl (e.g., phenylsulfonyl etc.);
(37) $C_{3-6}$ cycloalkyl-$C_{1-6}$ alkyl-sulfonyl (e.g., cyclopropylmethylsulfonyl etc.);
(38) $C_{3-6}$ cycloalkenyl-$C_{1-6}$ alkyl-sulfonyl (e.g., cyclopentenylmethylsulfonyl etc.);
(39) $C_{6-10}$ aryl-$C_{1-6}$ alkyl-sulfonyl (e.g., benzylsulfonyl etc.);
(40) 5- or 6-membered monocyclic aromatic heterocyclyl-sulfonyl (e.g., furylsulfonyl, thienylsulfonyl, pyridylsulfonyl etc.);
(41) 8- to 12-membered fused aromatic heterocyclyl-sulfonyl (e.g., benzofurylsulfonyl, isobenzofurylsulfonyl etc.);
(42) 3- to 6-membered non-aromatic heterocyclyl-sulfonyl (e.g., oxiranylsulfonyl, azetidinylsulfonyl etc.);
(43) amino;
(44) mono-$C_{1-6}$ alkylamino (e.g., methylamino, ethylamino, propylamino, isopropylamino, butylamino, isobutylamino, tert-butylamino etc.);
(45) di-$C_{1-6}$ alkylamino (e.g., dimethylamino, diethylamino, dipropylamino, diisopropylamino, dibutylamino, diisobutylamino, di-tert-butylamino etc.);
(46) mono-($C_{1-6}$ alkyl-carbonyl)amino (e.g., acetylamino, ethylcarbonylamino, propylcarbonylamino, tert-butylcarbonylamino etc.) optionally having 1 to 3 halogen atoms;
(47) mono-($C_{3-6}$ cycloalkyl-carbonyl)amino (e.g., cyclopropylcarbonylamino, cyclobutylcarbonylamino, cyclopentylcarbonylamino, cyclohexylcarbonylamino etc.);
(48) mono-($C_{3-6}$ cycloalkenyl-carbonyl)amino (e.g., cyclopropenylcarbonylamino, cyclobutenylcarbonylamino, cyclopentenylcarbonylamino, cyclohexenylcarbonylamino etc.);
(49) mono-($C_{6-10}$ aryl-carbonyl)amino (e.g., benzoylamino etc.) optionally having 1 to 3 halogen atoms;
(50) mono-(5- or 6-membered monocyclic aromatic heterocyclyl-carbonyl)amino (e.g., furylcarbonylamino, thienylcarbonylamino, pyrrolylcarbonylamino, oxazolylcarbonylamino, isooxazolylcarbonylamino, thiazolylcarbonylamino, isothiazolylcarbonylamino, imidazolylcarbonylamino, tetrazolylcarbonylamino, pyridylcarbonylamino, pyrazolylcarbonylamino etc.) optionally having 1 to 3 substituents selected from (a) halogen atom, (b) $C_{1-6}$ alkyl (e.g., methyl, ethyl, propyl etc.) optionally having 1 to 3 halogen atoms, (c) $C_{1-6}$ alkoxy (e.g., methoxy, ethoxy, propoxy etc.) and (d) $C_{3-6}$ cycloalkyl (e.g., cyclopropyl, cyclobutyl, cyclopentyl, cyclohexyl etc.);
(51) mono-(8- to 12-membered fused aromatic heterocyclyl-carbonyl)amino (e.g., benzofurylcarbonylamino, isobenzofurylcarbonylamino, benzothienylcarbonylamino, isobenzothienylcarbonylamino, benzopyrazolylcarbonylamino etc.) optionally having 1 to 3 substituents selected from (a) halogen atom, (b) $C_{1-6}$ alkyl (e.g., methyl, ethyl, propyl etc.) m optionally having 1 to 3 halogen atoms, (c) $C_{1-6}$ alkoxy (e.g., methoxy, ethoxy, propoxy etc.) and (d) $C_{3-6}$ cycloalkyl (e.g., cyclopropyl, cyclobutyl, cyclopentyl, cyclohexyl etc.);
(52) mono-(3- to 6-membered non-aromatic heterocyclyl-carbonyl)amino (e.g., oxiranylcarbonylamino, azetidinylcarbonylamino, oxetanylcarbonylamino, tetrahydrofurylcarbonylamino etc.);
(53) mono-$C_{1-6}$ alkoxy-carbonylamino (e.g., methoxycarbonylamino, ethoxycarbonylamino, tert-butoxycarbonylamino etc.);
(54) mercapto;
(55) $C_{1-6}$ alkylsulfanyl (e.g., methylsulfanyl, ethylsulfanyl etc.);
(56) $C_{2-6}$ alkenylsulfanyl (e.g., ethenylsulfanyl, propenylsulfanyl etc.);
(57) $C_{2-6}$ alkynylsulfanyl (e.g., ethynylsulfanyl, propynylsulfanyl, butynylsulfanyl, pentynylsulfanyl, hexynylsulfanyl etc.);
(58) $C_{3-6}$ cycloalkylsulfanyl (e.g., cyclopropylsulfanyl, cyclobutylsulfanyl etc.);
(59) $C_{3-6}$ cycloalkenylsulfanyl (e.g., cyclopropenylsulfanyl, cyclobutenylsulfanyl etc.);
(60) $C_{6-10}$ arylsulfanyl (e.g., phenylsulfanyl etc.);
(61) $C_{3-6}$ cycloalkyl-$C_{1-6}$ alkyl-sulfanyl (e.g., cyclopropylmethylsulfanyl etc.);
(62) $C_{3-6}$ cycloalkenyl-$C_{1-6}$ alkyl-sulfanyl (e.g., cyclopentenylmethylsulfanyl etc.);
(63) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.);
(64) a 8- to 12-membered fused aromatic heterocyclic group (e.g., benzofuryl, isobenzofuryl, benzothienyl, isobenzothienyl, indolyl, isoindolyl, 1H-indazolyl, benzimidazolyl, benzoxazolyl, isoquinolyl etc.);
(65) a 3- to 6-membered non-aromatic heterocyclic group (e.g., oxiranyl, azetidinyl, oxetanyl, thietanyl, pyrrolidinyl, tetrahydrofuryl, thioranyl, piperidinyl etc.);

(66) 5- or 6-membered monocyclic aromatic heterocyclyl-oxy (e.g., furyloxy, thienyloxy, pyrrolyloxy, oxazolyloxy, isooxazolyloxy, thiazolyloxy, isothiazolyloxy, imidazolyloxy, pyridyloxy, pyrazolyloxy etc.);
(67) 8- to 12-membered fused aromatic heterocyclyl-oxy (e.g., benzofuryloxy, isobenzofuryloxy, benzothienyloxy, isobenzothienyloxy, indolyloxy, isoindolyloxy, 1H-indazolyloxy, benzimidazolyloxy, benzoxazolyloxy etc.);
(68) 3- to 6-membered non-aromatic heterocyclyl-oxy (e.g., oxiranyloxy, azetidinyloxy, oxetanyloxy, thietanyloxy, pyrrolidinyloxy, tetrahydrofuryloxy, thioranyloxy, piperidinyloxy etc.);
(69) oxo;
(70) $C_{1-6}$ alkylsulfinyl (e.g., methylsulfinyl, ethylsulfinyl etc.);
(71) $C_{2-6}$ alkenylsulfinyl (e.g., ethenylsulfinyl, propenylsulfinyl etc.);
(72) $C_{2-6}$ alkynylsulfinyl (e.g., ethynylsulfinyl, propynylsulfinyl, butynylsulfinyl, pentynylsulfinyl, hexynylsulfinyl etc.);
(73) $C_{3-6}$ cycloalkylsulfinyl (e.g., cyclopropylsulfinyl, cyclobutylsulfinyl etc.);
(74) $C_{3-6}$ cycloalkenylsulfinyl (e.g., cyclopropenylsulfinyl, cyclobutenylsulfinyl etc.);
(75) $C_{6-10}$ arylsulfinyl (e.g., phenylsulfinyl etc.);
(76) $C_{3-6}$ cycloalkyl-$C_{1-6}$ alkyl-sulfinyl (e.g., cyclopropylmethylsulfinyl etc.);
(77) $C_{3-6}$ cycloalkenyl-$C_{1-6}$ alkyl-sulfinyl (e.g., cyclopentenylmethylsulfinyl etc.);
(78) $C_{1-6}$ alkyl-aminothiocarbonyl (e.g., methylaminothiocarbonyl, ethylaminothiocarbonyl, propylaminothiocarbonyl etc.);
(79) di-$C_{1-6}$ alkyl-aminothiocarbonyl (e.g., dimethylaminothiocarbonyl, diethylaminothiocarbonyl, dipropylaminothiocarbonyl etc.);
(80) carboxy;
(81) $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, tert-butoxycarbonyl etc.);
(82) $C_{2-6}$ alkenyloxy-carbonyl (e.g., ethenyloxycarbonyl, propenyloxycarbonyl, butenyloxycarbonyl, pentenyloxycarbonyl, hexenyloxycarbonyl etc.);
(83) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl etc.);
(84) $C_{3-6}$ cycloalkyloxy-carbonyl (e.g., cyclopropyloxycarbonyl, cyclobutyloxycarbonyl, cyclopentyloxycarbonyl, cyclohexyloxycarbonyl etc.);
(85) $C_{3-6}$ cycloalkenyloxy-carbonyl (e.g., cyclopropenyloxycarbonyl, cyclobutenyloxycarbonyl, cyclopentenyloxycarbonyl, cyclohexenyloxycarbonyl etc.);
(86) $C_{6-10}$ aryloxy-carbonyl (e.g., phenoxycarbonyl, 1-naphthyloxycarbonyl, 2-naphthyloxycarbonyl etc.);
(87) $C_{3-6}$ cycloalkyl-$C_{1-6}$ alkoxy-carbonyl (e.g., cyclopropylmethoxycarbonyl, cyclopropylethoxycarbonyl, cyclobutylmethoxycarbonyl, cyclopentylmethoxycarbonyl, cyclohexylmethoxycarbonyl, cyclohexylethoxycarbonyl etc.);
(88) $C_{3-6}$ cycloalkenyl-$C_{1-6}$ alkoxy-carbonyl (e.g., cyclopentenylmethoxycarbonyl, cyclohexenylmethoxycarbonyl, cyclohexenylethoxycarbonyl, cyclohexenylpropoxycarbonyl etc.);
(89) $C_{6-10}$ aryl-$C_{1-6}$ alkoxy-carbonyl (e.g., phenylmethoxycarbonyl, phenylethoxycarbonyl etc.);
(90) carbamoyl;
(91) $C_{1-6}$ alkylthio (e.g., methylthio etc.);
(92) alkylenedioxy (e.g., methylenedioxy etc.); and
(93) $C_{1-6}$ alkylsulfonylamino (e.g., methylsulfonylamino etc.).

Examples of the "alkenyl group optionally having substituent(s)" include $C_{2-6}$ alkenyl (e.g., ethenyl, propenyl, butenyl, pentenyl, hexenyl, butadienyl etc.) optionally having 1 to 3 substituents selected from Substituent Group A, and the like.

Examples of the "alkynyl group optionally having substituent(s)" include $C_{2-6}$ alkynyl (e.g., ethynyl, propynyl, butynyl, pentynyl, hexynyl etc.) optionally having 1 to 3 substituents selected from Substituent Group A, and the like.

Examples of the "cycloalkyl group optionally having substituent(s)" include $C_{3-7}$ cycloalkyl (e.g., cyclopropyl, cyclobutyl, cyclopentyl, cyclohexyl etc., or crosslinked cycloalkyl such as norbornyl etc.) optionally having 1 to 3 substituents selected from Substituent Group A and $C_{1-6}$ alkyl (e.g., methyl, ethyl, propyl, isopropyl, butyl, isobutyl, tert-butyl etc.) optionally having 1 to 3 halogen atoms, and the like.

Examples of the "cycloalkenyl group optionally having substituent(s)" include $C_{3-6}$ cycloalkenyl (e.g., cyclopropenyl, cyclobutenyl, cyclopentenyl, cyclohexenyl etc.) optionally having 1 to 3 substituents selected from Substituent Group A and $C_{1-6}$ alkyl (e.g., methyl, ethyl, propyl, isopropyl, butyl, isobutyl, tert-butyl etc.) optionally having 1 to 3 halogen atoms, and the like.

Examples of the "aryl group optionally having substituent(s)" include $C_{6-10}$ aryl (e.g., phenyl, 1-naphthyl, 2-naphthyl etc.) optionally having 1 to 3 substituents selected from Substituent Group A (excluding oxo) and $C_{1-6}$ alkyl (e.g., methyl, ethyl, propyl, isopropyl, butyl, isobutyl, tert-butyl etc.) optionally having 1 to 3 halogen atoms, and the like.

Examples of the "cycloalkylalkyl group optionally having substituent(s)" include $C_{3-6}$ cycloalkyl-$C_{1-4}$ alkyl (e.g., cyclopropylmethyl, cyclopropylethyl, cyclobutylmethyl, cyclopentylmethyl, cyclohexylmethyl, cyclohexylethyl etc.) optionally having 1 to 3 substituents selected from Substituent Group A and $C_{1-6}$ alkyl (e.g., methyl, ethyl, propyl, isopropyl, butyl, isobutyl, tert-butyl etc.) optionally having 1 to 3 halogen atoms, and the like.

Examples of the "cycloalkenylalkyl group optionally having substituent(s)" include $C_{3-6}$ cycloalkenyl-$C_{1-4}$ alkyl (e.g., cyclopentenylmethyl, cyclohexenylmethyl, cyclohexenylethyl, cyclohexenylpropyl, cycloheptenylmethyl, cycloheptenylethyl etc.) optionally having 1 to 3 substituents selected from Substituent Group A and $C_{1-6}$ alkyl (e.g., methyl, ethyl, propyl, isopropyl, butyl, isobutyl, tert-butyl etc.) optionally having 1 to 3 halogen atoms, and the like.

Examples of the "aralkyl group optionally having substituent(s)" include $C_{6-10}$ aryl-$C_{1-4}$ alkyl (e.g., benzyl, phenylethyl etc.) optionally having 1 to 3 substituents selected from Substituent Group A and $C_{1-6}$ alkyl (e.g., methyl, ethyl, propyl, isopropyl, butyl, isobutyl, tert-butyl etc.) optionally having 1 to 3 halogen atoms, and the like.

Examples of the "cycloalkanedienyl group optionally having substituent(s)" include $C_{4-6}$ cycloalkanedienyl (e.g., 2,4-cyclopentadien-1-yl, 2,4-cyclohexadien-1-yl, 2,5-cyclohexadien-1-yl etc.) optionally having 1 to 3 substituents selected from Substituent Group A and $C_{1-6}$ alkyl (e.g., methyl, ethyl, propyl, isopropyl, butyl, isobutyl, tert-butyl etc.) optionally having 1 to 3 halogen atoms, and the like.

Examples of the "heterocyclic group bonded via a carbon atom, which optionally has substituent(s)" include a heterocyclic group (a monocyclic aromatic heterocyclic group, a fused aromatic heterocyclic group, a non-aromatic heterocyclic group) bonded via a carbon atom; which optionally has 1 to 3 substituents selected from Substituent Group A and $C_{1-6}$ alkyl (e.g., methyl, ethyl, propyl, isopropyl, butyl, isobutyl, tert-butyl etc.) optionally having 1 to 3 halogen atoms.

Examples of the "monocyclic aromatic heterocyclic group" include a 5- to 7-membered monocyclic aromatic heterocyclic group containing, as a ring constituting atom besides carbon atoms, 1 to 4 hetero atoms selected from an oxygen atom, a sulfur atom and a nitrogen atom (e.g., furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 2-pyrrolyl, 3-pyrrolyl), imidazolyl (e.g., 2-imidazolyl, 4-imidazolyl, 5-imidazolyl), pyrazolyl (e.g., 3-pyrazolyl, 4-pyrazolyl), thiazolyl (e.g., 2-thiazolyl, 4-thiazolyl, 5-thiazolyl), isothiazolyl, oxazolyl (e.g., 2-oxazolyl, 4-oxazolyl, 5-oxazolyl), isoxazolyl (e.g., 4-isoxazolyl etc.), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-3-yl, 1,2,3-triazol-4-yl), tetrazolyl (e.g., tetrazol-5-yl), triazinyl etc.) and the like.

Examples of the "fused aromatic heterocyclic group" include a group derived from a fused ring wherein a 5- to 7-membered monocyclic aromatic heterocycle containing, as a ring constituting atom besides carbon atoms, 1 to 4 hetero atoms selected from an oxygen atom, a sulfur atom and a nitrogen atom, and the like and $C_{6-10}$ arene and the like are condensed; a group derived from a fused ring wherein the above-mentioned 5- to 7-membered monocyclic aromatic heterocycles are condensed (e.g., quinolyl (e.g., 2-quinolyl, 3-quinolyl, 4-quinolyl, isoquinolyl (e.g., 4-isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-2-yl, benzimidazol-5-yl), indolyl (e.g., indolyl-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl, benzotriazolyl, pyrazolopyridyl, pyrazolothienyl, pyrazolotriazinyl), dibenzofuryl, and the like.

Examples of the "non-aromatic heterocyclic group" include a 3- to 8-membered (preferably 5- or 6-membered) saturated or unsaturated (preferably saturated) non-aromatic heterocyclic group (e.g., oxiranyl (e.g., 2-oxiranyl), azetidinyl (e.g., 2-azetidinyl), oxetanyl (e.g., 2-oxetanyl), thietanyl (e.g., 2-thietanyl), pyrrolidinyl (e.g., 2-pyrrolidinyl, 3-pyrrolidinyl), tetrahydrofuryl (e.g., 2-tetrahydrofuryl, 3-tetrahydrofuryl), thioranyl (e.g., 2-thioranyl, 3-thioranyl), piperidinyl (e.g., 2-piperidinyl, 3-piperidinyl), tetrahydropyranyl (e.g., 2-tetrahydropyranyl, 3-tetrahydropyranyl), thianyl (e.g., 2-thianyl, 3-thianyl), morpholinyl (e.g., 2-morpholinyl), thiomorpholinyl (e.g., 2-thiomorpholinyl), piperazinyl (e.g., 2-piperazinyl), azepanyl (e.g., 2-azepanyl, 3-azepanyl), oxepanyl (e.g., 2-oxepanyl, 3-oxepanyl, 4-oxepanyl), thiepanyl (e.g., 2-thiepanyl, 3-thiepanyl, 4-thiopanyl), oxazepanyl (e.g., 1,4-oxazepan-2-yl, 1,4-oxazepan-3-yl, 1,4-oxazepan-5-yl, 1,4-oxazepan-6-yl, 1,4-oxazepan-7-yl), thiazepanyl (e.g., 1,4-thiazepan-2-yl, 1,4-thiazepan-3-yl, 1,4-thiazepan-5-yl, 1,4-thiazepan-6-yl, 1,4-thiazepan-7-yl), azocanyl (e.g., 2-azocanyl, 3-azocanyl, 4-azocanyl), oxocanyl (e.g., 2-oxocanyl, 3-oxocanyl, 4-oxocanyl), thiocanyl (e.g., 2-thiocanyl, 3-thiocanyl), oxazocanyl (e.g., 1,4-oxazocan-2-yl, 1,4-oxazocan-3-yl, 1,5-oxazocan-2-yl), thiazocanyl (e.g., 1,4-thiazocan-2-yl, 1,4-thiazocan-3-yl, 1,5-thiazocan-4-yl), dioxynyl (e.g., 1,4-dioxin-2-yl), diazetidinyl (3-diazetidinyl), hexahydropyridazinyl (3-hexahydropyridazinyl) etc.), and the like.

In the present specification, the "group via a nitrogen atom" is, for example, nitro group, an amino group optionally having substituent(s), a heterocyclic group bonded via a nitrogen atom, which optionally has substituent(s), or the like.

Examples of the substituent of the "amino group optionally having substituent(s)" include a group bonded via a carbon atom, a group represented by the formula —SO$_2$R$^a$ wherein R$^a$ is a group bonded via a carbon atom, and the like. The number of the substituent is 0 to 2.

Examples of the "heterocyclic group bonded via a nitrogen atom, which optionally has substituent(s)" include a heterocyclic group (a monocyclic aromatic heterocyclic group, a fused aromatic heterocyclic group, a non-aromatic heterocyclic group) bonded via a nitrogen atom, which optionally has 1 to 3 substituents selected from Substituent Group A and $C_{1-6}$ alkyl (e.g., methyl, ethyl, propyl, isopropyl, butyl, isobutyl, tert-butyl etc.) optionally having 1 to 3 halogen atoms.

Examples of the "monocyclic aromatic heterocyclic group" include a 5- to 7-membered monocyclic aromatic heterocyclic group containing, as a ring constituting atom besides carbon atoms and one nitrogen atom, 1 to 4 hetero atoms selected from an oxygen atom, a sulfur atom and a nitrogen atom (e.g., pyrrolyl (e.g., 1-pyrrolyl), imidazolyl (e.g., 1-imidazolyl), pyrazolyl (e.g., 1-pyrazolyl), triazolyl (e.g., 1,2,4-triazol-1-yl), tetrazolyl (e.g., tetrazol-1-yl) etc.), and the like.

Examples of the "fused aromatic heterocyclic group" include a group derived from a fused ring wherein a 5- to 7-membered monocyclic aromatic heterocycle containing, as a ring constituting atom besides carbon atoms and one nitrogen atom, 1 to 4 hetero atoms selected from an oxygen atom, a sulfur atom and a nitrogen atom, and the like and $C_{6-10}$ arene and the like are condensed; a group derived from a fused ring wherein the above-mentioned 5- to 7-membered monocyclic aromatic heterocycles are condensed (e.g., benzimidazolyl (e.g., benzimidazol-1-yl), indolyl (e.g., indol-1-yl etc.), and the like).

Examples of the "non-aromatic heterocyclic group" include a 3- to 8-membered (preferably 5- or 6-membered) saturated or unsaturated (preferably saturated) non-aromatic heterocyclic group (e.g., azetidinyl (e.g., 1-azetidinyl), pyrrolidinyl (e.g., 1-pyrrolidinyl), piperidinyl (e.g., 1-piperidinyl), morpholinyl (e.g., morpholino), thiomorpholinyl (e.g., thiomorpholino), piperazinyl (e.g., 1-piperazinyl), azepanyl (e.g., 1-azepanyl), oxazepanyl (e.g., 1,4-oxazepan-4-yl), thiazepanyl (e.g., 1,4-thiazepan-4-yl), azocanyl (e.g., 1-azocanyl) etc.), oxazolidinyl (e.g., oxazolidin-3-yl), and the like).

In the present specification, the "group via an oxygen atom" is, for example, hydroxy optionally having a substituent. Examples of the substituent of the "hydroxy group optionally having a substituent" include a group via a carbon atom, and the like.

In the present specification, the "group via a sulfur atom" is, for example, a mercapto group, or a group represented by the formula —S(O)$_m$R$^b$ wherein m is an integer of 0 to 2, R$^b$ is a group via a carbon atom or a group via a nitrogen atom.

In the present specification, the "monoalkylamino group" is, for example, mono-$C_{1-6}$ alkylamino (e.g., methylamino, ethylamino, propylamino, isopropylamino, butylamino, isobutylamino, sec-butylamino, tert-butylamino, pentylamino, hexylamino etc.), or the like.

In the present specification, the "dialkylamino group" of the "dialkylamino group optionally having substituent(s)" is, for example, di-$C_{1-6}$ alkylamino (e.g., dimethylamino, diethylamino, N-ethyl-N-methylamino, dipropylamino, N-isopropyl-N-methylamino, diisopropylamino, dibutylamino, diisobutylamino, di-tert-butylamino etc.), or the like.

In the present specification, the "substituent" of the "dialkylamino group optionally having substituent(s)" is substituent(s) selected from Substituent Group A. The number of substituent is 1 to 3.

In the present specification, the "non-aromatic heterocyclic group" of the "non-aromatic heterocyclic group optionally having substituent(s)" is, for example, a 3- to 8-membered (preferably 5- or 6-membered) saturated or unsaturated (preferably saturated) non-aromatic heterocyclic group (e.g., azetidinyl, pyrrolidinyl, piperidinyl, morpholinyl, thiomorpholinyl, piperazinyl, azepanyl, oxazepanyl, thiazepanyl, azocanyl, tetrahydrofuryl, oxazolidinyl etc.), or the like.

In the present specification, the "non-aromatic heterocyclyl-carbonyl group" is, for example, a carbonyl group having a 3- to 8-membered (preferably 5- or 6-membered) saturated or unsaturated (preferably saturated) non-aromatic heterocyclic group (e.g., azetidinylcarbonyl, pyrrolidinylcarbonyl, piperidinylcarbonyl, morpholinylcarbonyl, thiomorpholinylcarbonyl, piperazinylcarbonyl, azepanylcarbonyl, oxazepanylcarbonyl, thiazepanylcarbonyl, azocanylcarbonyl, tetrahydrofurylcarbonyl, oxazolidinylcarbonyl etc.), or the like.

In the present specification, the "aryl group" of the "aryl group optionally having substituent(s)" is, for example, $C_{6-10}$ aryl (e.g., phenyl, naphthyl etc.), or the like.

In the present specification, the "substituent" of the "non-aromatic heterocyclic group optionally having substituent(s)" or the "aryl group optionally having substituent(s)" is substituent(s) (excluding oxo) selected from Substituent Group A and $C_{1-6}$ alkyl (e.g., methyl, ethyl, propyl, isopropyl, butyl, isobutyl, tert-butyl etc.) optionally having 1 to 3 halogen atoms. The number of substituent is 1 to 3.

In the present specification, the "cycloalkyl group" of the "cycloalkyl group optionally having substituent(s)" is, for example, $C_{3-7}$ cycloalkyl (e.g., cyclopropyl, cyclobutyl, cyclopentyl, cyclohexyl etc., or crosslinked cycloalkyl such as norbornyl etc.), or the like.

In the present specification, the "substituent" of the "cycloalkyl group optionally having substituent(s)" is substituent(s) selected from Substituent Group A and $C_{1-6}$ alkyl (e.g., methyl, ethyl, propyl, isopropyl, butyl, isobutyl, tert-butyl etc.) optionally having 1 to 3 halogen atoms. The number of substituent is 1 to 3.

In the present specification, the "cycloalkenyl group" of the "cycloalkenyl group optionally having substituent(s)" is, for example, $C_{3-6}$ cycloalkenyl (e.g., cyclopropenyl, cyclobutenyl, cyclopentenyl, cyclohexenyl etc.), or the like.

In the present specification, the "substituent" of the "cycloalkenyl group optionally having substituent(s)" is substituent(s) selected from Substituent Group A and $C_{1-6}$ alkyl (e.g., methyl, ethyl, propyl, isopropyl, butyl, isobutyl, tert-butyl etc.) optionally having 1 to 3 halogen atoms. The number of substituent is 1 to 3.

In the present specification, the "aromatic heterocyclic group" of the "aromatic heterocyclic group optionally having substituent(s)" is a monocyclic aromatic heterocyclic group or a fused aromatic heterocyclic group.

Examples of the "monocyclic aromatic heterocyclic group" include a 5- to 7-membered monocyclic aromatic heterocyclic group containing, as a ring constituting atom besides carbon atoms, 1 to 4 hetero atoms selected from an oxygen atom, a sulfur atom and a nitrogen atom (e.g., furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 2-imidazolyl, 4-imidazolyl, 5-imidazolyl), pyrazolyl (e.g., 3-pyrazolyl, 4-pyrazolyl), thiazolyl (e.g., 2-thiazolyl, 4-thiazolyl, 5-thiazolyl), isothiazolyl, oxazolyl (e.g., 2-oxazolyl, 4-oxazolyl, 5-oxazolyl), isoxazolyl (e.g., 4-isoxazolyl etc.), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-3-yl, 1,2,3-triazol-4-yl), tetrazolyl (e.g., tetrazol-5-yl), triazinyl etc.), and the like.

Examples of the "fused aromatic heterocyclic group" include a group derived from a fused ring wherein a 5- to 7-membered monocyclic aromatic heterocycle containing, as a ring constituting atom besides carbon atoms, 1 to 4 hetero atoms selected from an oxygen atom, a sulfur atom and a nitrogen atom, and the like and $C_{6-10}$ arene and the like are condensed; a group derived from a fused ring wherein the above-mentioned 5- to 7-membered monocyclic aromatic heterocycles are condensed (e.g., quinolyl (e.g., 2-quinolyl, 3-quinolyl, 4-quinolyl), isoquinolyl (e.g., 4-isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-2-yl, benzimidazol-5-yl), indolyl (e.g., indolyl-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl, benzotriazolyl, pyrazolopyridyl, pyrazolothienyl, pyrazolotriazinyl etc.), dibenzofuryl and the like.

In the present specification, the "substituent" of the "aromatic heterocyclic group optionally having substituent(s)" is substituent(s) (excluding oxo) selected from Substituent Group A and $C_{1-6}$ alkyl (e.g., methyl, ethyl, propyl, isopropyl, butyl, isobutyl, tert-butyl etc.) optionally having 1 to 3 halogen atoms. The number of substituent is 1 to 3.

In the present specification, the "$C_{2-6}$ alkyl group" is straight chain or branched chain alkyl having 2 to 6 carbon atoms (e.g., ethyl, propyl, isopropyl, butyl, isobutyl, sec-butyl, tert-butyl, pentyl, hexyl etc.), or the like.

In the present specification, the "alkoxy-alkyl group" is $C_{1-6}$ alkyl (e.g., methyl, ethyl, propyl, isopropyl, butyl, isobutyl, sec-butyl, tert-butyl, pentyl, hexyl etc.) substituted by 1 to 3 $C_{1-6}$ alkoxy (e.g., methoxy, ethoxy, propoxy, isopropoxy, butoxy, isobutoxy, tert-butoxy etc.), or the like. Examples thereof include methoxymethyl, 2-methoxyethyl, 3-methoxypropyl and the like.

In the present specification, the "halo-$C_{2-6}$ alkyl group" is $C_{2-6}$ alkyl (e.g., ethyl, propyl, isopropyl, butyl, isobutyl, sec-butyl, tert-butyl, pentyl, hexyl etc.) substituted by 1 to 3 halogen atoms (a fluorine atom, a chlorine atom, a bromine atom or an iodine atom). Examples thereof include 2,2,2-trifluoroethyl, 2,2,2-trifluoro-1-methylethyl and the like.

In the present specification, the "alkenyl group" is straight chain or branched chain alkenyl having 2 to 6 carbon atoms (e.g., ethenyl, propenyl, butenyl, pentenyl, hexenyl, butadienyl etc.), or the like. Specific examples thereof include (E)-1-propenyl, (Z)-1-propenyl, (E)-1-butenyl and the like.

In the present specification, the "aryl-alkenyl group" is $C_{2-6}$ alkenyl (e.g., ethenyl, propenyl, butenyl, pentenyl, hexenyl, butadienyl etc.) substituted by 1 to 3 aryl group (e.g., phenyl, naphthyl etc.), or the like. Examples thereof include 2-phenylethenyl and the like.

In the present specification, the "alkoxy-alkenyl group" is $C_{2-6}$ alkenyl (e.g., ethenyl, propenyl, butenyl, pentenyl, hexenyl, butadienyl etc.) substituted by 1 to 3 $C_{1-6}$ alkoxy (e.g., methoxy, ethoxy, propoxy, isopropoxy, butoxy, isobutoxy, tert-butoxy etc.), or the like. Examples thereof include (E)-4-methoxy-1-butenyl and the like.

In compound (I) and compound (I'), $R^1$, $R^2$, $R^3$, $R^4$, $R^5$ and $R^6$ are the same or different and each is (1) a hydrogen atom, (2) a halogen atom, (3) a group via a carbon atom, (4) a group via a nitrogen atom, (5) a group via an oxygen atom, or (6) a group via a sulfur atom.

$R^1$ is preferably a hydrogen atom.
$R^2$ is preferably a hydrogen atom.
$R^3$ is preferably a hydrogen atom.
$R^4$ is preferably a hydrogen atom.
$R^5$ is preferably a hydrogen atom.
$R^6$ is preferably a hydrogen atom.

In compound (I), $R^7$ is (1) a mono-alkylamino group, (2) a di-alkylamino group optionally having substituent(s), (3) a non-aromatic heterocyclic group optionally having substituent(s), (4) an aryl group optionally having substituent(s), (5) a cycloalkyl group optionally having substituent(s), (6) a cycloalkenyl group optionally having substituent(s), (7) an aromatic heterocyclic group optionally having substituent(s), (8) a $C_{2-6}$ alkyl group, (9) an alkoxy-alkyl group, (10) a halo-$C_{2-6}$ alkyl group, (11) an alkenyl group, (12) an aryl-alkenyl group, (13) an alkoxy-alkenyl group, or (14) a non-aromatic heterocyclyl-carbonyl group, and in compound (I'), $R^{7'}$ is (1) a mono-alkylamino group, (2) a di-alkylamino group optionally having substituent(s), (3) a non-aromatic heterocyclic group optionally having substituent(s), (4) an aryl group optionally having substituent(s), (5) a cycloalkyl group optionally having substituent(s), (6) a cycloalkenyl group optionally having substituent(s), (7) an aromatic heterocyclic group optionally having substituent(s), (8) a $C_{2-6}$ alkyl group, (9) an alkoxy-alkyl group, (10) a halo-$C_{2-6}$ alkyl group, (11) an alkenyl group, (12) an aryl-alkenyl group, (13) an alkoxy-alkenyl group, (14) a non-aromatic heterocyclyl-carbonyl group, or (15) a carboxyl group.

$R^7$ is preferably (1) a di-alkylamino group optionally having substituent(s), (2) a non-aromatic heterocyclic group optionally having substituent(s), (3) an aryl group optionally having substituent(s), (4) a cycloalkyl group optionally having substituent(s), (5) a cycloalkenyl group optionally having substituent(s), (6) an aromatic heterocyclic group optionally having substituent(s), (7) a $C_{2-6}$ alkyl group, (8) an alkoxy-alkyl group, (9) a halo-$C_{2-6}$ alkyl group, (10) an alkenyl group, (11) an aryl-alkenyl group, (12) an alkoxy-alkenyl group, or (13) a non-aromatic heterocyclyl-carbonyl group, particularly preferably a non-aromatic heterocyclic group optionally having substituent(s), a cycloalkyl group optionally having substituent(s), a $C_{2-6}$ alkyl group, or a halo-$C_{2-6}$ alkyl group.

$R^{7'}$ is preferably (1) a di-alkylamino group optionally having substituent(s), (2) a non-aromatic heterocyclic group optionally having substituent(s), (3) an aryl group optionally having substituent(s), (4) a cycloalkyl group optionally having substituent(s), (5) a cycloalkenyl group optionally having substituent(s), (6) an aromatic heterocyclic group optionally having substituent(s), (7) a $C_{2-6}$ alkyl group, (8) an alkoxy-alkyl group, (9) a halo-$C_{2-6}$ alkyl group, (10) an alkenyl group, (11) an aryl-alkenyl group, (12) an alkoxy-alkenyl group, (13) a non-aromatic heterocyclyl-carbonyl group, or (14) a carboxyl group, particularly preferably a non-aromatic heterocyclic group optionally having substituent(s), a cycloalkyl group optionally having substituent(s), a $C_{2-6}$ alkyl group, or a halo-$C_{2-6}$ alkyl group.

Of these, $R^7$ is preferably (1) a di-$C_{1-6}$ alkylamino (particularly diethylamino, N-ethyl-N-methylamino, N-isopropyl-N-methylamino) optionally having 1 or 2 $C_{1-6}$ alkoxy (particularly methoxy), (2) a 5- or 6-membered saturated non-aromatic heterocyclic group (particularly pyrrolidinyl, piperidinyl, morpholinyl, tetrahydrofuryl, oxazolidinyl) optionally having 1 or 2 substituents selected from $C_{1-6}$ alkyl (particularly methyl), a halogen atom (particularly a fluorine atom) and oxo, (3) a $C_{6-10}$ aryl (particularly phenyl, 1-naphthyl) optionally having 1 or 2 substituents selected from (a) a halogen atom (particularly a fluorine atom, chlorine atom), (b) $C_{1-6}$ alkoxy optionally having 1 to 3 halogen atoms (particularly a fluorine atom) (particularly methoxy, ethoxy, isopropoxy, trifluoromethoxy), (c) $C_{1-6}$ alkyl-carbonyl (particularly acetyl), (d) $C_{1-6}$ alkylsulfanyl (particularly methylsulfanyl), (e) $C_{1-6}$ alkyl (particularly methyl) optionally having 1 to 3 halogen atoms (particularly a fluorine atom), (f) a cyano group, (g) a nitro group, (h) a hydroxyl group, (i) $C_{1-6}$ alkoxy-carbonyl (particularly methoxycarbonyl), (j) carbamoyl group, (k) $C_{1-6}$ alkyl-carbonyl-amino (particularly acetylamino), (l) $C_{1-6}$ alkylthio (particularly methylthio), (m) $C_{6-10}$ aryl-$C_{1-6}$ alkoxy (particularly benzyloxy), (n) $C_{1-6}$ alkylsulfonylamino (particularly methylsulfonylamino) and (o) alkylenedioxy group (particularly methylenedioxy), (4) a $C_{3-7}$ cycloalkyl (particularly cyclopropyl, cyclobutyl, cyclopentyl, cyclohexyl, norbornyl), (5) a $C_{3-6}$ cycloalkenyl (particularly cyclopentenyl, cyclohexenyl), (6) a 5- to 7-membered monocyclic or fused aromatic heterocyclic group, containing, as a ring constituting atom besides carbon atoms, 1 to 4 hetero atoms selected from an oxygen atom, a sulfur atom and a nitrogen atom (particularly a monocyclic aromatic heterocyclic group such as furyl (e.g., 2-furyl, 3-furyl), thienyl (e.g., 2-thienyl, 3-thienyl), pyridyl (e.g., 3-pyridyl, 4-pyridyl), isoxazolyl (e.g., 4-isoxazolyl), thiazolyl (e.g., 5-thiazolyl), pyrazolyl (e.g., 4-pyrazolyl) and the like; a fused aromatic heterocyclic group such as benzothienyl (e.g., 2-benzothienyl, 3-benzothienyl), isoquinolyl (e.g., 4-isoquinolyl), dibenzofuryl (e.g., 4-dibenzofuryl), and the like) optionally having 1 or 2 substituents selected from $C_{1-6}$ alkyl (particularly methyl) and $C_{1-6}$ alkoxy (particularly methoxy), (7) a $C_{2-6}$ alkyl group (particularly ethyl, propyl, isopropyl, isobutyl), (8) a $C_{1-6}$ alkyl group (particularly propyl) substituted by one $C_{1-6}$ alkoxy group (particularly methoxy) (e.g., 3-methoxypropyl), (9) a $C_{2-6}$ alkyl group (particularly isopropyl) substituted by 1 to 3 halogen atoms (particularly a fluorine atom) (e.g., 2,2,2-trifluoro-1-methylethyl),

(10) a $C_{2-6}$ alkenyl group (particularly (E)-1-propenyl, (Z)-1-propenyl),

(11) a $C_{2-6}$ alkenyl (particularly ethenyl) substituted by $C_{6-10}$ aryl (particularly phenyl) (e.g., 2-phenylethenyl),

(12) a $C_{2-6}$ alkenyl group (particularly butenyl) substituted by a $C_{1-6}$ alkoxy group (particularly methoxy) (e.g., (E)-4-methoxy-1-butenyl), or

(13) a 3- to 6-membered non-aromatic heterocyclyl-carbonyl group (particularly pyrrolidin-1-ylcarbonyl, morpholin-4-ylcarbonyl),
particularly preferably
(2') a 5-membered saturated non-aromatic heterocyclic group (particularly tetrahydrofuryl),
(4') a $C_{3-6}$ cycloalkyl (particularly cyclopropyl, cyclobutyl),
(7') a $C_{2-6}$ alkyl group (particularly isopropyl), or
(9') a $C_{2-6}$ alkyl group substituted by three halogen atoms (particularly a fluorine atom) (particularly 2,2,2-trifluoro-1-methylethyl).

$R^{7'}$ is preferably the above-mentioned (1) to (13) recited for $R^7$, or (14) a carboxyl group, particularly preferably the above-mentioned (2'), (4'), (7') or (9') recited for $R^7$.

In compound (I) and compound (I'), $R^8$ is (1) a halogen atom, (2) a group via a carbon atom, (3) a group via a nitrogen atom, (4) a group via an oxygen atom, or (5) a group via a sulfur atom.

$R^8$ is preferably a hydrogen atom or a halogen atom (particularly a fluorine atom).

In compound (I), n is an integer of 0 to 3.

n is preferably 0 or 1.

Examples of compound (I) include a compound wherein $R^7$ is bonded at the 6-position, 7-position, 8-position or 9-position of the benzoxazepine skeleton, that is, the following compound (Ia), compound (Ib), compound (Ic) and compound (Id).

Examples of compound (I') include a compound wherein $R^{7'}$ is bonded at the 6-position, 7-position, 8-position or 9-position of the benzoxazepine skeleton, that is, compounds represented by the following formulas (Ia'), (Ib'), (Ic') and (Id') (hereinafter sometimes to be abbreviated as compound (Ia'), compound (Ib'), compound (Ic') and compound (Id')).

Compound (Ia) and compound (Ia'):

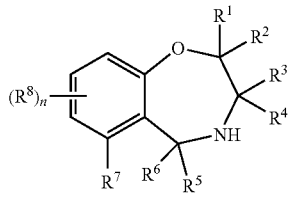
(Ia)

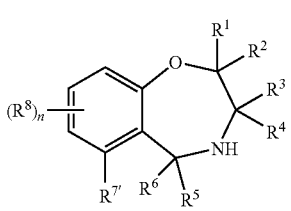
(Ia')

wherein each symbol is as defined above.

In compound (Ia) and compound (Ia'), $R^7$ and $R^{7'}$ are each preferably (1) a non-aromatic heterocyclic group or (2) an aryl group optionally having substituent(s).

Particularly, $R^7$ and $R^{7'}$ are each preferably
(1) a 5- or 6-membered saturated non-aromatic heterocyclic group (particularly morpholinyl) or
(2) a $C_{6-10}$ aryl (particularly phenyl).

Specific examples of compound (Ia) and compound (Ia') include the compounds of Examples 29 and 30.

Compound (Ib) and compound (Ib'):

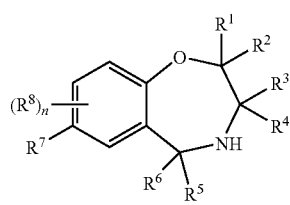
(Ib)

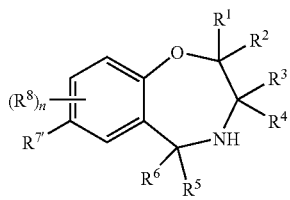
(Ib')

wherein each symbol is as defined above.

In compound (Ib) and compound (Ib'), $R^7$ and $R^{7'}$ are each preferably (1) a non-aromatic heterocyclic group, or (3) an aryl group optionally having substituent(s).

Particularly, $R^7$ and $R^{7'}$ are each preferably
(1) a 5- or 6-membered saturated non-aromatic heterocyclic group (particularly morpholinyl), or
(2) a $C_{6-10}$ aryl (particularly phenyl) optionally having one $C_{1-6}$ alkyl (particularly methyl).

Specific examples of compound (Ib) and compound (Ib') include the compounds of Examples 28, 33 and 34.

Compound (Ic):

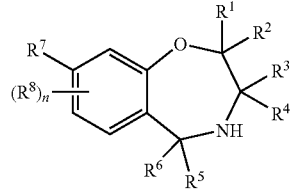
(Ic)

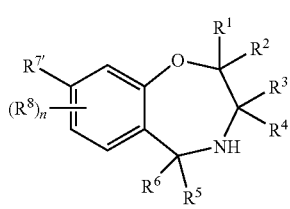
(Ic')

wherein each symbol is as defined above.

In compound (Ic) and compound (Ic'), $R^7$ and $R^{7'}$ are each preferably (1) a di-alkylamino group optionally having substituent(s), (2) a non-aromatic heterocyclic group optionally having substituent(s), or (3) an aryl group optionally having substituent(s).

Particularly, $R^7$ and $R^{7'}$ are each preferably
(1) a di-$C_{1-6}$ alkylamino (particularly diethylamino, N-ethyl-N-methylamino, N-isopropyl-N-methylamino) optionally having 1 or 2 $C_{1-6}$ alkoxy (particularly methoxy),
(2) a 5- or 6-membered saturated non-aromatic heterocyclic group (particularly pyrrolidinyl, piperidinyl, morpholinyl) optionally substituted by $C_{1-6}$ alkyl (particularly methyl), or
(3) $C_{6-10}$ aryl (particularly phenyl) optionally having one halogen atom (particularly chlorine atom).

Specific examples of compound (Ic) and compound (Ic') include the compounds of Examples 1 to 6, 8, 27, 36, 65 and 66.

Compound (Id):

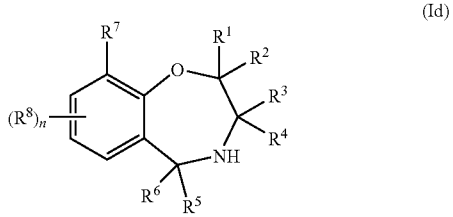

wherein each symbol is as defined above.

In compound (Id), $R^7$ is particularly preferably (1) a non-aromatic heterocyclic group optionally having substituent(s), (2) an aryl group optionally having substituent(s), (3) a cycloalkyl group optionally having substituent(s), (4) a cycloalkenyl group optionally having substituent(s), (5) an aromatic heterocyclic group optionally having substituent(s), (6) a $C_{2-6}$ alkyl group, (7) an alkoxy-alkyl group, (8) a halo-$C_{2-6}$ alkyl group, (9) an alkenyl group, (10) an aryl-alkenyl group, (11) an alkoxy-alkenyl group, or (12) a non-aromatic heterocyclyl-carbonyl group is preferable, and a non-aromatic heterocyclic group optionally having substituent(s), a cycloalkyl group optionally having substituent(s), a $C_{2-6}$ alkyl group or a halo-$C_{2-6}$ alkyl group.

Especially, $R^7$ is preferably
(1) a 5- or 6-membered saturated non-aromatic heterocyclic group (particularly pyrrolidinyl, piperidinyl, morpholinyl, tetrahydrofuryl, oxazolidinyl) optionally having 1 or 2 substituents selected from $C_{1-6}$ alkyl (particularly methyl), a halogen atom (particularly a fluorine atom) and oxo,
(2) a $C_{6-10}$ aryl (particularly phenyl, 1-naphthyl) optionally having 1 or 2 substituents selected from (a) a halogen atom (particularly a fluorine atom, a chlorine atom), (b) $C_{1-6}$ alkoxy (particularly methoxy, ethoxy, isopropoxy, trifluoromethoxy) optionally having 1 to 3 halogen atoms (particularly a fluorine atom), (c) $C_{1-6}$ alkyl-carbonyl (particularly acetyl), (d) $C_{1-6}$ alkylsulfanyl (particularly methylsulfanyl), (e) $C_{1-6}$ alkyl (particularly methyl) optionally having 1 to 3 halogen atoms (particularly a fluorine atom), (f) a cyano group, (g) a nitro group, (h) a hydroxyl group, (i) $C_{1-6}$ alkoxy-carbonyl (particularly methoxycarbonyl), (j) a carbamoyl group, (k) $C_{1-6}$ alkyl-carbonyl-amino (particularly acetylamino), (l) $C_{1-6}$ alkylthio (particularly methylthio), (m) $C_{6-10}$ aryl-$C_{1-6}$ alkoxy (particularly benzyloxy), (n) $C_{1-6}$ alkylsulfonylamino (particularly methylsulfonylamino) and (o) an alkylenedioxy group (particularly methylenedioxy),
(3) a $C_{3-7}$ cycloalkyl (particularly cyclopropyl, cyclobutyl, cyclopentyl, cyclohexyl, norbornyl),
(4) a $C_{3-6}$ cycloalkenyl (particularly cyclopentenyl, cyclohexenyl),
(5) a 5- to 7-membered monocyclic or fused aromatic heterocyclic group containing, as a ring constituting atom besides carbon atoms, 1 to 4 hetero atoms selected from an oxygen atom, a sulfur atom and a nitrogen atom (particularly a monocyclic aromatic heterocyclic group such as furyl(e.g., 2-furyl, 3-furyl), thienyl (e.g., 2-thienyl, 3-thienyl), pyridyl (e.g., 3-pyridyl, 4-pyridyl), isoxazolyl (e.g., 4-isoxazolyl), thiazolyl (e.g., 5-thiazolyl), pyrazolyl (e.g., 4-pyrazolyl) and the like; a fused aromatic heterocyclic group such as benzothienyl (e.g., 2-benzothienyl, 3-benzothienyl), isoquinolyl (e.g., 4-isoquinolyl), dibenzofuryl (e.g., 4-dibenzofuryl) etc.), which optionally has 1 or 2 substituents selected from $C_{1-6}$ alkyl (particularly methyl) and $C_{1-6}$ alkoxy (particularly methoxy),
(6) a $C_{2-6}$ alkyl group (particularly ethyl, propyl, isopropyl, isobutyl),
(7) a $C_{1-6}$ alkyl group (particularly propyl) substituted by one $C_{1-6}$ alkoxy group (particularly methoxy) (e.g., 3-methoxypropyl),
(8) a $C_{2-6}$ alkyl group (particularly isopropyl) substituted by 1 to 3 halogen atoms (particularly a fluorine atom) (e.g., 2,2,2-trifluoro-1-methylethyl),
(9) a $C_{2-6}$ alkenyl group (particularly (E)-1-propenyl, (Z)-1-propenyl),
(10) a $C_{2-6}$ alkenyl (particularly ethenyl) substituted by $C_{6-10}$ aryl (particularly phenyl) (e.g., 2-phenylethenyl),
(11) a $C_{2-6}$ alkenyl group (particularly butenyl) substituted by a $C_{1-6}$ alkoxy group (particularly methoxy) (e.g., (E)-4-methoxy-1-butenyl), or
(12) a 3- to 6-membered non-aromatic heterocyclyl-carbonyl (particularly pyrrolidin-1-ylcarbonyl, morpholin-4-ylcarbonyl). Furthermore, it is particularly preferably
(1') a 5-membered saturated non-aromatic heterocyclic group (particularly tetrahydrofuryl),
(3') a $C_{3-6}$ cycloalkyl (particularly cyclopropyl, cyclobutyl),
(6') a $C_{2-6}$ alkyl group (particularly isopropyl), or
(8') a $C_{2-6}$ alkyl group substituted by 3 halogen atoms (particularly a fluorine atom) (particularly 2,2,2-trifluoro-1-methylethyl).

Specific examples of compound (Id) include the compounds of Examples 7, 9 to 26, 31, 35, 37 to 59, 61 to 64 and 67 to 106.

Compound (Id'):

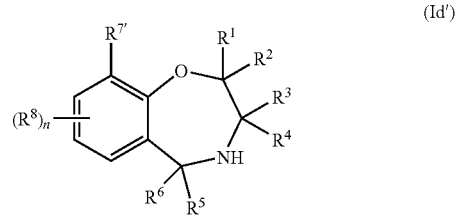

wherein each symbol is as defined above.

In compound (Id'), $R^{7'}$ is preferably the above-mentioned (1)-(12) recited as preferable $R^7$ of compound (Id), or (13) a carboxyl group, particularly preferably the above-mentioned (1'), (3'), (6') or (8').

Specific examples of compound (Id') include the compounds of Examples 7, 9 to 26, 31, 35, 37 to 64 and 67 to 106.

Compound (I) does not include 9-chloro-7-(1,1-dimethylethyl)-2,3,4,5-tetrahydro-1,4-benzoxazepine and N-[[(5S)-2-oxo-3-(2,3,4,5-tetrahydro-1,4-benzoxazepin-7-yl)-5-oxazolidinyl]methyl]acetamide.

Compound (I') does not include 9-chloro-7-(1,1-dimethylethyl)-2,3,4,5-tetrahydro-1,4-benzoxazepine and N-[[(5S)-2-oxo-3-(2,3,4,5-tetrahydro-1,4-benzoxazepin-7-yl)-5-oxazolidinyl]methyl]acetamide, and further, when the compound has $R^7$ or $R^8$ at the 9-position of 2,3,4,5-tetrahydro-1,4-benzoxazepine, the substituent at the 7-position is not
(i) a group represented by $-B_1-SO_2-Q_1$
wherein $B_1$ is an oxygen atom or an amino group optionally having substituent(s), and
$Q_1$ is a hydrocarbon group optionally having substituent(s) or a heterocyclic group optionally having substituent(s), or B₁ combined with Q₁ is a nitrogen-containing aromatic heterocyclic group optionally having substituent(s), nor (ii) a group represented by —SO₂—B₂-Q₂ wherein B₂ is an oxygen atom or an amino group optionally having substituent(s), and Q₂ is a hydrocarbon group optionally having substituent(s) or a heterocyclic group optionally having substituent(s), or —B₂-Q₂ is a nitrogen-containing aromatic heterocyclic group optionally having substituent(s).

As compound (I) and compound (I'), 8-(morpholin-4-yl)-2,3,4,5-tetrahydro-1,4-benzoxazepine or a salt thereof (Example 1), 8-(pyrrolidin-1-yl)-2,3,4,5-tetrahydro-1,4-benzoxazepine or a salt thereof (Example 2), 8-(piperidin-1-yl)-2,3,4,5-tetrahydro-1,4-benzoxazepine or a salt thereof (Example 3), N-isopropyl-N-methyl-2,3,4,5-tetrahydro-1,4-benzoxazepin-8-amine or a salt thereof (Example 4), N,N-diethyl-2,3,4,5-tetrahydro-1,4-benzoxazepin-8-amine or a salt thereof (Example 5), N-ethyl-N-methyl-2,3,4,5-tetrahydro-1,4-benzoxazepin-8-amine or a salt thereof (Example 6), 9-(pyrrolidin-1-yl)-2,3,4,5-tetrahydro-1,4-benzoxazepine or a salt thereof (Example 7), 9-phenyl-2,3,4,5-tetrahydro-1,4-benzoxazepine or a salt thereof (Example 9), 9-(2-chlorophenyl)-2,3,4,5-tetrahydro-1,4-benzoxazepine or a salt thereof (Example 10), 9-(2-methylphenyl)-2,3,4,5-tetrahydro-1,4-benzoxazepine or a salt thereof (Example 11), 9-[2-(trifluoromethyl)phenyl]-2,3,4,5-tetrahydro-1,4-benzoxazepine or a salt thereof (Example 12), 9-(3-furyl)-2,3,4,5-tetrahydro-1,4-benzoxazepine or a salt thereof (Example 15), 9-(3-thienyl)-2,3,4,5-tetrahydro-1,4-benzoxazepine or a salt thereof (Example 16), 9-(cyclopent-1-en-1-yl)-2,3,4,5-tetrahydro-1,4-benzoxazepine or a salt thereof (Example 26), 9-(1-methylethyl)-2,3,4,5-tetrahydro-1,4-benzoxazepine or a salt thereof (Example 54), 9-(tetrahydrofuran-3-yl)-2,3,4,5-tetrahydro-1,4-benzoxazepine or a salt thereof (Example 55), 9-(2,2,2-trifluoro-1-methylethyl)-2,3,4,5-tetrahydro-1,4-benzoxazepine or a salt thereof (Example 59), 9-cyclobutyl-2,3,4,5-tetrahydro-1,4-benzoxazepine or a salt thereof (Example 63) and 9-cyclopropyl-2,3,4,5-tetrahydro-1,4-benzoxazepine or a salt thereof (Example 64) are preferable. Particularly, 9-(1-methylethyl)-2,3,4,5-tetrahydro-1,4-benzoxazepine or a salt thereof (Example 54), 9-(tetrahydrofuran-3-yl)-2,3,4,5-tetrahydro-1,4-benzoxazepine or a salt thereof (Example 55), 9-(2,2,2-trifluoro-1-methylethyl)-2,3,4,5-tetrahydro-1,4-benzoxazepine or a salt thereof (Example 59), 9-cyclobutyl-2,3,4,5-tetrahydro-1,4-benzoxazepine or a salt thereof (Example 63) and 9-cyclopropyl-2,3,4,5-tetrahydro-1,4-benzoxazepine or a salt thereof (Example 64) are preferable.

When compound (I) and compound (I') are salts, examples of the salt include salt with inorganic base, ammonium salt, salt with organic base, salt with inorganic acid, salt with organic acid, salt with basic or acidic amino acid and the like.

Preferable examples of the salt with inorganic base include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Of these salts, pharmaceutically acceptable salts are preferable.

Compound (I) and compound (I') encompass a solvate, for example, hydrate.

Compound (I) and compound (I') may be deuterium converters.

In addition, compound (I) and compound (I') may be labeled with an isotope (e.g., ³H, ¹⁴C, ³⁵S, ¹²⁵I etc.) and the like.

When compound (I) and compound (I') of the present invention have an asymmetric center, isomers such as enantiomer, diastereomer and the like may be present. Such isomers and a mixture thereof are all encompassed in the scope of the present invention. When an isomer due to conformation is present, such isomer and a mixture thereof are also encompassed in compound (I) and compound (I') of the present invention.

The production methods of the compounds of the present invention are explained in the following. Compound (I) and compound (I') of the present invention can be produced by, for example, the following Method A, Method B, Method C, Method D or Method E.

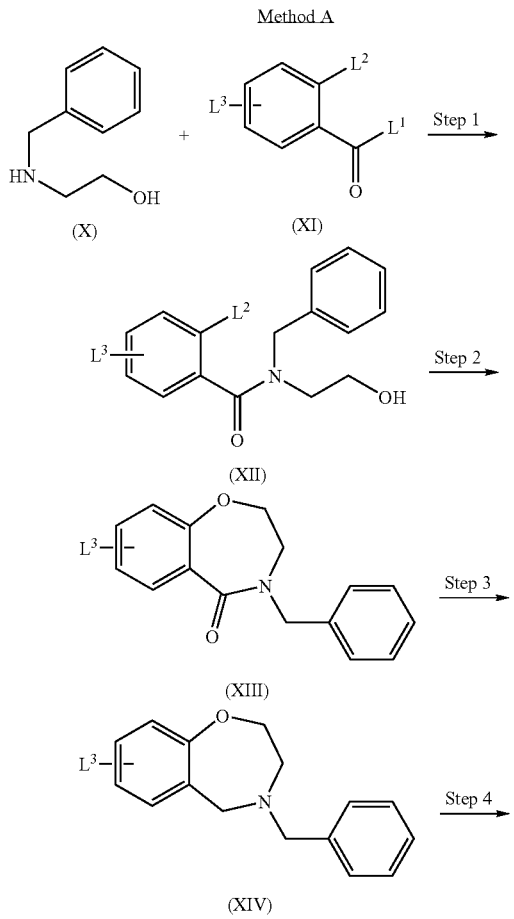

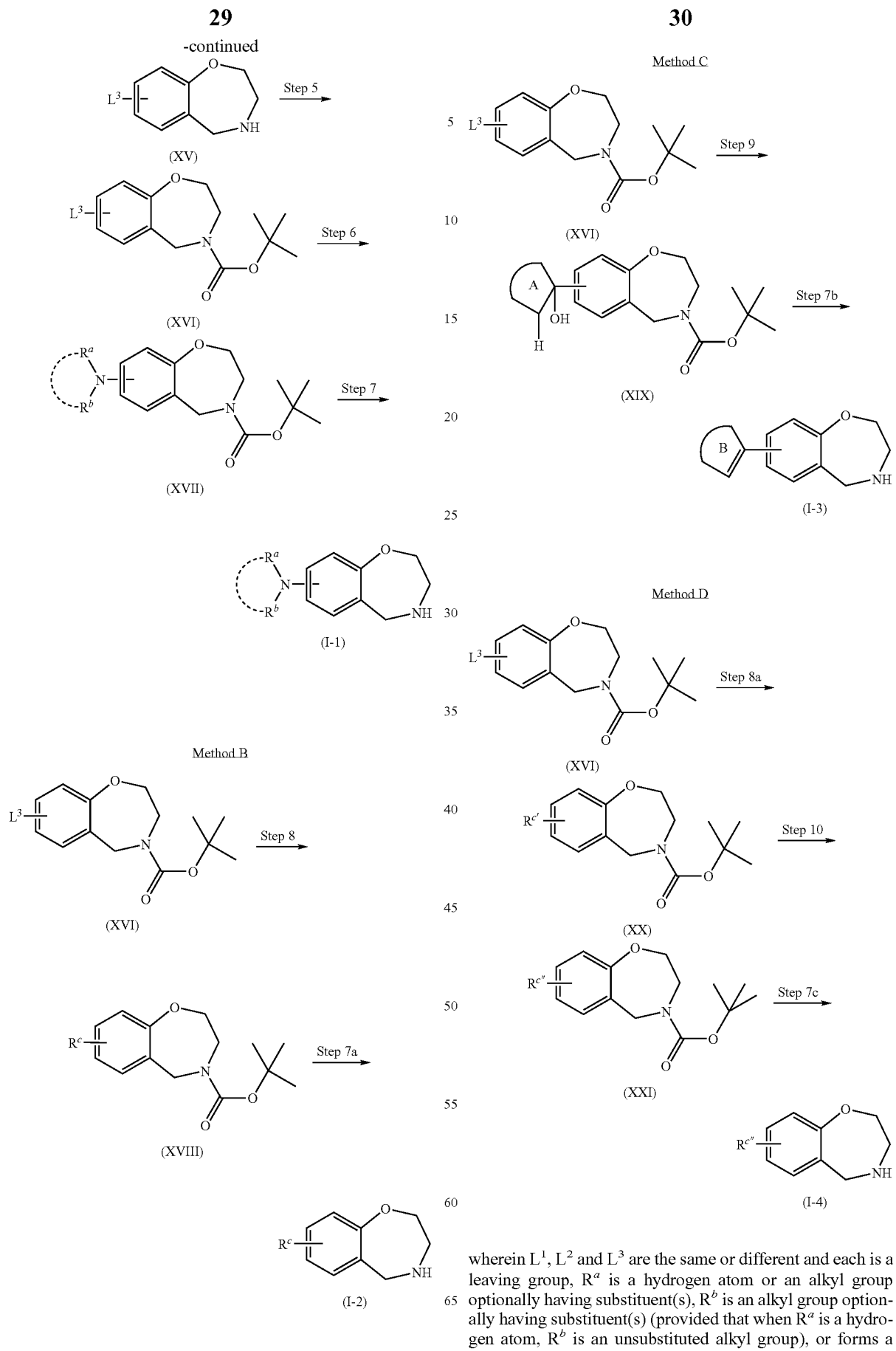
wherein $L^1$, $L^2$ and $L^3$ are the same or different and each is a leaving group, $R^a$ is a hydrogen atom or an alkyl group optionally having substituent(s), $R^b$ is an alkyl group optionally having substituent(s) (provided that when $R^a$ is a hydrogen atom, $R^b$ is an unsubstituted alkyl group), or forms a non-aromatic heterocyclic group optionally having substituent(s) as shown by —$NR^aR^b$, $R^c$ is an aryl group optionally having substituent(s), a cycloalkenyl group optionally having substituent(s) or an aromatic heterocyclic group optionally having substituent(s), ring A is a cycloalkyl ring optionally having substituent(s), ring B is a cycloalkenyl ring optionally having substituent(s), $R^{c'}$ is a cycloalkenyl group optionally having substituent(s), $R^{c''}$ is a cycloalkyl group optionally having substituent(s), and other symbols are as defined above.

Examples of the leaving group for $L^1$, $L^2$ or $L^3$ include a halogen atom (e.g., a fluorine atom, a chlorine atom, a bromine atom or an iodine atom), a $C_{1-6}$ alkylsulfonyloxy optionally having a halogen atom (e.g., methanesulfonyloxy, trifluoromethanesulfonyloxy), a benzenesulfonyloxy and the like.

Examples of the "alkyl group optionally having substituent(s)" for $R^a$ or $R^b$ include a $C_{1-6}$ alkyl optionally having 1 to 3 substituents selected from Substituent Group A and the like.

Examples of the "non-aromatic heterocyclic group" of the "non-aromatic heterocyclic group optionally having substituent(s)" formed by —$NR^aR^b$ include a 3- to 8-membered (preferably 5- or 6-membered) saturated or unsaturated (preferably saturated) non-aromatic heterocyclic group (e.g., 1-azetidinyl, 1-pyrrolidinyl, 1-piperidinyl, morpholino, thiomorpholino, 1-piperazinyl, 1-azepanyl, 1,4-oxazepan-4-yl, 1,4-thiazepan-4-yl, 1-azocanyl etc.) and the like.

Examples of the "substituent" of the "non-aromatic heterocyclic group optionally having substituent(s)" include a substituent group selected from $C_{1-6}$ alkyl (e.g., methyl, ethyl, propyl, isopropyl, butyl, isobutyl, tert-butyl etc.) optionally having 1 to 3 halogen atoms and Substituent Group A. The number of substituent is 1 to 3.

Examples of the "aryl group optionally having substituent(s)", "cycloalkenyl group optionally having substituent(s)" and "aromatic heterocyclic group optionally having substituent(s)" for $R^c$ include those similar to the "aryl group optionally having substituent(s)", "cycloalkenyl group optionally having substituent(s)" and "aromatic heterocyclic group optionally having substituent(s)" for $R^7$.

Examples of the "cycloalkyl ring optionally having substituent(s)" for ring A include a $C_{3-6}$ cycloalkyl ring (e.g., cyclopropane, cyclobutane, cyclopentane, cyclohexane etc.) optionally having 1 to 3 substituents selected from $C_{1-6}$ alkyl (e.g., methyl, ethyl, propyl, isopropyl, butyl, isobutyl, tert-butyl etc.) optionally having 1 to 3 halogen atoms and Substituent Group A, and the like.

Examples of the "cycloalkene ring optionally having substituent(s)" for ring B include a $C_{3-6}$ cycloalkene ring (e.g., cyclopropene, cyclobutene, cyclopentene, cyclohexene etc.) optionally having 1 to 3 substituents selected from $C_{1-6}$ alkyl (e.g., methyl, ethyl, propyl, isopropyl, butyl, isobutyl, tert-butyl etc.) optionally having 1 to 3 halogen atoms and Substituent Group A, and the like.

Examples of the "cycloalkenyl group optionally having substituent(s)" for $R^{c'}$ include those similar to the "cycloalkenyl group optionally having substituent(s)" for $R^7$.

Examples of the "cycloalkyl group optionally having substituent(s)" for $R^{c''}$ include those similar to the "cycloalkyl group optionally having substituent(s)" for $R^7$.

(Step 1)

This is a step for producing a compound represented by the formula (XII) or a salt thereof (hereinafter to be referred to as compound (XII)) by reacting a compound represented by the formula (X) or a salt thereof (hereinafter to be referred to as compound (X)) with a compound represented by the formula (XI) or a salt thereof (hereinafter to be referred to as compound (XI)).

Compound (X) and compound (XI) can be used as commercially available products or can be produced according to known methods.

The amount of compound (XI) to be used is generally about 1 mol to about 10 mol, preferably about 1 mol to about 2 mol, per 1 mol of compound (X).

The above-mentioned reaction is generally carried out in a solvent that does not adversely influence the reaction, and a base may be added to promote the reaction.

Examples of the solvent include hydrocarbons (e.g., benzene, toluene etc.), ethers (e.g., diethyl ether, dioxane, tetrahydrofuran etc.), esters (e.g., ethyl acetate etc.), halogenated hydrocarbons (e.g., chloroform, dichloromethane etc.), amides (e.g., N,N-dimethylformamide etc.), aromatic amines (e.g., pyridine etc.), water and the like. These solvents may be used in a mixture of two or more kinds at an appropriate ratio.

Examples of the base include alkali metal hydroxides (e.g., sodium hydroxide, potassium hydroxide etc.), hydrogen carbonates (e.g., sodium hydrogen carbonate, potassium hydrogen carbonate etc.), carbonates (e.g., sodium carbonate, potassium carbonate etc.), acetates (e.g., sodium acetate etc.), tertiary amines (e.g., trimethylamine, triethylamine, N-methylmorpholine etc.), aromatic amines (e.g., pyridine, picoline, N,N-dimethylaniline etc.) and the like. The amount of the base to be used is generally about 1 to about 100 mol, preferably about 1 to about 5 mol, per 1 mol of compound (X).

The reaction temperature is generally about −80° C. to about 150° C., preferably about −80° C. to about 50° C., and the reaction time is generally about 0.1 hr to about 48 hr, preferably about 0.5 hr to about 16 hr.

(Step 2)

This is a step for producing a compound represented by the formula (XIII) or a salt thereof (hereinafter to be referred to as compound (XIII)) by subjecting compound (XII) to intramolecular ring closure reaction. This reaction is performed by a method known per se, and generally in the presence of a base and, where necessary, in a solvent that does not adversely influence the reaction.

Examples of the base include metal hydrides (e.g., potassium hydride, sodium hydride etc.), inorganic bases (e.g., alkali metal hydroxides such as lithium hydroxide, sodium hydroxide, potassium hydroxide etc.; alkali metal hydrogen carbonates such as sodium hydrogen carbonate, potassium hydrogen carbonate etc.; alkali metal carbonates such as sodium carbonate, potassium carbonate etc.; alkoxides such as sodium methoxide, sodium ethoxide etc., and the like), organic bases (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.) and the like. Of these, metal hydrides such as sodium hydride and the like are preferable. While the amount of the base to be used varies depending on the kind of the solvent and other reaction conditions, it is generally about 0.1 to about 10 mol, preferably about 0.1 to about 5 mol, per 1 mol of compound (XII).

Examples of the solvent that does not adversely influence the reaction include alcohols (e.g., methanol, ethanol, propanol, 2-propanol, butanol, isobutanol, tert-butanol etc.), hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.), water and the like. These solvents may be used in a mixture of two or more kinds at an appropriate ratio.

The reaction temperature is generally within the range of about −50° C. to about 200° C., preferably about 0° C. to about 150° C. While the reaction time varies depending on the kind of compound (XII), reaction temperature and the like, it is generally about 0.1 hr to about 100 hr, preferably about 0.5 hr to about 24 hr.

(Step 3)

This is a step for producing a compound represented by the formula (XIV) or a salt thereof (hereinafter to be referred to as compound (XIV)) by subjecting compound (XIII) to a reduction reaction. This reaction can be performed according to a method known per se, and generally in the presence of a reducing agent and, where necessary, in a solvent that does not adversely influence the reaction.

Examples of the reducing agent include aluminum reagent (e.g., lithium aluminum hydride (LiAlH$_4$), diisobutylaluminum hydride (DIBAL-H), sodium bis(2-methoxyethoxy)aluminum hydride (Red-Al), alane (AlH$_3$) etc.), boron reagent (e.g., borane (BH$_3$), 9-borabicyclo[3.3.1]nonane (9-BBN), sodium borohydride (NaBH$_4$), sodium cyanoborohydride (NaBH$_3$CN), sodium triacetoxyborohydride (NaBH(OAc)$_3$) etc.) and the like. Of these, lithium aluminum hydride and borane are preferable. While the amount of the reducing agent to be used varies depending on the kind of the solvent and other reaction conditions, it is generally about 1 mol to about 10 mol, preferably about 1 mol to about 5 mol, per 1 mol of compound (XIII).

Examples of the solvent that does not adversely influence the reaction include alcohols (e.g., methanol, ethanol, propanol, 2-propanol, butanol, isobutanol, tert-butanol etc.), hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), carboxylic acid (e.g., acetic acid, trifluoroacetic acid etc.) and the like. These solvents may be used in a mixture of two or more kinds at an appropriate ratio.

The reaction temperature is generally within the range of about −80° C. to about 200° C., preferably about −80° C. to about 100° C. While the reaction time varies depending on the kind of compound (XIII), reaction temperature and the like, it is generally about 0.1 hr to about 100 hr, preferably about 0.5 hr to about 24 hr.

(Step 4)

This is a step for producing a compound represented by the formula (XV) or a salt thereof (hereinafter to be referred to as compound (XV)) by removing a benzyl group from compound (XIV).

As the method for removing the benzyl group, a method known per se or the method described in Wiley-InterScience, 1999, "Protective Groups in Organic Synthesis, 3rd Ed." (Theodara W. Greene, Peter G. M. Wuts) and the like, or a method analogous thereto can be employed. Examples thereof include a catalytic hydrogenation reaction, a method of treating with acyl halide and the like.

The catalytic hydrogenation reaction can be performed under a hydrogen atmosphere in the presence of a catalyst. Examples of the catalyst include palladiums (e.g., palladium carbon, palladium hydroxide carbon, palladium oxide etc.), nickels (e.g., Raney nickel catalyst etc.), platinums (e.g., platinum oxide, platinum carbon etc.), rhodiums (e.g., rhodium carbon etc.) and the like. The amount thereof to be used is generally about 0.001 mol to about 1 mol, preferably about 0.01 mol to about 0.5 mol, per 1 mol of compound (XIV).

The catalytic hydrogenation reaction is generally carried out in a solvent inert to the reaction. Examples of such solvent include alcohols (e.g., methanol, ethanol, propanol, butanol etc.), hydrocarbons (e.g., benzene, toluene, xylene etc.), halogenated hydrocarbons (e.g., dichloromethane, chloroform etc.), ethers (e.g., diethyl ether, dioxane, tetrahydrofuran etc.), esters (e.g., ethyl acetate etc.), amides (e.g., N,N-dimethylformamide etc.), carboxylic acids (e.g., acetic acid etc.), water or a mixture thereof.

The hydrogen pressure to be applied is generally about 1 atm to about 50 atm, preferably about 1 atm to about 10 atm. The reaction temperature is generally about 0° C. to about 150° C., preferably about 20° C. to about 100° C. The reaction time is generally about 5 min to about 72 hr, preferably about 0.5 hr to about 40 hr.

For the method for treating with acyl halide, for example, chloroformic acid 1-chloroethyl, chloroformic acid 2,2,2-trichloro-1,1-dimethylethyl, chloroformic acid β-trimethylsilylethyl and the like can be used. Of these, a method using chloroformic acid 1-chloroethyl is preferable. The amount of acid halide to be used is generally about 1 mol to about 10 mol, preferably about 1 mol to about 2 mol, per 1 mol of compound (XIV).

The reaction can be generally carried out in a solvent inert to the reaction. Examples of such solvent include hydrocarbons (e.g., benzene, toluene, xylene etc.), halogenated hydrocarbons (e.g., dichloromethane, chloroform etc.), ethers (e.g., diethyl ether, dioxane, tetrahydrofuran etc.), esters (e.g., ethyl acetate etc.), amides (e.g., N,N-dimethylformamide etc.), nitriles (e.g., acetonitrile etc.) or a mixture thereof.

The reaction temperature is generally about −80° C. to about 150° C., preferably about 0° C. to about 100° C. The reaction time is generally about 5 min to about 72 hr, preferably about 0.5 hr to about 20 hr.

When chloroformic acid 1-chloroethyl is used as acid halide, compound (XIV) is reacted with chloroformic acid 1-chloroethyl, and the resulting compound is treated with alcohols (e.g., methanol, ethanol etc.), aqueous solution (e.g., aqueous sodium hydroxide solution etc.) or water to give compound (XV). The reaction temperature is generally about 0° C. to about 150° C., preferably about 5° C. to about 100° C. The reaction time is generally about 5 min to about 24 hr, preferably about 0.5 hr to about 5 hr.

(Step 5)

This is a step for producing a compound represented by the formula (XVI) or a salt thereof (hereinafter to be referred to as compound (XVI)) by subjecting compound (XV) to a tert-butoxycarbonylation reaction.

The tert-butoxycarbonylation reaction is carried out according to a conventional method using di-tert-butyl dicarbonate in the presence of a base in a solvent inert to the reaction.

Examples of the base include triethylamine, tributylamine, diisopropylethylamine, potassium carbonate, sodium carbonate, sodium hydride, potassium hydride and the like. The amount of the base to be used is generally about 1 mol to about 5 mol, per 1 mol of compound (XV).

Examples of the solvent inert to the reaction include ethers such as tetrahydrofuran and the like; halogenated hydrocarbons such as chloroform and the like; aromatic hydrocarbons such as toluene and the like; amides such as N,N-dimethylformamide and the like; sulfoxides such as dimethyl sulfoxide and the like, and the like. These solvents may be used in a mixture of two or more kinds at an appropriate ratio. The amount of the solvent to be used is generally 1-fold volume to 100-fold volume relative to compound (XV).

The reaction temperature is generally about −50° C. to about 250° C., preferably 0° C. to 120° C. The reaction time is generally about 0.5 to about 24 hr.

The thus-obtained compound (XVI) can be isolated and purified by a known separation and purification means, for example, concentration, concentration under reduced pressure, solvent extraction, crystallization, recrystallization, phase transfer, chromatography and the like.

(Step 6)

This is a step for producing a compound represented by the formula (XVII) or a salt thereof (hereinafter to be referred to as compound (XVII)) by reacting compound (XVI) with $HNR^aR^b$.

This step can be performed according to a method known per se [e.g., J. Am. Chem. Soc., 2003, vol. 125, page 6653 or J. Org. Chem., 2000, vol. 65, page 1174 etc.]. For example, it is performed by reaction with $HNR^aR^b$ in the presence of a transition metal catalyst and a base in a solvent that does not adversely influence the reaction.

Examples of the transition metal catalyst include palladium catalyst (e.g., palladium(II) acetate, tris(dibenzylideneacetone)dipalladium(0), palladium(II) chloride, tetrakis(triphenylphosphine)palladium(0) etc.), nickel catalyst (e.g., nickel chloride etc.) and the like. Where necessary, a ligand (e.g., 2-dicyclohexylphosphino-2',4',6'-triisopropyl-1,1'-biphenyl, triphenylphosphine, tri-tert-butylphosphine etc.) may be added. While the amount of the transition metal catalyst to be used varies depending on the kind, it is generally about 0.0001 mol to about 1 mol, preferably about 0.01 mol to about 0.5 mol, per 1 mol of compound (XVI). The amount of the ligand to be used is generally about 0.0001 mol to about 4 mol, preferably about 0.01 mol to about 0.2 mol, per 1 mol of compound (XVI).

Preferable examples of the base include organic amines (e.g., trimethylamine, triethylamine, diisopropylamine, N-methylmorpholine, 1,8-diazabicyclo[5.4.0]undeca-7-ene, pyridine, N,N-dimethylaniline etc.), alkali metal salt (e.g., sodium hydrogen carbonate, potassium hydrogen carbonate, sodium carbonate, potassium carbonate, cesium carbonate, sodium phosphate, potassium phosphate, sodium hydroxide, potassium hydroxide etc.), metal hydride (e.g., potassium hydride, sodium hydride etc.), alkali metal alkoxide (e.g., sodium methoxide, sodium ethoxide, sodium-tert-butoxide, potassium-tert-butoxide etc.), alkali metal disilazide (e.g., lithium disilazide, sodium disilazide, potassium disilazide etc.) and the like. Of these, alkali metal salt such as potassium carbonate, cesium carbonate, sodium phosphate, potassium phosphate and the like; alkali metal alkoxide such as sodium-tert-butoxide, potassium-tert-butoxide and the like; organic amines such as triethylamine, diisopropylamine etc. and the like. The amount of the base to be used is generally about 0.1 mol to about 10 mol, preferably about 1 mol to about 5 mol, per 1 mol of compound (XVI).

The solvent may be one that does not adversely influence the reaction, for example, hydrocarbons (e.g., benzene, toluene, xylene etc.), halogenated hydrocarbons (e.g., chloroform, 1,2-dichloroethane etc.), nitriles (e.g., acetonitrile etc.), ethers (e.g., dimethoxyethane, tetrahydrofuran etc.), aprotic polar solvents (e.g., N,N-dimethylformamide, dimethyl sulfoxide, hexamethyl phosphoramide etc.) or a mixture thereof and the like.

The reaction temperature is generally about −10° C. to about 200° C., preferably 0° C. to about 150° C. The reaction time is generally about 0.5 hr to about 48 hr, preferably about 0.5 hr to about 16 hr.

(Step 7)

This is a step for producing a compound represented by the formula (I-1) or a salt thereof (hereinafter to be referred to as compound (1-1)) by removing a tert-butoxycarbonyl group from compound (XVII). This reaction can be performed according to a method known per se, generally by reaction with an acid in a solvent that does not adversely influence the reaction.

Examples of the acid include hydrochloric acid, hydrobromic acid, sulfuric acid, trifluoroacetic acid, trifluoromethanesulfonic acid, hydrogen chloride and the like. The amount of the acid to be used is preferably about 1 to about 100 mol, per 1 mol of compound (XVII).

Examples of the solvent that does not adversely influence the reaction include alcohols (e.g., methanol etc.), ethers (e.g., tetrahydrofuran etc.), halogenated hydrocarbons (e.g., chloroform etc.), aromatic hydrocarbons (e.g., toluene etc.), amides (e.g., N,N-dimethylformamide etc.), sulfoxides (e.g., dimethyl sulfoxide etc.), esters (e.g., ethyl acetate etc.) and the like. These solvents may be used in a mixture of two or more kinds at an appropriate ratio. The amount of the solvent to be used is generally 1-fold amount to 100-fold amount, relative to compound (XVII).

The reaction temperature is generally about −50° C. to about 250° C., preferably 0° C. to 120° C. The reaction time is generally about 0.5 hr to about 24 hr.

The thus-obtained compound (1-1) can be isolated and purified by known separation and purification means, for example, concentration, concentration under reduced pressure, solvent extraction, crystallization, recrystallization, phase transfer, chromatography and the like.

(Step 8)

This is a step for producing compound (XVIII) or a salt thereof (hereinafter to be referred to as compound (XVIII)) by coupling reaction of compound (XVI) with a compound represented by the formula: $R^c—B(OH)_2$ wherein each symbol is as defined above, or a salt thereof.

This step can be performed according to a method known per se [e.g., Chemical Reviews, 1995, vol. 95, page 2457 etc.], for example, it can be performed in the presence of a transition metal catalyst and a base in a solvent that does not adversely influence the reaction.

As the transition metal catalyst, for example, palladium catalyst (e.g., palladium acetate, palladium chloride, tetrakis (triphenylphosphine) palladium etc.), nickel catalyst (e.g., nickel chloride etc.) and the like can be used. Where necessary, a ligand (e.g., triphenylphosphine, tri-tert-butylphosphine etc.) may be added and used as a co-catalyst such as metal oxide (e.g., copper oxide, silver oxide etc.) and the like. While the amount of the transition metal catalyst to be used varies depending on the kind of the catalyst, it is generally about 0.0001 mol to 1 mol, preferably about 0.01 mol to 0.5 mol, per 1 mol of compound (XVI). The amount of the ligand to be used is generally about 0.0001 mol to 4 mol, preferably about 0.01 mol to 2 mol, per 1 mol of compound (XVI). The amount of the co-catalyst to be used is generally about 0.0001 mol to 4 mol, preferably about 0.01 mol to 2 mol, per 1 mol of compound (XVI).

Examples of the base include organic amines (e.g., trimethylamine, triethylamine, diisopropylamine, N-methylmorpholine, 1,8-diazabicyclo[5,4,0]undec-7-ene, pyridine, N,N-dimethylaniline etc.), alkali metal salt (e.g., sodium hydrogen carbonate, potassium hydrogen carbonate, sodium carbonate, potassium carbonate, cesium carbonate, sodium phosphate, potassium phosphate, sodium hydroxide, potassium hydroxide etc.), metal hydride (e.g., potassium hydride, sodium hydride etc.), alkali metal alkoxide (e.g., sodium methoxide, sodium ethoxide, sodium-tert-butoxide, potassium-tert-butoxide etc.), alkali metal disilazide (e.g., lithium disilazide, sodium disilazide, potassium disilazide etc.) and the like. Of these, alkali metal salt such as potassium carbonate, cesium carbonate, sodium phosphate, potassium phosphate and the like, alkali metal alkoxide such as sodium-tert-butoxide, potassium-tert-butoxide and the like, organic amines such as triethylamine, diisopropylamine and the like and the like are preferable. The amount of the base to be used is generally about 0.1 mol to 10 mol, preferably about 1 mol to 5 mol, per 1 mol of compound (XVI).

The solvent may be one that does not adversely influence the reaction, for example, hydrocarbons (e.g., benzene, toluene, xylene etc.), halogenated hydrocarbons (e.g., chloroform, 1,2-dichloroethane etc.), nitriles (e.g., acetonitrile etc.), ethers (e.g., dimethoxyethane, tetrahydrofuran), alcohols (e.g., methanol, ethanol etc.), aprotic polar solvent (e.g., dimethylformamide, dimethyl sulfoxide, hexamethylphosphoramide etc.), water or a mixture thereof and the like.

The reaction temperature is generally −10° C. to 200° C., preferably about 0° C. to about 150° C. The reaction time is generally 0.5 hr to 48 hr, preferably about 0.5 hr to 16 hr.

(Step 7a)

Step 7a can be performed in the same manner as in step 7.

(Step 9)

This is a step for producing compound (XIX) or a salt thereof (hereinafter to be referred to as compound (XIX)) by subjecting compound (XVI) to addition reaction with cycloalkanone optionally having substituent(s).

This reaction can be performed according to a method known per se [e.g., 4th ed. JIKKEN KAGAKU KOZA, organic synthesis II, alcohol-amine, MARUZEN Co., Ltd, pages 81-93 etc.]. For example, compound (XVI) wherein $L^3$ is a halogen atom (preferably, a bromine atom, an iodine atom) is converted to an organic metal compound, and cycloalkanone optionally having substituent(s) is added. The reaction can be performed in a solvent that does not adversely influence the reaction.

Examples of the organic metal compound include organic lithium reagent, Grignard reagent and the like. In the case of the former, the above-mentioned compound (XVI) is reacted with metal lithium, butyllithium and the like. The amount of the metal lithium, butyllithium and the like to be used is generally about 1 mol to about 5 mol, preferably about 1 mol to about 2 mol, per 1 mol of compound (XVI). In the case of the latter, the above-mentioned compound (XVI) is reacted with metal magnesium. The amount of the metal magnesium to be used is generally about 1 mol to about 5 mol, preferably about 1 mol to about 2 mol, per 1 mol of compound (XVI).

The amount of the cycloalkanone optionally having substituent(s) to be used is generally about 1 mol to about 5 mol, preferably about 1 mol to about 2 mol, per 1 mol of compound (XVI).

The solvent may be one that does not adversely influence the reaction, for example, ethers (e.g., dimethoxyethane, tetrahydrofuran etc.) and the like.

The reaction temperature is generally about −100° C. to about 100° C., preferably about −78° C. to about 50° C. The reaction time is generally about 0.5 hr to about 48 hr, preferably about 0.5 hr to about 16 hr.

(Step 7b)

Step 7b can be performed in the same manner as in step 7.

(Step 8a)

Step 8a can be performed in the same manner as in step 8.

(Step 10)

This is a step for producing compound (XXI) or a salt thereof (hereinafter to be referred to as compound (XXI)) by subjecting compound (XX) to a reduction reaction.

The reduction reaction can be performed according to a method known per se [e.g., Yuki Kagaku Jikken No Tebiki 3, synthesis reaction I, Kagaku Dojin, pages 38-40 etc.]. For example, the reaction can be performed in the presence of various transition metal catalysts under hydrogen gas in a solvent that does not adversely influence the reduction.

Examples of the transition metal catalyst include platinum, palladium, rhodium, ruthenium, nickel, palladium oxide, palladium carbon, Wilkinson complex and the like. While the amount of the transition metal catalyst to be used varies depending on the kind of the catalyst, it is generally about 0.1 mol to about 5 mol, preferably about 0.1 mol to about 2 mol, per 1 mol of compound (XX). The hydrogen gas may be used at normal pressure or under pressurization.

The solvent may be one that does not adversely influence the reaction, for example, hydrocarbons (e.g., benzene, toluene, xylene etc.), nitriles (e.g., acetonitrile etc.), ethers (e.g., dimethoxyethane, tetrahydrofuran), alcohols (e.g., methanol, ethanol etc.), aprotic polar solvent (e.g., dimethylformamide, dimethyl sulfoxide, hexamethylphosphoramide etc.), water or a mixture thereof and the like.

The reaction temperature is generally about −100° C. to about 100° C., preferably about −78° C. to about 50° C. The reaction time is generally about 0.5 hr to about 48 hr, preferably about 0.5 hr to about 16 hr.

(Step 7c)

Step 7c can be performed in the same manner as in step 7.

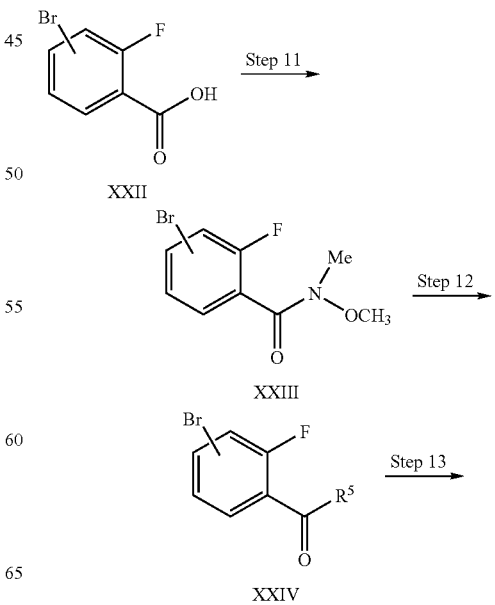

Method E

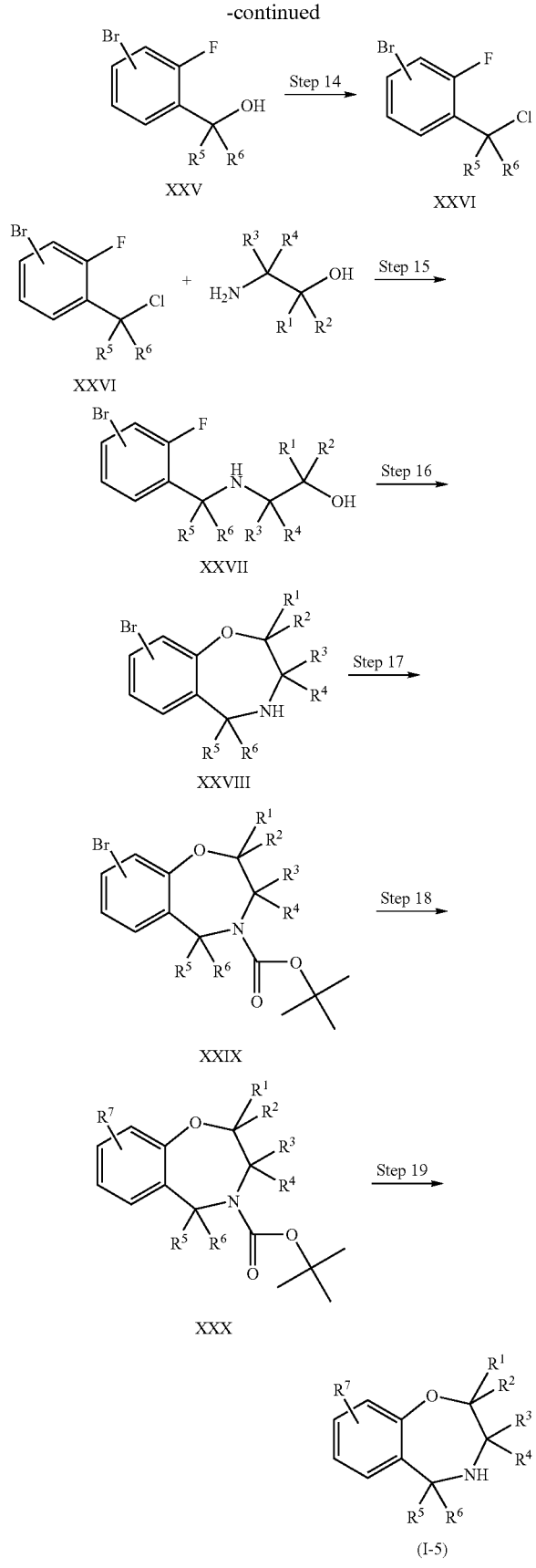

(Step 11)

This is a step for producing compound (XXIII) by reacting a compound represented by the formula (XXII) or a salt thereof (hereinafter to be referred to as compound (XXII)) with N,O-dimethylhydroxylamine or a salt thereof in the presence of a condensation agent. The reaction can be performed according to a method known per se. The amount of N,O-dimethylhydroxylamine or a salt thereof to be used for the reaction is generally 1 mol to 5 mol, preferably 1 mol to 2 mol, per 1 mol of compound (XXII). Examples of the condensation agent to be used for the reaction include 1-ethyl-3-(3-dimethylaminopropyl)carbodiimide hydrochloride and the like. The amount of the condensation agent to be used for the reaction is generally 1 mol to 5 mol, preferably about 1 mol to 2 mol, per 1 mol of compound (XXII).

Where necessary, an additive may be used in this reaction. Examples of the additive to be used for the reaction as necessary include 1-hydroxybenzotriazole and the like. The amount to be used is generally 1 mol to 5 mol, preferably about 1 mol to 2 mol, per 1 mol of compound (XXII).

Where necessary, a base may be used in this reaction. Examples of the base to be used as necessary include metal hydride (e.g., potassium hydride, sodium hydride etc.), inorganic base (e.g., alkali metal hydroxide such as lithium hydroxide, sodium hydroxide, potassium hydroxide and the like; alkali metal hydrogencarbonate such as sodium hydrogen carbonate, potassium hydrogen carbonate and the like; alkali metal carbonate such as sodium carbonate, potassium carbonate and the like; alkoxide such as sodium methoxide, sodium ethoxide etc. and the like), organic base (e.g., trimethylamine, triethylamine, diisopropylethylamine, N-methylmorpholine, 1,8-diazabicyclo[5.4.0]undeca-7-ene, pyridine, N,N-dimethylaniline, pyridazine, 4-dimethylaminopyridine etc.) and the like. While the amount of the base to be used as necessary varies depending on the kind of the solvent and other reaction conditions, it is generally about 0.1 mol to about 10 mol, preferably about 1 mol to about 5 mol, per 1 mol of compound (XXII).

This reaction can be performed, for example, in a solvent that does not adversely influence the reaction. Examples of the solvent that does not adversely influence the reaction include hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.), water and the like. These solvents may be used in a mixture of two or more kinds at an appropriate ratio.

The reaction temperature is generally within the range of about −50° C. to about 200° C., preferably about 0° C. to about 150° C. While the reaction time varies depending on the kind of compound (XXII), the reaction temperature and the like, it is generally about 0.1 hr to about 100 hr, preferably about 0.5 hr to about 24 hr.

The thus-obtained compound (XXIII) can be isolated and purified by known separation and purification means, for example, concentration, concentration under reduced pressure, solvent extraction, crystallization, recrystallization, phase transfer, chromatography and the like.

(Step 12)

This is a step for producing compound (XXIV) by reacting compound (XXIII) with an organic metal reagent. This reaction can be performed according to a method known per se. For example, the reaction can be performed in a solvent that does not adversely influence the reaction. Examples of the organic metal reagent include organic lithium reagent, organic magnesium reagent and the like. The amount of the organic metal reagent to be used is generally about 1 mol to about 5 mol, preferably about 1 mol to about 3 mol, per 1 mol of compound (XXIII). Examples of the solvent that does not adversely influence the reaction include hydrocarbons (e.g., benzene, toluene, xylene, hexane, heptane etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.), water and the like. These solvents may be used in a mixture of two or more kinds at an appropriate ratio.

The reaction temperature is generally within the range of about −78° C. to about 200° C., preferably about −78° C. to about 70° C. While the reaction time varies depending on the kind of compound (XXIII), reaction temperature and the like, it is generally about 0.1 hr to about 100 hr, preferably about 0.5 hr to about 24 hr.

The thus-obtained compound (XXIV) can be isolated and purified by known separation and purification means, for example, concentration, concentration under reduced pressure, solvent extraction, crystallization, recrystallization, phase transfer, chromatography and the like. In addition, compound (XXIV) may be used for the next reaction without isolation.

(Step 13)

This is a step for producing a compound represented by the formula (XXV) or a salt thereof (hereinafter to be referred to as compound (XXV)) from compound (XXIV).

When $R^6$ is not a hydrogen atom, compound (XXV) can be produced by reacting compound (XXIV) with an organic metal reagent. This reaction can be performed according to a method known per se, for example, in the same manner as in step 12.

On the other hand, when $R^6$ is a hydrogen atom, compound (XXV) can be produced by subjecting compound (XXIV) to a reduction reaction. This reaction can be performed according to a method known per se, generally in the presence of a reducing agent, and where necessary, in a solvent that does not adversely influence the reaction.

Examples of the reducing agent include aluminum reagents (e.g., lithium aluminum hydride ($LiAlH_4$), diisobutylaluminum hydride (DIBAL-H), sodium bis(2-methoxyethoxy)aluminum hydride (Red-Al), alane ($AlH_3$) etc.), boron reagents (e.g., borane ($BH_3$), 9-borabicyclo[3.3.1]nonane (9-BBN), sodium borohydride ($NaBH_4$), sodium cyanoborohydride ($NaBH_3CN$), sodium triacetoxyborohydride ($NaBH(OAc)_3$) etc.) and the like. Of these, sodium borohydride is preferable. While the amount of the reducing agent to be used varies depending on the kind of the solvent and other reaction conditions, it is generally about 1 mol to about 10 mol, preferably about 1 mol to about 5 mol, per 1 mol of compound (XXIV).

Examples of the solvent that does not adversely influence the reaction include alcohols (e.g., methanol, ethanol, propanol, 2-propanol, butanol, isobutanol, tert-butanol etc.), hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), carboxylic acids (e.g., acetic acid, trifluoroacetic acid etc.) and the like. These solvents may be used in a mixture of two or more kinds at an appropriate ratio.

The reaction temperature is generally within the range of about −80° C. to about 200° C., preferably about −80° C. to about 100° C. While the reaction time varies depending on the kind of compound (XXIV), reaction temperature and the like, it is generally about 0.1 hr to about 100 hr, preferably about 0.5 hr to about 24 hr.

The thus-obtained compound (XXV) can be isolated and purified by known separation and purification means, for example, concentration, concentration under reduced pressure, solvent extraction, crystallization, recrystallization, phase transfer, chromatography and the like. In addition, compound (XXV) may be used for the next reaction without isolation.

(Step 14)

This is a step for halogenating compound (XXV) by reaction with a halogenating agent to convert the compound to compound (XXVI).

The method for the halogenation can be performed according to a method known per se [e.g., 4th ed. JIKKENN KAGAKU KOZA, vol. 22, page 115 etc.]. For example, it can be performed in the presence of a halogenating agent in a solvent that does not adversely influence the reaction.

Examples of the halogenating agent include thionyl chloride, phosphorus pentachloride, phosphorus oxychloride, oxalyl chloride and the like. The amount thereof to be used is about 1 mol to about 10 mol, preferably about 1 mol to about 3 mol, per 1 mol compound (XXV).

The solvent to be used for the reaction may be one that does not adversely influence the reaction, for example, hydrocarbons (e.g., benzene, toluene, xylene etc.), halogenated hydrocarbons (e.g., chloroform, 1,2-dichloroethane etc.), nitriles (e.g., acetonitrile etc.), ethers (e.g., dimethoxyethane, tetrahydrofuran etc.), aprotic polar solvent (e.g., N,N-dimethylformamide, dimethyl sulfoxide, hexamethylphosphoramide etc.) or a mixture thereof.

The reaction temperature is generally about −10° C. to about 200° C., preferably about 0° C. to about 150° C. The reaction time is generally about 0.5 hr to about 48 hr, preferably about 0.5 hr to about 16 hr.

The thus-obtained compound (XXVI) can be isolated and purified by known separation and purification means, for example, concentration, concentration under reduced pressure, solvent extraction, crystallization, recrystallization, phase transfer, chromatography and the like. In addition, compound (XXVI) may be used for the next reaction without isolation.

(Step 15)

This is a step for producing a compound represented by the formula (XXVII) or a salt thereof (hereinafter to be referred to as compound (XXVII)) by reacting compound (XXVI) with an ethanolamine derivative or a salt thereof in the presence of a base. This reaction can be performed according to a method known per se. For example, it can be carried out in a solvent that does not adversely influence the reaction. The amount of the ethanolamine derivative or a salt thereof to be used is generally about 1 mol to 5 mol, preferably 1 mol to 2 mol, per 1 mol of compound (XXVI). Examples of the base include metal hydride (e.g., potassium hydride, sodium hydride etc.), inorganic base (e.g., alkali metal hydroxide such as lithium hydroxide, sodium hydroxide, potassium hydroxide and the like; alkali metal hydrogencarbonate such as sodium hydrogen carbonate, potassium hydrogen carbonate and the like; alkali metal carbonate such as sodium carbonate, potassium carbonate and the like; alkoxide such as sodium methoxide, sodium ethoxide, etc. and the like), organic base (e.g., trimethylamine, triethylamine, diisopropylethylamine, N-methylmorpholine, 1,8-diazabicyclo[5.4.0]undeca-7-ene, pyridine, N,N-dimethylaniline, pyridazine, 4-dimethylaminopyridine etc.) and the like. Of these, metal hydride such as sodium hydride and the like are preferable.

While the amount of the base to be used varies depending on the kind of the solvent and other reaction conditions, it is generally about 0.1 mol to about 10 mol, preferably about 0.1 mol to about 5 mol, per 1 mol compound (XXVI).

Examples of the solvent that does not adversely influence the reaction include hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.), water and the like. These solvents may be used in a mixture of two or more kinds at an appropriate ratio.

The reaction temperature is generally within the range of about −50° C. to about 200° C., preferably about 0° C. to about 150° C. While the reaction time varies depending on the kind of compound (XXVI), the reaction temperature and the like, it is generally about 0.1 hr to about 100 hr, preferably about 0.5 hr to about 24 hr.

The thus-obtained compound (XXVII) can be isolated and purified by known separation and purification means, for example, concentration, concentration under reduced pressure, solvent extraction, crystallization, recrystallization, phase transfer, chromatography and the like. In addition, compound (XXVII) may be used for the next reaction without isolation.

(Step 16)

This is a step for producing a compound represented by the formula (XXVIII) or a salt thereof (hereinafter to be referred to as compound (XXVIII)) by subjecting compound (XXVII) to intramolecular ring closure reaction. While this reaction can be performed by a method known per se, it can be generally carried out in the presence of a base and, where necessary, in a solvent that does not adversely influence the reaction.

Examples of the base include metal hydride (e.g., potassium hydride, sodium hydride etc.), inorganic base (e.g., alkali metal hydroxide such as lithium hydroxide, sodium hydroxide, potassium hydroxide and the like; alkali metal hydrogencarbonate such as sodium hydrogen carbonate, potassium hydrogen carbonate and the like; alkali metal carbonate such as sodium carbonate, potassium carbonate and the like; alkoxide such as sodium methoxide, sodium ethoxide etc. and the like), organic base (e.g., trimethylamine, triethylamine, diisopropylethylamine, N-methylmorpholine, 1,8-diazabicyclo[5.4.0]undec-7-ene, pyridine, N,N-dimethylaniline, pyridazine, 4-dimethylaminopyridine etc.) and the like. Of these, metal hydride such as sodium hydride and the like are preferable. While the amount of the base to be used varies depending on the kind of the solvent and other reaction conditions, it is generally about 0.1 mol to about 10 mol, preferably about 0.1 mol to about 5 mol, per 1 mol compound (XXVII).

Examples of the solvent that does not adversely influence the reaction to be used as necessary include alcohols (e.g., methanol, ethanol, propanol, 2-propanol, butanol, isobutanol, tert-butanol etc.), hydrocarbons (e.g., benzene, toluene, xylene, hexane, heptane etc.), halogenated hydrocarbons (e.g., dichloromethane, chloroform etc.), ethers (e.g., diethyl ether, diisopropyl ether, tert-butyl methyl ether, tetrahydrofuran, dioxane, dimethoxyethane etc.), nitriles (e.g., acetonitrile etc.), amides (e.g., N,N-dimethylformamide, N,N-dimethylacetamide etc.), sulfoxides (e.g., dimethyl sulfoxide etc.), water and the like. These solvents may be used in a mixture of two or more kinds at an appropriate ratio.

The reaction temperature is generally within the range of about −50° C. to about 200° C., preferably about 0° C. to about 150° C. While the reaction time varies depending on the kind of compound (XXVII), the reaction temperature and the like, it is generally about 0.1 hr to about 100 hr, preferably about 0.5 hr to about 24 hr.

The thus-obtained compound (XXVIII) can be isolated and purified by known separation and purification means, for example, concentration, concentration under reduced pressure, solvent extraction, crystallization, recrystallization, phase transfer, chromatography and the like. In addition, compound (XXVIII) may be used for the next reaction without isolation.

(Step 17)

This is a step for producing compound (XXIX) by subjecting compound (XXVIII) to tert-butoxycarbonylation reaction.

The tert-butoxycarbonylation reaction is carried out according to a conventional method using di-tert-butyl dicarbonate in the presence of a base in a solvent that does not adversely influence the reaction.

Examples of the base include triethylamine, tributylamine, diisopropylethylamine, potassium carbonate, sodium carbonate, sodium hydride, potassium hydride and the like. The amount of the base to be used is generally about 1 mol to about 5 mol, per 1 mol compound (XXVIII).

Examples of the solvent that does not adversely influence the reaction include ethers such as tetrahydrofuran and the like; halogenated hydrocarbons such as chloroform and the like; aromatic hydrocarbons such as toluene and the like; amides such as N,N-dimethylformamide and the like; sulfoxides such as dimethyl sulfoxide etc. and the like. These solvents may be used in a mixture of two or more kinds at an appropriate ratio. The amount of the solvent to be used is generally 1-fold amount to 100-fold amount relative to compound (XXVIII).

The reaction temperature is generally about −50° C. to about 250° C., preferably 0° C. to 120° C. The reaction time is generally about 0.5 hr to about 24 hr.

The thus-obtained compound (XXIX) can be isolated and purified by known separation and purification means, for example, concentration, concentration under reduced pressure, solvent extraction, crystallization, recrystallization, phase transfer, chromatography and the like. In addition, compound (XXIX) may be used for the next reaction without isolation.

(Step 18)

This is a step for producing compound (XXX) by subjecting compound (XXIX) to a coupling reaction with a compound represented by the formula: $R^7$—$B(OH)_2$ wherein each symbol is as defined above, or a salt thereof.

This step can be performed according to a method known per se [e.g., Chemical Reviews, 1995, vol. 95, page 2457 etc.]. For example, it can be performed in the presence of a transition metal catalyst and a base in a solvent that does not adversely influence the reaction.

As the transition metal catalyst, for example, palladium catalyst (e.g., palladium acetate, palladium chloride, tetrakis (triphenylphosphine) palladium etc.), nickel catalyst (e.g., nickel chloride etc.) and the like can be used. Where necessary, a ligand (e.g., triphenylphosphine, tri-tert-butylphosphine etc.) may be added, and metal oxide (e.g., copper oxide, silver oxide etc.) and the like may be used as a co-catalyst. While the amount of the transition metal catalyst to be used varies depending on the kind of the catalyst, it is generally about 0.0001 mol to 1 mol, preferably about 0.01 mol to 0.5 mol, per 1 mol of compound (XXIX). The amount of the ligand to be used is generally about 0.0001 mol to 4 mol, preferably about 0.01 mol to 2 mol, per 1 mol of compound (XXIX). The amount of the co-catalyst to be used is generally about 0.0001 mol to 4 mol, preferably about 0.01 mol to 2 mol, per 1 mol of compound (XXIX).

Examples of the base include organic amines (e.g., trimethylamine, triethylamine, diisopropylamine, N-methylmorpholine, 1,8-diazabicyclo[5,4,0]undec-7-ene, pyridine, N,N-dimethylaniline etc.), alkali metal salt (e.g., sodium hydrogen carbonate, potassium hydrogen carbonate, sodium carbonate, potassium carbonate, cesium carbonate, sodium phosphate, potassium phosphate, sodium hydroxide, potassium hydroxide etc.), metal hydride (e.g., potassium hydride, sodium hydride etc.), alkali metal alkoxide (e.g., sodium methoxide, sodium ethoxide, sodium-tert-butoxide, potassium-tert-butoxide etc.), alkali metal disilazide (e.g., lithium disilazide, sodium disilazide, potassium disilazide etc.) and the like. Of these, alkali metal salt such as potassium carbonate, cesium carbonate, sodium phosphate, potassium phosphate and the like, alkali metal alkoxide such as sodium-tert-butoxide, potassium-tert-butoxide and the like, organic amines such as triethylamine, diisopropylamine etc. and the like are preferable. The amount of the base to be used is generally about 0.1 mol to 10 mol, preferably about 1 mol to 5 mol, per 1 mol of compound (XXIX).

The solvent may be one that does not adversely influence the reaction, for example, hydrocarbons (e.g., benzene, toluene, xylene etc.), halogenated hydrocarbons (e.g., chloroform, 1,2-dichloroethane etc.), nitriles (e.g., acetonitrile etc.), ethers (e.g., dimethoxyethane, tetrahydrofuran), alcohols (e.g., methanol, ethanol etc.), aprotic polar solvent (e.g., dimethylformamide, dimethyl sulfoxide, hexamethylphosphoramide etc.), water or a mixture thereof and the like.

The reaction temperature is generally −10° C. to 200° C., preferably about 0° C. to 150° C. The reaction time is generally about 0.5 hr to 48 hr, preferably 0.5 hr to 16 hr.

The thus-obtained compound (XXX) can be isolated and purified by known separation and purification means, for example, concentration, concentration under reduced pressure, solvent extraction, crystallization, recrystallization, phase transfer, chromatography and the like. In addition, compound (XXX) may be used for the next reaction without isolation.

(Step 19)

This is a step for producing a compound represented by the formula (I-5) or a salt thereof (hereinafter to be referred to as compound (1-5)) by removing a tert-butoxycarbonyl group from compound (XXX). While this reaction can be performed according to a method known per se, it is generally carried out by reacting compound (XXX) with an acid, where necessary, in a solvent that does not adversely influence the reaction.

Examples of the acid include hydrochloric acid, hydrobromic acid, sulfuric acid, trifluoroacetic acid, trifluoromethanesulfonic acid, hydrogen chloride and the like. The amount of the acid to be used is preferably about 1 mol to about 100 mol, per 1 mol of compound (XXX).

Examples of the solvent that does not adversely influence the reaction to be used as necessary include alcohols (e.g., methanol etc.), ethers (e.g., tetrahydrofuran etc.), halogenated hydrocarbons (e.g., chloroform etc.), aromatic hydrocarbons (e.g., toluene etc.), amides (e.g., N,N-dimethylformamide etc.), sulfoxides (e.g., dimethyl sulfoxide etc.), esters (e.g., ethyl acetate etc.) and the like. These solvents may be used in a mixture of two or more kinds at an appropriate ratio. The amount of the solvent to be used is generally 1-fold amount to 100-fold amount, relative to compound (XXX).

The reaction temperature is generally about −50° C. to about 250° C., preferably 0° C. to 120° C. The reaction time is generally about 0.5 hr to about 24 hr.

The thus-obtained compound (1-5) can be isolated and purified by known separation and purification means, for example, concentration, concentration under reduced pressure, solvent extraction, crystallization, recrystallization, phase transfer, chromatography and the like.

When compound (I) and compound (I') are obtained as free compounds by the above-mentioned methods, they can be converted to salts according to a conventional method. When compound (I) and compound (I') are obtained in the form of salts, they can be converted to free compounds or other salts according to a conventional method.

In addition, in each reaction mentioned above, when the starting material compound can form a salt, the compound may be used as a salt. Examples of such salt include those exemplified as the salts of compound (I) and compound (I').

Compound (I) and compound (I') produced by such method can be isolated and purified by a typical separation means such as recrystallization, distillation, chromatography, etc.

When compound (I) and compound (I') contain an optical isomer, a stereoisomer, a regioisomer or a rotamer, these are also encompassed in compound (I) and compound (I'), and can be obtained as a single product according to synthetic methods or separation methods known per se (e.g., concentration, solvent extraction, column chromatography, recrystallization, etc.). For example, when compound (I) and compound (I') have an optical isomer, an optical isomer resolved from this compound is also encompassed in compound (I) and compound (I').

The optical isomer can be produced by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method, etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) is formed, which is separated by a fractional recrystallization method, and if desired, a free optical isomer is obtained by a neutralization step.

2) a Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method, etc.) and the like, and is subjected to a chemical treatment such as hydrolysis and the like to separate an optically active reagent moiety, whereby an optical isomer is obtained. For example, when compound (I) and compound (I') contain a hydroxyl group, or primary or secondary amino group(s) in a molecule, the compound and an optically active organic acid (e.g., (−)-MTPA [α-methoxy-α-(trifluoromethyl)phenylacetic acid], (+)-MTPA, (−)-menthoxyacetic acid, (+)-menthoxyacetic acid etc.) and the like are subjected to condensation reaction to give diastereomers in the ester form or in the amide form, respectively. When compound (I) and compound (I') have a carboxyl group, this compound and an optically active amine or alcohol reagent are subjected to condensation reaction to give diastereomers in the amide form or in the ester form, respectively. The separated diastereomer is converted to an optical isomer of the original compound by acid hydrolysis or base hydrolysis.

The compound (I) and compound (I') may be a crystal.

The crystal of the compound (I) and compound (I') can be produced by crystallization of compound (I) and compound (I') according to crystallization methods known per se.

Examples of the crystallization method include a method of crystallization from a solution, a method of crystallization from vapor, a method of crystallization from the melts and the like.

The "crystallization from a solution" is typically a method of shifting a non-saturated state to supersaturated state by varying factors involved in solubility of compounds (solvent composition, pH, temperature, ionic strength, redox state, etc.) or the amount of solvent. Specific examples thereof include a concentration method, a slow cooling method, a reaction method (a diffusion method, an electrolysis method), a hydrothermal growth method, a flux method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, isopropyl alcohol, etc.), water and the like. These solvents are used alone or in a combination of two or more at a suitable ratio (e.g., 1:1 to 1:100 (a volume ratio)). Where necessary, a seed crystal can be used.

The "crystallization from vapor" is, for example, a vaporization method (a sealed tube method, a gas stream method), a gas phase reaction method, a chemical transportation method and the like.

The "crystallization from the melts" is, for example, a normal freezing method (a Czockralski method, a temperature gradient method and a Bridgman method, etc.), a zone melting method (a zone leveling method and a floating zone method, etc.), a special growth method (a VLS method and a liquid phase epitaxy method, etc.) and the like.

Preferable examples of the crystallization method include a method of dissolving compound (I) and compound (I') in a suitable solvent (e.g., alcohols such as methanol, ethanol, etc., and the like) at a temperature of 20 to 120° C., and cooling the resulting solution to a temperature not higher than the temperature of dissolution (e.g., 0 to 50° C., preferably 0 to 20° C.) and the like.

The thus obtained crystals of the present invention can be isolated, for example, by filtration and the like.

As an analysis method of the obtained crystal is generally a method of crystal analysis by powder X-ray diffraction. As a method of determining crystal orientation, a mechanical method or an optical method and the like can also be used.

The crystal of compound (I) and compound (I') obtained by the above-mentioned production method (hereinafter to be abbreviated as "the crystal of the present invention") has high purity, high quality, and low hygroscopicity, is not denatured even after a long-term preservation under general conditions, and is extremely superior in the stability. In addition, it is also superior in the biological properties (e.g., pharmacokinetics (absorption, distribution, metabolism, excretion), efficacy expression etc.) and is extremely useful as a pharmaceutical composition.

In the present specification, specific optical rotation ($[α]_D$) means a specific optical rotation measured with, for example, a polarimeter (JASCO Corporation), P-1030 type polarimeter (No. AP-2)) and the like.

In the present specification, the melting point means a melting point measured using, for example, a micro melting point apparatus (YANACO, MP-500D), a DSC (differential scanning calorimetry) apparatus (SEIKO, EXSTAR6000) and the like.

A prodrug of the compound (I) and compound (I') means a compound which is converted to the compound (I) and compound (I') with a reaction due to an enzyme, an gastric acid, etc. under the physiological condition in the living body, that is, a compound which is converted to the compound (I) and compound (I') with oxidation, reduction, hydrolysis, etc. according to an enzyme; a compound which is converted to the compound (I) and compound (I') by hydrolysis etc. due to gastric acid, etc. A prodrug for compound (I) and compound (I') may be a compound obtained by subjecting an amino in compound (I) and compound (I') to an acylation, alkylation or phosphorylation [e.g., a compound obtained by subjecting an amino in compound (I) and compound (I') to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.]; a compound obtained by subjecting a hydroxy group in compound (I) and compound (I') to an acylation, alkylation, phosphorylation or boration (e.g., a compound obtained by subjecting a hydroxy group in compound (I) and compound (I') to an acetylation, palmitoylation, propanoylation, pivaloylation, succinylation, fumarylation, alanylation, dimethylaminomethylcarbonylation, etc.); a compound obtained by subjecting a carboxy group in compound (I) and compound (I') to an esterification or amidation [e.g., a compound obtained by subjecting a carboxy group in compound (I) and compound (I') to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, methylamidation, etc.] and the like. Any of these compounds can be produced from compound (I) and compound (I') by a method known per se.

A prodrug of compound (I) and compound (I') may also be one which is converted into compound (I) and compound (I') under a physiological condition, such as those described in IYAKUHIN no KAIHATSU (Development of Pharmaceuticals), Vol. 7, Design of Molecules, p. 163-198, Published by HIROKAWA SHOTEN (1990).

Compound (I) and compound (I') of the present invention or a salt thereof or a prodrug thereof (hereinafter to be abbreviated as compound (I)) has superior serotonin $5-HT_{2C}$ receptor activation action, particularly an action to activate serotonin 5-HT$_{2C}$ receptor selectively.

In addition, compound (I) and compound (I') of the present invention have low toxicity and are safe.

Accordingly, compound (I) of the present invention having a superior serotonin 5-HT$_{2C}$ receptor activating action is useful as a prophylaxis or therapeutic drug for all serotonin 5-HT$_{2C}$ associated diseases in mammals (e.g., mouse, rat, hamster, rabbit, cat, dog, bovine, sheep, monkey, human and the like), for example, (1) lower urinary tract symptoms [for example, abnormal urination such as overactive bladder, stress urinary incontinence, mixed urinary incontinence, post-micturition dribble, lower urinary tract symptoms associated with benign prostatic hyperplasia, pelvic visceral pain, lower urinary tract symptoms associated with chronic prostatitis, lower urinary tract symptoms associated with interstitial cystitis etc. and the like]

(2) metabolic diseases [for example, diabetes (insulin dependent diabetes, diabetic complications, diabetic retinopathy, diabetic microangiopathy, diabetic neuropathy etc.), impaired glucose tolerance, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity], benign prostatic hyperplasia, sexual dysfunction and the like]

(3) central nervous system diseases [for example, neurodegenerative diseases (e.g., Alzheimer's disease, Down's disease, Parkinson's disease, Creutzfeldt-Jakob disease, amyotrophic lateral sclerosis (ALS), Huntington chorea, diabetic neuropathy, multiple sclerosis etc.), mental diseases (e.g., schizophrenia, depression, mania, anxiety neurosis, obsessive-compulsive neurosis, panic disorder, epilepsy, alcohol dependence, drug dependence, anxiety, anxious mental state, emotional abnormality, cyclothymia, nervous erethism, autism, faint, addiction, low sex drive etc.), disorders such as central nervous system and peripheral nerve disorders (e.g., head trauma, spinal trauma, brain edema, disorders of sensory function, abnormality of sensory function, disorders of autonomic nervous function, abnormality of autonomic nervous function, whiplash injury etc.), memory disorders (e.g., senile dementia, amnesia, cerebrovascular dementia etc.), cerebrovascular disorder (e.g., cerebral hemorrhage, cerebral infarction and the like and sequelae or complication thereof, asymptomatic cerebrovascular accident, transient cerebral ischemic attack, hypertensive encephalopathia, blood-brain barrier disorder, etc.), recurrence and sequelae of cerebrovascular disorders (e.g., neural symptoms, mental symptoms, subjective symptoms, disorders of daily living activities etc.), central nervous system hypofunction after brain blood vessel occlusion, disorder or abnormality of autoregulation ability of brain circulation or renal circulation etc.], sleep disorder (4) genital insufficiency diseases [for example, male erectile dysfunction, dysspermia, female genital insufficiency etc.]

(5) digestive organ diseases [for example, an irritable bowel syndrome, inflammatory bowel disease, ulcerative colitis, Crohn's disease, diseases caused by a spiral urease-positive gram-negative bacterium (e.g., *Helicobacter pylori*, etc.) (e.g., gastritis, gastric ulcer, etc.), gastric cancer, postgastrostomy disorder, indigestion, esophageal ulcer, pancreatitis, polyp of the colon, cholelithiasis, hemorrhoids, peptic ulcer, situational ileitis, gluttony, constipation, diarrhea, borborygmus, etc.]

(6) inflammatory or allergic diseases [for example, allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, meningitidis, inflammatory ophthalmic diseases, etc.]

(7) osteoarthropathy diseases [for example, rheumatoid arthritis (chronic rheumatoid arthritis), arthritis deformans, rheumatoid myelitis, osteoporosis, abnormal growth of cells, bone fracture, bone refracture, osteomalacia, osteopenia, Paget's disease of bone, rigid myelitis, articular tissue destruction by gonarthrosis deformans and similar diseases thereto, etc.]

(8) respiratory diseases [for example, cold syndrome, pneumonia, asthma, pulmonary hypertension, pulmonary thrombi/pulmonary obliteration, pulmonary sarcoidosis, pulmonary tuberculosis, interstitial pneumonia, silicosis, adult respiratory distress syndrome, chronic obstructive pulmonary disease, cough, etc.]

(9) infectious diseases [HIV infectious diseases, virus infectious diseases due to cytomegalo virus, influenza virus, herpes virus and the like, *rickettsia* infectious diseases, bacterial infectious diseases, sexually-transmitted diseases, carinii pneumonia, *Helicobacter pylori* infectious disease, systemic fungal infectious diseases, tuberculosis, invasive staphylococcal infectious diseases, acute viral encephalitis, acute bacterial meningitidis, AIDS encephalitis, septicemia, sepsis, sepsis gravis, septic shock, endotoxin shock, toxic shock syndromes, etc.]

(10) cancers [for example, primary, metastatic or recurrent breast cancer, prostatic cancer, pancreatic cancer, gastric cancer, lung cancer, colorectal cancer (colon cancer, rectal cancer, anal cancer), esophagus cancer, duodenal cancer, head and neck cancer (cancer of the tongue, pharynx cancer, laryngeal cancer), brain tumor, schwannoma, non-small cell lung cancer, small cell lung cancer, liver cancer, kidney cancer, biliary tract cancer, uterus cancer (uterine body cancer, uterine cervical cancer), ovary cancer, urinary bladder cancer, skin cancer, hemangioma, malignant lymphoma, malignant melanoma, thyroid cancer, bone tumor, hemangioma, vascular fibroma, retinosarcoma, penile cancer, solid cancer in childhood, Kaposi's sarcoma, Kaposi's sarcoma caused by AIDS, maxillary tumor, fibrous histiocytoma, leiomyosarcoma, rhabdomyosarcoma, liposarcoma, fibroid tumors of the uterus, osteoblastoma, osteosarcoma, chondrosarcoma, cancerous mesothelioma, tumors such as leukemia, Hodgkin's disease, etc.]

(11) circulatory diseases [for example, acute coronary artery syndromes (e.g., acute myocardial infarction, unstable angina, etc.), peripheral arterial occlusion, Raynaud's disease, Buerger's disease, restenosis after coronary-artery intervention (percutaneous transluminal coronary angioplasty (PTCA), directional coronary atherectomy (DCA), stenting, etc.), restenosis after coronary-artery bypass operation, restenosis after intervention (angioplasty, atherectomy, stenting, etc.) or bypass operation in other peripheral artery, ischemic cardiac diseases (e.g., myocardial infarction, angina, etc.), myocarditis, intermittent claudication, lacunar infarction, arteriosclerosis (e.g., atherosclerosis, etc.), cardiac failure (acute cardiac failure, chronic cardiac failure including congestive cardiac failure), arrhythmia, progress of atherosclerotic plaque, thrombosis, hypertension, hypertensive tinnitus, hypotension, etc.]

(12) pains [e.g., headache, migraine, neuralgia, pelvic visceral pain (including cystalgia), etc.]
(13) autoimmune diseases [for example, collagen disease, systemic lupus erythematosus, scleroderma, polyarteritis, myasthenia gravis, multiple sclerosis, Sjogren's syndrome, Behcet's disease, etc.]
(14) hepatic diseases [e.g., hepatitis (including chronic hepatitis), cirrhosis, interstitial hepatic diseases, etc.]
(15) pancreatic diseases [e.g., pancreatitis (including chronic pancreatitis), etc.]
(16) renal diseases [e.g., nephritis, glomerulonephritis, glomerulosclerosis, renal failure, thrombotic microangiopathy, dialysis complications, organ disorders including nephropathia by radiation, diabetic nephropathy, etc.]
(17) endocrine diseases [e.g., Addison's disease, Cushing's syndrome, melanocytoma, primary aldosteronism, etc.]
(18) other diseases
(a) transplant rejection [e.g., posttransplantational rejection, posttransplantational polycythemia, hypertension, organ disorder and/or vascular hypertrophy, graft-versus-host disease, etc.]
(b) abnormality in characteristic of blood and/or blood components [e.g., enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy, etc.]
(c) gynecologic diseases [for example, climacteric disorder, gestational toxicosis, endometriosis, hysteromyoma, ovarian disease, mammary disease, premenstrual syndrome, pelvic organ prolapse (pelvic organ prolapse; anterior vaginal wall prolapse, posterior vaginal wall prolapse, uterine prolapse, prolapse of the apical segment of the vagina, rectal prolapse [rectocele], enterocele, cystocele, urethral prolapse and the like)]
(d) dermatic diseases [e.g., keloid, hemangioma, psoriasis, pruritus, etc.]
(e) ophthalmic diseases [e.g., glaucoma, ocular hypertension disease, etc.]
(f) otolaryngological diseases [e.g., Menuel syndrome, tinnitus, gustation disorder, dizziness, disequilibrium, dysphagia, etc.]
(g) diseases due to environmental and/or occupational factors (e.g., radiation disorder, disorders by ultraviolet ray/infrared ray/laser ray, altitude sickness, etc.)
(h) ataxia, stiffness, tremor, motion impairment, akinesia
(i) chronic fatigue syndrome
(j) sudden infant death syndrome
(k) hiccup
(l) diseases causing palpitation, vertigo, heartburn, and the like.

Of these diseases, the compound of the present invention is particularly useful as a serotonin 5-HT$_{2c}$ receptor activator, an agent for improving lower urinary tract symptoms (including stress urinary incontinence, mixed urinary incontinence, post-micturition dribble), a drug for the prophylaxis or treatment of pelvic organ prolapse (anterior vaginal wall prolapse, posterior vaginal wall prolapse, uterine prolapse, prolapse of the apical segment of the vagina, rectal prolapse [rectocele], enterocele, cystocele, urethral prolapse and the like) and/or obesity.

A preparation containing compound (I) (or compound (I')) of the present invention may be any of solid preparations including powder, granule, tablet, capsule, orally disintegrating tablet, orally disintegrable films and the like, and liquid agents such as syrup, emulsion, injection and the like.

The preparation for the prophylaxis or treatment of the present invention can be produced by a conventional method such as blending, kneading, granulation, tabletting, coating, sterilization treatment, emulsification and the like according to the form of the preparation. As for the production of the preparation, for example, each item of the Japanese Pharmacopoeia Preparation General Rules and the like can be referred to. In addition, the agent of the present invention may be formed into a sustained-release preparation containing an active ingredient and a biodegradable polymer compound. The sustained-release preparation can be produced according to the method described in JP-A-9-263545.

In the preparations of the present invention, the content of the compound (I) (or compound (I')) varies depending on the forms of the preparations, but is generally in the order of 0.01 to 100% by weight, preferably 0.1 to 50% by weight, more preferably 0.5 to 20% by weight, relative to the total weight of each preparation.

When the compound (I) (or compound (I')) of the present invention is used in the above-mentioned pharmaceutical products, it may be used alone, or in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by ordinary methods. It can be formulated into the solid preparations such as powders, fine granules, granules, tablets, capsules, etc., or into the liquid preparations such as injections, etc., and can be administered orally or parenterally. When compound (I) (or compound (I')) is formed as a preparation for topical administration and administered, it can also be directly administered to the affected part of an articular disease. In this case, an injection is preferable. It can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) (or compound (I')) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing compound (I) together with vegetable oil such as sesame oil, corn oil and the like or a mixture thereof with a phospholipid such as lecithin and the like, or medium-chain triglyceride (e.g., miglyol 812 etc.) to give an injection to be actually used.

An agent for the prophylaxis or treatment of the present invention can be used along with other pharmaceutical composition.

As a drug that can be blended or combined with the substance of the present invention (hereinafter to be abbreviated as concomitant drug), the following drugs and the like can be used.

(1) Other Drugs for Treating Stress Urinary Incontinence

Adrenaline al receptor agonists (e.g., ephedrine hydrochloride, midodrine hydrochloride), adrenaline 132 receptor agonists (e.g., Clenbuterol), noradrenaline uptake inhibitory substances, noradrenaline and serotonin uptake inhibitory substances (e.g., duloxetine), tricyclic antidepressants (e.g., imipramine hydrochloride), anticholinergic agents or smooth muscle stimulants (e.g., oxybutynin hydrochloride, propiverine hydrochloride, celimeverine hydrochloride), female hormone drugs (e.g., conjugated estrogen (premarin), estriol) and the like.

(2) Agent for Treating Diabetes

Insulin preparations [e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1, etc.)], insulin sensitizers (e.g., pioglitazone hydrochloride, troglitazone, rosiglitazone or its maleate, JTT-501, MCC-555, YM-440, GI-262570, KRP-297, FK-614, CS-011, etc.), α-glucosidase inhibitors (e.g., voglibose, acarbose, miglitol, emiglitate, etc.), biguanides (e.g., phenformin, metformin, buformin, etc.), sulfonylureas (e.g., tolbutamide, glibenclamide, gliclazide, chlorpropamide, tolazamide, acetohexamide, glyclopyramide, glimepiride, etc.) and other insulin secretagogues (e.g., repaglinide, senaglinide, mitiglinide or its calcium salt hydrate, GLP-1, nateglinide, etc.), dipeptidylpeptidase IV inhibitors (e.g., vildagliptin, sitagliptin, saxagliptin, alogliptin, NVP-DPP-728, PT-100, P32/98, etc.), β3 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.) and the like.

(3) Agent for Treating Diabetic Complications

Aldose reductase inhibitors (e.g., tolrestat, epalrestat, zenarestat, zopolrestat, fidarestat (SNK-860), minalrestat (ARI-509), CT-112, etc.), neurotrophic factors (e.g., NGF, NT-3, etc.), AGE inhibitors (e.g., ALT-945, pimagedine, pyratoxathine, N-phenacylthiazolium bromide (ALT-766), EXO-226, etc.), active oxygen scavengers (e.g., thioctic acid, etc.), cerebral vasodilators (e.g., tiapride, etc.) and the like.

(4) Antihyperlipidemic Agent

Statin compounds inhibiting cholesterol synthesis (e.g., pravastatin, simvastatin, lovastatin, atorvastatin, fluvastatin, cerivastatin or their salt (e.g., sodium salt, etc.), etc.), squalene synthase inhibitors, fibrate compounds having triglyceride lowering action (e.g., bezafibrate, clofibrate, simfibrate, clinofibrate, etc.) and the like.

(5) Hypotensive Agent

Angiotensin converting enzyme inhibitors (e.g., captopril, enalapril, delapril, etc.), angiotensin II antagonists (e.g., losartan, candesartan cilexetil, etc.), calcium antagonists (e.g., manidipine, nifedipine, amlodipine, efonidipine, nicardipine, etc.), clonidine, and the like.

(6) Antiobesity Agent

Antiobesity drugs acting on the central nervous system (e.g. dexfenfluramine, fenfluramine, phentermine, sibutramine, anfepramone, dexamphetamine, mazindol, phenylpropanolamine, clobenzorex, etc.), pancreatic lipase inhibitors (e.g. orlistat, etc.), β3 agonists (e.g. CL-316243, SR-58611-A, UL-TG-307, AJ-9677, AZ40140, etc.), anorectic peptides (e.g. leptin, CNTF (Ciliary Neurotrophic Factor), etc.), cholecystokinin agonists (e.g. lintitript, FPL-15849, etc.).

(7) Diuretic Agent

Xanthine derivatives (e.g., theobromine sodium salicylate, theobromine calcium salicylate, etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonic anhydrase inhibitors (e.g., acetazolamide, etc.), chlorobenzenesulfonamide preparations (e.g., chlorthalidone, mefruside, indapamide, etc.), azosemide, isosorbide, ethacrynic acid, piretanide, bumetanide, furosemide, etc.

(8) Chemotherapeutic Agent

Alkylating agents (e.g., cyclophosphamide, ifosamide, etc.), metabolic antagonists (e.g., methotrexate, 5-fluorouracil, etc.), antitumor antibiotics (e.g., mitomycin, adriamycin, etc.), plant-derived antitumor agents (e.g., vincristine, vindesine, taxol, etc.), cisplatin, carboplatin, etoposide, etc. Among these, 5-fluorouracil derivatives such as Furtulon and Neo-Furtulon are preferred.

(9) Immunotherapeutic Agent

Microorganism- or bacterium-derived components (e.g., muramyl dipeptide derivatives, Picibanil, etc.), immunopotentiator polysaccharides (e.g., lentinan, schizophyllan, krestin, etc.), genetically engineered cytokines (e.g., interferons, interleukins (IL), etc.), colony stimulating factors (e.g., granulocyte colony stimulating factor, erythropoietin, etc.) and the like. Among these, IL-1, IL-2, IL-12, etc. are preferred.

(10) Therapeutic Agent Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above references are applied to both), fat metabolism ameliorating agents (e.g., eicosapentaenoic acid) [British Journal of Cancer, vol. 68, pp. 314-318, 1993], growth hormones, IGF-1, and antibodies to the cachexia-inducing factors such as TNF-α, LIF, IL-6 and oncostatin M.

(11) Antiinflammatory Agent

Steroids (e.g., dexamethasone, etc.), sodium hyaluronate, cyclooxygenase inhibitors (e.g., indomethacin, ketoprofen, loxoprofen, meloxicam, ampiroxicam, celecoxib, rofecoxib, etc.) and the like.

(12) Miscellaneous

Glycosylation inhibitors (e.g., ALT-711, etc.), nerve regeneration promoting drugs (e.g., Y-128, VX853, prosaptide, etc.), drugs acting on the central nervous system (e.g., antidepressants such as desipramine, amitriptyline, imipramine, fluoxetine, paroxetine, doxepin, etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), GABA receptor agonists (e.g., gabapentin), GABA uptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), hypnotics (e.g., triazolam, zolpidem), anticholinergic agents, $\alpha_1$ receptor blocking agents (e.g., tamsulosin, silodosin, naftopidil), muscle relaxants (e.g., baclofen), potassium channel openers (e.g., nicorandil), calcium channel blocking agents (e.g., nifedipine), agents for preventing and/or treating Alzheimer's disease (e.g., donepezil, rivastigmine, galanthamine), agents for treating Parkinson's disease (e.g., L-dopa), agents for preventing and/or treating multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents of treating HIV infection (saquinavir, zidovudine, lamivudine, nevirapine), agents of treating chronic obstructive pulmonary diseases (salmeterol, thiotropium bromide, cilomilast), etc.

Anticholinergic agents include, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrogen bromide, homatropine hydrogen bromide, cyclopentolate hydrochloride, flavoxate hydrochloride, pirenzepine hydrochloride, trihexyphenidyl hydrochloride, oxybutynin hydrochloride, tolterodine tartrate, etc.), preferably, oxybutynin, propiverine, darifenacin, tolterodine, temiverine, trospium chloride or a salt thereof (e.g., oxybutynin hydrochloride, tolterodine tartrate, etc.). In addition, acetylcholinesterase inhibitors (e.g., distigmine, etc.) and the like can be used.

NK-2 receptor antagonists include, for example, a piperidine derivative such as GR159897, GR149861, SR48968% (saredutant), SR144190, YM35375, YM38336, ZD7944, L-743986, MDL105212A, ZD6021, MDL105172A, SCH205528, SCH62373, R-113281, etc., a perhydroisoindole derivative such as RPR-106145, etc., a quinoline derivative such as SB-414240, etc., a pyrrolopyrimidine derivative such as ZM-253270, etc., a pseudopeptide derivative such as MEN11420 (nepadutant), SCH217048, L-659877, PD-147714 (CAM-2291), MEN10376, S16474, etc., and others such as GR100679, DNK333, GR94800, UK-224671, MEN10376, MEN10627, or a salt thereof, and the like.

In combination of the compound of the present invention and the concomitant drug, the administration time of the compound (I) (or the compound (I')) and the concomitant drug is not restricted, and the compound (I) (or the compound (I')) or a pharmaceutical composition thereof and the concomitant drug or a pharmaceutical composition thereof can be administered to the administration subject simultaneously, or may be administered at different times. The dosage of the concomitant drug may be determined according to the dose clinically used, and can be appropriately selected depending on the administration subject, administration route, disease, combination and the like.

The concomitant administration mode is not particularly restricted, and it is sufficient that the compound (I) (or the compound (I')) and the concomitant drug are combined in administration. Examples of such administration mode include the following methods:
(1) The compound (I) (or the compound (I')) or a pharmaceutical composition thereof and the concomitant drug are simultaneously produced to give a single preparation which is administered. (2) The compound (I) (or the compound (I')) or a pharmaceutical composition thereof and the concomitant drug or a pharmaceutical composition thereof are separately produced to give two kinds of preparations which are administered simultaneously by the same administration route. (3) The compound (I) (or the compound (I')) or a pharmaceutical composition thereof and the concomitant drug or a pharmaceutical composition thereof are separately produced to give two kinds of preparations which are administered by the same administration route at different times. (4) The compound (I) (or the compound (I')) or a pharmaceutical composition thereof and the concomitant drug or a pharmaceutical composition thereof are separately produced to give two kinds of preparations which are administered simultaneously by different administration routes. (5) The compound (I) (or the compound (I')) or a pharmaceutical composition thereof and the concomitant drug or a pharmaceutical composition thereof are separately produced to give two kinds of preparations which are administered by different administration routes at different times (e.g., the compound (I) (or the compound (I')) or a pharmaceutical composition thereof; the concomitant drug or a pharmaceutical composition thereof are administered in this order, or in the reverse order).

The mixing ratio of compound (I) (or the compound (I')) and a concomitant drug in the combination drug of the present invention can be appropriately determined according to the subject of administration, administration route, disease and the like.

For example, while the content of compound (I) (or the compound (I')) in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the concomitant drug in the combination drug of the present invention varies depending on the form of the preparation, it is generally about 0.01 to about 100 wt %, preferably about 0.1 to about 50 wt %, more preferably about 0.5 to about 20 wt %, relative to the whole preparation.

While the content of the additive such as a carrier and the like in the combination drug of the present invention varies depending on the form of the preparation, it is generally about 1 to about 99.99 wt %, preferably about 10 to about 90 wt %, relative to the whole preparation.

Similar contents can be employed when compound (I) (or the compound (I')) and the concomitant drug are independently formulated.

While the dose varies depending on the kind of compound (I) (or the compound (I')) or a pharmaceutically acceptable a salt thereof, administration route, symptom, age of patients and the like, for example, for oral administration to an adult patient with stress urinary incontinence, it is about 0.005 to 50 mg, preferably about 0.05 to 10 mg, more preferably about 0.2 to 4 mg/kg body weight/day as compound (I) (or the compound (I')), which can be administered in 1 to about 3 portions.

When the pharmaceutical composition of the present invention is a sustained-release preparation, the dose varies depending on the kind and content of compound (I) (or the compound (I')), dosage form, period of sustained drug release, subject animal of administration (e.g., mammals such as human, rat, mouse, cat, dog, rabbit, bovine, swine and the like) and administration object. For parenteral administration, for example, about 0.1 to about 100 mg of compound (I) (or the compound (I')) only needs to be released in one week from the administered preparation.

The dose of the concomitant drug may be set within the range such that it causes no problems of side effects. The daily dose as the concomitant drug varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of drugs is usually in the order of about 0.001 to 2000 mg, preferably about 0.01 to 500 mg, and more preferably about 0.1 to 100 mg, per 1 kg body weight of mammals, which may be administered once a day or in two to four divided portions a day.

In administering the combination drug of the present invention, it may be administered at the same time or, the concomitant drug may be administered before administering the compound (I) (or the compound (I')), or vice versa. In case of staggered administration, the time interval varies depending on the active ingredients to be administered, a formulation and an administration route. For example, if the concomitant drug is administered first, the compound (I) (or the compound (I')) may be administered 1 minute to 3 days, preferably 10 minutes to 1 day, more preferably 15 minutes to 1 hour after administering the concomitant drug. If the compound (I) (or the compound (I')) is administered first, the concomitant drug may be administered 1 minute to 1 day, preferably 10 minutes to 6 hours, more preferably 15 minutes to 1 hour after administering the compound (I) (or the compound (I')).

The pharmaceutical composition of the present invention shows low toxicity and can be used safely. Particularly, since the Example compounds shown below are superior in the absorption by oral administration, they can be advantageously used for oral preparations.

A screening method of an agent for the prophylaxis or treatment of pelvic organ prolapse or post-micturition dribble, namely, a screening method of a substance that increases the contractile force of the pelvic floor muscles is described in the following.

In this screening method, an animal with bilaterally cut hypogastric nerve and pudendal nerve is used. The muscular tissues which are related to the closing pressure include internal urethral sphincter (smooth muscle), external urethral sphincter (striated muscle), and pelvic floor muscles and the like. The pelvic floor muscles include the iliococcygeus muscle and the pubococcygeus muscle. The internal urethral sphincter is innervated by the hypogastric nerve, the external urethral sphincter is innervated by the pudendal nerves, and the iliococcygeus muscle and the pubococcygeus muscle are innervated by the nerves to the iliococcygeus muscle and the pubococcygeus muscle (common name beyond species does not exist). When the level of the aquatic reservoir connected to the bladder is raised to a certain level, reflective urethral contractile responses are observed in the middle urethra (see "American Journal of Physiology Renal Physiology", 2004, vol. 287, p. F434-441). Using an animal with bilaterally cut hypogastric nerve and pudendal nerves, the bladder pressure is increased and the urethral contractile responses are observed. As a result, a urethral closure response mainly caused by the pelvic floor muscles (the iliococcygeus muscle and the pubococcygeus muscle) can be measured, based on which the contractile responses of the pelvic floor muscles can be evaluated.

A concrete measurement method of the "reflective urethral contractile responses of pelvic floor muscles when bladder pressure is increased" is described in detail in the below-mentioned Experimental Example 3.

EXAMPLES

The present invention is further described in detail with reference to Reference Examples, Examples, Formulation Examples and Experimental Examples which are not intended to restrict the invention and may be modified without departing from the scope of the invention.

Elution in the column chromatography in the following Reference Examples and Examples was conducted under observation by TLC (thin layer chromatography), unless otherwise specifically indicated. In the TLC observation, 60F254, TLC plates, produced by Merck & Co., Inc. was used, and the solvent employed as an elution solvent in the column chromatography was used as a developing solvent. For the detection, a UV detector was employed. As silica gel for column chromatography, silica gel 60 (70-230 mesh) manufactured by Merck & Co or Purif-Pack manufactured by MORITEX was used. As basic silica gel (hereinafter to be referred to as NH silica gel), Chromatorex NH (100-200 mesh) manufactured by Fuji Silysia Chemical was used.

The room temperature referred herein means temperature generally from about 10° C. to 30° C.

The melting point was measured by a melting point measurement apparatus MP-500D (Yanaco Co., Ltd.) or OptiMelt MPA-100 (Stanford Research Systems).

LC-MS analysis was performed under the following conditions.

measurement device: Waters LC-MS system
HPLC: Agilent HP1100
MS: Micromass ZQ
HPLC conditions
column: CAPCELL PAK C18UG120, S-3 µM, 1.5×35 mm (Shiseido Co., Ltd.)
solvent: SOLUTION A; 0.05% trifluoroacetic acid-containing water, SOLUTION B; 0.05% trifluoroacetic acid-containing acetonitrile
gradient cycle: 0.00 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.60 min (SOLUTION A/SOLUTION B=90/10)
injection volume: 2 µL, flow rate: 0.5 mL/min, detection method: UV220 nm
MS conditions
ionization method: ESI
Purification by high-polar preparative HPLC was conducted under the following conditions.
device: Gilson Inc. High-Throughput Purification System
column: CombiPrep ODS-A S-5 µm, 50×20 mm (YMC)
solvent: SOLUTION A; 0.1% trifluoroacetic acid-containing water, SOLUTION B; 0.1% trifluoroacetic acid-containing acetonitrile
gradient cycle: 0.00 min (SOLUTION A/SOLUTION B=95/5), 1.00 min (SOLUTION A/SOLUTION B=95/5), 5.20 min (SOLUTION A/SOLUTION B=5/95), 6.40 min (SOLUTION A/SOLUTION B=5/95), 6.50 min (SOLUTION A/SOLUTION B=95/5), 6.60 min (SOLUTION A/SOLUTION B=95/5)
flow rate: 25 mL/min, detection method: UV220 nm The abbreviations in Examples and Reference Examples mean the following.

LC: liquid chromatography
MS: mass spectrometry spectrum
ESI: electrospray method
M: molecular ion peak
NMR: nuclear magnetic resonance spectrum
Hz: hertz
J: coupling constant
m: multiplet
q: quartet
t: triplet d: doublet
dd: double doublet
ddd: double double doublet
s: singlet
br s: broad singlet
br: broad
N: normal concentration
DMSO: dimethyl sulfoxide
MeOH: methanol
DMF: N,N-dimethylformamide
THF: tetrahydrofuran
TFA: trifluoroacetic acid
X-phos: 2-dicyclohexylphosphino-2',4',6'-triisopropyl-1,1'-biphenyl
5-HT: serotonin (or 5-hydroxytryptamine)

Example 1

8-(morpholin-4-yl)-2,3,4,5-tetrahydro-1,4-benzoxazepine hydrochloride (1) N-benzyl-4-bromo-2-fluoro-N-(2-hydroxyethyl)benzamide To a solution of N-benzylethanolamine (6.37 g, 42.1 mmol), triethylamine (8.81 ml, 63.2 mmol) in tetrahydrofuran (200 ml) was added under ice-cooling 4-bromo-2-fluorobenzoylchloride (10.0 g, 42.1 mmol), and the mixture was stirred at room temperature for 1 hr. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (1.45 g, 98.0%) as an oil.
$^1$H-NMR (CDCl$_3$) δ; 1.97 (0.3H, t, J=5.4 Hz), 2.90 (0.7H, t, J=5.1 Hz), 3.26-3.30 (0.6H, m), 3.55-3.60 (0.6H, m), 3.63-3.66 (1.4H, m), 3.75-3.81 (1.4H, m), 4.50 (1.4H, s), 4.86 (0.6H, s), 7.12 (2H, d, J=6.3 Hz), 7.25-7.38 (6H, m).

(2) 4-benzyl-8-bromo-3,4-dihydro-1,4-benzoxazepine-5 (2H)-one

To a solution of N-benzyl-4-bromo-2-fluoro-N-(2-hydroxyethyl)benzamide (14.5 g, 41.2 mmol) in N,N-dimethylformamide (200 ml) was added under ice-cooling sodium hydride (60%, 2.14 g, 53.5 mmol), and the mixture was stirred under ice-cooling for 1 hr. The reaction mixture was poured into ice water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (10.1 g, 73.7%) as an oil.
$^1$H-NMR (CDCl$_3$) δ; 3.46 (2H, t, J=4.8 Hz), 4.17 (2H, t, J=4.8 Hz), 4.81 (2H, s), 7.17 (1H, s), 7.25-7.35 (6H, m), 7.77 (1H, d, J=8.4 Hz).

(3) 4-benzyl-8-bromo-2,3,4,5-tetrahydro-1,4-benzoxazepine

To a solution of 4-benzyl-8-bromo-3,4-dihydro-1,4-benzoxazepine-5 (2H)-one (4.50 g, 13.5 mmol) in tetrahydrofuran (45 ml) was added 1M borane-tetrahydrofuran solution (54 ml, 54.0 mmol), and the mixture was stirred at 65° C. for 4 hr. Under ice-cooling, methanol (135 ml) and sodium hydroxide (11.7 g, 294 mmol) were added, and the mixture was stirred at room temperature for 1 hr. The solvent was evaporated under reduced pressure. The residue was poured into water and the mixture was extracted with ethyl acetate. The extract was dried over anhydrous magnesium sulfate. The solvent was evaporated under reduced pressure to give the desired product (4.30 g, 100%) as an oil.
$^1$H-NMR (CDCl$_3$) δ; 3.07 (2H, br s), 3.63 (2H, s), 3.75 (2H, s), 4.07-4.10 (2H, m), 6.85 (1H, d, J=7.8 Hz), 7.10 (1H, dd, J=2.1, 7.8 Hz), 7.18 (1H, d, J=2.1 Hz), 7.24-7.32 (5H, m).

(4) tert-butyl 8-bromo-2,3-dihydro-1,4-benzoxazepine-4(5H)-carboxylate

A solution of 4-benzyl-8-bromo-2,3,4,5-tetrahydro-1,4-benzoxazepine (1.00 g, 3.14 mmol) and 1-chloroethyl chloroformate (0.591 ml, 5.49 mmol) in 1,2-dichloroethane (20 ml) was stirred for 1 hr at 90° C. The solvent was evaporated under reduced pressure. To the residue was added methanol (20 ml), and the mixture was stirred for 1 hr at 80° C. The solvent was evaporated under reduced pressure and the residue was washed with ether. To the residue were added 1N aqueous sodium hydroxide solution (7 ml), dioxane (7 ml) and di-t-butyl-dicarbonate (1.13 g, 5.18 mmol) under ice-cooling, and the mixture was stirred for 1 hr at room temperature. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (670 mg, 65.0%) as a solid.
$^1$H-NMR (CDCl$_3$) δ; 1.41 (9H, s), 3.77-3.80 (2H, m), 4.02-4.05 (2H, m), 4.36-4.42 (2H, m), 7.02-7.20 (3H, m).

(5) tert-butyl 8-(morpholin-4-yl)-2,3-dihydro-1,4-benzoxazepine-4(5H)-carboxylate A solution of tert-butyl 8-bromo-2,3-dihydro-1,4-benzoxazepine-4(5H)-carboxylate (100 mg, 0.305 mmol), morpholine (0.0292 ml, 0.335 mmol), X-phos (8.70 mg, 0.0182 mmol), tris(dibenzylideneacetone)dipalladium(0) (5.52 mg, 0.00604 mmol) and sodium tert-butoxide (43.8 mg, 0.456 mmol) in dioxane (2 ml) was stirred under an argon atmosphere for 7 hr at 80° C. The reaction mixture was poured into water, and the mixture was extracted with ethyl acetate. The extract was washed with water and dried over anhydrous magnesium sulfate. The solvent was evaporated under reduced pressure. The residue was purified by NH silica gel column chromatography (hexane:ethyl acetate=1:1) to give the desired product (50.0 mg, 49.0%) as an oil.
$^1$H-NMR (CDCl$_3$) δ; 1.41 (9H, s), 3.12-3.15 (4H, m), 3.75-3.78 (2H, m), 3.82-3.85 (4H, m), 4.01-4.04 (2H, m), 4.34-4.41 (2H, m), 6.53-6.59 (2H, m), 7.04-7.18 (1H, m).

(6) 8-(morpholin-4-yl)-2,3,4,5-tetrahydro-1,4-benzoxazepine hydrochloride

A solution of tert-butyl 8-(morpholin-4-yl)-2,3-dihydro-1,4-benzoxazepine-4(5H)-carboxylate (50.0 mg, 0.150 mmol) in 4N hydrogen chloride-ethyl acetate (1 ml) was stirred for 1 hr at room temperature, and the solvent was evaporated under reduced pressure. The residue was recrystallized from a mixed solvent of methanol and ether to give the desired product (25.0 mg, 54.5%) as a solid.
$^1$H-NMR (DMSO-d$_6$) δ; 3.11-3.16 (4H, m), 3.40 (2H, br s), 3.70-3.73 (4H, m), 4.17 (4H, br s), 6.65 (1H, s), 6.70 (1H, d, J=8.7 Hz), 7.25 (1H, d, J=8.7 Hz), 9.43 (2H, br s).

Example 2

8-(pyrrolidin-1-yl)-2,3,4,5-tetrahydro-1,4-benzoxazepine dihydrochloride

(1) tert-butyl 8-(pyrrolidin-1-yl)-2,3-dihydro-1,4-benzoxazepine-4(5H)-carboxylate A solution of tert-butyl 8-bromo-2,3-dihydro-1,4-benzoxazepine-4(5H)-carboxylate (300 mg, 0.915 mmol), pyrrolidine (0.250 ml, 3.00 mmol), X-phos (26.1 mg, 0.0546 mmol), tris(dibenzylideneacetone)dipalladium(0) (16.6 mg, 0.00187 mmol) and sodium tert-butoxide (131 mg, 1.37 mmol) in dioxane (6 ml) was stirred under an argon atmosphere for 1 hr at 80° C. The reaction mixture was poured into water, and the mixture was extracted with ethyl acetate. The extract was washed with water and dried over anhydrous magnesium sulfate. The solvent was evaporated under reduced pressure and the residue was purified by NH silica gel column chromatography (hexane:ethyl acetate=1:1) to give the desired product (110 mg, 37.8%) as an oil.

$^1$H-NMR (CDCl$_3$) δ; 1.42 (9H, s), 1.96-2.00 (4H, m), 3.22-3.26 (4H, m), 3.74-3.76 (2H, m), 4.01-4.04 (2H, m), 4.32-4.39 (2H, m), 6.18-6.25 (2H, m), 6.97-7.03 (1H, m).

(2) 8-(pyrrolidin-1-yl)-2,3,4,5-tetrahydro-1,4-benzoxazepine dihydrochloride A solution of tert-butyl 8-(pyrrolidin-1-yl)-2,3-dihydro-1,4-benzoxazepine-4(5H)-carboxylate (110 mg, 0.345 mmol) in 4N hydrogen chloride-ethyl acetate (2 ml) was stirred for 1 hr at room temperature, and the solvent was evaporated under reduced pressure. The residue was recrystallized from a mixed solvent of methanol and ether to give the desired product (74.0 mg, 73.3%) as a solid.

$^1$H-NMR (DMSO-d$_6$) δ; 1.91-1.96 (4H, m), 3.16-3.22 (4H, m), 3.37 (2H, br s), 4.13-4.14 (4H, m), 5.51 (1H, br s), 6.22 (1H, d, J=2.4 Hz), 6.27 (1H, dd, J=2.4, 8.1 Hz), 7.16 (1H, d, J=8.1 Hz), 9.36-9.43 (2H, m).

Example 3

8-(piperidin-1-yl)-2,3,4,5-tetrahydro-1,4-benzoxazepine dihydrochloride

(1) tert-butyl 8-(piperidin-1-yl)-2,3-dihydro-1,4-benzoxazepine-4(5H)-carboxylate A solution of tert-butyl 8-bromo-2,3-dihydro-1,4-benzoxazepine-4(5H)-carboxylate (300 mg, 0.915 mmol), piperidine (0.297 ml, 3.00 mmol), X-phos (26.1 mg, 0.0546 mmol), tris(dibenzylideneacetone)dipalladium(0) (16.6 mg, 0.00187 mmol) and sodium tert-butoxide (131 mg, 1.37 mmol) in dioxane (6 ml) was stirred under an argon atmosphere for 1 hr at 80° C. The reaction mixture was poured into water, and the mixture was extracted with ethyl acetate. The extract was washed with water and dried over anhydrous magnesium sulfate. The solvent was evaporated under reduced pressure and the residue was purified by NH silica gel column chromatography (hexane:ethyl acetate=2:1) to give the desired product (280 mg, 92.1%) as an oil.

$^1$H-NMR (CDCl$_3$) δ; 1.41 (9H, s), 1.53-1.59 (2H, m), 1.64-1.71 (4H, m), 3.11-3.15 (4H, m), 3.74-3.77 (2H, m), 4.00-4.03 (2H, m), 4.32-4.39 (2H, m), 6.54-6.60 (2H, m), 6.97-7.03 (1H, m).

(2) 8-(piperidin-1-yl)-2,3,4,5-tetrahydro-1,4-benzoxazepine dihydrochloride A solution of tert-butyl 8-(piperidin-1-yl)-2,3-dihydro-1,4-benzoxazepine-4(5H)-carboxylate (280 mg, 0.843 mmol) in 4N hydrogen chloride-ethyl acetate (6 ml) was stirred for 1 hr at room temperature, and the solvent was evaporated under reduced pressure. The residue was recrystallized from a mixed solvent of methanol and ether to give the desired product (210 mg, 81.7%) as a solid.

$^1$H-NMR (DMSO-d$_6$) δ; 1.62 (2H, br s), 1.85 (4H, br s), 3.38-3.44 (7H, m), 4.24-4.29 (4H, m), 7.33-7.47 (3H, m), 9.71 (2H, br s).

Example 4

N-isopropyl-N-methyl-2,3,4,5-tetrahydro-1,4-benzoxazepine-8-amine dihydrochloride

(1) tert-butyl 8-[isopropyl(methyl)amino]-2,3-dihydro-1,4-benzoxazepine-4(5H)-carboxylate A solution of tert-butyl 8-bromo-2,3-dihydro-1,4-benzoxazepine-4(5H)-carboxylate (300 mg, 0.915 mmol), N-methyl-N-isopropylamine (0.313 ml, 3.00 mmol), X-phos (26.1 mg, 0.0546 mmol), tris(dibenzylideneacetone)dipalladium(0) (16.6 mg, 0.00187 mmol) and sodium tert-butoxide (131 mg, 1.37 mmol) in dioxane (6 ml) was stirred under an argon atmosphere at 80° C. for 1.5 hr. The reaction mixture was poured into water, and the mixture was extracted with ethyl acetate. The extract was washed with water and dried over anhydrous magnesium sulfate. The solvent was evaporated under reduced pressure and the residue was purified by NH silica gel column chromatography (hexane:ethyl acetate=1:1) to give the desired product (270 mg, 92.1%) as an oil.

$^1$H-NMR (CDCl$_3$) δ; 1.14 (6H, d, J=6.6 Hz), 1.42 (9H, s), 2.70 (3H, s), 3.74-3.81 (2H, m), 4.00-4.15 (3H, m), 4.32-4.40 (2H, m), 6.39-6.46 (2H, m), 6.98-7.04 (1H, m).

(2) N-isopropyl-N-methyl-2,3,4,5-tetrahydro-1,4-benzoxazepine-8-amine dihydrochloride A solution of tert-butyl 8-[isopropyl(methyl)amino]-2,3-dihydro-1,4-benzoxazepine-4(5H)-carboxylate (270 mg, 0.843 mmol) in 4N hydrogen chloride-ethyl acetate (6 ml) was stirred for 1 hr at room temperature, and the solvent was evaporated under reduced pressure. The residue was recrystallized from a mixed solvent of methanol and ether to give the desired product (123 mg, 49.8%) as a solid.

$^1$H-NMR (CD$_3$OD) δ; 1.33 (6H, d, J=6.3 Hz), 3.24 (3H, s), 3.64-3.67 (2H, m), 3.93-4.00 (1H, m), 4.35-4.38 (2H, m), 4.48 (2H, s), 4.86 (3H, br s), 7.37-7.40 (2H, m), 7.62 (1H, d, J=8.1 Hz).

Example 5

N,N-diethyl-2,3,4,5-tetrahydro-1,4-benzoxazepine-8-amine dihydrochloride

(1) tert-butyl 8-(diethylamino)-2,3-dihydro-1,4-benzoxazepine-4(5H)-carboxylate A solution of tert-butyl 8-bromo-2,3-dihydro-1,4-benzoxazepine-4(5H)-carboxylate (300 mg, 0.915 mmol), diethylamine (0.310 ml, 3.00 mmol), X-phos (26.1 mg, 0.0546 mmol), tris(dibenzylideneacetone)dipalladium(0) (16.6 mg, 0.00187 mmol) and sodium tert-butoxide (131 mg, 1.37 mmol) in dioxane (6 ml) was stirred under an argon atmosphere for 1 hr at 80° C. The reaction mixture was poured into water, and the mixture was extracted with ethyl acetate. The extract was washed with water and dried over anhydrous magnesium sulfate. The solvent was evaporated under reduced pressure and the residue was purified by NH silica gel column chromatography (hexane:ethyl acetate=2:1) to give the desired product (250 mg, 85.3%) as an oil.

$^1$H-NMR (CDCl$_3$) δ; 1.15 (6H, t, J=7.2 Hz), 1.42 (9H, s), 3.31 (4H, q, J=7.2 Hz), 3.74-3.77 (2H, m), 4.01-4.04 (2H, m), 4.31-4.38 (2H, m), 6.29-6.36 (2H, m), 6.96-7.04 (1H, m).

(2) N,N-diethyl-2,3,4,5-tetrahydro-1,4-benzoxazepine-8-amine dihydrochloride

A solution of tert-butyl 8-(diethylamino)-2,3-dihydro-1,4-benzoxazepine-4(5H)-carboxylate (250 mg, 0.780 mmol) in 4N hydrogen chloride-ethyl acetate (6 ml) was stirred for 1 hr at room temperature, and the solvent was evaporated under reduced pressure. The residue was recrystallized from a mixed solvent of methanol and ether to give the desired product (144 mg, 62.9%) as a solid.

$^1$H-NMR (CD$_3$OD) δ; 1.16 (6H, t, J=7.2 Hz), 3.62-3.69 (6H, m), 4.36-4.39 (2H, m), 4.49 (2H, s), 4.85 (3H, br s), 7.37-7.40 (2H, m), 7.65 (1H, d, J=8.4 Hz).

Example 6

N-ethyl-N-methyl-2,3,4,5-tetrahydro-1,4-benzoxazepine-8-amine dihydrochloride (1) tert-butyl 8-[ethyl(methyl)amino]-2,3-dihydro-1,4-benzoxazepine-4(5H)-carboxylate A solution of tert-butyl 8-bromo-2,3-dihydro-1,4-benzoxazepine-4(5H)-carboxylate (300 mg, 0.915 mmol), N-ethyl-N-methylamine (0.258 ml, 3.00 mmol), X-phos (26.1 mg, 0.0546 mmol), tris(dibenzylideneacetone)dipalladium(0) (16.6 mg, 0.00187 mmol) and sodium tert-butoxide (131 mg, 1.37 mmol) in dioxane (6 ml) was stirred under an argon atmosphere for 2 hr at 80° C. The reaction mixture was poured into water, and the mixture was extracted with ethyl acetate. The extract was washed with water and dried over anhydrous magnesium sulfate. The solvent was evaporated under reduced pressure and the residue was purified by NH silica gel column chromatography (hexane:ethyl acetate=1:1) to give the desired product (230 mg, 82.1%) as an oil.

$^1$H-NMR (CDCl$_3$) δ; 1.08-1.14 (3H, m), 1.43 (9H, s), 2.87 (3H, s), 3.33-3.38 (2H, m), 3.74-3.77 (2H, m), 4.02-4.04 (2H, m), 4.33-4.40 (2H, m), 6.33-6.40 (2H, m), 7.00-7.12 (1H, m).

(2) N-ethyl-N-methyl-2,3,4,5-tetrahydro-1,4-benzoxazepine-8-amine dihydrochloride A solution of tert-butyl 8-[ethyl(methyl)amino]-2,3-dihydro-1,4-benzoxazepine-4(5H)-carboxylate (230 mg, 0.751 mmol) in 4N hydrogen chloride-ethyl acetate (4 ml) was stirred for 1 hr at room temperature, and the solvent was evaporated under reduced pressure. The residue was recrystallized from a mixed solvent of methanol and ether to give the desired product (143 mg, 68.1%) as a solid.

$^1$H-NMR (CD$_3$OD) δ; 1.19 (3H, t, J=7.2 Hz), 3.24 (3H, s), 3.60-3.67 (4H, m), 4.34-4.37 (2H, m), 4.47 (2H, s), 4.86 (3H, s), 7.33-7.36 (2H, m), 7.61 (1H, d, J=8.1 Hz).

Example 7

9-(pyrrolidin-1-yl)-2,3,4,5-tetrahydro-1,4-benzoxazepine dihydrochloride (1) N-benzyl-3-bromo-2-fluoro-N-(2-hydroxyethyl) benzamide A solution of 3-bromo-2-fluorobenzoic acid (10.0 g, 45.9 mmol) and N,N-dimethylformamide (0.100 ml) in thionylchloride (10 ml) was stirred for 3 hr at 85° C., and the solvent was evaporated under reduced pressure. The residue was added to a solution of N-benzylethanolamine (6.94 g, 45.8 mmol) and triethylamine (9.60 ml, 68.9 mmol) in tetrahydrofuran (140 ml) under ice-cooling, and the mixture was stirred at room temperature for 1 hr. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (11.5 g, 68.9%) as an oil.

$^1$H-NMR (CDCl$_3$) δ; 1.58 (0.3H, t, J=6.0 Hz), 2.71 (0.7H, t, J=5.1 Hz), 3.27-3.31 (0.6H, m), 3.57-3.68 (2H, m), 3.78-3.83 (1.4H, m), 4.50 (1.4H, s), 4.90 (0.6H, s), 7.04-7.14 (2H, m), 7.28-7.40 (5H, m), 7.56-7.62 (1H, m).

(2) 4-benzyl-9-bromo-3,4-dihydro-1,4-benzoxazepine-5 (2H)-one

To a solution of N-benzyl-3-bromo-2-fluoro-N-(2-hydroxyethyl)benzamide (11.4 g, 32.4 mmol) in N,N-dimethylformamide (160 ml) was added under ice-cooling sodium hydride (60%, 1.68 g, 42.1 mmol), and the mixture was stirred under ice-cooling for 1 hr. The reaction mixture was poured into ice water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (8.08 g, 74.8%) as an oil.

$^1$H-NMR (CDCl$_3$) δ; 3.41-3.44 (2H, m), 4.16-4.20 (2H, m), 4.84 (2H, s), 7.05-7.11 (1H, m), 7.25-7.38 (5H, m), 7.66-7.76 (2H, m).

(3) 4-benzyl-9-bromo-2,3,4,5-tetrahydro-1,4-benzoxazepine

To a solution of 4-benzyl-9-bromo-3,4-dihydro-1,4-benzoxazepine-5 (2H)-one (8.00 g, 24.1 mmol) in tetrahydrofuran (80 ml) was added 1M borane-tetrahydrofuran solution (96.4 ml, 96.4 mmol), and the mixture was stirred at 60° C. for 2 hr. Under ice-cooling, methanol (240 ml) and sodium hydroxide (20.8 g, 519 mmol) were added, and the mixture was stirred at room temperature for 2 hr, and the solvent was evaporated under reduced pressure. The residue was poured into water and the mixture was extracted with ethyl acetate. The extract was dried over anhydrous magnesium sulfate, and the solvent was evaporated under reduced pressure to give the desired product (6.20 g, 80.8%) as an oil.

$^1$H-NMR (CDCl$_3$) δ; 3.12-3.14 (2H, m), 3.63 (2H, s), 3.83 (2H, s), 4.14-4.15 (2H, m), 6.82-6.94 (2H, m), 7.25-7.35 (5H, m), 7.43-7.47 (1H, m).

(4) tert-butyl 9-bromo-2,3-dihydro-1,4-benzoxazepine-4(5H)-carboxylate

A solution of 4-benzyl-9-bromo-2,3,4,5-tetrahydro-1,4-benzoxazepine (6.00 g, 18.9 mmol) and 1-chloroethyl chloroformate (3.24 ml, 30.0 mmol) in 1,2-dichloroethane (120 ml) was stirred at 90° C. for 1 hr, and the solvent was evaporated under reduced pressure. Methanol (120 ml) was added to the residue, the mixture was stirred at 80° C. for 1 hr, and the solvent was evaporated under reduced pressure. The residue was washed with ether, and 1N aqueous sodium hydroxide solution (42 ml), dioxane (42 ml) and di-tert-butyl dicarbonate (6.92 ml, 31.0 mmol) were added to the residue under ice-cooling, and the mixture was stirred at room temperature for 2 hr. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (6.00 g, 96.7%) as a solid.

$^1$H-NMR (CDCl$_3$) δ; 1.40 (9H, s), 3.82-3.84 (2H, m), 4.07-4.13 (2H, m), 4.42-4.48 (2H, m), 6.87-6.92 (1H, m), 7.11-7.26 (1H, m), 7.44-7.47 (1H, m).

(5) tert-butyl 9-(pyrrolidin-1-yl)-2,3-dihydro-1,4-benzoxazepine-4(5H)-carboxylate A solution of tert-butyl 9-bromo-2,3-dihydro-1,4-benzoxazepine-4(5H)-carboxylate (350 mg, 1.07 mmol), pyrrolidine (0.274 ml, 3.27 mmol), X-phos (30.5 mg, 0.064 mmol), tris(dibenzylideneacetone)dipalladium(0) (19.3 mg, 0.0212 mmol) and sodium tert-butoxide (154 mg, 1.60 mmol) in dioxane (7 ml) was stirred under an argon atmosphere for 2 hr at 80° C. The reaction mixture was poured into water, and the mixture was extracted with ethyl acetate. The extract was washed with water and dried over anhydrous magnesium sulfate. The solvent was evaporated under reduced pressure and the residue was purified by NH silica gel column chromatography (hexane:ethyl acetate=3:1) to give the desired product (90.0 mg, 26.4%) as an oil.

$^1$H-NMR (CDCl$_3$) δ; 1.42 (9H, s), 1.90-1.94 (4H, m), 3.34-3.39 (4H, m), 3.78-3.81 (2H, m), 3.96-3.99 (2H, m), 4.38-4.43 (2H, m), 6.59-6.63 (2H, m), 6.86-6.92 (1H, m).

(6) 9-(pyrrolidin-1-yl)-2,3,4,5-tetrahydro-1,4-benzoxazepine dihydrochloride

A solution of tert-butyl 9-(pyrrolidin-1-yl)-2,3-dihydro-1,4-benzoxazepine-4(5H)-carboxylate (90.0 mg, 0.283 mmol) in 4N hydrogen chloride-ethyl acetate (3 ml) was stirred for 1 hr at room temperature, and the solvent was evaporated under reduced pressure. The residue was recrystallized from a mixed solvent of methanol and ether to give the desired product (25.4 mg, 30.9%) as a solid.

$^1$H-NMR (CD$_3$OD) δ; 2.29-2.33 (4H, m), 3.70-3.73 (2H, m), 4.80 (4H, br s), 4.48-4.51 (4H, m), 4.85 (3H, s), 7.33-7.38 (1H, m), 7.55 (1H, d, J=7.5 Hz), 7.72 (1H, d, J=8.1 Hz).

Example 8

8-phenyl-2,3,4,5-tetrahydro-1,4-benzoxazepine hydrochloride (1) tert-butyl 8-phenyl-2,3-dihydro-1,4-benzoxazepine-4(5H)-carboxylate A mixture of tert-butyl 8-bromo-2,3-dihydro-1,4-benzoxazepine-4(5H)-carboxylate (200 mg, 0.609 mmol), a solution of phenylboronic acid (111 mg, 0.912 mmol) in ethanol (0.7 ml), 2N aqueous sodium carbonate solution (2.5 ml) and tetrakis(triphenylphosphine)palladium(0) (84.2 mg, 0.0729 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=1:1) to give the desired product (180 mg, 90.9%) as an oil.

$^1$H-NMR (CDCl$_3$) δ; 1.43 (9H, s), 3.80-3.83 (2H, m), 4.07-4.10 (2H, m), 4.45-4.52 (2H, m), 7.18-7.44 (6H, m), 7.56 (2H, d, J=7.5 Hz).

(2) 8-phenyl-2,3,4,5-tetrahydro-1,4-benzoxazepine hydrochloride

A mixture of tert-butyl 8-phenyl-2,3-dihydro-1,4-benzoxazepine-4(5H)-carboxylate (180 mg, 0.553 mmol), ethyl acetate (1 ml) and 4N hydrogen chloride-ethyl acetate solution (5 ml) was stirred for 1 hr at room temperature, and the solvent was evaporated under reduced pressure. The residue was recrystallized from a mixed solvent of methanol and ether to give the desired product (131 mg, 90.3%) as a solid.

$^1$H-NMR (CD$_3$OD) δ; 3.60-3.63 (2H, m), 4.29-4.32 (2H, m), 4.43 (2H, s), 4.86 (2H, s), 7.36-7.48 (6H, m), 7.60-7.63 (2H, m).

Example 9

9-phenyl-2,3,4,5-tetrahydro-1,4-benzoxazepine hydrochloride (1) tert-butyl 9-phenyl-2,3-dihydro-1,4-benzoxazepine-4(5H)-carboxylate A mixture of tert-butyl 9-bromo-2,3-dihydro-1,4-benzoxazepine-4(5H)-carboxylate (400 mg, 1.21 mmol), a solution of phenylboronic acid (222 mg, 1.82 mmol) in ethanol (1.4 ml), 2N aqueous sodium carbonate solution (5 ml) and tetrakis(triphenylphosphine)palladium(0) (168 mg, 0.146 mmol) in toluene (10 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=1:1) to give the desired product (390 mg, 99.0%) as an oil.

$^1$H-NMR (CDCl$_3$) δ; 1.45 (9H, s), 3.78-3.81 (2H, m), 3.96-3.99 (2H, m), 4.46-4.52 (2H, m), 7.05-7.45 (8H, m).

(2) 9-phenyl-2,3,4,5-tetrahydro-1,4-benzoxazepine hydrochloride

A solution (5 ml) of tert-butyl 9-phenyl-2,3-dihydro-1,4-benzoxazepine-4(5H)-carboxylate (390 mg, 1.20 mmol) and ethyl acetate (1 ml) in 4N hydrogen chloride-ethyl acetate was stirred for 1 hr at room temperature, and the solvent was evaporated under reduced pressure. The residue was recrystallized from a mixed solvent of methanol and ether to give the desired product (232 mg, 73.9%) as a solid.

$^1$H-NMR (DMSO-d$_6$) δ; 3.43-3.46 (2H, m), 4.15-4.18 (2H, m), 4.34 (2H, s), 7.19-7.24 (1H, m), 7.33-7.48 (7H, m), 9.66 (2H, s).

Example 10

9-(2-chlorophenyl)-2,3,4,5-tetrahydro-1,4-benzoxazepine hydrochloride

(1) tert-butyl 9-(2-chlorophenyl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 2-chlorophenylboronic acid (143 mg, 0.912 mmol) in ethanol (0.7 ml), 2N aqueous sodium carbonate solution (2.5 ml) and tetrakis(triphenylphosphine)palladium(0) (84.0 mg, 0.0730 mmol) in toluene (5 ml) were stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (180 mg, 82.5%) as an oil.

$^1$H-NMR (CDCl$_3$) δ; 1.44 (9H, s), 3.75 (2H, br s), 3.96 (2H, br s), 4.47 (2H, br s), 7.05-7.14 (2H, m), 7.19-7.31 (4H, m), 7.44-7.47 (1H, m).

(2) 9-(2-chlorophenyl)-2,3,4,5-tetrahydro-1,4-benzoxazepine hydrochloride

A mixture of tert-Butyl 9-(2-chlorophenyl)-2,3-dihydro-1,4-benzoxazepine-4(5H)-carboxylate (180 mg, 0.500 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (110 mg, 74.3%) as a solid.

$^1$H-NMR (DMSO-d$_6$) δ; 3.40 (2H, br s), 4.13 (2H, br s), 4.36 (2H, br s), 7.21-7.27 (3H, m), 7.37-7.42 (2H, m), 7.50-7.57 (2H, m), 9.51 (2H, br s).

Example 11

9-(2-methylphenyl)-2,3,4,5-tetrahydro-1,4-benzoxazepine hydrochloride

(1) tert-butyl 9-(2-methylphenyl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 2-methylphenylboronic acid (124 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (180 mg, 87.8%) as an oil.

$^1$H-NMR (CDCl$_3$) δ; 1.45 (9H, s), 2.12 (3H, s), 3.86 (4H, br s), 4.46 (2H, br s), 7.00-7.25 (7H, m).

(2) 9-(2-methylphenyl)-2,3,4,5-tetrahydro-1,4-benzoxazepine hydrochloride

A mixture of tert-butyl 9-(2-methylphenyl)-2,3-dihydro-1,4-benzoxazepine-4(5H)-carboxylate (180 mg, 0.530 mmol), ethyl acetate (1 ml) and 4N hydrogen chloride-ethyl acetate solution (4 ml) were stirred for 1 hr at room temperature, and the solvent was evaporated under reduced pressure. The residue was recrystallized from a mixed solvent of methanol and ether to give the desired product (120 mg, 82.2%) as a solid.

$^1$H-NMR (DMSO-d$_6$) δ; 2.07 (3H, s), 3.39 (2H, br s), 4.05 (2H, br s), 4.35 (2H, s), 7.04-7.06 (1H, m), 7.18-7.28 (5H, m), 7.45-7.48 (1H, m), 9.55 (2H, br s).

Example 12

9-[2-(trifluoromethyl)phenyl]-2,3,4,5-tetrahydro-1,4-benzoxazepine hydrochloride

(1) tert-butyl 9-[2-(trifluoromethyl)phenyl]-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 2-trifluoromethylphenylboronic acid (173 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (200 mg, 84.0%) as an oil.

$^1$H-NMR (CDCl$_3$) δ; 1.43 (9H, s), 3.71-3.74 (2H, m), 3.83-3.85 (2H, m), 4.46-4.52 (2H, m), 7.00-7.56 (6H, m), 7.73 (1H, d, J=8.1 Hz).

(2) 9-[2-(trifluoromethyl)phenyl]-2,3,4,5-tetrahydro-1,4-benzoxazepine hydrochloride A mixture of tert-butyl 9-[2-(trifluoromethyl)phenyl]-2,3-dihydro-1,4-benzoxazepine-4(5H)-carboxylate (200 mg, 0.508 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (144 mg, 86.2%) as a solid.

$^1$H-NMR (DMSO-d$_6$) δ; 3.38-3.40 (2H, m), 4.02-4.04 (2H, m), 4.32 (1H, d, J=14.4 Hz), 4.38 (1H, d, J=14.4 Hz), 7.16-7.29 (3H, m), 7.51-7.73 (3H, m), 7.83 (1H, d, J=7.2 Hz), 9.55 (2H, br s).

Example 13

9-(2-methoxyphenyl)-2,3,4,5-tetrahydro-1,4-benzoxazepine hydrochloride

(1) tert-butyl 9-(2-methoxyphenyl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 2-methoxyphenylboronic acid (139 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (180 mg, 83.7%) as an oil.

$^1$H-NMR (CDCl$_3$) δ; 1.46 (9H, s), 3.76 (5H, s), 3.98 (2H, br s), 4.44-4.50 (2H, m), 6.94-7.35 (7H, m).

(2) 9-(2-methoxyphenyl)-2,3,4,5-tetrahydro-1,4-benzoxazepine hydrochloride

A mixture of tert-butyl 9-(2-methoxyphenyl)-2,3-dihydro-1,4-benzoxazepine-4(5H)-carboxylate (180 mg, 0.506 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (134 mg, 90.5%) as a solid.

$^1$H-NMR (DMSO-d$_6$) δ; 3.39 (2H, br s), 3.73 (3H, s), 4.12 (2H, br s), 4.30 (2H, s), 6.96-7.46 (7H, m), 9.44 (2H, br s).

Example 14

9-(2-fluorophenyl)-2,3,4,5-tetrahydro-1,4-benzoxazepine hydrochloride

(1) tert-butyl 9-(2-fluorophenyl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 2-fluorophenylboronic acid (128 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (150 mg, 72.1%) as an oil.

$^1$H-NMR (CDCl$_3$) δ; 1.45 (9H, s), 3.76-3.79 (2H, m), 3.99-4.02 (2H, m), 4.46-4.52 (2H, m), 7.06-7.36 (7H, m).

(2) 9-(2-fluorophenyl)-2,3,4,5-tetrahydro-1,4-benzoxazepine hydrochloride

A mixture of tert-butyl 9-(2-fluorophenyl)-2,3-dihydro-1,4-benzoxazepine-4(5H)-carboxylate (150 mg, 0.437 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (103 mg, 84.4%) as a solid.

$^1$H-NMR (DMSO-d$_6$) δ; 3.43 (2H, br s), 4.16 (2H, br s), 4.35 (2H, s), 7.21-7.53 (7H, m), 9.49 (2H, br s).

Example 15

9-(3-furyl)-2,3,4,5-tetrahydro-1,4-benzoxazepine hydrochloride

(1) tert-butyl 9-(3-furyl)-2,3-dihydro-1,4-benzoxazepine-4(5H)-carboxylate

A mixture of tert-butyl 9-bromo-2,3-dihydro-1,4-benzoxazepine-4(5H)-carboxylate (200 mg, 0.605 mmol), a solution of 3-furan boronic acid (102 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (190 mg, 99.5%) as an oil.

$^1$H-NMR (CDCl$_3$) δ; 1.42 (9H, s), 3.83-3.86 (2H, m), 4.03-4.06 (2H, m), 4.45-4.50 (2H, m), 6.74-6.75 (1H, m), 7.02-7.11 (2H, m), 7.39-7.47 (2H, m), 7.94-7.95 (1H, m).

(2) 9-(3-furyl)-2,3,4,5-tetrahydro-1,4-benzoxazepine hydrochloride

A mixture of tert-butyl 9-(3-furyl)-2,3-dihydro-1,4-benzoxazepine-4(5H)-carboxylate (190 mg, 0.602 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (131 mg, 86.2%) as a solid.

$^1$H-NMR (DMSO-d$_6$) δ; 3.51 (2H, br s), 4.26 (2H, br s), 4.33 (2H, s), 7.01-7.03 (1H, m), 7.14-7.19 (1H, m), 7.34-7.37 (1H, m), 7.67-7.77 (2H, m), 8.18-8.19 (1H, m), 9.49 (2H, br s).

Example 16

9-(3-thienyl)-2,3,4,5-tetrahydro-1,4-benzoxazepine hydrochloride

(1) tert-butyl 9-(3-thienyl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 3-thiopheneboronic acid (117 mg, 0.912 mmol) in methanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (140 mg, 69.7%) as an oil.

$^1$H-NMR (CDCl$_3$) δ; 1.43 (9H, s), 3.81-3.84 (2H, m), 4.01-4.04 (2H, m), 4.45-4.51 (2H, m), 7.03-7.54 (6H, m).

(2) 9-(3-thienyl)-2,3,4,5-tetrahydro-1,4-benzoxazepine hydrochloride

A mixture of tert-butyl 9-(3-thienyl)-2,3-dihydro-1,4-benzoxazepine-4(5H)-carboxylate (140 mg, 0.422 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (105 mg, 92.9%) as a solid.

¹H-NMR (DMSO-d₆) δ; 3.47-3.50 (2H, m), 4.21-4.22 (2H, m), 4.34 (2H, s), 7.16-7.21 (1H, m), 7.39-7.46 (2H, m), 7.60-7.65 (2H, m), 7.80-7.82 (1H, m), 9.53 (2H, br s).

Example 17

9-[3-(trifluoromethyl)phenyl]-2,3,4,5-tetrahydro-1,4-benzoxazepine hydrochloride (1) tert-butyl 9-[3-(trifluoromethyl)phenyl]-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 3-trifluoromethylphenylboronic acid (173 mg, 0.912 mmol) in ethanol (0.7 ml), 2N aqueous sodium carbonate solution (2.5 ml), and tetrakis(triphenylphosphine)palladium (0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (210 mg, 88.2%) as an oil.
¹H-NMR (CDCl₃) δ; 1.45 (9H, s), 3.79-3.82 (2H, m), 3.96-3.99 (2H, m), 4.47-4.53 (2H, m), 7.11-7.71 (7H, m).

(2) 9-[3-(trifluoromethyl)phenyl]-2,3,4,5-tetrahydro-1,4-benzoxazepine hydrochloride A mixture of tert-butyl 9-[3-(trifluoromethyl)phenyl]-2,3-dihydro-1,4-benzoxazepine-4(5H)-carboxylate (210 mg, 0.534 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (121 mg, 68.8%) as a solid.
¹H-NMR (DMSO-d₆) δ; 3.46 (2H, br s), 4.18 (2H, br s), 4.37 (2H, s), 7.23-7.28 (1H, m), 7.47-7.55 (2H, m), 7.69-7.76 (4H, m), 9.49 (2H, br s).

Example 18

9-[4-(trifluoromethyl)phenyl]-2,3,4,5-tetrahydro-1,4-benzoxazepine hydrochloride (1) tert-butyl 9-[4-(trifluoromethyl)phenyl]-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 4-trifluoromethylphenylboronic acid (173 mg, 0.912 mmol) in ethanol (0.7 ml), 2N aqueous sodium carbonate solution (2.5 ml), and tetrakis(triphenylphosphine)palladium (0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (210 mg, 83.7%) as an oil.
¹H-NMR (CDCl₃) δ; 1.45 (9H, s), 3.79-3.82 (2H, m), 3.95-3.98 (2H, m), 4.47-4.53 (2H, m), 7.09-7.14 (1H, m), 7.24-7.35 (2H, m), 7.55 (2H, d, J=8.4 Hz), 7.65 (2H, d, J=8.4 Hz).

(2) 9-[4-(trifluoromethyl)phenyl]-2,3,4,5-tetrahydro-1,4-benzoxazepine hydrochloride A mixture of tert-butyl 9-[4-(trifluoromethyl)phenyl]-2,3-dihydro-1,4-benzoxazepine-4(5H)-carboxylate (210 mg, 0.534 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (143 mg, 81.3%) as a solid.
¹H-NMR (DMSO-d₆) δ; 3.47 (2H, br s), 4.19 (2H, br s), 4.37 (2H, br s), 7.24-7.29 (1H, m), 7.45-7.55 (2H, m), 7.66 (2H, d, J=7.8 Hz), 7.81 (2H, d, J=7.8 Hz), 9.65 (2H, br s).

Example 19

9-(2-furyl)-2,3,4,5-tetrahydro-1,4-benzoxazepine hydrochloride (1) tert-butyl 9-(2-furyl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 2-furanboronic acid (102 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (150 mg, 78.5%) as an oil.
¹H-NMR (CDCl₃) δ; 1.41 (9H, s), 3.82-3.87 (2H, m), 4.07-4.10 (2H, m), 4.42-4.45 (2H, m), 6.48-6.50 (1H, m), 6.90-6.91 (1H, m), 7.05-7.10 (2H, m), 7.45-7.47 (1H, m), 7.73-7.77 (1H, m).

(2) 9-(2-furyl)-2,3,4,5-tetrahydro-1,4-benzoxazepine hydrochloride

A mixture of tert-butyl 9-(2-furyl)-2,3-dihydro-1,4-benzoxazepine-4(5H)-carboxylate (150 mg, 0.476 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (100 mg, 83.3%) as a solid.
¹H-NMR (DMSO-d₆) δ; 3.53 (2H, br s), 4.28-4.31 (2H, br s), 4.36 (2H, br s), 6.62-6.64 (1H, m), 6.98-6.99 (1H, m), 7.19-7.25 (1H, m), 7.38-7.40 (1H, m), 7.77-7.80 (2H, m), 9.56 (2H, br s).

Example 20

9-[2-(methylthio)phenyl]-2,3,4,5-tetrahydro-1,4-benzoxazepine hydrochloride (1) tert-butyl 9-[2-(methylthio)phenyl]-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 2-methylthiophenylboronic acid (153 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (170 mg, 80.0%) as an oil.

$^1$H-NMR (CDCl$_3$) δ; 1.45 (9H, s), 2.36 (3H, s), 3.74 (2H, br s), 3.86 (1H, br s), 4.03 (1H, br s), 4.47-4.53 (2H, m), 7.04-7.36 (7H, m).

(2) 9-[2-(methylthio)phenyl]-2,3,4,5-tetrahydro-1,4-benzoxazepine hydrochloride A mixture of tert-butyl 9-[2-(methylthio)phenyl]-2,3-dihydro-1,4-benzoxazepine-4(5H)-carboxylate (170 mg, 0.458 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (133 mg, 94.3%) as a solid.

$^1$H-NMR (DMSO-d$_6$) δ; 2.37 (3H, s), 3.38 (2H, br s), 4.11 (2H, br s), 4.32 (2H, br s), 7.02-7.50 (7H, m), 9.52 (2H, br s).

Example 21

9-(2-thienyl)-2,3,4,5-tetrahydro-1,4-benzoxazepine hydrochloride

(1) tert-butyl 9-(2-thienyl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 2-thiopheneboronic acid (117 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (160 mg, 79.6%) as an oil.

$^1$H-NMR (CDCl$_3$) δ; 1.42 (9H, s), 3.86-3.89 (2H, m), 4.08-4.10 (2H, m), 4.45-4.50 (2H, m), 7.01-7.13 (3H, m), 7.33-7.35 (1H, m), 7.45-7.47 (1H, m), 7.61-7.64 (1H, m).

(2) 9-(2-thienyl)-2,3,4,5-tetrahydro-1,4-benzoxazepine hydrochloride

A mixture of tert-butyl 9-(2-thienyl)-2,3-dihydro-1,4-benzoxazepine-4(5H)-carboxylate (160 mg, 0.483 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (111 mg, 86.0%) as a solid.

$^1$H-NMR (DMSO-d$_6$) δ; 3.53 (2H, br s), 4.25 (2H, br s), 4.35 (2H, br s), 7.14-7.23 (2H, m), 7.38-7.40 (1H, m), 7.62-7.69 (2H, m), 7.87-7.90 (1H, m), 9.54 (2H, br s).

Example 22

1-[2-(2,3,4,5-tetrahydro-1,4-benzoxazepine-9-yl) phenyl]ethanone hydrochloride

(1) tert-butyl 9-(2-acetylphenyl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 2-acetylphenylboronic acid (150 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (190 mg, 85.6%) as an oil.

$^1$H-NMR (CDCl$_3$) δ; 1.43 (9H, s), 2.17 (3H, s), 3.74 (2H, br s), 3.84 (2H, br s), 4.46-4.53 (2H, m), 7.05-7.66 (7H, m).

(2) 1-[2-(2,3,4,5-tetrahydro-1,4-benzoxazepine-9-yl) phenyl]ethanone hydrochloride A mixture of tert-butyl 9-(2-acetylphenyl)-2,3-dihydro-1,4-benzoxazepine-4(5H)-carboxylate (190 mg, 0.517 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (132 mg, 84.1%) as a solid.

$^1$H-NMR (DMSO-d$_6$) δ; 2.34 (3H, s), 3.37 (2H, br s), 4.01 (2H, br s), 4.32 (2H, br s), 7.15-7.26 (3H, m), 7.43-7.61 (3H, m), 7.77-7.80 (1H, m), 9.53 (2H, br s).

Example 23

9-(pyridin-3-yl)-2,3,4,5-tetrahydro-1,4-benzoxazepine dihydrochloride

(1) tert-butyl 9-(pyridin-3-yl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 3-pyridineboronic acid (112 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=1:1) to give the desired product (190 mg, 96.4%) as an oil.

$^1$H-NMR (CDCl$_3$) δ; 1.44 (9H, s), 3.80 (2H, br s), 3.96-3.99 (2H, m), 4.48-4.53 (2H, m), 7.10-7.35 (3H, m), 7.52-7.67 (1H, m), 7.76-7.79 (1H, m), 8.56 (1H, br s), 8.71 (1H, br s).

(2) 9-(pyridin-3-yl)-2,3,4,5-tetrahydro-1,4-benzoxazepine dihydrochloride

A mixture of tert-butyl 9-(pyridin-3-yl)-2,3-dihydro-1,4-benzoxazepine-4(5H)-carboxylate (190 mg, 0.582 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (109 mg, 62.6%) as a solid.

$^1$H-NMR (CD$_3$OD) δ; 3.63-3.65 (2H, m), 4.26-4.29 (2H, m), 4.52 (2H, s), 4.86 (3H, br s), 7.37-7.42 (1H, m), 7.61-7.69 (2H, m), 8.15-8.20 (1H, m), 8.78-8.87 (2H, m), 9.05 (1H, s).

Example 24

9-(pyridin-4-yl)-2,3,4,5-tetrahydro-1,4-benzoxazepine dihydrochloride

(1) tert-butyl 9-(pyridin-4-yl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 4-pyridineboronic acid (112 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=1:1) to give the desired product (109 mg, 55.3%) as an oil.

$^1$H-NMR (CDCl$_3$) δ; 1.44 (9H, s), 3.80-3.82 (2H, m), 3.96-3.99. (2H, m), 4.48-4.53 (2H, m), 7.10-7.29 (3H, m), 7.38 (2H, d, J=5.4 Hz), 8.62 (2H, d, J=5.4 Hz).

(2) 9-(pyridin-4-yl)-2,3,4,5-tetrahydro-1,4-benzoxazepine dihydrochloride

A mixture of tert-butyl 9-(pyridin-4-yl)-2,3-dihydro-1,4-benzoxazepine-4(5H)-carboxylate (109 mg, 0.334 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from methanol to give the desired product (19.0 mg, 19.0%) as a solid.

$^1$H-NMR (CD$_3$OD) δ; 3.65-3.68 (2H, m), 4.29-4.33 (2H, m), 4.53 (2H, s), 4.88 (3H, s), 7.39-7.44 (1H, m), 7.66-7.75 (2H, m), 8.26 (2H, d, J=6.9 Hz), 8.89 (2H, d, J=6.9 Hz).

Example 25

9-[2-(trifluoromethoxy)phenyl]-2,3,4,5-tetrahydro-1,4-benzoxazepine hydrochloride

(1) tert-butyl 9-[2-(trifluoromethoxy)phenyl]-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of 2-trifluoromethoxyphenylboronic acid (188 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (190 mg, 76.6%) as an oil.

$^1$H-NMR (CDCl$_3$) δ; 1.43 (9H, s), 3.73-3.76 (2H, m), 3.95 (2H, br s), 4.45-4.51 (2H, m), 7.05-7.41 (7H, m).

(2) 9-[2-(trifluoromethoxy)phenyl]-2,3,4,5-tetrahydro-1,4-benzoxazepine hydrochloride A mixture of tert-butyl 9-[2-(trifluoromethoxy)phenyl]-2,3-dihydro-1,4-benzoxazepine-4(5H)-carboxylate (190 mg, 0.464 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from methanol to give the desired product (158 mg, 98.8%) as a solid.

$^1$H-NMR (DMSO-d$_6$) δ; 3.42 (2H, br s), 4.12 (2H, br s), 4.35 (2H, s), 7.20-7.57 (7H, m), 9.44 (2H, br s).

Example 26

9-(cyclopenta-1-en-1-yl)-2,3,4,5-tetrahydro-1,4-benzoxazepine hydrochloride

(1) tert-butyl 9-(1-hydroxycyclopentyl)-2,3-dihydro-1,4-benzoxazepine-4(5H)-carboxylate To a solution of tert-butyl 9-bromo-2,3-dihydro-1,4-benzoxazepine-4(5H)-carboxylate (200 mg, 0.605 mmol) in tetrahydrofuran (4 ml) was added dropwise 1.6 M solution of n-butyllithium in hexane (0.396 ml, 0.634 mmol) at −78° C., and the mixture was stirred at −78° C. for 10 min. A solution of cyclopentanone (0.0696 ml, 0.787 mmol) in tetrahydrofuran (2 ml) was added dropwise, and the mixture was stirred at 78° C. for 2 hr. The reaction mixture was poured into saturated aqueous ammonium chloride solution, and the mixture was extracted with ethyl acetate. The extract was dried over anhydrous magnesium sulfate, and the solvent was evaporated under reduced pressure. The residue was purified by silica gel column chromatography (hexane:ethyl acetate=1:1) to give the desired product (30.0 mg, 14.9%) as an oil.

$^1$H-NMR (CDCl$_3$) δ; 1.42 (9H, s), 1.57-2.04 (8H, m), 3.27 (0.3H, s), 3.40 (0.7H, s), 3.82-3.85 (2H, m), 4.05-4.09 (2H, m), 4.41-4.46 (2H, m), 6.87-7.30 (3H, m).

(2) 9-(cyclopenta-1-en-1-yl)-2,3,4,5-tetrahydro-1,4-benzoxazepine hydrochloride A mixture of tert-butyl 9-(1-hydroxycyclopentyl)-2,3-dihydro-1,4-benzoxazepine-4(5H)-carboxylate (30.0 mg, 0.0899 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (18.0 mg, 79.3%) as a solid.

$^1$H-NMR (CD$_3$OD) δ; 1.96-2.03 (2H, m), 2.51-2.55 (2H, m), 2.72-2.78 (2H, m), 3.31-3.63 (2H, m), 4.20 (2H, br s), 4.37 (2H, s), 4.88 (2H, s), 6.33 (1H, br s), 7.10-7.15 (1H, m), 7.25-7.27 (1H, m), 7.38-7.41 (1H, m).

Example 27

8-(4-chlorophenyl)-2,3,4,5-tetrahydro-1,4-benzoxazepine hydrochloride

(1) tert-butyl 8-(4-chlorophenyl)-2,3-dihydro-1,4-benzoxazepine-4(5H)-carboxylate A mixture of tert-butyl 8-bromo-2,3-dihydro-1,4-benzoxazepine-4(5H)-carboxylate (200 mg, 0.605 mmol), a solution of 4-chlorophenylboronic acid (143 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (210 mg, 95.9%) as an oil.
$^1$H-NMR (CDCl$_3$) δ; 1.43 (9H, s), 3.81-3.84 (2H, m), 4.07-4.10 (2H, m), 4.45-4.51 (2H, m), 7.22-7.25 (3H, m), 7.38 (2H, d, J=8.7 Hz), 7.49 (2H, d, J=8.7 Hz).

(2) 8-(4-chlorophenyl)-2,3,4,5-tetrahydro-1,4-benzoxazepine hydrochloride

A mixture of tert-butyl 8-(4-chlorophenyl)-2,3-dihydro-1,4-benzoxazepine-4(5H)-carboxylate (210 mg, 0.584 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (145 mg, 83.8%) as a solid.
$^1$H-NMR (DMSO-d$_6$) δ; 3.48 (2H, br s), 4.26 (2H, br s), 4.35 (2H, s), 7.39 (1H, s), 7.45 (1H, d, J=7.8 Hz), 7.50-7.54 (3H, m), 7.72 (2H, d, J=8.7 Hz), 9.62 (2H, br s).

Example 28

7-phenyl-2,3,4,5-tetrahydro-1,4-benzoxazepine hydrochloride

(1) N-benzyl-5-bromo-2-fluoro-N-(2-hydroxyethyl)benzamide

A solution of 5-bromo-2-fluorobenzoic acid (3.00 g, 13.7 mmol) and N,N-dimethylformamide (0.100 ml) in thionyl chloride (20 ml) was stirred at 85° C. for 2 hr, and the solvent was evaporated under reduced pressure. The residue was added under ice-cooling to a solution of N-benzylethanolamine (2.07 g, 13.7 mmol) and triethylamine (2.87 ml, 20.6 mmol) in tetrahydrofuran (30 ml), and the mixture was stirred under ice-cooling for 1 hr and at room temperature for 12 hr. The reaction mixture was poured into water, and the mixture was extracted with ethyl acetate. The extract was washed with water and dried over anhydrous magnesium sulfate. The solvent was evaporated under reduced pressure to give the desired product (4.75 g, 98.3%) as an oil.
$^1$H-NMR (CDCl$_3$) δ; 2.04 (1H, br s), 3.30 (0.7H, t, J=5.4 Hz), 3.59-3.68 (2H, m), 3.79 (1.3H, t, J=5.4 Hz), 4.51 (1.3H, s), 4.87 (0.7H, s), 6.97-7.39 (1H, m), 7.13-7.15 (1H, m), 7.25-7.39 (4H, m), 7.45-7.55 (2H, m).

(2) 4-benzyl-7-bromo-3,4-dihydro-1,4-benzoxazepine-5 (2H)-one

To a solution of N-benzyl-5-bromo-2-fluoro-N-(2-hydroxyethyl)benzamide (4.70 g, 13.3 mmol) in N,N-dimethylformamide (100 ml) was added under ice-cooling sodium hydride (60%, 691 mg, 17.3 mmol), and the mixture was stirred under ice-cooling for 1 hr, and poured into ice water. The mixture was extracted with ethyl acetate and the extract was washed with water, and dried over anhydrous magnesium sulfate. The solvent was evaporated under reduced pressure to give the desired product (4.20 g, 96.3%) as an oil.
$^1$H-NMR (CDCl$_3$) δ; 3.45 (2H, t, J=5.1 Hz), 4.16 (2H, t, J=5.1 Hz), 4.81 (2H, s), 6.87 (1H, d, J=9.0 Hz), 7.25-7.38 (5H, m), 7.48 (1H, dd, J=2.7, 9.0 Hz), 8.01 (1H, d, J=2.7 Hz).

(3) 4-benzyl-7-bromo-2,3,4,5-tetrahydro-1,4-benzoxazepine

To a solution of 4-benzyl-7-bromo-3,4-dihydro-1,4-benzoxazepine-5 (2H)-one (4.20 g, 12.8 mmol) in tetrahydrofuran (400 ml) was added 1M borane-tetrahydrofuran solution (52.8 ml, 52.8 mmol) and the mixture was stirred at 80° C. for 2 hr. Under ice-cooling, methanol (240 ml) and sodium hydroxide (20.8 g, 519 mmol) were added, and the mixture was stirred at room temperature for 2 hr. The solvent was evaporated under reduced pressure. The residue was poured into water and the mixture was extracted with ethyl acetate. The extract was dried over anhydrous magnesium sulfate, and the solvent was evaporated under reduced pressure. The residue was purified by silica gel column chromatography (hexane:ethyl acetate=1:1) to give the desired product (2.42 g, 59.5%) as an oil.
$^1$H-NMR (CDCl$_3$) δ; 3.05-3.08 (2H, m), 3.63 (2H, s), 3.75 (2H, s), 4.03-4.07 (2H, m), 6.86-6.90 (1H, m), 7.11-7.12 (1H, m), 7.24-7.35 (6H, m).

(4) tert-butyl 7-bromo-2,3-dihydro-1,4-benzoxazepine-4(5H)-carboxylate

A solution of 4-benzyl-7-bromo-2,3,4,5-tetrahydro-1,4-benzoxazepine (2.30 g, 7.22 mmol) and 1-chloroethyl chloroformate (1.24 ml, 11.5 mmol) in 1,2-dichloroethane (46 ml) was stirred at 90° C. for 1 hr, and the solvent was evaporated under reduced pressure. Methanol (46 ml) was added to the residue, and the mixture was stirred at 80° C. for 1 hr, and the solvent was evaporated under reduced pressure. The residue was washed with ether, 1N aqueous sodium hydroxide solution (16 ml), dioxane (16 ml) and di-tert-butyl dicarbonate (2.64 ml, 11.8 mmol) were added to the residue under ice-cooling, and the mixture was stirred under ice-cooling for 1 hr and at room temperature for 12 hr. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (2.01 g, 84.8%) as a solid.
$^1$H-NMR (CDCl$_3$) δ; 1.42 (9H, s), 3.76-3.79 (2H, m), 4.00-4.03 (2H, m), 4.35 (2H, br s), 6.89 (1H, br s), 7.28-7.28 (2H, m).

(5) tert-butyl 7-phenyl-2,3-dihydro-1,4-benzoxazepine-4(5H)-carboxylate

A mixture of tert-butyl 7-bromo-2,3-dihydro-1,4-benzoxazepine-4(5H)-carboxylate (200 mg, 0.605 mmol), a solution of phenylboronic acid (111 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (160 mg, 77.3%) as an oil.

$^1$H-NMR (CDCl$_3$) δ; 1.43 (9H, s), 3.81-3.84 (2H, m), 4.05-4.09 (2H, m), 4.48-4.55 (2H, m), 7.07-7.10 (2H, m), 7.32-7.34 (1H, m), 7.40-7.43 (3H, m), 7.53-7.55 (2H, m).

(6) 7-phenyl-2,3,4,5-tetrahydro-1,4-benzoxazepine hydrochloride

A mixture of tert-butyl 7-phenyl-2,3-dihydro-1,4-benzoxazepine-4(5H)-carboxylate (160 mg, 0.471 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (112 mg, 91.1%) as a solid.

$^1$H-NMR (DMSO-d$_6$) δ; 3.49 (2H, br s), 4.24 (2H, br s), 4.39 (2H, s), 7.16 (1H, d, J=8.7 Hz), 7.33-7.38 (1H, m), 7.44-7.49 (2H, m), 7.63-7.65 (3H, m), 7.79 (1H, d, J=2.4 Hz), 9.66 (2H, br s).

Example 29

6-phenyl-2,3,4,5-tetrahydro-1,4-benzoxazepine hydrochloride (1) N-benzyl-6-bromo-2-fluoro-N-(2-hydroxyethyl) benzamide A solution of 6-bromo-2-fluorobenzoic acid (10.0 g, 45.7 mmol) and N,N-dimethylformamide (0.100 ml) in thionyl-chloride (40 ml) was stirred at 85° C. for 12 hr, and the solvent was evaporated under reduced pressure. The residue was added to a solution of N-benzylethanolamine (6.91 g, 45.7 mmol) and triethylamine (9.55 ml, 68.6 mmol) in tetrahydrofuran (100 ml) under ice-cooling, and the mixture was stirred for 1 hr under ice-cooling and at room temperature for 1 hr. The reaction mixture was poured into water, and the mixture was extracted with ethyl acetate. The extract was washed with water and dried over anhydrous magnesium sulfate. The solvent was evaporated under reduced pressure to give the desired product (15.7 g, 97.5%) as an oil.

$^1$H-NMR (CDCl$_3$) δ; 3.25-3.29 (1H, m), 3.40-3.50 (1H, m), 3.56-3.67 (1H, m), 3.81-3.88 (2H, m), 4.43 (0.5H, d, J=15.6 Hz), 4.51 (0.5H, d, J=15.6 Hz), 4.82 (0.5H, d, J=15.0 Hz), 4.98 (0.5H, d, J=15.0 Hz), 7.06-7.13 (1H, m), 7.21-7.45 (7H, m).

(2) 4-benzyl-6-bromo-3,4-dihydro-1,4-benzoxazepine-5 (2H)-one

To a solution of N-benzyl-6-bromo-2-fluoro-N-(2-hydroxyethyl)benzamide (15.5 g, 44.0 mmol) in N,N-dimethylformamide (200 ml) was added sodium hydride (60%, 2.29 g, 57.2 mmol) under ice-cooling, and the mixture was stirred for 1 hr under ice-cooling. The reaction mixture was poured into ice water, and the mixture was extracted with ethyl acetate. The extract was washed with water, and dried over anhydrous magnesium sulfate. The solvent was evaporated under reduced pressure. The residue was purified by silica gel column chromatography (hexane:ethyl acetate=2:1) to give the desired product (4.94 g, 33.8%) as an oil.

$^1$H-NMR (CDCl$_3$) δ; 3.36-3.40 (1H, m), 3.98-4.02 (1H, m), 4.29-4.31 (1H, m), 4.51-4.56 (1H, m), 4.86 (1H, s), 5.02-5.17 (1H, m), 6.48-6.56 (1H, m), 6.77-7.48 (7H, m).

(3) 4-benzyl-6-bromo-2,3,4,5-tetrahydro-1,4-benzoxazepine

To a solution of 4-benzyl-6-bromo-3,4-dihydro-1,4-benzoxazepine-5 (2H)-one (4.94 g, 14.9 mmol) in tetrahydrofuran (60 ml) was added 1M borane-tetrahydrofuran solution (61.5 ml, 61.5 mmol), and the mixture was stirred at 80° C. for 2 hr. Under ice-cooling, methanol (140 ml) and sodium hydroxide (13.2 g, 331 mmol) were added, and the mixture was stirred at room temperature for 1 hr. The solvent was evaporated under reduced pressure. The residue was poured into water and the mixture was extracted with ethyl acetate. The extract was dried over anhydrous magnesium sulfate, and the solvent was evaporated under reduced pressure. The residue was purified by silica gel column chromatography (hexane:ethyl acetate=10:1) to give the desired product (450 mg, 9.5%) as an oil.

$^1$H-NMR (CDCl$_3$) δ; 2.99-3.02 (2H, m), 3.70 (2H, s), 4.08-4.10 (2H, m), 4.15 (2H, s), 6.94-7.04 (2H, m), 7.22-7.35 (6H, m).

(4) tert-butyl 6-bromo-2,3-dihydro-1,4-benzoxazepine-4(5H)-carboxylate

A solution of 4-benzyl-6-bromo-2,3,4,5-tetrahydro-1,4-benzoxazepine (450 mg, 1.41 mmol) and 1-chloroethyl chloroformate (0.242 ml, 2.25 mmol) in 1,2-dichloroethane (5 ml) was stirred at 90° C. for 1 hr, and the solvent was evaporated under reduced pressure. Methanol (9 ml) was added to the residue, and the mixture was stirred at 80° C. for 1 hr. The solvent was evaporated under reduced pressure. The residue was washed with ether, and 1N aqueous sodium hydroxide solution (3 ml), dioxane (3 ml) and di-tert-butyl dicarbonate (0.513 ml, 2.30 mmol) were added to the residue under ice-cooling. The mixture was stirred under ice-cooling for 1 hr and at room temperature for 12 hr. The reaction mixture was poured into water, and the mixture was extracted with ethyl acetate. The extract was washed with water and dried over anhydrous magnesium sulfate. The solvent was evaporated under reduced pressure and the residue was purified by silica gel column chromatography (hexane:ethyl acetate=2:1) to give the desired product (450 mg, 97.4%) as a solid.

$^1$H-NMR (CDCl$_3$) δ; 1.45 (9H, s), 3.82 (2H, br s), 4.10-4.13 (2H, m), 4.76 (2H, s), 6.94-7.05 (2H, m), 7.25-7.29 (1H, m).

(5) tert-butyl 6-phenyl-2,3-dihydro-1,4-benzoxazepine-4(5H)-carboxylate

A mixture of tert-butyl 6-bromo-2,3-dihydro-1,4-benzoxazepine-4(5H)-carboxylate (150 mg, 0.457 mmol), a solution of phenylboronic acid (83.4 mg, 0.684 mmol) in ethanol (0.525 ml), 2N aqueous sodium carbonate solution (2 ml), and tetrakis(triphenylphosphine)palladium(0) (63.2 mg, 0.0547 mmol) in toluene (4 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (90.0 mg, 58.0%) as an oil.

¹H-NMR (CDCl₃) δ; 1.13 (9H, s), 3.81 (2H, br s), 4.16-4.19 (2H, m), 4.63 (2H, br s), 6.79-7.02 (2H, m), 7.18-7.43 (6H, m).

(6) 6-phenyl-2,3,4,5-tetrahydro-1,4-benzoxazepine hydrochloride

A mixture of tert-butyl 6-phenyl-2,3-dihydro-1,4-benzoxazepine-4(5H)-carboxylate (90.0 mg, 0.265 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (68.5 mg, 98.7%) as a solid.
¹H-NMR (DMSO-d₆) δ; 3.45-3.49 (2H, m), 4.12 (2H, s), 4.28-4.31 (2H, m), 7.07-7.15 (2H, m), 7.38-7.50 (6H, m), 9.64 (2H, br s).

Example 30

6-(morpholin-4-yl)-2,3,4,5-tetrahydro-1,4-benzoxazepine dihydrochloride (1) tert-butyl 6-(morpholin-4-yl)-2,3-dihydro-1,4-benzoxazepine-4(5H)-carboxylate A solution of tert-butyl 6-bromo-2,3-dihydro-1,4-benzoxazepine-4(5H)-carboxylate (150 mg, 0.457 mmol), morpholine (0.120 ml, 1.37 mmol), X-phos (13.0 mg, 0.0274 mmol), tris(dibenzylideneacetone)dipalladium(0) (82.4 mg, 0.00900 mmol), sodium tert-butoxide (65.8 mg, 0.684 mmol) and dioxane (3 ml) was stirred under an argon atmosphere for 2 hr at 80° C. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=2:1) to give the desired product (120 mg, 78.4%) as an oil.
¹H-NMR (CDCl₃) δ; 1.38 (9H, s), 2.88 (4H, br s), 3.76-3.82 (2H, m), 3.87 (4H, br s), 4.19 (2H, br s), 4.74 (2H, br s), 6.72-6.79 (2H, m), 7.10-7.15 (1H, m).

(2) 6-(morpholin-4-yl)-2,3,4,5-tetrahydro-1,4-benzoxazepine dihydrochloride

A mixture of tert-butyl 6-(morpholin-4-yl)-2,3-dihydro-1,4-benzoxazepine-4(5H)-carboxylate (120 mg, 0.359 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (77.4 mg, 92.0%) as a solid.
¹H-NMR (DMSO-d₆) δ; 2.84-2.87 (4H, m), 3.45 (2H, br s), 3.73-3.76 (4H, m), 4.25 (2H, br s), 4.43 (2H, br s), 5.02 (1H, br s), 6.81 (1H, d, J=8.1 Hz), 6.96 (1H, d, J=7.5 Hz), 7.26-7.32 (1H, m), 9.66 (2H, br s).

Example 31

9-(piperidin-1-yl)-2,3,4,5-tetrahydro-1,4-benzoxazepine dihydrochloride (1) tert-butyl 9-(piperidin-1-yl)-2,3-dihydro-1,4-benzoxazepine-4(5H)-carboxylate A solution of tert-butyl 9-bromo-2,3-dihydro-1,4-benzoxazepine-4(5H)-carboxylate (200 mg, 0.609 mmol), piperidine (0.522 ml, 6.13 mmol), X-phos (17.4 mg, 0.0365 mmol), tris(dibenzylideneacetone)dipalladium(0) (11.0 mg, 0.0120 mmol), sodium tert-butoxide (87.5 mg, 0.912 mmol) and dioxane (4 ml) was stirred at 80° C. for 3 hr under an argon atmosphere. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=2:1) to give the desired product (130 mg, 64.3%) as an oil.
¹H-NMR (CDCl₃) δ; 1.42 (9H, s), 1.52-1.59 (2H, m), 1.68-1.76 (4H, m), 2.94-2.98 (4H, m), 3.78-3.81 (2H, m), 4.03-4.05 (2H, m), 4.37-4.44 (2H, m), 6.79-7.03 (3H, m).

(2) 9-(piperidin-1-yl)-2,3,4,5-tetrahydro-1,4-benzoxazepine dihydrochloride

A solution of tert-butyl 9-(piperidin-1-yl)-2,3-dihydro-1,4-benzoxazepine-4(5H)-carboxylate (130 mg, 0.391 mmol) and 4N hydrogen chloride-ethyl acetate (4 ml) in ethyl acetate (1 ml) was stirred for 1 hr at room temperature, and the solvent was evaporated under reduced pressure. The residue was recrystallized from a mixed solvent of methanol and ether to give the desired product (93.6 mg, 78.7%) as a solid.
¹H-NMR (CD₃OD) δ; 1.82 (2H, br s), 2.11 (4H, br s), 3.65-3.74 (6H, m), 4.53-4.55 (4H, m), 4.85 (3H, s), 7.36-7.41 (1H, m), 7.60 (1H, d, J=8.1 Hz), 7.82 (1H, d, J=8.4 Hz).

Example 32

8-(cis-2,6-dimethylmorpholin-4-yl)-2,3,4,5-tetrahydro-1,4-benzoxazepine dihydrochloride (1) tert-butyl 8-(cis-2,6-dimethylmorpholin-4-yl)-2,3-dihydro-1,4-benzoxazepine-4(5H)-carboxylate A solution of tert-butyl 8-bromo-2,3-dihydro-1,4-benzoxazepine-4(5H)-carboxylate (300 mg, 0.609 mmol), cis-2,6-dimethylmorpholine (0.370 ml, 3.00 mmol), X-phos (26.1 mg, 0.0548 mmol), tris(dibenzylideneacetone)dipalladium(0) (16.6 mg, 0.0181 mmol), sodium tert-butoxide (131 mg, 1.37 mmol) and dioxane (6 ml) was stirred under an argon atmosphere for 2 hr at 80° C. The reaction mixture was poured into water, and the mixture was extracted with ethyl acetate. The extract was washed with water and dried over anhydrous magnesium sulfate. The solvent was evaporated under reduced pressure and the residue was purified by silica gel column chromatography (hexane:ethyl acetate=1:1) to give the desired product (300 mg, 90.4%) as an oil.
¹H-NMR (CDCl₃) δ; 1.21-1.26 (6H, m), 1.41 (9H, s), 2.36-2.43 (2H, m), 3.40-3.44 (2H, m), 3.75-3.77 (4H, m), 4.01-4.03 (2H, m), 4.33 (2H, br s), 6.52-6.58 (2H, m), 7.03-7.15 (1H, m).

(2) 8-(cis-2,6-dimethylmorpholin-4-yl)-2,3,4,5-tetrahydro-1,4-benzoxazepine dihydrochloride A mixture of tert-butyl 8-(cis-2,6-dimethylmorpholin-4-yl)-2,3-dihydro-1,4-benzoxazepine-4(5H)-carboxylate (300 mg, 0.828 mmol), ethyl acetate (1 ml) and 4N hydrogen chloride-ethyl acetate solution (6 ml) was stirred for 1 hr at room temperature, and the solvent was evaporated under reduced pressure. The residue was recrystallized from a mixed solvent of methanol and ether to give the desired product (225 mg, 81.2%) as a solid.

$^1$H-NMR (DMSO-d$_6$) δ; 1.14 (6H, d, J=6.0 Hz), 2.23-2.30 (2H, m), 3.40 (2H, br s), 3.56-3.69 (4H, m), 4.13-4.18 (4H, m), 5.46 (1H, br s), 6.61 (1H, s), 6.70 (1H, d, J=8.4 Hz), 7.23 (1H, d, J=8.4 Hz), 9.43 (2H, br s).

Example 33

7-(2-methylphenyl)-2,3,4,5-tetrahydro-1,4-benzoxazepine hydrochloride (1) tert-butyl 7-(2-methylphenyl)-2,3-dihydro-1,4-benzoxazepine-4(5H)-carboxylate A mixture of tert-butyl 7-bromo-2,3-dihydro-1,4-benzoxazepine-4(5H)-carboxylate (200 mg, 0.609 mmol), a solution of 2-methylphenylboronic acid (124 mg, 0.912 mmol) in ethanol (0.7 ml), 2N aqueous sodium carbonate solution (2.5 ml), and tetrakis(triphenylphosphine)palladium(0) (84.2 mg, 0.0729 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (200 mg, 96.6%) as an oil.
$^1$H-NMR (CDCl$_3$) δ; 1.42 (9H, s), 2.27 (3H, s), 3.83 (2H, s), 4.08 (2H, s), 4.45-4.51 (2H, m), 7.01-7.24 (7H, m).

(2) 7-(2-methylphenyl)-2,3,4,5-tetrahydro-1,4-benzoxazepine hydrochloride

A mixture of tert-butyl 7-(2-methylphenyl)-2,3-dihydro-1,4-benzoxazepine-4(5H)-carboxylate (200 mg, 0.589 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (133 mg, 82.1%) as a solid.
$^1$H-NMR (DMSO-d$_6$) δ; 2.24 (3H, s), 3.46-3.49 (2H, m), 4.24-4.27 (2H, m), 4.36 (2H, s), 7.11-7.32 (6H, m), 7.44 (1H, s), 9.62 (2H, br s).

Example 34

7-(morpholin-4-yl)-2,3,4,5-tetrahydro-1,4-benzoxazepine dihydrochloride (1) tert-butyl 7-(morpholin-4-yl)-2,3-dihydro-1,4-benzoxazepine-4(5H)-carboxylate A solution of tert-butyl 7-bromo-2,3-dihydro-1,4-benzoxazepine-4(5H)-carboxylate (200 mg, 0.609 mmol), morpholine (0.159 ml, 1.83 mmol), X-phos (17.4 mg, 0.0365 mmol), tris(dibenzylideneacetone)dipalladium(0) (11.0 mg, 0.0120 mmol), sodium tert-butoxide (87.5 mg, 0.912 mmol) and dioxane (4 ml) was stirred under an argon atmosphere for 2 hr at 80° C. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (180 mg, 88.4%) as an oil.
$^1$H-NMR (CDCl$_3$) δ; 1.42 (9H, s), 3.07-3.11 (4H, m), 3.76-3.78 (2H, m), 3.85 (4H, br s), 3.96-3.99 (2H, m), 4.37-4.44 (2H, m), 6.73-6.86 (2H, m), 6.93-6.96 (1H, m).

(2) 7-(morpholin-4-yl)-2,3,4,5-tetrahydro-1,4-benzoxazepine dihydrochloride

A mixture of tert-butyl 7-(morpholin-4-yl)-2,3-dihydro-1,4-benzoxazepine-4(5H)-carboxylate (180 mg, 0.538 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (134 mg, 81.2%) as a solid.
$^1$H-NMR (DMSO-d$_6$) δ; 3.12 (4H, br s), 3.42 (2H, br s), 3.78 (4H, br s), 4.13 (2H, br s), 4.26 (2H, br s), 5.49 (1H, br s), 7.00 (2H, br s), 7.17 (1H, s), 9.55 (2H, br s).

Example 35

9-(morpholin-4-yl)-2,3,4,5-tetrahydro-1,4-benzoxazepine dihydrochloride (1) tert-butyl 9-(morpholin-4-yl)-2,3-dihydro-1,4-benzoxazepine-4(5H)-carboxylate A solution of tert-butyl 9-bromo-2,3-dihydro-1,4-benzoxazepine-4(5H)-carboxylate (200 mg, 0.609 mmol), morpholine (0.159 ml, 1.83 mmol), X-phos (17.4 mg, 0.0365 mmol), tris(dibenzylideneacetone)dipalladium(0) (11.0 mg, 0.0120 mmol), sodium tert-butoxide (87.5 mg, 0.912 mmol) and dioxane (4 ml) was stirred under an argon atmosphere for 2 hr at 80° C. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (150 mg, 73.7%) as an oil.
$^1$H-NMR (CDCl$_3$) δ; 1.42 (9H, s), 3.04-3.07 (4H, m), 3.79-3.82 (2H, m), 3.84-3.87 (4H, m), 4.02-4.04 (2H, m), 4.39-4.45 (2H, m), 6.82-6.85 (2H, m), 6.85-6.99 (1H, m).

(2) 9-(morpholin-4-yl)-2,3,4,5-tetrahydro-1,4-benzoxazepine dihydrochloride

A mixture of tert-butyl 9-(morpholin-4-yl)-2,3-dihydro-1,4-benzoxazepine-4(5H)-carboxylate (150 mg, 0.449 mmol), ethyl acetate (1 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (97.5 mg, 70.8%) as a solid.
$^1$H-NMR (DMSO-d$_6$) δ; 3.07 (4H, br s), 3.44 (2H, br s), 3.78 (4H, br s), 4.20 (2H, br s), 4.26 (2H, br s), 5.11 (1H, br s), 7.10 (3H, br s), 9.59 (2H, br s).

Example 36

N,N-bis(2-methoxyethyl)-2,3,4,5-tetrahydro-1,4-benzoxazepine-8-amine dihydrobromide (1) tert-butyl 8-[bis(2-methoxyethyl)amino]-2,3-dihydro-1,4-benzoxazepine-4(5H)-carboxylate A solution of tert-butyl 8-bromo-2,3-dihydro-1,4-benzoxazepine-4(5H)-carboxylate (200 mg, 0.609 mmol), bis(2-methoxyethyl)amine (0.270 ml, 1.83 mmol), X-phos (17.4 mg, 0.0365 mmol), tris(dibenzylideneacetone)dipalladium(0) (11.0 mg, 0.0120 mmol), sodium tert-butoxide (87.5 mg, 0.912 mmol) and dioxane (4 ml) was stirred under an argon atmosphere for 2 hr at 80° C. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (230 mg, 99.1%) as an oil.

$^1$H-NMR (CDCl$_3$) δ; 1.42 (9H, s), 3.34 (6H, s), 3.52 (8H, s), 3.69-3.76 (2H, m), 4.01-4.04 (2H, m), 4.31-4.38 (2H, m), 6.32-6.39 (2H, m), 6.97-6.99 (1H, m).

(2) N,N-bis(2-methoxyethyl)-2,3,4,5-tetrahydro-1,4-benzoxazepine-8-amine dihydrobromide A mixture of tert-butyl 8-[bis(2-methoxyethyl)amino]-2,3-dihydro-1,4-benzoxazepine-4(5H)-carboxylate (230 mg, 0.828 mmol), ethyl acetate (1 ml) and 4N hydrogen chloride-ethyl acetate solution (6 ml) was stirred for 1 hr at room temperature, and the solvent was evaporated under reduced pressure. 1N Aqueous sodium hydroxide solution (10 ml) was added to the residue, and the mixture was extracted with ethyl acetate. The extract was dried over anhydrous magnesium sulfate, and the solvent was evaporated under reduced pressure and the residue was purified by NH silica gel column chromatography (ethyl acetate) to give the desired product (120 mg) as an oil. 20% Hydrogen bromide ethanol solution (1 ml) was added thereto and the mixture was concentrated to give the desired product (136 mg, 50.9%) as an oil.

$^1$H-NMR (DMSO-d$_6$) δ; 3.24 (6H, s), 3.44-3.49 (10H, m), 4.15-4.17 (4H, m), 4.80 (1H, br s), 6.38-6.44 (2H, m), 7.14 (1H, d, J=8.4 Hz), 8.89 (2H, br s).

Example 37

9-(cyclohexa-1-en-1-yl)-2,3,4,5-tetrahydro-1,4-benzoxazepine hydrochloride (1) tert-butyl 9-(cyclohexa-1-en-1-yl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), a solution of cyclohexen-1-ylboronic acid (115 mg, 0.912 mmol) in ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (170 mg, 85.4%) as an oil.

$^1$H-NMR (CDCl$_3$) δ; 1.42 (9H, s), 1.64-1.77 (4H, m), 2.16 (2H, br s), 2.33 (2H, br s), 3.77-3.80 (2H, m), 3.97-4.00 (2H, m), 4.39-4.45 (2H, m), 5.68 (1H, br s), 6.92-6.97 (2H, m), 7.05-7.08 (1H, m).

(2) 9-(cyclohexa-1-en-1-yl)-2,3,4,5-tetrahydro-1,4-benzoxazepine hydrochloride

A mixture of tert-butyl 9-(cyclohexa-1-en-1-yl)-2,3-dihydro-1,4-benzoxazepine-4(5H)-carboxylate (170 mg, 0.516 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (112 mg, 81.8%) as a solid.

$^1$H-NMR (DMSO-d$_6$) δ; 1.61-1.69 (4H, m), 2.14 (2H, br s), 2.27 (2H, br s), 3.39-3.44 (2H, m), 4.14 (2H, br s), 4.25 (2H, s), 5.66 (1H, br s), 7.04-7.09 (1H, m), 7.15-7.19 (1H, m), 7.31-7.33 (1H, m), 9.46 (2H, br s).

Example 38

9-cyclohexyl-2,3,4,5-tetrahydro-1,4-benzoxazepine hydrochloride (1) tert-butyl 9-cyclohexyl-2,3-dihydro-1,4-benzoxazepine-4(5H)-carboxylate A mixture of tert-butyl 9-(cyclohexa-1-en-1-yl)-2,3-dihydro-1,4-benzoxazepine-4(5H)-carboxylate (160 mg, 0.486 mmol) and 10% palladium on carbon (100 mg) in methanol (5 ml) was stirred under a hydrogen atmosphere for 12 hr. The reaction mixture was filtered, and the filtrate was concentrated to give the desired product (150 mg, 93.2%) as an oil.

$^1$H-NMR (CDCl$_3$) δ; 1.21-1.42 (14H, m), 1.81 (5H, br s), 2.95 (1H, br s), 3.79-3.82 (2H, m), 3.98-4.01 (2H, m), 4.40-4.45 (2H, m), 6.94-7.00 (2H, m), 7.05-7.14 (1H, m).

(2) 9-cyclohexyl-2,3,4,5-tetrahydro-1,4-benzoxazepine hydrochloride

A mixture of tert-butyl 9-cyclohexyl-2,3-dihydro-1,4-benzoxazepine-4(5H)-carboxylate (150 mg, 0.453 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (112 mg, 92.6%) as a solid.

$^1$H-NMR (DMSO-d$_6$) δ; 1.25-1.39 (5H, m), 1.67-1.80 (5H, m), 2.91 (1H, br s), 3.45 (2H, br s), 4.15 (2H, br s), 4.25 (2H, s), 7.05-7.10 (1H, m), 7.24-7.28 (2H, m), 9.36 (2H, br s).

Example 39

9-cyclopentyl-2,3,4,5-tetrahydro-1,4-benzoxazepine hydrochloride (1) tert-butyl 9-(cyclopenta-1-en-1-yl)-2,3-dihydro-1,4-benzoxazepine-4(5H)-carboxylate A mixture of tert-butyl 9-bromo-2,3-dihydro-1,4-benzoxazepine-4(5H)-carboxylate (400 mg, 1.21 mmol), a solution of cyclopenten-1-ylboronic acid (204 mg, 1.82 mmol) in ethanol (1.4 ml), 2N aqueous sodium carbonate solution (5 ml), and tetrakis(triphenylphosphine)palladium(0) (168 mg, 0.146 mmol) in toluene (10 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (260 mg, 68.1%) as an oil.

$^1$H-NMR (CDCl$_3$) δ; 1.42 (9H, s), 1.93-2.10 (2H, m), 2.48-2.56 (2H, m), 2.70-2.77 (2H, m), 3.80-3.83 (2H, m), 3.99-4.02 (2H, m), 4.41-4.46 (2H, m), 6.25-6.27 (1H, m), 6.95-7.08 (2H, m), 7.19-7.25 (1H, m).

(2) tert-butyl 9-cyclopentyl-2,3-dihydro-1,4-benzoxazepine-4(5H)-carboxylate A mixture of tert-butyl 9-(cyclopenta-1-en-1-yl)-2,3-dihydro-1,4-benzoxazepine-4(5H)-carboxylate (140 mg, 0.444 mmol) and 10% palladium on carbon (100 mg) in methanol (5 ml) was stirred under a hydrogen atmosphere for 12 hr. The reaction mixture was filtered, and the filtrate was concentrated to give the desired product (130 mg, 92.2%) as an oil.
$^1$H-NMR (CDCl$_3$) δ; 1.42 (9H, s), 1.47-2.05 (8H, m), 3.27-3.40 (1H, m), 3.80-3.83 (2H, m), 3.95-4.02 (2H, m), 4.40-4.46 (2H, m), 6.94-7.04 (2H, m), 7.14-7.18 (1H, m).

(3) 9-cyclopentyl-2,3,4,5-tetrahydro-1,4-benzoxazepine hydrochloride

A mixture of tert-butyl 9-cyclopentyl-2,3-dihydro-1,4-benzoxazepine-4(5H)-carboxylate (130 mg, 0.410 mmol), ethyl acetate (1 ml) and 4N hydrogen chloride-ethyl acetate solution (4 ml) was stirred for 1 hr at room temperature, and the solvent was evaporated under reduced pressure. The residue was recrystallized from a mixed solvent of methanol and ether to give the desired product (81.3 mg, 78.2%) as a solid.
$^1$H-NMR (DMSO-d$_6$) δ; 1.51-1.93 (8H, m), 3.25-3.34 (1H, m), 3.44 (2H, br s), 4.15 (2H, br s), 4.26 (2H, br s), 7.04-7.10 (1H, m), 7.25-7.31 (2H, m), 9.47 (2H, br s).

Example 40

9-(5-methyl-3-furyl)-2,3,4,5-tetrahydro-1,4-benzoxazepine hydrochloride

(1) tert-butyl 9-(5-formyl-3-furyl)-2,3-dihydro-1,4-benzoxazepine-4(5H)-carboxylate A mixture of tert-butyl 9-bromo-2,3-dihydro-1,4-benzoxazepine-4(5H)-carboxylate (1.18 g, 3.60 mmol), 5-formylfuran-3-boronic acid pinacol ester (800 mg, 3.60 mmol), saturated aqueous sodium carbonate solution (15 ml), and tetrakis (triphenylphosphine)palladium(0) (118 mg, 0.102 mmol) in ethylene glycol dimethyl ether (20 ml) was stirred under a nitrogen atmosphere at 85° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=1:1) to give the desired product (900 mg, 72.6%) as an oil.
$^1$H-NMR (CDCl$_3$) δ; 1.41 (9H, s), 3.84-3.87 (2H, m), 4.05-4.08 (2H, m), 4.46-4.52 (2H, m), 7.07-7.12 (1H, m), 7.17-7.32 (1H, m), 7.40-7.43 (1H, m), 7.58 (1H, s), 8.15 (1H, s), 9.70 (1H, s).

(2) tert-butyl 9-(5-methyl-3-furyl)-2,3-dihydro-1,4-benzoxazepine-4(5H)-carboxylate A mixture of tert-butyl 9-(5-formyl-3-furyl)-2,3-dihydro-1,4-benzoxazepine-4(5H)-carboxylate (300 mg, 0.874 mmol), hydrazine monohydrate (0.100 ml, 2.06 mmol), ethylene glycol (6 ml) and methanol (4 ml) was stirred at 70° C. for 10 min. After cooling to room temperature, potassium hydroxide (147 mg, 2.62 mmol) was added, and the mixture was stirred at 100° C. for 1 hr. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=2:1) to give the desired product (72.0 mg, 25.0%) as an oil.
$^1$H-NMR (CDCl$_3$) δ; 1.42 (9H, s), 2.33 (3H, s), 3.84-3.85 (2H, m), 4.02-4.04 (2H, m), 4.44-4.49 (2H, m), 6.33 (1H, s), 6.99-7.25 (2H, m), 7.34-7.37 (1H, m), 7.77 (1H, s).

(3) 9-(5-methyl-3-furyl)-2,3,4,5-tetrahydro-1,4-benzoxazepine hydrochloride A mixture of tert-Butyl 9-(5-methyl-3-furyl)-2,3-dihydro-1,4-benzoxazepine-4(5H)-carboxylate (92.0 mg, 0.279 mmol), ethyl acetate (2 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (60.0 mg, 81.0%) as a solid.
$^1$H-NMR (DMSO-d$_6$) δ; 2.30 (3H, s), 3.50 (2H, br s), 4.24 (2H, br s), 4.33 (2H, s), 6.61 (1H, s), 7.13-7.18 (1H, m), 7.31-7.34 (1H, m), 7.59-7.62 (1H, m), 8.00 (1H, s), 9.38 (2H, br s).

Example 41

9-(2-methyl-3-furyl)-2,3,4,5-tetrahydro-1,4-benzoxazepine hydrochloride

(1) tert-butyl 9-(2-formyl-3-furyl)-2,3-dihydro-1,4-benzoxazepine-4(5H)-carboxylate A mixture of tert-butyl 9-bromo-2,3-dihydro-1,4-benzoxazepine-4(5H)-carboxylate (1.48 g, 4.50 mmol), 2-formylfuran-3-boronic acid pinacol ester (1.00 g, 4.50 mmol), saturated aqueous sodium carbonate solution (20 ml), and tetrakis (triphenylphosphine)palladium(0) (147 mg, 0.127 mmol) in ethylene glycol dimethyl ether (25 ml) was stirred under a nitrogen atmosphere at 85° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=1:1) to give the desired product (750 mg, 48.4%) as an oil.
$^1$H-NMR (CDCl$_3$) δ; 1.43 (9H, s), 3.80-3.81 (2H, m), 3.95-3.98 (2H, m), 4.48-4.54 (2H, m), 6.66-6.67 (1H, m), 7.08-7.51 (3H, m), 7.67-7.68 (1H, m), 9.60 (1H, s).

(2) tert-butyl 9-(2-methyl-3-furyl)-2,3-dihydro-1,4-benzoxazepine-4(5H)-carboxylate A mixture of tert-butyl 9-(2-formyl-3-furyl)-2,3-dihydro-1,4-benzoxazepine-4(5H)-carboxylate (750 mg, 2.18 mmol), hydrazine monohydrate (0.300 ml, 6.18 mmol), ethylene glycol (15 ml) and methanol (5 ml) was stirred at 85° C. for 10 min. After cooling to room temperature, potassium hydroxide (500 mg, 8.91 mmol) was added, and the mixture was stirred at 100° C. for 0.5 hr. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (300 mg, 41.8%) as an oil.
$^1$H-NMR (CDCl$_3$) δ; 1.44 (9H, s), 3.79-3.81 (2H, m), 3.97-4.00 (2H, m), 4.45-4.51 (2H, m), 6.44 (1H, d, J=2.1 Hz), 7.01-7.18 (3H, m), 7.33 (1H, d, J=2.1 Hz).

(3) 9-(2-methyl-3-furyl)-2,3,4,5-tetrahydro-1,4-benzoxazepine hydrochloride

A mixture of tert-butyl 9-(2-methyl-3-furyl)-2,3-dihydro-1,4-benzoxazepine-4(5H)-carboxylate (300 mg, 0.911 mmol), ethyl acetate (1 ml) and 4N hydrogen chloride-ethyl acetate solution (3 ml) was stirred at room temperature for 0.5 hr, and the solvent was evaporated under reduced pressure. The residue was recrystallized from a mixed solvent of methanol and ether to give the desired product (230 mg, 95.0%) as a solid.

$^1$H-NMR (DMSO-d$_6$) δ; 2.27 (3H, s), 3.43 (2H, br s), 4.15 (2H, br s), 4.32 (2H, s), 6.51 (1H, d, J=1.8 Hz), 7.14-7.19 (1H, m), 7.31-7.34 (1H, m), 7.40-7.42 (1H, m), 7.57 (1H, d, J=1.8 Hz), 9.60 (2H, br s).

Example 42

9-bicyclo[2.2.1]hepta-2-yl-2,3,4,5-tetrahydro-1,4-benzoxazepine hydrochloride

(1) tert-butyl 9-bicyclo[2.2.1]hepta-2-en-2-yl-2,3-dihydro-1,4-benzoxazepine-4(5H)-carboxylate A mixture of tert-butyl 9-bromo-2,3-dihydro-1,4-benzoxazepine-4(5H)-carboxylate (594 mg, 1.81 mmol), bicyclo[2.2.1]-2-hepten-2-ylboronic acid (250 mg, 1.81 mmol), ethanol (2 ml), 2N aqueous sodium carbonate solution (10 ml), and tetrakis(triphenylphosphine)palladium(0) (253 mg, 0.219 mmol) in toluene (20 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (282 mg, 45.6%) as an oil.

$^1$H-NMR (CDCl$_3$) δ; 1.15-1.23 (4H, m), 1.42 (9H, s), 1.72-1.78 (2H, m), 2.98 (1H, br s), 3.27 (1H, br s), 3.75-3.83 (2H, m), 3.99-4.06 (2H, m), 4.41 (2H, br s), 6.42-6.43 (1H, m), 6.95-7.25 (3H, m).

(2) tert-butyl 9-bicyclo[2.2.1]hepta-2-yl-2,3-dihydro-1,4-benzoxazepine-4(5H)-carboxylate A mixture of tert-butyl 9-bicyclo[2.2.1]hepta-2-en-2-yl-2,3-dihydro-1,4-benzoxazepine-4(5H)-carboxylate (160 mg, 0.469 mmol) and 10% palladium carbon (100 mg) in methanol (10 ml) was stirred under a hydrogen atmosphere for 12 hr. The reaction mixture was filtered, and the filtrate was concentrated. The residue was purified by silica gel column chromatography (hexane:ethyl acetate=2:1) to give the desired product (100 mg, 62.1%) as an oil.

$^1$H-NMR (CDCl$_3$) δ; 1.21-1.33 (6H, m), 1.42 (9H, s), 1.52-1.64 (2H, m), 1.82-1.93 (1H, m), 2.32-2.33 (1H, br s), 3.49-3.56 (1H, m), 3.80-3.81 (2H, m), 3.97-4.05 (2H, m), 4.40-4.45 (2H, m), 6.96-7.19 (3H, m).

(3) 9-bicyclo[2.2.1]hepta-2-yl-2,3,4,5-tetrahydro-1,4-benzoxazepine hydrochloride A mixture of tert-butyl 9-bicyclo[2.2.1]hepta-2-yl-2,3-dihydro-1,4-benzoxazepine-4(5H)-carboxylate (100 mg, 0.292 mmol), ethyl acetate (1 ml) and 4N hydrogen chloride-ethyl acetate solution (2 ml) was stirred at room temperature for 0.5 hr, and the solvent was evaporated under reduced pressure. The residue was recrystallized from a mixed solvent of methanol and ether to give the desired product (24.0 mg, 29.4%) as a solid.

$^1$H-NMR (DMSO-d$_6$) δ; 1.06-1.83 (8H, m), 2.30 (2H, br s), 3.15-3.16 (1H, m), 3.45 (2H, br s), 4.12 (2H, br s), 4.27 (2H, br s), 7.11-7.13 (1H, m), 7.27-7.30 (2H, m), 9.17 (2H, br s).

Example 43

9-(3,5-dimethylisoxazol-4-yl)-2,3,4,5-tetrahydro-1,4-benzoxazepine hydrochloride

(1) tert-butyl 9-(3,5-dimethylisoxazol-4-yl)-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), 3,5-dimethylisoxazol-4-ylboronic acid (129 mg, 0.912 mmol), ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water and dried over anhydrous magnesium sulfate. The solvent was evaporated under reduced pressure, and the residue was purified by silica gel column chromatography (hexane:ethyl acetate=2:1) to give the desired product (120 mg, 57.7%) as an oil.

$^1$H-NMR (CDCl$_3$) δ; 1.43 (9H, s), 2.17 (3H, s), 2.29 (3H, s), 3.76-3.79 (2H, m), 3.86-3.89 (2H, m), 4.47-4.54 (2H, m), 7.04-7.07 (2H, m), 7.22-7.33 (1H, m).

(2) 9-(3,5-dimethylisoxazol-4-yl)-2,3,4,5-tetrahydro-1,4-benzoxazepine hydrochloride A mixture of tert-butyl 9-(3,5-dimethylisoxazol-4-yl)-2,3-dihydro-1,4-benzoxazepine-4(5H)-carboxylate (120 mg, 0.348 mmol), ethyl acetate (1 ml) and 4N hydrogen chloride-ethyl acetate solution (2 ml) was stirred at room temperature for 1 hr, and the solvent was evaporated under reduced pressure. The residue was recrystallized from a mixed solvent of methanol and ether to give the desired product (67.4 mg, 69.0%) as a solid.

$^1$H-NMR (DMSO-d$_6$) δ; 2.08 (3H, s), 2.26 (3H, s), 3.44 (2H, br s), 4.14 (2H, br s), 4.37 (2H, s), 7.19-7.24 (1H, m), 7.30-7.33 (1H, m), 7.49-7.52 (1H, m), 9.56 (2H, br s).

Example 44

9-(3-fluorophenyl)-2,3,4,5-tetrahydro-1,4-benzoxazepine hydrochloride

(1) tert-butyl 9-(3-fluorophenyl)-2,3-dihydro-1,4-benzoxazepine-4(5H)-carboxylate A mixture of tert-butyl 9-bromo-2,3-dihydro-1,4-benzoxazepine-4(5H)-carboxylate (400 mg, 1.22 mmol), 3-fluorophenylboronic acid (171 mg, 1.22 mmol), ethanol (1 ml), 2N aqueous sodium carbonate solution (5 ml), and tetrakis(triphenylphosphine)palladium(0) (170 mg, 0.147 mmol) in toluene (10 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (390 mg, 93.1%) as an oil.

$^1$H-NMR (CDCl$_3$) δ; 1.44 (9H, s), 3.78-3.81 (2H, m), 3.96-3.99 (2H, m), 4.46-4.52 (2H, m), 6.98-7.39 (7H, m).

(2) 9-(3-fluorophenyl)-2,3,4,5-tetrahydro-1,4-benzoxazepine hydrochloride

A mixture of tert-butyl 9-(3-fluorophenyl)-2,3-dihydro-1,4-benzoxazepine-4(5H)-carboxylate (390 mg, 1.14 mmol), ethyl acetate (4 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (309 mg, 97.2%) as a solid.

$^1$H-NMR (DMSO-d$_6$) δ; 3.46 (2H, br s), 4.18 (2H, br s), 4.36 (2H, s), 7.18-7.29 (4H, m), 7.43-7.53 (3H, m), 9.57 (2H, br s).

Example 45

9-[(1E)-propa-1-ene-1-yl]-2,3,4,5-tetrahydro-1,4-benzoxazepine hydrochloride (1) tert-butyl 9-[(1E)-propa-1-ene-1-yl]-2,3-dihydro-1,4-benzoxazepine-4(5H)-carboxylate A mixture of tert-butyl 9-bromo-2,3-dihydro-1,4-benzoxazepine-4(5H)-carboxylate (400 mg, 1.22 mmol), trans-1-propen-1-ylboronic acid (157 mg, 1.82 mmol), ethanol (1.4 ml), 2N aqueous sodium carbonate solution (5 ml), and tetrakis(triphenylphosphine)palladium(0) (170 mg, 0.147 mmol) in toluene (10 ml) was stirred under a nitrogen atmosphere at 95° C. for 12 hr. The reaction mixture was poured into water, and the mixture was extracted with ethyl acetate. The extract was washed with water and dried over anhydrous magnesium sulfate. The solvent was evaporated under reduced pressure, and the residue was purified by silica gel column chromatography (hexane:ethyl acetate=2:1) to give the desired product (340 mg, 97.1%) as an oil.

$^1$H-NMR (CDCl$_3$) δ; 1.41 (9H, s), 1.88-1.91 (3H, m), 3.79-3.82 (2H, m), 4.01-4.04 (2H, m), 4.38-4.45 (2H, m), 6.15-6.27 (1H, m), 6.68-6.74 (1H, m), 6.92-6.97 (1H, m), 7.04-7.16 (1H, m), 7.35-7.36 (1H, m).

(2) 9-[(1E)-propa-1-ene-1-yl]-2,3,4,5-tetrahydro-1,4-benzoxazepine hydrochloride A mixture of tert-butyl 9-[(1E)-propa-1-ene-1-yl]-2,3-dihydro-1,4-benzoxazepine-4(5H)-carboxylate (178 mg, 0.615 mmol), ethyl acetate (1 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (121 mg, 87.7%) as a solid.

$^1$H-NMR (DMSO-d$_6$) δ; 1.87 (3H, d, J=6.6 Hz), 3.42-3.46 (2H, m), 4.17-4.19 (2H, m), 4.26 (2H, s), 6.27-6.39 (1H, m), 6.66 (1H, d, J=16.8 Hz), 7.04-7.09 (1H, m), 7.28 (1H, d, J=7.5 Hz), 7.54 (1H, d, J=8.1 Hz), 9.60 (2H, br s).

Example 46

9-isoxazol-4-yl-2,3,4,5-tetrahydro-1,4-benzoxazepine hydrochloride (1) tert-butyl 9-isoxazol-4-yl-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.605 mmol), 4-isooxazolylboronic acid pinacol ester (119 mg, 0.609 mmol), tripotassium phosphate (194 mg, 0.914 mmol), and [1,1'-bis(diphenylphosphino)ferrocene]palladium(II) dichloride dichloromethane complex (24.9 mg, 0.0305 mmol) in dioxane (2 ml) was stirred at 85° C. for 12 hr under a nitrogen atmosphere. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (120 mg, 62.2%) as an oil.

$^1$H-NMR (CDCl$_3$) δ; 1.41 (9H, s), 3.84-3.87 (2H, m), 4.04-4.07 (2H, m), 4.45-4.51 (2H, m), 7.05-7.53 (3H, m), 8.62 (1H, s), 8.84 (1H, s).

(2) 9-isoxazol-4-yl-2,3,4,5-tetrahydro-1,4-benzoxazepine hydrochloride

A mixture of tert-butyl 9-isoxazol-4-yl-2,3-dihydro-1,4-benzoxazepine-4(5H)-carboxylate (120 mg, 0.379 mmol), ethyl acetate (2 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (13.3 mg, 13.9%) as a solid.

$^1$H-NMR (DMSO-d$_6$) δ; 3.53 (2H, br s), 4.31-4.40 (4H, m), 7.20-7.25 (1H, m), 7.41-7.44 (1H, m), 7.77-7.80 (1H, m), 9.17 (1H, s), 9.39 (1H, s), 9.36 (2H, br s).

Example 47

9-propyl-2,3,4,5-tetrahydro-1,4-benzoxazepine hydrochloride (1) tert-butyl 9-propyl-2,3-dihydro-1,4-benzoxazepine-4(5H)-carboxylate A mixture of tert-butyl 9-[(1E)-propa-1-ene-1-yl]-2,3-dihydro-1,4-benzoxazepine-4(5H)-carboxylate (170 mg, 0.587 mmol) and 10% palladium on carbon (100 mg) in methanol (5 ml) was stirred under a hydrogen atmosphere for 12 hr. The reaction mixture was filtered, and the filtrate was concentrated. The residue was purified by silica gel column chromatography (hexane:ethyl acetate=2:1) to give the desired product (140 mg, 81.9%) as an oil.

$^1$H-NMR (CDCl$_3$) δ; 0.95 (3H, t, J=7.5 Hz), 1.41 (9H, s), 1.52-1.64 (2H, m), 2.59 (2H, t, J=8.1 Hz), 3.78-3.81 (2H, m), 3.98-4.01 (2H, m), 4.39-4.45 (2H, m), 6.90-6.95 (1H, m), 7.01-7.09 (2H, m).

(2) 9-propyl-2,3,4,5-tetrahydro-1,4-benzoxazepine hydrochloride

A mixture of tert-butyl 9-propyl-2,3-dihydro-1,4-benzoxazepine-4(5H)-carboxylate (140 mg, 0.480 mmol), ethyl acetate (1 ml) and 4N hydrogen chloride-ethyl acetate solution (2 ml) was stirred at room temperature for 1 hr, and the solvent was evaporated under reduced pressure. The residue was recrystallized from a mixed solvent of methanol and ether to give the desired product (106 mg, 97.2%) as a solid.

$^1$H-NMR (DMSO-d$_6$) δ; 0.90 (3H, t, J=7.2 Hz), 1.49-1.57 (2H, m), 2.55-2.60 (2H, m), 3.42-3.45 (2H, m), 4.15-4.18 (2H, m), 4.25 (2H, s), 7.02-7.07 (1H, m), 7.22-7.28 (2H, m), 9.53 (2H, br s).

Example 48

9-[(1Z)-propa-1-ene-1-yl]-2,3,4,5-tetrahydro-1,4-benzoxazepine hydrochloride (1) tert-butyl 9-[(1Z)-propa-1-ene-1-yl]-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.61 mmol), cis-1-propen-1-ylboronic acid (78.5 mg, 0.910 mmol), ethanol (0.7 ml), 2N aqueous sodium carbonate solution (2.5 ml), and tetrakis(triphenylphosphine)palladium(0) (84.0 mg, 0.0730 mmol) in toluene (5 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=2:1) to give the desired product (170 mg, 97.1%) as an oil.
$^1$H-NMR (CDCl$_3$) δ; 1.42 (9H, s), 1.80-1.83 (3H, m), 3.78-3.81 (2H, m), 4.00-4.41 (2H, m), 4.41-4.48 (2H, m), 5.78-5.89 (1H, m), 6.51-6.56 (1H, m), 6.93-7.04 (1H, m), 7.20-7.25 (2H, m).

(2) 9-[(1Z)-propa-1-ene-1-yl]-2,3,4,5-tetrahydro-1,4-benzoxazepine hydrochloride A mixture of tert-butyl 9-[(1Z)-propa-1-ene-1-yl]-2,3-dihydro-1,4-benzoxazepine-4(5H)-carboxylate (170 mg, 0.587 mmol), ethyl acetate (1 ml) and 4N hydrogen chloride-ethyl acetate solution (2 ml) was stirred at room temperature for 1 hr, and the solvent was evaporated under reduced pressure. The residue was recrystallized from a mixed solvent of methanol and ether to give the desired product (120 mg, 90.9%) as a solid.
$^1$H-NMR (DMSO-d$_6$) δ; 1.76-1.79 (3H, m), 3.42-3.45 (2H, m), 4.15-4.18 (2H, m), 4.29 (2H, s), 5.79-5.90 (1H, m), 6.50 (1H, d, J=11.1 Hz), 7.09-7.14 (1H, m), 7.32-7.36 (2H, m), 9.53 (2H, br s).

Example 49

9-ethyl-2,3,4,5-tetrahydro-1,4-benzoxazepine hydrochloride (1) tert-butyl 9-ethenyl-2,3-dihydro-1,4-benzoxazepine-4(5H)-carboxylate A mixture of tert-Butyl 9-bromo-2,3-dihydro-1,4-benzoxazepine-4(5H)-carboxylate (852 mg, 2.60 mmol), vinylboronic acid pinacol ester (400 mg, 2.60 mmol), saturated aqueous sodium carbonate solution (12 ml), and tetrakis(triphenylphosphine)palladium(0) (84.8 mg, 0.0734 mmol) in dimethoxyethane (15 ml) was stirred under a nitrogen atmosphere at 85° C. for 12 hr. The reaction mixture was poured into water, and the mixture was extracted with ethyl acetate. The extract was washed with water and dried over anhydrous magnesium sulfate. The solvent was evaporated under reduced pressure, and the residue was purified by silica gel column chromatography (hexane:ethyl acetate=3:1) to give the desired product (250 mg, 34.9%) as an oil.
$^1$H-NMR (CDCl$_3$) δ; 1.41 (9H, s), 3.79-3.82 (2H, m), 4.02-4.05 (2H, m), 4.40-4.46 (2H, m), 5.27 (1H, d, J=11.4 Hz), 5.73 (1H, d, J=15.9 Hz), 6.96-7.12 (3H, m), 7.42 (1H, d, J=9.0 Hz).

(2) tert-butyl 9-ethyl-2,3-dihydro-1,4-benzoxazepine-4(5H)-carboxylate

A mixture of tert-butyl 9-ethenyl-2,3-dihydro-1,4-benzoxazepine-4(5H)-carboxylate (349 mg, 1.27 mmol) and 10% palladium on carbon (50.0 mg) in methanol (6 ml) was stirred under a hydrogen atmosphere for 12 hr. The reaction mixture was filtered, and the filtrate was concentrated. The residue was poured into water, and the mixture was extracted with ethyl acetate. The extract was dried over anhydrous magnesium sulfate, and the solvent was evaporated under reduced pressure to give the desired product (260 mg, 73.9%) as an oil.
$^1$H-NMR (CDCl$_3$) δ; 1.18 (3H, t, J=7.8 Hz), 1.41 (9H, s), 2.64 (2H, q, J=7.8 Hz), 3.79-3.32 (1H, m), 3.99-4.05 (2H, m), 4.40-4.45 (2H, m), 6.92-7.19 (3H, m).

(3) 9-ethyl-2,3,4,5-tetrahydro-1,4-benzoxazepine hydrochloride

A mixture of tert-butyl 9-ethyl-2,3-dihydro-1,4-benzoxazepine-4(5H)-carboxylate (260 mg, 0.937 mmol), ethyl acetate (2 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (166 mg, 83.0%) as a solid.
$^1$H-NMR (DMSO-d$_6$) δ; 1.13 (3H, t, J=7.8 Hz), 2.61 (2H, q, J=7.8 Hz), 3.43-3.50 (2H, m), 4.16-4.19 (2H, m), 4.25 (2H, s), 7.02-7.07 (1H, m), 7.23-7.28 (2H, m), 9.62 (2H, br s).

Example 50

9-(3-methoxypropyl)-2,3,4,5-tetrahydro-1,4-benzoxazepine hydrochloride (1) tert-butyl 9-[(1E)-3-methoxypropa-1-ene-1-yl]-2,3-dihydro-1,4-benzoxazepine-4(5H)-carboxylate A mixture of tert-butyl 9-bromo-2,3-dihydro-1,4-benzoxazepine-4(5H)-carboxylate (328 mg, 1.00 mmol), trans-2-methoxy-1-propenylboronic acid pinacol ester (198 mg, 1.00 mmol), saturated aqueous sodium carbonate solution (6 ml), and tetrakis(triphenylphosphine)palladium(0) (32.6 mg, 0.0282 mmol) in dimethoxyethane (10 ml) was stirred at 85° C. for 12 hr under a nitrogen atmosphere. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=1:1) to give the desired product (200 mg, 62.3%) as an oil.
$^1$H-NMR (CDCl$_3$) δ; 1.41 (9H, s), 3.38 (3H, s), 3.79-3.82 (2H, m), 4.02-4.11 (4H, m), 4.39-4.45 (2H, m), 6.23-6.32 (1H, m), 6.90-7.14 (3H, m), 7.39-7.41 (1H, m).

(2) tert-butyl 9-(3-methoxypropyl)-2,3-dihydro-1,4-benzoxazepine-4(5H)-carboxylate A mixture of tert-butyl 9-[(1E)-3-methoxypropa-1-ene-1-yl]-2,3-dihydro-1,4-benzoxazepine-4(5H)-carboxylate (200 mg, 0.622 mmol) and 10% palladium on carbon (50.0 mg) in methanol (4 ml) was stirred under a hydrogen atmosphere for 12 hr. The reaction mixture was filtered, and the filtrate was concentrated. The residue was poured into water, and the mixture was extracted with ethyl acetate. The extract was dried over anhydrous magnesium sulfate, and the solvent was evaporated under reduced pressure to give the desired product (170 mg, 85.0%) as an oil.

$^1$H-NMR (CDCl$_3$) δ; 1.41 (9H, s), 1.81-1.88 (2H, m), 2.66-2.71 (2H, m), 3.34 (3H, s), 3.37-3.41 (2H, m), 3.78-3.81 (2H, m), 3.99-4.02 (2H, m), 4.40 (2H, s), 6.91-7.09 (3H, m).

(3) 9-(3-methoxypropyl)-2,3,4,5-tetrahydro-1,4-benzoxazepine hydrochloride

A mixture of tert-butyl 9-(3-methoxypropyl)-2,3-dihydro-1,4-benzoxazepine-4(5H)-carboxylate (170 mg, 0.529 mmol), ethyl acetate (1 ml) and 4N hydrogen chloride-ethyl acetate solution (2 ml) was stirred at room temperature for 1 hr, and the solvent was evaporated under reduced pressure. The residue was recrystallized from a mixed solvent of isopropyl alcohol and diisopropyl ether to give the desired product (106 mg, 77.9%) as a solid.

$^1$H-NMR (DMSO-d$_6$) δ; 1.68-1.78 (2H, m), 2.60-2.65 (2H, m), 3.23 (3H, s), 3.30-3.33 (2H, m), 3.43 (2H, br s), 4.17 (2H, br s), 4.25 (2H, s), 7.02-7.07 (1H, m), 7.21-7.28 (2H, m), 9.58 (2H, br s).

Example 51

9-(2-methylpropyl)-2,3,4,5-tetrahydro-1,4-benzoxazepine hydrochloride

(1) tert-butyl 9-(2-methylpropa-1-ene-1-yl)-2,3-dihydro-1,4-benzoxazepine-4(5H)-carboxylate A mixture of tert-butyl 9-bromo-2,3-dihydro-1,4-benzoxazepine-4(5H)-carboxylate (328 mg, 1.00 mmol), 2,2-dimethylethenylboronic acid (98.0 mg, 1.00 mmol), saturated aqueous sodium carbonate solution (14 ml) and tetrakis(triphenylphosphine)palladium(0) (32.6 mg, 0.0282 mmol) in dimethoxyethane (10 ml) was stirred at 85° C. for 12 hr under a nitrogen atmosphere. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=9:1) to give the desired product (270 mg, 89.1%) as an oil.

$^1$H-NMR (CDCl$_3$) δ; 1.42 (9H, s), 1.79 (3H, s), 1.92 (3H, s), 3.77-3.80 (2H, m), 4.00-4.03 (2H, m), 4.40-4.46 (2H, m), 6.29 (1H, s), 6.93-7.14 (3H, m).

(2) tert-butyl 9-(2-methylpropyl)-2,3-dihydro-1,4-benzoxazepine-4(5H)-carboxylate A solution of tert-butyl 9-(2-methylpropa-1-ene-1-yl)-2,3-dihydro-1,4-benzoxazepine-4(5H)-carboxylate (270 mg, 0.890 mmol) and 10% palladium on carbon (50.0 mg) in methanol (6 ml) was stirred under a hydrogen atmosphere for 12 hr. The reaction mixture was filtered, and the filtrate was concentrated. The residue was poured into water, and the mixture was extracted with ethyl acetate. The extract was dried over anhydrous magnesium sulfate, and the solvent was evaporated under reduced pressure to give the desired product (260 mg, 95.6%) as an oil.

$^1$H-NMR (CDCl$_3$) δ; 0.90 (6H, d, J=6.6 Hz), 1.41 (9H, s), 1.81-1.90 (1H, m), 2.48 (2H, d, J=7.2 Hz), 3.78-3.81 (2H, m), 3.97-4.00 (2H, m), 4.39 (2H, br s), 6.90-7.04 (3H, m).

(3) 9-(2-methylpropyl)-2,3,4,5-tetrahydro-1,4-benzoxazepine hydrochloride

A mixture of tert-butyl 9-(2-methylpropyl)-2,3-dihydro-1,4-benzoxazepine-4(5H)-carboxylate (260 mg, 0.937 mmol), ethyl acetate (2 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (192 mg, 93.7%) as a solid.

$^1$H-NMR (DMSO-d$_6$) δ; 0.86 (6H, d, J=6.6 Hz), 1.77-1.86 (1H, m), 2.47 (2H, d, J=7.5 Hz), 3.41-3.44 (2H, m), 4.14-4.15 (2H, m), 4.25 (2H, s), 7.01-7.06 (1H, m), 7.18 (1H, d, J=7.2 Hz), 7.28 (1H, d, J=7.5 Hz), 9.58 (2H, br s).

Example 52

9-(2,4-dimethyl-1,3-thiazol-5-yl)-2,3,4,5-tetrahydro-1,4-benzoxazepine hydrochloride

(1) tert-butyl 9-(2,4-dimethyl-1,3-thiazol-5-yl)-2,3-dihydro-1,4-benzoxazepine-4(5H)-carboxylate A mixture of tert-butyl 9-bromo-2,3-dihydro-1,4-benzoxazepine-4(5H)-carboxylate (328 mg, 1.00 mmol), 2,4-dimethyl-1,3-thiazol-5-ylboronic acid pinacol ester (239 mg, 1.00 mmol), saturated aqueous sodium carbonate solution (6 ml) and tetrakis(triphenylphosphine)palladium(0) (32.6 mg, 0.0282 mmol) in dimethoxyethane (10 ml) was stirred at 85° C. for 12 hr under a nitrogen atmosphere. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=1:1) to give the desired product (240 mg, 66.7%) as an oil.

$^1$H-NMR (CDCl$_3$) δ; 1.44 (9H, s), 2.35 (3H, s), 2.69 (3H, s), 3.79-3.82 (2H, m), 3.97-4.00 (2H, m), 4.45-4.51 (2H, m), 7.04-7.51 (3H, m).

(2) 9-(2,4-dimethyl-1,3-thiazol-5-yl)-2,3,4,5-tetrahydro-1,4-benzoxazepine hydrochloride A mixture of tert-butyl 9-(2,4-dimethyl-1,3-thiazol-5-yl)-2,3-dihydro-1,4-benzoxazepine-4(5H)-carboxylate (240 mg, 0.666 mmol), ethyl acetate (2 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (180 mg, 90.9%) as a solid.

$^1$H-NMR (DMSO-d$_6$) δ; 2.30 (3H, s), 2.70 (3H, s), 3.46 (2H, br s), 4.18-4.21 (2H, m), 4.36 (2H, br s), 7.21-7.62 (3H, m), 9.75 (2H, br s).

Example 53

9-[(1E)-3-methoxypropa-1-ene-1-yl]-2,3,4,5-tetrahydro-1,4-benzoxazepine hydrochloride A mixture of tert-butyl 9-[(1E)-3-methoxypropa-1-ene-1-yl]-2,3-dihydro-1,4-benzoxazepine-4(5H)-carboxylate (90.0 mg, 0.282 mmol), ethyl acetate (1 ml) and 4N hydrogen chloride-ethyl acetate solution (2 ml) was stirred at room temperature for 1 hr, and the solvent was evaporated under reduced pressure. The residue was recrystallized from a mixed solvent of methanol and ether to give the desired product (60.0 mg, 83.4%) as a solid.

$^1$H-NMR (DMSO-d$_6$) δ; 3.29 (3H, s), 3.46 (2H, br s), 4.04-4.06 (2H, m), 4.20 (2H, br s), 4.29 (2H, s), 6.34-6.43

(1H, m), 6.82-6.88 (1H, m), 7.08-7.13 (1H, m), 7.33-7.35 (1H, m), 7.59-7.62 (1H, m), 9.48 (2H, br s).

Example 54

9-(1-methylethyl)-2,3,4,5-tetrahydro-1,4-benzoxazepine hydrochloride (1) tert-butyl 9-(1-methylethenyl)-2,3-dihydro-1,4-benzoxazepine-4(5H)-carboxylate A mixture of tert-butyl 9-bromo-2,3-dihydro-1,4-benzoxazepine-4(5H)-carboxylate (1.00 g, 3.05 mmol), isopropenyl boronic acid pinacol ester (513 mg, 3.05 mmol), saturated aqueous sodium carbonate solution (14 ml) and tetrakis(triphenylphosphine)palladium(0) (99.5 mg, 0.0861 mmol) in dimethoxyethane (17 ml) was stirred at 85° C. for 12 hr under a nitrogen atmosphere. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=3:1) to give the desired product (680 mg, 77.0%) as an oil.
$^1$H-NMR (CDCl$_3$) δ; 1.43 (9H, s), 2.11 (3H, s), 3.79-3.82 (2H, m), 4.00-4.03 (2H, m), 4.41-4.47 (2H, m), 4.98-4.99 (1H, m), 5.14-5.15 (1H, m), 6.95-7.00 (1H, m), 7.11-7.14 (2H, m).

(2) tert-butyl 9-(1-methylethyl)-2,3-dihydro-1,4-benzoxazepine-4(5H)-carboxylate A mixture of tert-butyl 9-(1-methylethenyl)-2,3-dihydro-1,4-benzoxazepine-4(5H)-carboxylate (480 mg, 1.66 mmol) and 10% palladium on carbon (30.0 mg) in methanol (10 ml) was stirred under a hydrogen atmosphere for 12 hr. The reaction mixture was filtered, and the filtrate was concentrated. The residue was purified by silica gel column chromatography (hexane:ethyl acetate=3:1) to give the desired product (330 mg, 68.1%) as an oil.
$^1$H-NMR (CDCl$_3$) δ; 1.21 (6H, d, J=7.2 Hz), 1.42 (9H, s), 3.29-3.38 (1H, m), 3.79-3.82 (2H, m), 3.99-4.02 (2H, m), 4.40-4.45 (2H, m), 6.95-7.16 (3H, m).

(3) 9-(1-methylethyl)-2,3,4,5-tetrahydro-1,4-benzoxazepine hydrochloride

A mixture of tert-butyl 9-(1-methylethyl)-2,3-dihydro-1,4-benzoxazepine-4(5H)-carboxylate (330 mg, 1.13 mmol), ethyl acetate (6 ml) and 4N hydrogen chloride-ethyl acetate solution (3 ml) was stirred at room temperature for 1 hr, and the solvent was evaporated under reduced pressure. The residue was recrystallized from a mixed solvent of methanol and ether to give the desired product (106 mg, 97.2%) as a solid.
$^1$H-NMR (DMSO-d$_6$) δ; 1.17 (6H, d, J=6.0 Hz), 3.23-3.33 (1H, m), 3.40-3.45 (2H, m), 4.16-4.19 (2H, m), 4.25 (2H, s), 7.06-7.11 (1H, m), 7.26-7.31 (2H, m), 9.55 (2H, br s).
melting point 191° C.

Example 55

9-(tetrahydrofuran-3-yl)-2,3,4,5-tetrahydro-1,4-benzoxazepine hydrochloride (1) tert-butyl 9-(tetrahydrofuran-3-yl)-2,3-dihydro-1,4-benzoxazepine-4(5H)-carboxylate A mixture of tert-butyl 9-(tetrahydrofuran-3-yl)-2,3-dihydro-1,4-benzoxazepine-4(5H)-carboxylate (430 mg, 1.36 mmol) and 10% palladium on carbon (100 mg) in methanol (8 ml) was stirred under a hydrogen atmosphere at room temperature for 12 hr, and the insoluble material was filtered off. The filtrate was concentrated to give the desired product (430 mg, 99.1%) as an oil.
$^1$H-NMR (CDCl$_3$) δ; 1.42 (9H, s), 1.93-2.02 (1H, m), 2.24-2.35 (1H, m), 3.65-4.15 (9H, m), 4.40-4.46 (2H, m), 6.96-7.19 (3H, m).

(2) 9-(tetrahydrofuran-3-yl)-2,3,4,5-tetrahydro-1,4-benzoxazepine hydrochloride

A mixture of tert-butyl 9-(tetrahydrofuran-3-yl)-2,3-dihydro-1,4-benzoxazepine-4(5H)-carboxylate (430 mg, 1.35 mmol), ethyl acetate (2 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (320 mg, 92.8%) as a solid.
$^1$H-NMR (CD$_3$OD) δ; 1.96-2.07 (1H, m), 2.28-2.39 (1H, m), 3.58-4.13 (7H, m), 4.23-4.26 (2H, m), 4.37 (2H, s), 4.85 (2H, br s), 7.11-7.17 (1H, m), 7.27 (1H, d, J=7.5 Hz), 7.38 (1H, d, J=7.5 Hz).
melting point 183° C.

Example 56

9-(pyrrolidin-1-ylcarbonyl)-2,3,4,5-tetrahydro-1,4-benzoxazepine hydrobromide (1) 4-(tert-butoxycarbonyl)-2,3,4,5-tetrahydro-1,4-benzoxazepine-9-carboxylic acid To a solution of tert-butyl 9-bromo-2,3-dihydro-1,4-benzoxazepine-4(5H)-carboxylate (200 mg, 0.605 mmol) in tetrahydrofuran (4 ml) was added 1.6N solution of n-butyllithium in hexane (0.396 ml, 0.634 mmol) at −78° C., and the mixture was stirred at 78° C. for 1 hr. At −78° C., pulverized dry ice (2 g) was added to the reaction mixture, and the mixture was stirred for 1 hr. Saturated aqueous ammonium chloride solution (5 ml) and 1N hydrochloric acid (5 ml) were added, and the mixture was extracted with ethyl acetate. The extract was washed with water and dried over anhydrous magnesium sulfate. The solvent was evaporated under reduced pressure. The residue was purified by silica gel column chromatography (ethyl acetate) to give the desired product (40.0 mg, 22.6%) as an oil.
$^1$H-NMR (CDCl$_3$) δ; 1.42 (9H, s), 3.90-3.93 (2H, m), 4.27-4.30 (2H, m), 4.48-4.53 (2H, m), 7.18-7.23 (1H, m), 7.43-7.56 (1H, m), 8.07-8.10 (1H, m).

(2) tert-butyl 9-(pyrrolidin-1-ylcarbonyl)-2,3-dihydro-1,4-benzoxazepine-4(5H)-carboxylate To a solution of 4-(tert-butoxycarbonyl)-2,3,4,5-tetrahydro-1,4-benzoxazepine-9-carboxylic acid (40.0 mg, 0.136 mmol), 1-hydroxybenzotriazole (18.4 mg, 0.136 mmol) and pyrrolidine (0.017 ml, 0.204 mmol) in DMF (1 ml) was added 1-(3-dimethylaminopropyl)-3-ethylcarbodiimide hydrochloride (52.2 mg, 0.272 mmol), and the mixture was stirred at room temperature for 12 hr. The reaction mixture was poured into water, and the mixture was extracted with ethyl acetate. The extract was washed with water and dried over anhydrous magnesium sulfate. The solvent was evaporated under reduced pressure to give the desired product (42.0 mg, 89.2%) as an oil.

$^1$H-NMR (CDCl$_3$) δ; 1.41 (9H, s), 1.82-2.04 (4H, m), 3.18-3.23 (2H, m), 3.62-3.67 (2H, m), 3.79 (2H, br s), 4.06-4.09 (2H, m), 4.42-4.48 (2H, m), 7.00-7.30 (3H, m).

(3) 9-(pyrrolidin-1-ylcarbonyl)-2,3,4,5-tetrahydro-1,4-benzoxazepine hydrobromide A mixture of tert-butyl 9-(pyrrolidin-1-ylcarbonyl)-2,3-dihydro-1,4-benzoxazepine-4(5H)-carboxylate (42.0 mg, 0.121% mmol), ethyl acetate (2 ml) and 4N hydrogen chloride-ethyl acetate solution (2 ml) was stirred at room temperature for 1 hr, and the solvent was evaporated under reduced pressure. The residue was added to 1N aqueous sodium hydroxide solution (2 ml), and the mixture was extracted with ethyl acetate:tetrahydrofuran (1:1). The extract was dried over anhydrous magnesium sulfate, and the solvent was evaporated under reduced pressure. 10% Hydrogen bromide ethanol solution (2 ml) was added to the residue, and the mixture was concentrated. The residue was recrystallized from a mixed solvent of ethanol and ether to give the desired product (10.0 mg, 25.2%) as a solid.
$^1$H-NMR (CD$_3$OD) δ; 1.88-2.01 (4H, m), 3.21-3.27 (2H, m), 3.57-3.63 (4H, m), 4.28 (2H, br s), 4.45 (2H, s), 4.87 (2H, br s), 7.25 (1H, t, J=7.5 Hz), 7.37 (1H, d, J=7.5 Hz), 7.49 (1H, d, J=7.5 Hz).

Example 57

1-(2,3,4,5-tetrahydro-1,4-benzoxazepine-9-yl)pyrrolidin-2-one hydrobromide (1) tert-butyl 9-(2-oxopyrrolidin-1-yl)-2,3-dihydro-1,4-benzoxazepine-4(5H)-carboxylate tert-Butyl 9-bromo-2,3-dihydro-1,4-benzoxazepine-4(5H)-carboxylate (328 mg, 1.00 mmol), 2-pyrrolidone (85.1 mg, 1.00 mmol), tripotassium phosphate (318 mg, 1.50 mmol), N,N-dimethylformamide (3 ml), dioxane (3 ml) and 1,2-trans-cyclohexanediamine (0.025 ml) mixture were stirred at room temperature under a nitrogen atmosphere for 5 min. Copper iodide(I) (35.0 mg, 0.184 mmol) was added, and the mixture was stirred at 110° C. under a nitrogen atmosphere for 20 hr. The reaction mixture was poured into water (10 ml) and ethyl acetate (10 ml), and filtered through celite. The organic layer was separated, washed with water, and dried over anhydrous magnesium sulfate. The solvent was evaporated under reduced pressure. The residue was purified by silica gel column chromatography (hexane:ethyl acetate=1:1) to give the desired product (260 mg, 86.4%) as an oil.
$^1$H-NMR (CDCl$_3$) δ; 1.42 (9H, s), 2.14-2.24 (2H, m), 2.53-2.59 (2H, m), 3.73-3.79 (4H, m), 4.05-4.06 (2H, m), 4.42-4.47 (2H, m), 7.01-7.27 (3H, m).

(2) 1-(2,3,4,5-tetrahydro-1,4-benzoxazepine-9-yl)pyrrolidin-2-one hydrobromide

A mixture of tert-butyl 9-(2-oxopyrrolidin-1-yl)-2,3-dihydro-1,4-benzoxazepine-4(5H)-carboxylate (260 mg, 0.782 mmol), ethyl acetate (5 ml) and 4N hydrogen chloride-ethyl acetate solution (5 ml) was stirred at room temperature for 1 hr, and the solvent was evaporated under reduced pressure. The residue was added to 1N aqueous sodium hydroxide solution (3 ml), and the mixture was extracted with ethyl acetate:tetrahydrofuran (1:1). The extract was dried over anhydrous magnesium sulfate, and the solvent was evaporated under reduced pressure. 10% Hydrogen bromide ethanol solution (3 ml) was added to the residue and concentrated to give the desired product (43.6 mg, 17.8%) as an oil.
$^1$H-NMR (CD$_3$OD) δ; 2.20-2.29 (2H, m), 2.54-2.60 (2H, m), 3.59-3.62 (2H, m), 3.78-3.82 (2H, m), 4.26-4.29 (2H, m), 4.43 (2H, s), 4.88 (2H, br s), 7.19-7.25 (1H, m), 7.36-7.42 (2H, m).

Example 58

9-(3,3-difluoropyrrolidin-1-yl)-2,3,4,5-tetrahydro-1,4-benzoxazepine (1) tert-butyl 9-(3,3-difluoropyrrolidin-1-yl)-2,3-dihydro-1,4-benzoxazepine-4(5H)-carboxylate A solution of tert-butyl 9-bromo-2,3-dihydro-1,4-benzoxazepine-4(5H)-carboxylate (328 mg, 1.04 mmol), 3,3-difluoropyrrolidine hydrochloride (150 mg, 1.04 mmol), 2-dicyclohexylphosphino-2',4',6'-triisopropylbiphenyl(X-phos) m (39.8 mg, 0.0835 mmol), tris(dibenzylideneacetone)dipalladium(0) (19.0 mg, 0.0208 mmol) and sodium tert-butoxide (250 mg, 2.60 mmol) in toluene (10 ml) was stirred under an argon atmosphere at 100° C. for 12 hr. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (110 mg, 29.8%) as an oil.
$^1$H-NMR (CDCl$_3$) δ; 1.42 (9H, s), 2.33-2.47 (2H, m), 3.45-3.51 (2H, m), 3.74-3.83 (4H, m), 3.97-4.02 (2H, m), 4.38-4.44 (2H, m), 6.60-6.95 (3H, m).

(2) 9-(3,3-difluoropyrrolidin-1-yl)-2,3,4,5-tetrahydro-1,4-benzoxazepine

A mixture of tert-butyl 9-(3,3-difluoropyrrolidin-1-yl)-2,3-dihydro-1,4-benzoxazepine-4(5H)-carboxylate (110 mg, 0.310 mmol), ethyl acetate (2 ml) and 4N hydrogen chloride-ethyl acetate solution (2 ml) was stirred at room temperature for 1 hr, and the solvent was evaporated under reduced pressure. The residue was added to 1N aqueous sodium hydroxide solution (2 ml), and the mixture was extracted with ethyl acetate:tetrahydrofuran (1:1). The extract was dried over anhydrous magnesium sulfate, and the solvent was evaporated under reduced pressure. The residue was purified by NH silica gel column chromatography (hexane:ethyl acetate=1:1) to give the desired product (41.0 mg, 52.0%) as a solid.
$^1$H-NMR (CDCl$_3$) δ; 2.36-2.43 (2H, m), 3.23 (2H, br s), 3.46 (2H, br s), 3.75-3.83 (2H, m), 3.94-3.98 (4H, m), 6.59-6.91 (3H, m), 7.25 (1H, br s).
melting point 54° C.

Example 59

9-(2,2,2-trifluoro-1-methylethyl)-2,3,4,5-tetrahydro-1,4-benzoxazepine hydrochloride (1) tert-butyl 9-[1-(trifluoromethyl)ethenyl]-2,3-dihydro-1,4-benzoxazepine-4(5H)-carboxylate A mixture of tert-butyl 9-bromo-2,3-dihydro-1,4-benzoxazepine-4(5H)-carboxylate (328 mg, 1.00 mmol), 1-(trifluoromethyl)vinylboronic acid pinacol ester (222 mg, 1.00 mmol), saturated aqueous sodium carbonate solution (6 ml) and tetrakis(triphenylphosphine)palladium(0) (32.6 mg, 0.0282 mmol) in dimethoxyethane (10 ml) was stirred at 85°

C. for 12 hr under a nitrogen atmosphere. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=10:1) to give the desired product (300 mg, 87.5%) as an oil.

$^1$H-NMR (CDCl$_3$) δ; 1.41 (9H, s), 3.78-3.81 (2H, m), 3.96-4.05 (2H, m), 4.43-4.48 (2H, m), 5.56 (1H, s), 6.07 (1H, s), 6.99-7.25 (3H, m).

(2) tert-butyl 9-(2,2,2-trifluoro-1-methylethyl)-2,3-dihydro-1,4-benzoxazepine-4(5H)-carboxylate A mixture of tert-butyl 9-[1-(trifluoromethyl)ethenyl]-2,3-dihydro-1,4-benzoxazepine-4(5H)-carboxylate (300 mg, 0.874 mmol) and 10% palladium on carbon (50.0 mg) in methanol (6 ml) was stirred under a hydrogen atmosphere for 12 hr. The reaction mixture was filtered, and the filtrate was concentrated. The residue was poured into water, and the mixture was extracted with ethyl acetate. The extract was dried over anhydrous magnesium sulfate, and the solvent was evaporated under reduced pressure to give the desired product (100 mg, 33.1%) as an oil.

$^1$H-NMR (CDCl$_3$) δ; 1.42-1.45 (12H, m), 3.66-4.50 (7H, m), 7.01-7.30 (3H, m).

(3) 9-(2,2,2-trifluoro-1-methylethyl)-2,3,4,5-tetrahydro-1,4-benzoxazepine hydrochloride A mixture of tert-butyl 9-(2,2,2-trifluoro-1-methylethyl)-2,3-dihydro-1,4-benzoxazepine-4(5H)-carboxylate (100 mg, 0.290 mmol), ethyl acetate (2 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (60.0 mg, 73.4%) as a solid.

$^1$H-NMR (DMSO-d$_6$) δ; 1.43 (3H, d, J=7.2 Hz), 3.45-3.48 (2H, m), 4.09-4.36 (5H, m), 7.17-7.22 (1H, m), 7.45-7.48 (2H, m), 9.75 (2H, br s).
melting point 227° C.

Example 60

2,3,4,5-tetrahydro-1,4-benzoxazepine-9-carboxylic acid hydrochloride 4-(tert-Butoxycarbonyl)-2,3,4,5-tetrahydro-1,4-benzoxazepine-9-carboxylic acid (110 mg, 0.375 mmol), ethyl acetate (1 ml) and 4N hydrogen chloride-ethyl acetate solution (2 ml) were stirred at room temperature for 1 hr, and the solvent was evaporated under reduced pressure. The residue was recrystallized from a mixed solvent of methanol and ether to give the desired product (72.0 mg, 83.6%) as a solid.

$^1$H-NMR (CD$_3$OD) δ; 3.32-3.63 (2H, m), 4.29-4.32 (2H, m), 4.46 (2H, s), 4.85 (3H, br s), 7.23-7.28 (1H, m), 7.57-7.61 (1H, m), 7.79-7.82 (1H, m).

Example 61

9-(morpholin-4-ylcarbonyl)-2,3,4,5-tetrahydro-1,4-benzoxazepine hydrobromide (1) tert-butyl 9-(morpholin-4-ylcarbonyl)-2,3-dihydro-1,4-benzoxazepine-4(5H)-carboxylate To a solution of 4-(tert-butoxycarbonyl)-2,3,4,5-tetrahydro-1,4-benzoxazepine-9-carboxylic acid (125 mg, 0.426 mmol) and 1-hydroxybenzotriazole (57.6 mg, 0.426 mmol), morpholine (0.0743 ml, 0.852 mmol) in DMF (3 ml) was added 1-(3-dimethylaminopropyl)-3-ethylcarbodiimide hydrochloride (163 mg, 0.852 mmol), and the mixture was stirred at room temperature for 12 hr. The reaction mixture was poured into water, and the mixture was extracted with ethyl acetate. The extract was washed with water and dried over anhydrous magnesium sulfate. The solvent was evaporated under reduced pressure, and the residue was purified by silica gel column chromatography (hexane:ethyl acetate=1:2) to give the desired product (130 mg, 84.4%) as a solid.

$^1$H-NMR (CDCl$_3$) δ; 1.41 (9H, s), 3.26 (2H, br s), 3.57-3.64 (3H, m), 3.76-4.33 (8H, m), 4.50-4.70 (1H, m), 7.03-7.32 (3H, m).

(2) 9-(morpholin-4-ylcarbonyl)-2,3,4,5-tetrahydro-1,4-benzoxazepine hydrobromide A mixture of tert-butyl 9-(morpholin-4-ylcarbonyl)-2,3-dihydro-1,4-benzoxazepine-4(5H)-carboxylate (130 mg, 0.359 mmol), ethyl acetate (1 ml) and 4N hydrogen chloride-ethyl acetate solution (2 ml) was stirred at room temperature for 1 hr, and the solvent was evaporated under reduced pressure. The residue was added to 1N aqueous sodium hydroxide solution (5 ml), and the mixture was extracted with ethyl acetate:tetrahydrofuran (1:1). The extract was dried over anhydrous magnesium sulfate, and the solvent was evaporated under reduced pressure. 10% Hydrogen bromide methanol solution (0.800 ml) was added to the residue and the mixture was concentrated. The residue was recrystallized from a mixed solvent of methanol and ether to give the desired product (40.0 mg, 32.5%) as a solid.

$^1$H-NMR (CD$_3$OD) δ; 3.59-3.63 (5H, m), 3.71-3.81 (5H, m), 4.07-4.15 (1H, m), 4.39-4.49 (3H, m), 4.85 (2H, br s), 7.23-7.28 (1H, m), 7.34-7.37 (1H, m), 7.48-7.52 (1H, m).

Example 62

3-(2,3,4,5-tetrahydro-1,4-benzoxazepine-9-yl)-1,3-oxazolidin-2-one hydrochloride (1) tert-butyl 9-(2-oxo-1,3-oxazolidin-3-yl)-2,3-dihydro-1,4-benzoxazepine-4(5H)-carboxylate A mixture of tert-Butyl 9-bromo-2,3-dihydro-1,4-benzoxazepine-4(5H)-carboxylate (328 mg, 1.00 mmol), 2-oxazolidone (87.0 mg, 1.00 mmol), tripotassium phosphate (318 mg, 1.50 mmol), N,N-dimethylformamide (3 ml), dioxane (3 ml) and 1,2-trans-cyclohexanediamine (0.025 ml) was stirred at room temperature under a nitrogen atmosphere for 5 min. Copper iodide(I) (35.0 mg, 0.184 mmol) was added, and the mixture was stirred at 110° C. under a nitrogen atmosphere for 20 hr. The reaction mixture was poured into water (10 ml) and ethyl acetate (10 ml), and filtered through celite. The organic layer was separated, washed with water, and dried over anhydrous magnesium sulfate. The solvent was evaporated under reduced pressure. The residue was purified by silica gel column chromatography (hexane:ethyl acetate=1:1) to give the desired product (230 mg, 68.9%) as an oil.

$^1$H-NMR (CDCl$_3$) δ; 1.42 (9H, s), 3.81 (2H, br s), 3.96-4.01 (2H, br s), 4.08-4.10 (2H, m), 4.43-4.49 (4H, m), 7.02-7.30 (3H, m).

(2) 3-(2,3,4,5-tetrahydro-1,4-benzoxazepine-9-yl)-1,3-oxazolidin-2-one hydrochloride A mixture of tert-butyl 9-(2-oxo-1,3-oxazolidin-3-yl)-2,3-dihydro-1,4-benzoxazepine-4(5H)-carboxylate (230 mg, 0.688 mmol), ethyl acetate (3 ml) and 4N hydrogen chloride-ethyl acetate solution (3 ml) was stirred at room temperature for 1 hr, and the solvent was evaporated under reduced pressure. The residue was recrystallized from a mixed solvent of methanol and ether to give the desired product (118 mg, 63.4%) as a solid.

$^1$H-NMR (CD$_3$OD) δ; 3.59-3.62 (2H, m), 3.99-4.04 (2H, m), 4.30-4.33 (2H, m), 4.42 (2H, s), 4.51-4.57 (2H, br s), 7.20-7.25 (1H, m), 7.39-7.42 (1H, m), 7.46-7.49 (1H, m).

Example 63

9-cyclobutyl-2,3,4,5-tetrahydro-1,4-benzoxazepine hydrochloride (1) tert-butyl 9-(1-hydroxycyclobutyl)-2,3-dihydro-1,4-benzoxazepine-4(5H)-carboxylate To a solution of tert-butyl 9-bromo-2,3-dihydro-1,4-benzoxazepine-4(5H)-carboxylate (328 mg, 1.00 mmol) in tetrahydrofuran (3 ml) was added 1.6N solution of n-butyllithium in hexane (0.829 ml, 1.33 mmol) at −78° C., and the mixture was stirred at −78° C. for 15 min. At −78° C., a solution of cyclobutanone (0.0747 ml, 1.00 mmol) in tetrahydrofuran (1 ml) was added, and the mixture was stirred at −78° C. for 30 min. Saturated aqueous ammonium chloride solution (3 ml) was added, and the mixture was stirred at room temperature for 1 hr. The reaction mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (108 mg, 33.8%) as an oil.

$^1$H-NMR (CDCl$_3$) δ; 1.42 (9H, s), 1.74-2.98 (6H, m), 3.43 (1H, br s), 3.80-3.83 (2H, m), 4.04-4.07 (2H, m), 4.41-4.46 (2H, m), 6.99-7.26 (3H, m).

(2) tert-butyl 9-cyclobutyl-2,3-dihydro-1,4-benzoxazepine-4(5H)-carboxylate

A mixture of tert-butyl 9-(1-hydroxycyclobutyl)-2,3-dihydro-1,4-benzoxazepine-4(5H)-carboxylate (108 mg, 0.338 mmol) and 10% palladium on carbon (100 mg) in methanol (10 ml) was stirred at room temperature for 24 hr under a hydrogen atmosphere, and the insoluble material was filtered off. The filtrate was concentrated, and the residue was purified by silica gel column chromatography (hexane:ethyl acetate=1:1) to give the desired product (40.0 mg, 39.0%) as an oil.

$^1$H-NMR (CDCl$_3$) δ; 1.41 (9H, s), 1.78-2.37 (6H, m), 3.70-3.80 (3H, m), 3.95-3.98 (2H, m), 4.38-4.44 (2H, m), 6.96-7.16 (3H, m).

(3) 9-cyclobutyl-2,3,4,5-tetrahydro-1,4-benzoxazepine hydrochloride

A mixture of tert-butyl 9-cyclobutyl-2,3-dihydro-1,4-benzoxazepine-4(5H)-carboxylate (40.0 mg, 0.132 mmol), ethyl acetate (2 ml) and 4N hydrogen chloride-ethyl acetate solution (2 ml) was stirred at room temperature for 1 hr, and the solvent was evaporated under reduced pressure. The residue was recrystallized from a mixed solvent of methanol and ether to give the desired product (25.0 mg, 79.1%) as a solid.

$^1$H-NMR (CD$_3$OD) δ; 1.82-2.40 (6H, m), 3.54-3.57 (2H, m), 3.74-3.83 (1H, m), 4.16-4.19 (2H, m), 4.34 (2H, s), 4.85 (2H, br s), 7.10-7.35 (3H, m).

melting point 207° C.

Example 64

9-cyclopropyl-2,3,4,5-tetrahydro-1,4-benzoxazepine hydrochloride (1) tert-butyl 9-cyclopropyl-2,3-dihydro-1,4-benzoxazepine-4(5H)-carboxylate A mixture of tert-butyl 9-bromo-2,3-dihydro-1,4-benzoxazepine-4(5H)-carboxylate (200 mg, 0.609 mmol), cyclopropylboronic acid (78.5 mg, 0.914 mmol), saturated aqueous sodium carbonate solution (3 ml), and tetrakis(triphenylphosphine)palladium(0) (19.0 mg, 0.0172 mmol) in dimethoxyethane (5 ml) was stirred at 90° C. for 12 hr under a nitrogen atmosphere. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=1:1) to give the desired product (70.0 mg, 39.8%) as an oil.

$^1$H-NMR (CDCl$_3$) δ; 0.61-0.67 (2H, m), 0.91-0.97 (2H, m), 1.41 (9H, s), 2.16-2.25 (1H, m), 3.81-3.84 (2H, m), 4.02-4.07 (2H, m), 4.40-4.46 (2H, m), 6.72-7.10 (3H, m).

(2) 9-cyclopropyl-2,3,4,5-tetrahydro-1,4-benzoxazepine hydrochloride

A mixture of tert-butyl 9-cyclopropyl-2,3-dihydro-1,4-benzoxazepine-4(5H)-carboxylate (70.0 mg, 0.242 mmol), ethyl acetate (1 ml) and 4N hydrogen chloride-ethyl acetate solution (2 ml) was stirred at room temperature for 1 hr, and the solvent was evaporated under reduced pressure. The residue was recrystallized from a mixed solvent of methanol and ether to give the desired product (29.5 mg, 54.0%) as a solid.

$^1$H-NMR (DMSO-d$_6$) δ; 0.62-0.67 (2H, m), 0.90-0.97 (2H, m), 2.18-2.22 (1H, m), 3.44-3.47 (2H, m), 4.18-4.21 (2H, m), 4.26 (2H, s), 6.88-6.91 (1H, m), 6.99-7.04 (1H, m), 7.19-7.22 (1H, m), 9.45 (2H, br s).

melting point 187° C.

Example 65

8-[(3S)-3-methylmorpholin-4-yl]-2,3,4,5-tetrahydro-1,4-benzoxazepine dihydrochloride (1) tert-butyl 8-[(3S)-3-methylmorpholin-4-yl]-2,3-dihydro-1,4-benzoxazepine-4(5H)-carboxylate A solution of tert-butyl 6-bromo-2,3-dihydro-1,4-benzoxazepine-4(5H)-carboxylate (500 mg, 1.52 mmol), (3S)-3-methylmorpholine p-toluenesulfonate (416 mg, 1.52 mmol), 2-dicyclohexylphosphino-2',4',6'-triisopropylbiphenyl(X-phos) (58.0 mg, 0.122 mmol), tris(dibenzylideneacetone)dipalladium(0) (27.8 mg, 0.0304 mmol), sodium tert-butoxide (365 mg, 3.80 mmol) and toluene (6 ml) was stirred under an argon atmosphere at 100° C. for 12 hr. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (420 mg, 79.2%) as an oil.

¹H-NMR (CDCl₃) δ; 1.09 (3H, d, J=6.6 Hz), 1.42 (9H, s), 3.12 (2H, br s), 3.63-3.83 (6H, m), 3.94-4.13 (3H, m), 4.34-4.39 (2H, m), 6.49-6.55 (2H, m), 6.97-7.26 (1H, m).

(2) (3S)-3-methylmorpholin-4-yl]-2,3,4,5-tetrahydro-1,4-benzoxazepine dihydrochloride A mixture of tert-butyl 8-[(3S)-3-methylmorpholin-4-yl]-2,3-dihydro-1,4-benzoxazepine-4(5H)-carboxylate (400 mg, 1.15 mmol), ethyl acetate (4 ml) and 4N hydrogen chloride-ethyl acetate solution (8 ml) was stirred at room temperature for 1 hr, and the solvent was evaporated under reduced pressure. The residue was recrystallized from a mixed solvent of methanol and ether to give the desired product (300 mg, 81.3%) as a solid.

¹H-NMR (CD₃OD) δ; 1.08 (3H, d, J=6.3 Hz), 3.55-3.67 (3H, m), 3.74-3.90 (2H, m), 4.00-4.19 (4H, m), 4.35-4.38 (2H, m), 4.48 (2H, s), 4.85 (3H, br s), 7.50-7.64 (3H, m).

$[\alpha]_D^{20}$ (c=0.879, MeOH)=19.7

Example 66

8-[(3R)-3-methylmorpholin-4-yl]-2,3,4,5-tetrahydro-1,4-benzoxazepine dihydrochloride

(1) tert-butyl (3R)-3-methylmorpholin-4-yl]-2,3-dihydro-1,4-benzoxazepine-4(5H)-carboxylate A mixture of tert-butyl 6-bromo-2,3-dihydro-1,4-benzoxazepine-4(5H)-carboxylate (500 mg, 1.52 mmol), (3R)-3-methylmorpholine-toluenesulfonate (416 mg, 1.52 mmol), 2-dicyclohexylphosphino-2',4',6'-triisopropylbiphenyl (X-phos) (58.0 mg, 0.122 mmol), tris(dibenzylideneacetone)dipalladium(0) (27.8 mg, 0.0304 mmol), and sodium tert-butoxide (365 mg, 3.80 mmol) in toluene (6 ml) was stirred under an argon atmosphere at 100° C. for 12 hr. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=1:1) to give the desired product (460 mg, 86.8%) as an oil.

¹H-NMR (CDCl₃) δ; 1.09 (3H, d, J=6.6 Hz), 1.42 (9H, s), 3.12 (2H, br s), 3.63-3.83 (6H, m), 3.94-4.13 (3H, m), 4.34-4.39 (2H, m), 6.49-6.55 (2H, m), 6.97-7.26 (1H, m).

(2) (3R)-3-methylmorpholin-4-yl]-2,3,4,5-tetrahydro-1,4-benzoxazepine dihydrochloride A mixture of tert-butyl 8-[(3R)-3-methylmorpholin-4-yl]-2,3-dihydro-1,4-benzoxazepine-4(5H)-carboxylate (460 mg, 1.32 mmol), ethyl acetate (4 ml) and 4N hydrogen chloride-ethyl acetate solution (8 ml) was stirred at room temperature for 1 hr, and the solvent was evaporated under reduced pressure. The residue was recrystallized from a mixed solvent of methanol and ether to give the desired product (320 mg, 75.5%) as a solid.

¹H-NMR (CD₃OD) δ; 1.08 (3H, d, J=6.3 Hz), 3.55-3.67 (3H, m), 3.74-3.90 (2H, m), 4.00-4.19 (4H, m), 4.35-4.38 (2H, m), 4.48% (2H, s), 4.85 (3H, br s), 7.50-7.64 (3H, m).

$[\alpha]_D^{20}$ (c=0.821, MeOH)=−19.5

Example 67

6-fluoro-9-furan-3-yl-2,3,4,5-tetrahydro-1,4-benzoxazepine hydrochloride

(1) 3-bromo-2,6-difluorobenzoic acid

To a mixed solution of 1.6N solution of n-butyllithium in hexane (9.4 ml, 15.0 mmol) and tetrahydrofuran (20 ml) were successively added 2,2,6,6-tetramethylpiperidine (2.50 ml, 15.0 mmol) and 1-bromo-2,4-difluorobenzene (2.90 g, 15.0 mmol) at −78° C., and the mixture was stirred at −78° C. for 1 hr. The pulverized dry ice (5 g) was added, and the mixture was stirred at −78° C. for 2 hr. Saturated aqueous ammonium chloride solution (5 ml) was added to the reaction mixture, and the mixture was stirred at room temperature for 30 min. Water (10 ml) and 1N hydrochloric acid (30 ml) were added, and the mixture was extracted with ethyl acetate. The extract was washed with water and dried over anhydrous magnesium sulfate. The solvent was evaporated under reduced pressure. Hexane was added to the residue, and desired product (2.30 g, 64.6%) was collected by filtration as a solid.

¹H-NMR (CDCl₃) δ; 6.91-6.97 (1H, m), 7.66-7.73 (1H, m).

(2) N-benzyl-3-bromo-2,6-difluoro-N-(2-hydroxyethyl)benzamide

To a solution of 3-bromo-2,6-difluorobenzoic acid (2.00 g, 8.44 mmol) and N,N-dimethylformamide (0.1 ml) in tetrahydrofuran (40 ml) was added dropwise oxalyl chloride (1.47 ml, 16.9 mmol) in a water bath, and the mixture was stirred at room temperature for 2 hr. The solvent was evaporated under reduced pressure. The residue was added under ice-cooling to a solution of N-benzylethanolamine (1.28 ml, 8.44 mmol) and triethylamine (1.77 ml, 12.7 mmol) in tetrahydrofuran (50 ml), and the mixture was stirred at 0° C. for 15 min and at room temperature for 1 hr. The reaction mixture was poured into ice water, and the mixture was extracted with ethyl acetate. The extract was washed with water and dried over anhydrous magnesium sulfate. The solvent was evaporated under reduced pressure. The residue was recrystallized from a mixed solution of diethyl ether and diisopropyl ether to give the desired product (2.10 g, 67.3%) as a solid.

¹H-NMR (CDCl₃) δ; 3.28-3.84 (5H, m), 4.51 (1H, m), 4.81-4.99 (1H, m), 6.85-6.93 (1H, m), 7.15-7.37 (5H, m), 7.51-7.60 (1H, m).

(3) 4-benzyl-9-bromo-6-fluoro-3,4-dihydro-1,4-benzoxazepine-5 (2H)-one

To a solution of N-benzyl-3-bromo-2,6-difluoro-N-(2-hydroxyethyl)benzamide (1.50 g, 4.05 mmol) in N,N-dimethylformamide (30 ml) under ice-cooling, 60% sodium hydride (210 mg, 5.27 mmol) was added, and the mixture was stirred for 1 hr under ice-cooling. The reaction mixture was poured into ice water, and the mixture was extracted with ethyl acetate. The extract was washed with water and dried over anhydrous magnesium sulfate. The solvent was evaporated under reduced pressure to give the desired product (1.40 g, 98.6%) as an oil.

¹H-NMR (CDCl₃) δ; 3.40-3.44 (2H, m), 4.02-4.15 (2H, m), 4.83 (2H, s), 6.86-6.92 (1H, m), 7.25-7.37 (5H, m), 7.59-7.62 (1H, m).

(4) 4-benzyl-9-bromo-6-fluoro-2,3,4,5-tetrahydro-1,4-benzoxazepine

To a solution of 4-benzyl-9-bromo-6-fluoro-3,4-dihydro-1,4-benzoxazepine-5 (2H)-one (1.40 g, 4.00 mmol) in tetrahydrofuran (30 ml) was added under ice-cooling 1M borane tetrahydrofuran solution (16.0 ml, 16.0 mmol), and the mixture was stirred at 60° C. for 3 hr. Under ice-cooling, methanol (20 ml) and sodium hydroxide (1.60 g, 40.0 mmol) were added, and the mixture was stirred at room temperature for 1 hr. The solvent was evaporated under reduced pressure. The residue was added to water, and the mixture was extracted with ethyl acetate. The extract was washed with water and dried over anhydrous magnesium sulfate, and the solvent was evaporated under reduced pressure. The residue was purified by silica gel column chromatography (hexane:ethyl acetate=1:1) to give the desired product (350 mg, 26.1%) as an oily substance.

$^1$H-NMR (CDCl$_3$) δ; 3.06 (2H, br s), 3.66 (2H, br s), 3.95 (2H, br s), 4.13 (2H, br s), 6.66-6.72 (1H, m), 7.29-7.41 (6H, m).

(5) tert-butyl 9-bromo-6-fluoro-2,3-dihydro-1,4-benzoxazepine-4(5H)-carboxylate

A solution of 4-benzyl-9-bromo-6-fluoro-2,3,4,5-tetrahydro-1,4-benzoxazepine (350 mg, 1.04 mmol), 1-chloroethyl chloroformate (0.178 ml, 1.65 mmol) and 1,2-dichloroethane (10 ml) was stirred at 90° C. for 1 hr, and the solvent was evaporated under reduced pressure. Methanol (10 ml) was added to the residue, and the mixture was stirred at 80° C. for 1 hr. The solvent was evaporated under reduced pressure. The residue was washed with ether, and 1N aqueous sodium hydroxide solution (2 ml), dioxane (4 ml) and di-tert-butyl dicarbonate (0.390 ml, 1.75 mmol) were added to the residue under ice-cooling. The mixture was stirred under ice-cooling for 1 hr and at room temperature for 12 hr. The reaction mixture was poured into water, and the mixture was extracted with ethyl acetate. The extract was washed with water and dried over anhydrous magnesium sulfate. The solvent was evaporated under reduced pressure. The residue was purified by silica gel column chromatography (hexane:ethyl acetate=2:1) to give the desired product (260 mg, 72.2%) as a solid.

$^1$H-NMR (CDCl$_3$) δ; 1.41 (9H, s), 3.83-3.86 (2H, m), 4.11-4.14 (2H, m), 4.56 (2H, br s), 6.70-6.76 (1H, m), 7.37-7.42 (1H, m).

(6) 6-fluoro-tert-butyl 9-furan-3-yl-2,3-dihydro-1,4-benzoxazepine-4(5H)-carboxylate A mixture of tert-butyl 9-bromo-6-fluoro-2,3-dihydro-1,4-benzoxazepine-4(5H)-carboxylate (260 mg, 0.751 mmol), a solution of 3-furanboronic acid (126 mg, 1.13 mmol) in ethanol (1 ml), 2N aqueous sodium carbonate solution (3 ml), and tetrakis(triphenylphosphine)palladium(0) (105 mg, 0.0906 mmol) in toluene (6 ml) was stirred under a nitrogen atmosphere at 95° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=10:1) to give the desired product (190 mg, 76.0%) as an oil.

$^1$H-NMR (CDCl$_3$) δ; 1.42 (9H, s), 3.85-3.88 (2H, m), 4.06-4.09 (2H, m), 4.59 (2H, br s), 6.68-6.69 (1H, m), 6.81-6.87 (1H, m), 7.31-7.36 (1H, m), 7.45-7.46 (1H, m), 7.87-7.88 (1H, m).

(7) 6-fluoro-9-furan-3-yl-2,3,4,5-tetrahydro-1,4-benzoxazepine hydrochloride

6-Fluoro-tert-butyl 9-furan-3-yl-2,3-dihydro-1,4-benzoxazepine-4(5H)-carboxylate (190 mg, 0.570 mmol), ethyl acetate (2 ml) and 4N hydrogen chloride-ethyl acetate solution (4 ml) were stirred at room temperature for 1 hr, and the solvent was evaporated under reduced pressure. The residue was recrystallized from a mixed solvent of methanol and ether to give the desired product (143 mg, 93.5%) as a solid.

$^1$H-NMR (DMSO-d$_6$) δ; 3.56 (2H, br s), 4.34 (4H, br s), 7.00 (1H, s), 7.09-7.16 (1H, m), 7.69-7.76 (2H, m), 8.15 (1H, s), 9.73 (2H, br s).

Example 68

6-fluoro-9-(1-methylethyl)-2,3,4,5-tetrahydro-1,4-benzoxazepine hydrochloride (1) 6-fluoro-tert-butyl 9-(1-methylethenyl)-2,3-dihydro-1,4-benzoxazepine-4(5H)-carboxylate A mixture of tert-butyl 9-bromo-6-fluoro-2,3-dihydro-1,4-benzoxazepine-4(5H)-carboxylate (500 mg, 1.44 mmol), isopropenyl boronic acid pinacol ester (336 mg, 2.00 mmol), saturated aqueous sodium carbonate solution (7 ml), and tetrakis(triphenylphosphine)palladium(0) (50.0 mg, 0.0433 mmol) in dimethoxyethane (10 ml) was stirred at 85° C. for 12 hr under a nitrogen atmosphere. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=3:1) to give the desired product (440 mg, 99.3%) as an oil.

$^1$H-NMR (CDCl$_3$) δ; 1.43 (9H, s), 2.08 (3H, s), 3.80-3.83 (2H, m), 4.02-4.05 (2H, m), 4.55 (2H, m), 4.95-4.96 (1H, m), 5.11-5.13 (1H, m), 6.72-6.79 (1H, m), 7.03-7.08 (1H, m).

(2) 6-fluoro-tert-butyl 9-(1-methylethyl)-2,3-dihydro-1,4-benzoxazepine-4(5H)-carboxylate A mixture of 6-fluoro-tert-butyl 9-(1-methylethenyl)-2,3-dihydro-1,4-benzoxazepine-4(5H)-carboxylate (440 mg, 1.43 mmol) and 10% palladium on carbon (100 mg) in methanol (10 ml) was stirred under a hydrogen atmosphere at room temperature for 12 hr, and insoluble material was filtered off. The filtrate was concentrated to give the desired product (360 mg, 81.4%) as an oil.

$^1$H-NMR (CDCl$_3$) δ; 1.18 (6H, d, J=8.7 Hz), 1.42 (9H, s), 3.22-3.31 (1H, m), 3.81-3.84 (2H, m), 4.02-4.05 (2H, m), 4.54 (2H, s), 6.73-6.79 (1H, m), 7.03-7.09 (1H, m).

(3) 6-fluoro-9-(1-methylethyl)-2,3,4,5-tetrahydro-1,4-benzoxazepine hydrochloride 6-Fluoro-tert-butyl 9-(1-methylethyl)-2,3-dihydro-1,4-benzoxazepine-4(5H)-carboxylate (360 mg, 1.16 mmol), ethyl acetate (4 ml) and 4N hydrogen chloride-ethyl acetate solution (4 ml) were stirred at room temperature for 1 hr, and the solvent was evaporated under reduced pressure. The residue was recrystallized from a mixed solvent of methanol and ether to give the desired product (217 mg, 75.9%) as a solid.

$^1$H-NMR (CD$_3$OD) δ; 1.22 (6H, d, J=7.2 Hz), 3.26-3.35 (1H, m), 3.61-3.63 (2H, m), 4.25-4.27 (2H, m), 4.41 (2H, s), 4.85 (2H, br s), 6.93-6.99 (1H, m), 7.32-7.37 (1H, m).

Example 69

9-cyclopropyl-6-fluoro-2,3,4,5-tetrahydro-1,4-benzoxazepine hydrochloride (1) tert-butyl 9-cyclopropyl-6-fluoro-2,3-dihydro-1,4-benzoxazepine-4(5H)-carboxylate A mixture of tert-butyl 9-bromo-6-fluoro-2,3-dihydro-1,4-benzoxazepine-4(5H)-carboxylate (400 mg, 1.16 mmol), cyclopropylboronic acid (298 mg, 3.47 mmol), saturated aqueous sodium carbonate solution (6 ml), and tetrakis(triphenylphosphine)palladium(0) (36.1 mg, 0.0313 mmol) in dimethoxyethane (10 ml) was stirred under a nitrogen atmosphere at 90° C. for 12 hr. The reaction mixture was poured into water, and the mixture was extracted with ethyl acetate. The extract was washed with water, and dried over anhydrous magnesium sulfate. The solvent was evaporated under reduced pressure, and the residue was purified by silica gel column chromatography (hexane:ethyl acetate=3:1) to give the desired product (270 mg, 75.7%) as an oil.

$^1$H-NMR (CDCl$_3$) δ; 0.55-0.61 (2H, m), 0.86-0.91 (2H, m), 1.42 (9H, s), 2.04-2.14 (1H, m), 3.81-3.85 (2H, m), 4.07-4.10 (2H, m), 4.54 (2H, s), 6.68-6.71 (2H, m).

(2) 9-cyclopropyl-6-fluoro-2,3,4,5-tetrahydro-1,4-benzoxazepine hydrochloride

A mixture of tert-butyl 9-cyclopropyl-6-fluoro-2,3-dihydro-1,4-benzoxazepine-4(5H)-carboxylate (270 mg, 0.878 mmol), ethyl acetate (4 ml) and 4N hydrogen chloride-ethyl acetate solution (4 ml) was stirred at room temperature for 1 hr, and the solvent was evaporated under reduced pressure. The residue was recrystallized from a mixed solvent of methanol and ether to give the desired product (144 mg, 67.3%) as a solid.

$^1$H-NMR (CD$_3$OD) δ; 0.62-0.67 (2H, m), 0.93-0.99 (2H, m), 2.14-2.19 (1H, m), 3.61-3.66 (2H, m), 4.28-4.32 (2H, m), 4.47 (2H, s), 4.85 (2H, br s), 6.87-6.99 (2H, m).

Example 70

9-cyclopropyl-8-fluoro-2,3,4,5-tetrahydro-1,4-benzoxazepine hydrochloride (1) N-benzyl-3-bromo-2,4-difluoro-N-(2-hydroxyethyl)benzamide To a mixture of 3-bromo-2,4-difluorobenzoic acid (1.00 g, 4.22 mmol), N,N-dimethylformamide (0.2 ml) and toluene (20 ml) was added under ice-cooling oxalyl dichloride (0.434 ml). The mixture was stirred at room temperature for 1 hr, and the solvent was evaporated under reduced pressure. To a solution of the residue in tetrahydrofuran (30 ml) were added N-benzylethanolamine (702 mg) and 1N aqueous sodium hydroxide solution (10 ml), and the mixture was stirred at room temperature for 0.5 hr. The reaction mixture was extracted with ethyl acetate. The extract was washed with water and brine and dried over anhydrous sodium sulfate, and the solvent was evaporated under reduced pressure. The residue was purified by silica gel column chromatography (hexane:ethyl acetate=1:1) to give the desired product (1.41 g, 90.3%) as a solid.

$^1$H-NMR (CDCl$_3$) δ; 1.40-1.50 (0.4H, m), 2.55-2.65 (0.6H, m), 3.29-3.32 (0.6H, m), 3.55-3.64 (0.6H, m), 3.64-3.69 (1.4H, m), 3.79-3.82 (1.4H, m), 4.51 (1.4H, s), 4.88 (0.6H, br s), 6.97-7.06 (1H, m), 7.12-7.15 (1H, m), 7.26-7.43 (5H, m).

(2) 4-benzyl-9-bromo-8-fluoro-3,4-dihydro-1,4-benzoxazepin-5 (2H)-one

To a solution of N-benzyl-3-bromo-2,4-difluoro-N-(2-hydroxyethyl)benzamide (4.57 g, 12.3 mmol) in N,N-dimethylformamide (60 ml) was added under ice-cooling sodium hydride (60%, 593 mg, 14.8 mmol), and the mixture was stirred for 2 hr. The reaction mixture was poured into ice water, and the mixture was extracted with ethyl acetate. The extract was washed with water and brine, and dried over anhydrous sodium sulfate, and the solvent was evaporated under reduced pressure. The residue was purified by silica gel column chromatography (hexane:ethyl acetate=2:1) to give the desired product (3.23 g, 75.0%) as an oil.

$^1$H-NMR (CDCl$_3$) δ; 3.43-3.47 (2H, m), 4.21-4.24 (2H, m), 4.82 (2H, s), 6.98-7.01 (1H, m), 7.27-7.40 (5H, m), 7.81 (1H, dd, J=6.4 Hz, 8.7 Hz).

(3) 4-benzyl-9-bromo-8-fluoro-2,3,4,5-tetrahydro-1,4-benzoxazepine

To a solution of 4-benzyl-9-bromo-8-fluoro-3,4-dihydro-1,4-benzoxazepine-5 (2H)-one (3.23 g, 9.22 mmol) in tetrahydrofuran (10 ml) was added under ice-cooling 1M borane-tetrahydrofuran solution (46 ml, 46.1 mmol), and the mixture was refluxed for 2 hr. Under ice-cooling, methanol was added, and the solvent was evaporated under reduced pressure. 6N hydrochloric acid (46 ml) was added, and the mixture was stirred at 100° C. for 1 hr. The solution was basified with 8N sodium hydroxide solution, and the mixture was extracted with ethyl acetate. The extract was washed with water and brine, and dried over anhydrous sodium sulfate, and the solvent was evaporated under reduced pressure. The residue was purified by silica gel column chromatography (hexane:ethyl acetate=2:1) to give the desired product (2.94 g, 94.8%) as an oil.

$^1$H-NMR (CDCl$_3$) δ; 3.12-3.15 (2H, m), 3.62 (2H, s), 3.80 (2H, s), 4.15-4.18 (2H, m), 6.74-6.80 (1H, m), 6.87-6.92 (1H, m), 7.25-7.35 (5H, m).

(4) 4-benzyl-9-cyclopropyl-8-fluoro-2,3,4,5-tetrahydro-1,4-benzoxazepine

A mixture of 4-benzyl-9-bromo-8-fluoro-2,3,4,5-tetrahydro-1,4-benzoxazepine (500 mg, 1.49 mmol), cyclopropylboronic acid (153 mg, 1.78 mmol), potassium carbonate (617 mg, 4.46 mmol), dioxane (3 ml) and water (3 ml) was deaerated with argon gas, and bis(triphenylphosphine)palladium (2) dichloride (52.2 mg, 0.0744 mmol) was added. The mixture was stirred under an argon atmosphere for 3 hr at 100° C. The reaction mixture was poured into water, and the mixture was extracted with ethyl acetate. The extract was washed with water and brine, and dried over anhydrous sodium sulfate. The solvent was evaporated under reduced pressure, and the residue was purified by silica gel column chromatography (hexane:ethyl acetate=2:1) to give the desired product (408 mg, 92.1%) as an oil.

$^1$H-NMR (CDCl$_3$) δ; 0.85-0.95 (2H, m), 0.95-1.05 (2H, m), 1.85-2.00 (1H, m), 3.07-3.10 (2H, m), 3.62 (2H, s), 3.74 (2H, s), 4.06-4.09 (2H, m), 6.63 (1H, dd, J=8.3 Hz, 10.4 Hz), 6.75 (1H, dd, J=6.4 Hz, 8.3 Hz), 7.26-7.35 (5H, m).

(5) 9-cyclopropyl-8-fluoro-2,3,4,5-tetrahydro-1,4-benzoxazepine hydrochloride

A solution of 4-benzyl-9-cyclopropyl-8-fluoro-2,3,4,5-tetrahydro-1,4-benzoxazepine (408 mg, 1.37 mmol) and 1-chloroethyl chloroformate (0.178 ml, 1.65 mmol) in toluene (10 ml) was stirred at 90° C. for 2 hr, and the solvent was evaporated under reduced pressure. Methanol (10 ml) was added to the residue, the mixture was stirred at 80° C. for 1 hr, and diisopropyl ether (10 ml) was added. The precipitate was collected by filtration and recrystallized from a mixed solvent of ethanol and diisopropyl ether to give the desired product (295 mg, 88.5%) as a solid.

$^1$H-NMR (CDCl$_3$) δ; 0.84-0.94 (4H, m), 1.85-2.00 (1H, m), 3.44-3.47 (2H, m), 4.18-4.21 (2H, m), 4.25 (2H, s), 6.93 (1H, dd, J=8.5 Hz, 10.6 Hz), 7.29 (1H, dd, J=6.2 Hz, 8.5 Hz), 9.43 (2H, br s).

Example 71

8-fluoro-9-furan-3-yl-2,3,4,5-tetrahydro-1,4-benzoxazepine hydrochloride (1) 4-benzyl-8-fluoro-9-furan-3-yl-2,3,4,5-tetrahydro-1,4-benzoxazepine A mixture of 4-benzyl-9-bromo-8-fluoro-2,3,4,5-tetrahydro-1,4-benzoxazepine (500 mg, 1.49 mmol), 3-furanboronic acid (250 mg, 2.23 mmol), potassium carbonate (206 mg, 1.49 mmol), tetrakis(triphenylphosphine)palladium(0) (172 mg, 0.149 mmol), 1,2-dimethoxyethane (5 ml) and water (0.5 ml) was stirred under an argon atmosphere at 100° C. for 3 hr. The reaction mixture was poured into water, and the mixture was extracted with ethyl acetate. The extract was washed with water and brine, and dried over anhydrous sodium sulfate. The solvent was evaporated under reduced pressure, and the residue was purified by silica gel column chromatography (hexane:ethyl acetate=1:1) and preparative HPLC to give the desired product (104 mg, 21.7%) as an oil.
$^1$H-NMR (CDCl$_3$) δ; 3.11-3.14 (2H, m), 3.65 (2H, s), 3.81 (2H, s), 4.08-4.11 (2H, m), 6.76-6.91 (3H, m), 7.26-7.35 (5H, m), 7.49 (1H, s), 7.94 (1H, s).

(2) 8-fluoro-9-furan-3-yl-2,3,4,5-tetrahydro-1,4-benzoxazepine hydrochloride

A solution of 4-benzyl-8-fluoro-9-furan-3-yl-2,3,4,5-tetrahydro-1,4-benzoxazepine (104 mg, 0.323 mmol), 1-chloroethyl chloroformate (0.0418 ml, 0.387 mmol) in toluene (2 ml) was stirred at 90° C. for 2 hr, and the solvent was evaporated under reduced pressure. Water and 1N sodium hydroxide were added to the residue, and the mixture was extracted with ethyl acetate. The extract was washed with water and brine, and dried over anhydrous sodium sulfate. The solvent was evaporated under reduced pressure, and the residue was purified by NH silica gel column chromatography (hexane:ethyl acetate=4:1). To ethyl acetate solution of the residue was added 4N hydrogen chloride-ethyl acetate. The precipitate was collected by filtration and was recrystallized from a mixed solvent of ethanol and diisopropyl ether to give the desired product (28 mg, 32.3%) as a solid.
$^1$H-NMR (CDCl$_3$) δ; 3.50-3.53 (2H, m), 4.25-4.28 (2H, m), 4.34 (2H, s), 6.86 (1H, s), 7.14 (1H, dd, J=8.6 Hz, 10.5 Hz), 7.44 (1H, dd, J=6.4 Hz, 8.6 Hz), 7.82 (1H, s), 8.09 (1H, s), 9.29 (2H, br s).

Example 72

9-(4-methylphenyl)-2,3,4,5-tetrahydro-1,4-benzoxazepine trifluoroacetate

A solution (500 µl; 100 µmol) of tert-butyl 9-bromo-2,3-dihydro-1,4-benzoxazepine-4(5H)-carboxylate (concentration 0.2 mol) in dimethoxyethane, a solution (500 µl; 110 µmol) of 4-methylphenylboronic acid (0.22 mol concentration) in dimethoxyethane, tetrakistriphenylphosphine palladium(0) (12 mg; 10 µmol) and 2N aqueous potassium carbonate solution (150 µl: 300 µmol) were mixed at room temperature. The reaction container was purged with argon and exposed to the irradiation by a microwave reactor apparatus at 150° C. for 8 min. Water (2 ml) was added to the reaction mixture, and the mixture was extracted with ethyl acetate (3 ml). The ethyl acetate solvent was evaporated under reduced pressure, the residue was dissolved in dimethylsulfoxide (1 ml) and purified by preparative HPLC to give an N-protected form of the title compound. Then, trifluoroacetic acid (1.5 ml) was added to the protected form, and the mixture was stirred at room temperature for 14 hr. Trifluoroacetic acid was evaporated under reduced pressure, and the residue was dissolved in water (1 ml) and purified by high-polar preparative HPLC to give the title compound as trifluoroacetate.
yield: 9.4 mg
LC-MS analysis: purity 97%
MS (ESI+): 240 (M+H)

Examples 73-106

Using tert-butyl 9-bromo-2,3-dihydro-1,4-benzoxazepine-4(5H)-carboxylate and the corresponding boronic acid reagent and in the same manner as in Example 72, the following title compounds were obtained.

Example 73

9-(4-fluorophenyl)-2,3,4,5-tetrahydro-1,4-benzoxazepine trifluoroacetate yield: 12.6 mg
LC-MS analysis: purity 98%
MS (ESI+): 244 (M+H)

Example 74

4-(2,3,4,5-tetrahydro-1,4-benzoxazepine-9-yl)benzonitrile trifluoroacetate yield: 13.4 mg
LC-MS analysis: purity 100%
MS (ESI+): 251 (M+H)

Example 75

9-(4-methoxyphenyl)-2,3,4,5-tetrahydro-1,4-benzoxazepine trifluoroacetate yield: 11.3 mg
LC-MS analysis: purity 99%
MS (ESI+): 256 (M+H)

Example 76

4-(2,3,4,5-tetrahydro-1,4-benzoxazepine-9-yl)benzamide trifluoroacetate yield: 10.7 mg
LC-MS analysis: purity 100%
MS (ESI+): 269 (M+H)

Example 77

9-(1,3-benzodioxoyl-5-yl)-2,3,4,5-tetrahydro-1,4-benzoxazepine trifluoroacetate yield: 11.3 mg
LC-MS analysis: purity 97%
MS (ESI+): 270 (M+H)

Example 78

9-[4-(methylsulfanyl)phenyl]-2,3,4,5-tetrahydro-1,4-benzoxazepine trifluoroacetate yield: 9.6 mg
LC-MS analysis: purity 98%
MS (ESI+): 272 (M+H)

Example 79

9-(1-benzothiophen-2-yl)-2,3,4,5-tetrahydro-1,4-benzoxazepine trifluoroacetate yield: 15.5 mg
LC-MS analysis: purity 98%
MS (ESI+): 282 (M+H)

Example 80

N-[3-(2,3,4,5-tetrahydro-1,4-benzoxazepin-9-yl)phenyl]acetamide trifluoroacetate yield: 14.2 mg
LC-MS analysis: purity 99%
MS (ESI+): 283 (M+H)

Example 81 methyl 4-(2,3,4,5-tetrahydro-1,4-benzoxazepin-9-yl)benzoate trifluoroacetate yield: 12.0 mg
LC-MS analysis: purity 97%
MS (ESI+): 284 (M+H)

Example 82

9-(2,4-dimethoxyphenyl)-2,3,4,5-tetrahydro-1,4-benzoxazepine trifluoroacetate yield: 7.7 mg
LC-MS analysis: purity 99%
MS (ESI+): 286 (M+H)

Example 83

9-[4-(trifluoromethoxy)phenyl]-2,3,4,5-tetrahydro-1,4-benzoxazepine trifluoroacetate yield: 14.6 mg
LC-MS analysis: purity 97%
MS (ESI+): 310 (M+H)

Example 84

9-(3-chloro-2-methylphenyl)-2,3,4,5-tetrahydro-1,4-benzoxazepine trifluoroacetate yield: 5.6 mg
LC-MS analysis: purity 98%
MS (ESI+): 274 (M+H)

Example 85

9-[2-(1-methylethoxy)phenyl]-2,3,4,5-tetrahydro-1,4-benzoxazepine trifluoroacetate yield: 10.9 mg
LC-MS analysis: purity 98%
MS (ESI+): 284 (M+H)

Example 86

9-(2-ethoxyphenyl)-2,3,4,5-tetrahydro-1,4-benzoxazepine trifluoroacetate yield: 9.2 mg
LC-MS analysis: purity 97%
MS (ESI+): 270 (M+H)

Example 87

2-(2,3,4,5-tetrahydro-1,4-benzoxazepin-9-yl)phenol trifluoroacetate yield: 9.2 mg
LC-MS analysis: purity 98%
MS (ESI+): 242 (M+H)

Example 88

9-[3-(benzyloxy)phenyl]-2,3,4,5-tetrahydro-1,4-benzoxazepine trifluoroacetate yield: 6.4 mg
LC-MS analysis: purity 91%
MS (ESI+): 332 (M+H)

Example 89

N-[2-(2,3,4,5-tetrahydro-1,4-benzoxazepin-9-yl)phenyl]acetamide trifluoroacetate yield: 18.0 mg
LC-MS analysis: purity 98%
MS (ESI+): 283 (M+H)

Example 90

9-(2,4-dichlorophenyl)-2,3,4,5-tetrahydro-1,4-benzoxazepine trifluoroacetate yield: 17.4 mg
LC-MS analysis: purity 99%
MS (ESI+): 295 (M+H)

Example 91

9-(2-ethoxy-5-methylphenyl)-2,3,4,5-tetrahydro-1,4-benzoxazepine trifluoroacetate yield: 14.0 mg
LC-MS analysis: purity 98%
MS (ESI+): 284 (M+H)

Example 92

N-[2-(2,3,4,5-tetrahydro-1,4-benzoxazepin-9-yl)phenyl]methanesulfoneamide trifluoroacetate yield: 20.5 mg
LC-MS analysis: purity 99%
MS (ESI+): 319 (M+H)

Example 93

9-(2-nitrophenyl)-2,3,4,5-tetrahydro-1,4-benzoxazepine trifluoroacetate yield: 4.0 mg
LC-MS analysis: purity 96%
MS (ESI+): 271 (M+H)

Example 94

9-(2-methoxypyridin-3-yl)-2,3,4,5-tetrahydro-1,4-benzoxazepine ditrifluoroacetate yield: 16.2 mg
LC-MS analysis: purity 97%
MS (ESI+): 257 (M+H)

Example 95 methyl 2-(2,3,4,5-tetrahydro-1,4-benzoxazepin-9-yl)benzoate trifluoroacetate yield: 10.7 mg
LC-MS analysis: purity 99%
MS (ESI+): 284 (M+H)

Example 96

9-dibenzo[b,d]furan-4-yl-2,3,4,5-tetrahydro-1,4-benzoxazepine trifluoroacetate yield: 13.4 mg
LC-MS analysis: purity 99%
MS (ESI+): 334 (M+H)

Example 97

9-(1-methyl-1H-pyrazol-4-yl)-2,3,4,5-tetrahydro-1,4-benzoxazepine ditrifluoroacetate yield: 3.7 mg
LC-MS analysis: purity 97%
MS (ESI+): 230 (M+H)

Example 98

9-(1-benzothiophen-3-yl)-2,3,4,5-tetrahydro-1,4-benzoxazepine trifluoroacetate yield: 14.8 mg
LC-MS analysis: purity 98%
MS (ESI+): 282 (M+H)

Example 99

9-[(E)-2-phenylethenyl]-2,3,4,5-tetrahydro-1,4-benzoxazepine trifluoroacetate yield: 6.1 mg
LC-MS analysis: purity 99%
MS (ESI+): 252 (M+H)

Example 100

9-naphthalen-1-yl-2,3,4,5-tetrahydro-1,4-benzoxazepine trifluoroacetate yield: 14.8 mg
LC-MS analysis: purity 100%
MS (ESI+): 276 (M+H)

Example 101

9-(4-chloro-2-methylphenyl)-2,3,4,5-tetrahydro-1,4-benzoxazepine trifluoroacetate yield: 12.7 mg
LC-MS analysis: purity 100%
MS (ESI+): 274 (M+H)

Example 102

9-(4-methoxy-2-methylphenyl)-2,3,4,5-tetrahydro-1,4-benzoxazepine trifluoroacetate yield: 9.5 mg
LC-MS analysis: purity 90%
MS (ESI+): 270 (M+H)

Example 103

9-(4-nitrophenyl)-2,3,4,5-tetrahydro-1,4-benzoxazepine trifluoroacetate yield: 18.4 mg
LC-MS analysis: purity 90%
MS (ESI+): 271 (M+H)

Example 104

9-(3,4-difluorophenyl)-2,3,4,5-tetrahydro-1,4-benzoxazepine trifluoroacetate yield: 15.1 mg
LC-MS analysis: purity 100%
MS (ESI+): 262 (M+H)

Example 105

9-isoquinolin-4-yl-2,3,4,5-tetrahydro-1,4-benzoxazepine ditrifluoroacetate yield: 14.8 mg
LC-MS analysis: purity 97%
MS (ESI+): 277 (M+H)

Example 106

9-(1H-pyrazol-4-yl)-2,3,4,5-tetrahydro-1,4-benzoxazepine ditrifluoroacetate yield: 1.2 mg
LC-MS analysis: purity 97%
MS (ESI+): 216 (M+H)

The compounds synthesized in the Examples are shown in Table 1-Table 7 (in the Tables, salt form is abbreviated).

TABLE 1
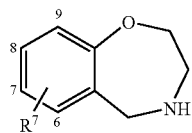
| Ex. No. | position of substitution of R⁷ | R⁷ |
|---|---|---|
| 1 | 8 | morpholin-4-yl |
| 2 | 8 | pyrrolidin-1-yl |
| 3 | 8 | piperidin-1-yl |
| 4 | 8 | N(CH₃)(CH(CH₃)₂) |
| 5 | 8 | N(CH₂CH₃)₂ |
| 6 | 8 | N(CH₃)(CH₂CH₃) |
| 7 | 9 | pyrrolidin-1-yl |
| 8 | 8 | phenyl |
| 9 | 9 | phenyl |
| 10 | 9 | 2-chlorophenyl |
| 11 | 9 | 2-methylphenyl |
| 12 | 9 | 2-(trifluoromethyl)phenyl |
| 13 | 9 | 2-methoxyphenyl |
| 14 | 9 | 2-fluorophenyl |
| 15 | 9 | furan-3-yl |
| 16 | 9 | thiophen-3-yl |
| 17 | 9 | 3-(trifluoromethyl)phenyl |
| 18 | 9 | 4-(trifluoromethyl)phenyl |
| 19 | 9 | furan-2-yl |
| 20 | 9 | 2-(methylthio)phenyl |

TABLE 2

[Structure: benzoxazepine core with R⁷ at position 6/7, O at 1, positions 8,9 on benzene, NH in 7-membered ring]

| Ex. No. | position of substitution of R⁷ | R⁷ |
|---|---|---|
| 41 | 9 | 2,3-dimethylfuran-yl |
| 42 | 9 | norbornyl |
| 43 | 9 | 3,4,5-trimethylisoxazol-yl |
| 44 | 9 | 3-fluorophenyl |
| 45 | 9 | CH₃CH=CH–CH₂– (but-2-enyl) |
| 46 | 9 | 4-methylisoxazol-yl |
| 47 | 9 | CH₃CH₂CH₂ |
| 48 | 9 | cis-CH=CH–CH₃ |
| 49 | 9 | CH₃CH₂ |
| 50 | 9 | CH₃OCH₂CH₂CH₂ |
| 51 | 9 | (CH₃)₂CH–CH(CH₃)– (2-methylbutan-2-yl type) |
| 52 | 9 | 2,4,5-trimethylthiazolyl |
| 53 | 9 | CH₃O–CH₂–CH=CH– |

TABLE 2-continued

| Ex. No. | position of substitution of R⁷ | R⁷ |
|---|---|---|
| 54 | 9 | (H₃C)₂CH– (isopropyl) |
| 55 | 9 | tetrahydrofuran-3-yl |
| 56 | 9 | 1-(pyrrolidin-1-yl)ethan-1-one |
| 57 | 9 | 1-methylpyrrolidin-2-one-yl |
| 58 | 9 | 3,3-difluoro-1-methylpyrrolidin-yl |
| 59 | 9 | CH(CH₃)CF₃ |
| 60 | 9 | –C(=O)OH |

TABLE 3

[Structure: benzoxazepine core with R⁷]

| Ex. No. | position of substitution of R⁷ | R⁷ |
|---|---|---|
| 21 | 9 | thiophen-2-yl |

TABLE 3-continued

Structure: 2,3,4,5-tetrahydro-1,4-benzoxazepine core with positions labeled 6, 7, 8, 9 on the benzene ring (O at position adjacent to 9, NH in the seven-membered ring), with R⁷ substituent.

| Ex. No. | position of subsitution of R⁷ | R⁷ |
|---|---|---|
| 22 | 9 | 2-acetylphenyl (phenyl with -C(O)CH₃ ortho) |
| 23 | 9 | pyridin-3-yl |
| 24 | 9 | pyridin-4-yl |
| 25 | 9 | 2-(trifluoromethoxy)phenyl |
| 26 | 9 | cyclopent-1-en-1-yl |
| 27 | 8 | 4-chlorophenyl |
| 28 | 7 | phenyl |
| 29 | 6 | phenyl |
| 30 | 6 | morpholin-4-yl |
| 31 | 9 | piperidin-1-yl |
| 32 | 8 | (2R,6S)-2,6-dimethylmorpholin-4-yl |
| 33 | 7 | 2-methylphenyl |
| 34 | 7 | morpholin-4-yl |
| 35 | 9 | morpholin-4-yl |
| 36 | 8 | bis(2-methoxyethyl)amino (N(CH₂CH₂OCH₃)₂) |
| 37 | 9 | cyclohex-1-en-1-yl |
| 38 | 9 | cyclohexyl |
| 39 | 9 | cyclopentyl |
| 40 | 9 | 5-methylfuran-3-yl (2-methyl-4-furyl) |

TABLE 4
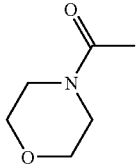
| Ex. No. | position of subsitution of R⁷ | R⁷ |
|---|---|---|
| 61 | 9 | 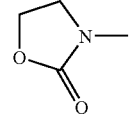 |
| 62 | 9 | 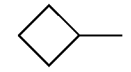 |
| 63 | 9 | 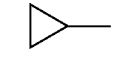 |
| 64 | 9 | 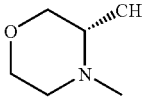 |
| 65 | 8 | 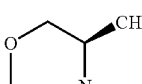 |
| 66 | 8 | 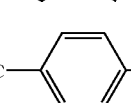 |
| 72 | 9 | 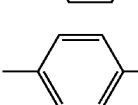 |
| 73 | 9 | 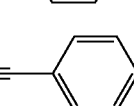 |
| 74 | 9 | 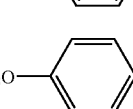 |
| 75 | 9 | 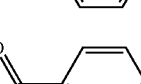 |
| 76 | 9 | 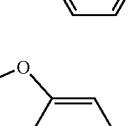 |
| 77 | 9 | 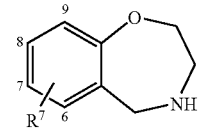 |
TABLE 4-continued
| Ex. No. | position of subsitution of R⁷ | R⁷ |
|---|---|---|
| 78 | 9 |  |
| 79 | 9 |  |
| 80 | 9 | 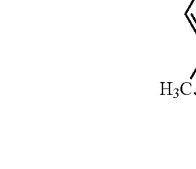 |
| 81 | 9 | 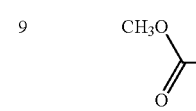 |
| 82 | 9 |  |
| 83 | 9 |  |
| 84 | 9 |  |
| 85 | 9 |  |

TABLE 5

| Ex. No. | position of substitution of R⁷ | R⁷ |
|---|---|---|
| 86 | 9 | 2-methylphenyl ethyl ether (OCH₂CH₃) |
| 87 | 9 | 2-methylphenol (OH) |
| 88 | 9 | 3-methylphenyl benzyl ether |
| 89 | 9 | 2-methylphenyl acetamide (NHC(O)CH₃) |
| 90 | 9 | 2,4-dichlorophenyl (methyl) |
| 91 | 9 | 2,4-dimethylphenyl ethyl ether |
| 92 | 9 | 2-methylphenyl methanesulfonamide (NHSO₂CH₃) |
| 93 | 9 | 2-methylnitrobenzene (NO₂) |

TABLE 5-continued

| Ex. No. | position of substitution of R⁷ | R⁷ |
|---|---|---|
| 94 | 9 | 3-methyl-2-methoxypyridine |
| 95 | 9 | methyl 2-methylbenzoate |
| 96 | 9 | methyldibenzofuran |
| 97 | 9 | 1,4-dimethylpyrazole |
| 98 | 9 | 3-methylbenzothiophene |
| 99 | 9 | styryl (phenyl-CH=CH-) |
| 100 | 9 | 1-methylnaphthalene |
| 101 | 9 | 4-chloro-2-methylphenyl (methyl) |

TABLE 6

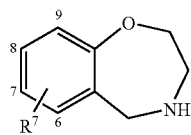

| Ex. No. | position of substution of R⁷ | R⁷ |
|---|---|---|
| 102 | 9 | 4-methoxy-2,3-dimethylphenyl (CH₃O, CH₃) |
| 103 | 9 | 4-nitrophenyl (O₂N-) |
| 104 | 9 | 3,4-difluorophenyl (F, F) |
| 105 | 9 | isoquinolin-4-yl |
| 106 | 9 | 1H-pyrazol-4-yl |

TABLE 7

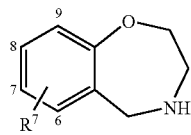

| Ex. No. | position of substution of R₇ | R⁷ | position of substution of R⁸ | R⁸ |
|---|---|---|---|---|
| 67 | 9 | furan-3-yl | 6 | F— |
| 68 | 9 | isopropyl | 6 | F— |
| 69 | 9 | cyclopropyl | 6 | F— |

TABLE 7-continued

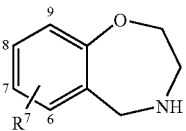

| Ex. No. | position of substution of R₇ | R⁷ | position of substution of R⁸ | R⁸ |
|---|---|---|---|---|
| 70 | 9 | cyclopropyl | 8 | F— |
| 71 | 9 | furan-3-yl | 8 | F— |

Formulation Example 1

| | |
|---|---|
| (1) compound of Example 1 | 10 mg |
| (2) Lactose | 60 mg |
| (3) Cornstarch | 35 mg |
| (4) hydroxypropylmethylcellulose | 3 mg |
| (5) Magnesium stearate | 2 mg |

A mixture of 10 mg of the compound obtained in Example 1, 60 mg of lactose and 35 mg of corn starch is granulated using 0.03 mL of an aqueous solution of 10 wt % hydroxypropylmethylcellulose (3 mg as hydroxypropylmethylcellulose), and then dried at 40° C. and sieved. The obtained granules are mixed with 2 mg of magnesium stearate and compressed. The obtained uncoated tablets are sugar-coated with an aqueous suspension of sucrose, titanium dioxide, talc and gum arabic. The thus-coated tablets are glazed with beeswax to give finally-coated tablets.

Formulation Example 2

| | |
|---|---|
| (1) compound of Example 1 | 10 mg |
| (2) Lactose | 70 mg |
| (3) Cornstarch | 50 mg |
| (4) Soluble starch | 7 mg |
| (5) Magnesium stearate | 3 mg |

The compound (10 mg) obtained in Example 1 and 3 mg of magnesium stearate are granulated with 0.07 mL of an aqueous solution of soluble starch (7 mg as soluble starch), dried, and mixed with 70 mg of lactose and 50 mg of corn starch. The mixture is compressed to give tablets.

Reference Formulation Example 1

| | |
|---|---|
| (1) Rofecoxib | 5.0 mg |
| (2) Sodium chloride | 20.0 mg |
| (3) Distilled water | amount to make total volume 2.0 mL |

Rofecoxib (5.0 mg) and 20.0 mg of Sodium chloride are dissolved in distilled water, and water is added to make the total volume 2.0 mL. The solution is filtered, and filled into 2 mL of ampoule under sterile condition. The ampoule is sterilized, and then sealed to give a solution for injection.

Reference Formulation Example 2

| | |
|---|---|
| (1) Rofecoxib | 50 mg |
| (2) Lactose | 34 mg |
| (3) Cornstarch | 10.6 mg |
| (4) Cornstarch (paste) | 5 mg |
| (5) Magnesium stearate | 0.4 mg |
| (6) Calcium carboxymethylcellulose | 20 mg |
| total | 120 mg |

The above-mentioned (1) to (6) are mixed according to a conventional method and the mixture is tableted by a tableting machine to give a tablet.

Formulation Example 3

The formulation prepared in Formulation Example 1 or 2, and the formulation prepared in Reference Formulation Example 1 or 2 are combined.

Experimental Example 1

The serotonin $5\text{-HT}_{2C}$ receptor agonist activity of the Example compounds was evaluated based on the changes in the intracellular calcium concentration by the following method. After transcription, $5\text{-HT}_{2C}$ undergoes RNA editing of the second intracellular loop, which results in the change of three amino acids and 14 receptor isoforms. $5\text{-HT}_{2C}$ stably expressing CHO cell that expresses isoform type VSV stably was purchased from Euroscreen S.A., and cultured in Ultra-CHO (BioWhittaker) medium containing 1% dialyzed bovine serum and 400 μg/mL G418. The cells were plated in a 384-well black clear bottom plate (PE Biosystems) at 5000 cells/well, cultured for 24 hr in a $CO_2$ incubator, and changes in the intracellular calcium concentration mediated by the $5\text{-HT}_{2C}$ receptor were evaluated using Calcium Kit-Fluo 3 (Dojindo Laboratories). A calcium kit buffer containing 2.5 mM probenecid, 0.04% Pluronic F-127 and 2.5 μg Fluo-3 AM (calcium indicator fluorescent dye) was prepared and used as a Fluo-3 loading solution (contained in Dojindo Laboratories Calcium Kit). The loading solution was incubated at 37° C., the medium in the wells of the cell culture plate was removed, and the loading solution was added to each well by 40 μL. The cells were reacted at 37° C. for 1 hr to allow uptake of Fluo-3 AM into the cells and washed. The Example compound was diluted with a calcium kit buffer, and dispensed to each well of the 384-well plate (REMP) by 40 μL to give a Example compound plate. The cell culture plate and test compound plate were set on a Fluometric Imaging Plate Reader (FLIPR, Molecular Devices), and changes in the intracellular calcium concentration were measured. An increase in the fluorescence intensity of Fluo-3 matches with an increase in the intracellular calcium concentration mediated by a receptor. The changes in the intracellular fluorescence intensity were measured every second with a CCD camera of FLIPR and, after measurement for 5 seconds before addition of the compound, a diluted solution of the Example compound was added by 20 μL to each well of the cell culture plate using an automatic dispenser in FLIPR.

The agonist activity was evaluated based on the difference in the fluorescence level obtained by subtracting the fluorescence intensity before addition of the compound from the maximum fluorescence intensity after the addition thereof. The activity of the test compound is shown by the ratio relative to the maximum response by 5-HT (Tables 8 and 9).

TABLE 8

| Ex. No. | ratio to maximum response by 5-HT (1 μM) |
|---|---|
| 1 | 95.4 |
| 2 | 93.1 |
| 3 | 94.3 |
| 4 | 100.2 |
| 5 | 91.9 |
| 6 | 101.6 |
| 7 | 107.2 |
| 9 | 93.1 |
| 10 | 94.0 |
| 11 | 92.7 |
| 12 | 93.6 |
| 15 | 96.2 |
| 16 | 99.1 |
| 26 | 100.8 |

TABLE 9

| Ex. No. | ratio to maximum response by 5-HT (1 μM) |
|---|---|
| 54 | 107.4 |
| 55 | 102.7 |
| 58 | 95.5 |
| 59 | 95.2 |
| 63 | 97.6 |
| 64 | 94.6 |

From Tables 8 and 9, it found that the compound of the present invention has a superior serotonin $5\text{-HT}_{2C}$ receptor agonistic activity.

Experimental Example 2

SD female rats (body weight 190-310 g) were anesthetized with urethane (Wako Pure Chemical Industries, Ltd.), and the spinal cord was cut at T8-9 level to eliminate the micturition reflex. During the operation, halothane (Takeda Pharmaceutical Company Limited) anesthesia was added as necessary. The abdomen was opened, the bladder neck was ligated with a suture thread, and then, the hypogastric nerve and the pudendal nerves were bilaterally cut. In some animals, the nerves to the iliococcygeus muscle and the pubococcygeus muscle were also cut bilaterally. A catheter (PE-90, Clay Adams) was inserted in the bladder, and the other end of the bladder catheter was connected to the pressure transducer and an aquatic reservoir (60 ml syringe) of saline via a three-way cock. A microchip transducer catheter (SPR-524, Millar Instruments Inc.) was inserted from the urethral orifice toward the bladder, and the transducer part was adjusted to be in the urethra at 10.0-15.0 mm from the urethral orifice using the scale on the catheter surface.

The topical changes in the urethral pressure (hereinafter to be referred to as urethral pressure for convenience) measured by the microchip transducer were input into a computer via an amplifier (blood pressure amplification unit AP-641G; NIHON KOHDEN CORPORATION) and a data analyzer (MP-100; biopack; sampled at 500 Hz), and recorded on a hard disk. The bladder pressure was rapidly increased to 50 cm $H_2O$ for 30 seconds by raising the position of the saline aquatic reservoir by 50 cm, and changes in the urethral pressure were observed. The response of the urethra induced by the increased bladder pressure was measured 3 times, and the average value of the last two measures was taken as the value before drug administration. The evaluation item was reflective urethral closure response, and the average urethral pressure per second was calculated by a smoothing treatment of the recorded value at 500 points. Then, the value immediately before bladder pressure increase was subtracted from the maximum value during bladder pressure increase and taken as the urethral closing responses.

Using the rat deprived of the micturition reflex by cutting the spinal cord, the hypogastric nerve and the pudendal nerves controlling the internal urethral sphincter, external urethral sphincter and coccygeus muscle were cut, the bladder pressure was rapidly raised from 0 cm $H_2O$ to 50 cm $H_2O$. As a result, a urethral pressure increasing response (urethral closure response) was observed. The mean±SEM of the urethral closure response of 20 rats subjected to the test was 5.6±0.7 cm $H_2O$.

In the rat whose nerves to the iliococcygeus muscle and the pubococcygeus muscle were bilaterally cut in addition to the hypogastric nerve and pudendal nerves, mean±SEM of the urethral closure response due to the increased bladder pressure was 1.3±0.4 cm $H_2O$ (4 rats), showing a significant decrease as compared to the rats free of cutting of the nerves to the iliococcygeus muscle and the pubococcygeus muscle ($P<0.05$, two-tail test, Student's t-test). These results reveal that the urethral closure response obtained by rapidly raising the bladder pressure of the rat whose hypogastric nerve and pudendal nerves were bilaterally cut from 0 cm $H_2O$ to 50 cm $H_2O$ is mainly caused by the contractile responses of the iliococcygeus muscle and the pubococcygeus muscle.

Experimental Example 3

SD female rats (body weight 230-274 g) were anesthetized with urethane (Wako Pure Chemical Industries, Ltd.), and the spinal cord was cut at T8-9 level to eliminate the micturition reflex. During the operation, halothane (Takeda Pharmaceutical Company Limited) anesthesia was added as necessary. The abdomen was opened, the bladder neck was ligated with a suture thread, and then, the hypogastric nerve and the pudendal nerves were bilaterally cut. A catheter (PE-90, Clay Adams) was inserted in the bladder, and the other end of the bladder catheter was connected to the pressure transducer and an aquatic reservoir (60 ml syringe) of saline via a three-way cock. A microchip transducer catheter (SPR-524, Millar Instruments Inc.) was inserted from the urethral orifice toward the bladder, and the transducer part was adjusted to be in the urethra at 10.0-15.0 mm from the urethral orifice using the scale on the catheter surface.

The topical changes in the urethral pressure (hereinafter to be referred to as urethral pressure for convenience) measured by the microchip transducer were input into a computer via an amplifier (BP Amp; ADINSTRUMENTS) and a data analyzer (Powerlab 4/25; ADINSTRUMENTS; sampled at 1000 Hz), and recorded on a hard disk. The bladder pressure was rapidly increased to 50 cm $H_2O$ for 30 seconds by raising the position of the saline aquatic reservoir by 50 cm, and changes in the urethral pressure were observed. The response of the urethra induced by the increased bladder pressure was repeatedly measured, and the average value of the last two measures was taken as the value before drug administration. The evaluation item was reflective urethral closure response, and the average urethral pressure for 30 seconds before increasing the bladder pressure and 30 seconds when the bladder pressure was raised to 50 cm was calculated. Then, the value before bladder pressure increase was subtracted from the value during bladder pressure increase and taken as the urethral closure response. The value before drug administration was measured, the compound of Example 63 was intravenously administered and, 10 min later, the urethral closure response was evaluated again. The drug was dissolved in saline with dimethylformamide, and intravenously administered at 1 ml/kg.

Using a female spinal cord transected rat whose hypogastric nerve and pudendal nerves were bilaterally cut, the effects of the compound of Example 63 on the urethral pressure increasing reaction (urethral closure response) induced by rapidly increasing the bladder pressure from 0 cm $H_2O$ to 50 cm $H_2O$ was investigated. As a result, the present compound significantly increased the urethral closure response induced by increased bladder pressure (Table 10 and FIG. 1). These results reveal that the urethral closure response by the iliococcygeus muscle and the pubococcygeus muscle, which are pelvic floor muscles, is enhanced by the compound of the present invention.

TABLE 10

Effects of compound on the urethral closure response induced by increased bladder pressure in female spinal cord transected rat whose hypogastric nerve and pudendal nerves were bilaterally cut

| | Dose (mg/kg, i.v.) | n | Urethral closure response (cm $H_2O$) | | |
|---|---|---|---|---|---|
| | | | Before drug administration | After drug administration | Increase |
| Vehicle | — | 4 | 2.0 ± 0.8 | 1.9 ± 0.7 | −0.1 ± 0.1 |
| Compound | 3 | 6 | 1.8 ± 0.5 | 6.2 ± 0.9 | 4.4 ± 0.7*** |

***$P<0.001$, the difference between before and after drug administration in urethral closure response was compared with vehicle administration group (two-tail test, Student's t-test)

INDUSTRIAL APPLICABILITY

Since compound (I) and compound (I') of the present invention and a prodrug thereof have a superior serotonin 5-$HT_{2C}$ receptor activation action, they are useful as safe drugs for the prophylaxis or treatment of any serotonin 5-$HT_{2C}$-related diseases, for example, lower urinary tract symptom (including stress urinary incontinence, mixed urinary incontinence, post-micturition dribble), obesity or pelvic organ prolapse (anterior vaginal wall prolapse, posterior vaginal wall prolapse, uterine prolapse, prolapse of the apical segment of the vagina, rectal prolapse [rectocele], enterocele, cystocele, urethral prolapse etc.), and the like.

This application is based on a patent application No. 2007-057857 filed in Japan, the contents of which are incorporated in full herein by this reference.

The invention claimed is:
1. A compound represented by the formula (I):

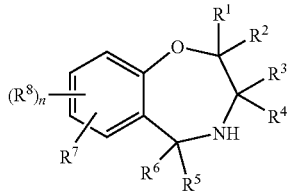

wherein
$R^1$, $R^2$, $R^3$ and $R^4$ are the same or different and each is
(1) a hydrogen atom,
(2) a halogen atom,
(3) a group via a carbon atom,
(4) a group via a nitrogen atom,
(5) a group via an oxygen atom, or
(6) a group via a sulfur atom;
$R^5$ and $R^6$ are the same or different and each is
(1) a hydrogen atom,
(2) a halogen atom,
(3) a cyano group,
(4) an alkyl group optionally having substituent(s),
(5) an alkenyl group optionally having substituent(s),
(6) an alkynyl group optionally having substituent(s),
(7) a cycloalkyl group optionally having substituent(s),
(8) a cycloalkenyl group optionally having substituent(s),
(9) a cycloalkylalkyl group optionally having substituent(s),
(10) a cycloalkenylalkyl group optionally having substituent(s),
(11) an aralkyl group optionally having substituent(s),
(12) a cycloalkanedienyl group optionally having substituent(s),
(13) a heterocyclic group bonded via a carbon atom, which optionally has substituent(s),
(14) a group via a nitrogen atom,
(15) a group via an oxygen atom, or
(16) a group via a sulfur atom;
$R^7$ is
(1) a mono-alkylamino group,
(2) a di-alkylamino group optionally having substituent(s),
(3) a non-aromatic heterocyclic group optionally having substituent(s),
(4) an aryl group optionally having substituent(s),
(5) a cycloalkyl group optionally having substituent(s),
(6) a cycloalkenyl group optionally having substituent(s),
(7) an aromatic heterocyclic group optionally having substituent(s),
(8) a $C_{2-6}$ alkyl group,
(9) an alkoxy-alkyl group,
(10) a halo-$C_{2-6}$ alkyl group,
(11) an alkenyl group,
(12) an aryl-alkenyl group,
(13) an alkoxy-alkenyl group, or
(14) a non-aromatic heterocyclyl-carbonyl group;
$R^8$ is
(1) a halogen atom,
(2) a group via a carbon atom,
(3) a group via a nitrogen atom,
(4) a group via an oxygen atom, or
(5) a group via a sulfur atom;
n is an integer of 0 to 3;
the group via a sulfur atom is
(1) a mercapto group, or
(2) a group represented by the formula $-S(O)_m R^b$ wherein m is an integer of 0 to 2, and $R^b$ is a group via a carbon atom or a group via a nitrogen atom;
the group via a nitrogen atom is
(1) a nitro group,
(2) an amino group optionally having substituents) selected from the group consisting of a group bonded via a carbon atom, and a group represented by the formula $-SO_2 R^a$ wherein $R^a$ is a group bonded via a carbon atom, or
(3) a heterocyclic group bonded via a nitrogen atom, which optionally has substituent(s);
the group via an oxygen atom is a hydroxy group optionally having a group via a carbon atom; and
the group via a carbon atom is
(1) a cyano group,
(2) an alkyl group optionally having substituent(s),
(3) an alkenyl group optionally having substituent(s),
(4) an alkynyl group optionally having substituent(s),
(5) a cycloalkyl group optionally having substituent(s),
(6) a cycloalkyenyl group optionally having substituent(s),
(7) an aryl group optionally having substituent(s),
(8) a cycloalkylalkyl group optionally having substituent(s),
(9) a cycloalkenylalkyl group optionally having substituent(s),
(10) an aralkyl group optionally having substituent(s),
(11) a cycloalkanedienyl group optionally having substituent(s), or
(12) a heterocyclic group bonded via a carbon atom, which optionally has substituent(s);
[excluding 9-chloro-7-(1,1-dimethylethyl)-2,3,4,5-tetrahydro-1,4-benzoxazepine and N-[[(5S)-2-oxo-3-(2,3,4,5-tetrahydro-1,4-benzoxazepin-7-yl)-5-oxazolidinyl]methyl]acetamide],
or a salt thereof.

2. The compound of claim 1, which is represented by the formula (Ia):

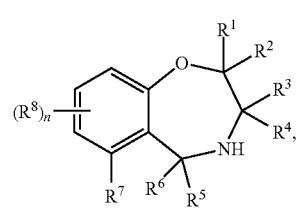

wherein each symbol is as defined in claim 1.

3. The compound of claim 1, which is represented by the formula (Ib):

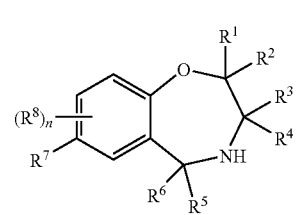

wherein each symbol is as defined in claim 1.

4. The compound of claim 1, which is represented by the formula (Ic):

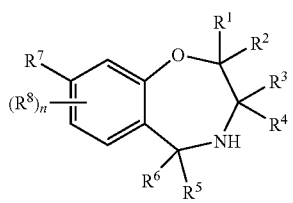

wherein each symbol is as defined in claim 1.

5. The compound of claim 1, which is represented by the formula (Id):

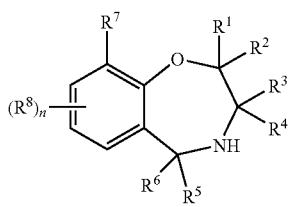

wherein each symbol is as defined in claim 1.

6. The compound of claim 1, wherein $R^7$ is
(1) a mono-alkylamino group,
(2) a di-alkylamino group optionally having substituent(s),
(3) a non-aromatic heterocyclic group,
(4) an aryl group optionally having substituent(s),
(5) a cycloalkyl group optionally having substituent(s),
(6) a cycloalkenyl group optionally having substituent(s), or
(7) an aromatic heterocyclic group optionally having substituent(s).

7. The compound of claim 1, wherein $R^7$ is
(1) a non-aromatic heterocyclic group optionally having substituent(s),
(2) a cycloalkyl group optionally having substituent(s),
(3) a $C_{2-6}$ alkyl group, or
(4) a halo-$C_{2-6}$ alkyl group.

8. The compound of claim 1, wherein n is 0 or 1.

9. 9-(1-Methylethyl)-2,3,4,5-tetrahydro-1,4-benzoxazepine,
9-(tetrahydrofuran-3-yl)-2,3,4,5-tetrahydro-1,4-benzoxazepine,
9-(2,2,2-trifluoro-1-methylethyl)-2,3,4,5-tetrahydro-1,4-benzoxazepine,
9-cyclobutyl-2,3,4,5-tetrahydro-1,4-benzoxazepine, or
9-cyclopropyl-2,3,4,5-tetrahydro-1,4-benzoxazepine,
or a salt thereof.

10. A pharmaceutical composition comprising a compound represented by the formula (I'):

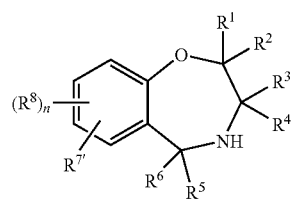

wherein
$R^1$, $R^2$, $R^3$ and $R^4$ are the same or different and each is
(1) a hydrogen atom,
(2) a halogen atom,
(3) a group via a carbon atom,
(4) a group via a nitrogen atom,
(5) a group via an oxygen atom, or
(6) a group via a sulfur atom;
$R^5$ and $R^6$ are the same or different and each is
(1) a hydrogen atom,
(2) a halogen atom,
(3) a cyano group,
(4) an alkyl group optionally having substituent(s),
(5) an alkenyl group optionally having substituent(s),
(6) an alkynyl group optionally having substituent(s),
(7) a cycloalkyl group optionally having substituent(s),
(8) a cycloalkenyl group optionally having substituent(s),
(9) a cycloalkylalkyl group optionally having substituent(s),
(10) a cycloalkenylalkyl group optionally having substituent(s),
(11) an aralkyl group optionally having substituent(s),
(12) a cycloalkanedienyl group optionally having substituent(s),
(13) a heterocyclic group bonded via a carbon atom, which optionally has substituent(s),
(14) a group via a nitrogen atom,
(15) a group via an oxygen atom, or
(16) a group via a sulfur atom;
$R^{7'}$ is
(1) a mono-alkylamino group,
(2) a di-alkylamino group optionally having substituent(s),
(3) a non-aromatic heterocyclic group optionally having substituent(s),
(4) an aryl group optionally having substituent(s),
(5) a cycloalkyl group optionally having substituent(s),
(6) a cycloalkenyl group optionally having substituent(s),
(7) an aromatic heterocyclic group optionally having substituent(s),
(8) a $C_{2-6}$ alkyl group,
(9) an alkoxy-alkyl group,
(10) a halo-$C_{2-6}$ alkyl group,
(11) an alkenyl group,
(12) an aryl-alkenyl group,
(13) an alkoxy-alkenyl group,
(14) a non-aromatic heterocyclyl-carbonyl group, or
(15) a carboxyl group;
$R^8$ is
(1) a halogen atom,
(2) a group via a carbon atom,
(3) a group via a nitrogen atom, (4) a group via an oxygen atom, or
(5) a group via a sulfur atom; and
n is an integer of 0 to 3;
the group via a sulfur atom is
(1) a mercapto group, or
(2) a group represented by the formula —S(O)$_m$R$^b$ wherein m is an integer of 0 to 2, and R$^b$ is a group via a carbon atom or a group via a nitrogen atom;
the group via a nitrogen atom is
(1) a nitro group,
(2) an amino group optionally having substituents) selected from the group consisting of a group bonded via a carbon atom, and a group represented by the formula —SO$_2$R$^a$ wherein R$^a$ is a group bonded via a carbon atom, or
(3) a heterocyclic group bonded via a nitrogen atom, which optionally has substituent(s);
the group via an oxygen atom is a hydroxy group optionally having a group via a carbon atom; and
the group via a carbon atom is
(1) a cyano group,
(2) an alkyl group optionally having substituent(s),
(3) an alkenyl group optionally having substituent(s),
(4) an alkynyl group optionally having substituent(s),
(5) a cycloalkyl group optionally having substituent(s),
(6) a cycloalkenyl group optionally having substituent(s),
(7) an aryl group optionally having substituent(s),
(8) a cycloalkylalkyl group optionally having substituent(s),
(9) a cycloalkenylalkyl group optionally having substituent(s),
(10) an aralkyl group optionally having substituent(s),
(11) a cycloalkanedienyl group optionally having substituent(s), or
(12) a heterocyclic group bonded via a carbon atom, which optionally has substituent(s);
provided that 9-chloro-7-(1,1-dimethylethyl)-2,3,4,5-tetrahydro-1,4-benzoxazepine and N-[[(5S)-2-oxo-3-(2,3,4,5-tetrahydro-1,4-benzoxazepin-7-yl)-5-oxazolidinyl]methyl]acetamide are excluded, and
provided that when the 2,3,4,5-tetrahydro-1,4-benzoxazepine has R$^7$ or R$^8$ at the 9-position of the 1,4-benzoxazepine ring, then the substituent at the 7-position of the 1,4-benzoxazepine ring is not
(i) a group represented by —B$_1$—SO$_2$-Q$_1$
wherein
B$_1$ is an amino group optionally having substituent(s), and
Q$_1$ is a hydrocarbon group optionally having substituent(s) or a heterocyclic group optionally having substituent(s), or B$_1$ combined with Q$_1$ is a nitrogen-containing aromatic heterocyclic group optionally having substituent(s), nor
(ii) a group represented by —SO$_2$—B$_2$-Q$_2$
wherein
B$_2$ is an amino group optionally having substituent(s), and
Q$_2$ is a hydrocarbon group optionally having substituent(s) or a heterocyclic group optionally having substituent(s), or —B$_2$-Q$_2$ is a nitrogen-containing aromatic heterocyclic group optionally having substituent(s),
or a salt thereof.

11. A method for the treatment of lower urinary tract symptom, obesity, pelvic organ prolapse, anterior vaginal wall prolapse, posterior vaginal wall prolapse, uterine prolapse, prolapse of the apical segment of the vagina, rectal prolapse, enterocele, cystocele, urethral prolapse or post-micturition dribble in a mammal, which comprises administering an effective amount of a compound represented by the formula (I'):

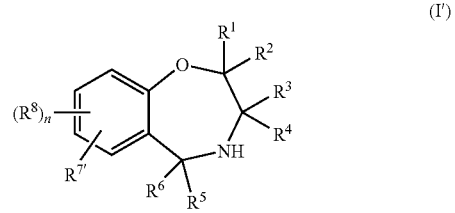

wherein
R$^1$, R$^2$, R$^3$, R$^4$, R$^5$ and R$^6$ are the same or different and each is
(1) a hydrogen atom,
(2) a halogen atom,
(3) a group via a carbon atom,
(4) a group via a nitrogen atom,
(5) a group via an oxygen atom, or
(6) a group via a sulfur atom;
R$^7$ is
(1) a mono-alkylamino group,
(2) a di-alkylamino group optionally having substituent(s),
(3) a non-aromatic heterocyclic group optionally having substituent(s),
(4) an aryl group optionally having substituent(s),
(5) a cycloalkyl group optionally having substituent(s),
(6) a cycloalkenyl group optionally having substituent(s),
(7) an aromatic heterocyclic group optionally having substituent(s),
(8) a C$_{2-6}$ alkyl group,
(9) an alkoxy-alkyl group,
(10) a halo-C$_{2-6}$ alkyl group,
(11) an alkenyl group,
(12) an aryl-alkenyl group,
(13) an alkoxy-alkenyl group,
(14) a non-aromatic heterocyclyl-carbonyl group, or
(15) a carboxyl group;
R$^8$ is
(1) a halogen atom,
(2) a group via a carbon atom,
(3) a group via a nitrogen atom,
(4) a group via an oxygen atom, or
(5) a group via a sulfur atom;
n is an integer of 0 to 3;
the group via a sulfur atom is
(1) a mercapto group, or
(2) a group represented by the formula —S(O)$_m$R$^b$ wherein m is an integer of 0 to 2, and R$^b$ is a group via a carbon atom or a group via a nitrogen atom;
the group via a nitrogen atom is
(1) a nitro group,
(2) an amino group optionally having substituents) selected from the group consisting of a group bonded via a carbon atom, and a group represented by the formula —SO$_2$R$^a$ wherein R$^a$ is a group bonded via a carbon atom, or (3) a heterocyclic group bonded via a nitrogen atom, which optionally has substituent(s);

the group via an oxygen atom is a hydroxy group optionally having a group via a carbon atom; and the group via a carbon atom is (1) a cyano group,
(2) an alkyl group optionally having substituent(s),
(3) an alkenyl group optionally having substituent(s),
(4) an alkynyl group optionally having substituent(s),
(5) a cycloalkyl group optionally having substituent(s),
(6) a cycloalkyl group optionally having substituent(s),
(7) an aryl group optionally having substituent(s),
(8) a cycloalkylalkyl group optionally having substituent(s),
(9) a cycloalkenylalkyl group optionally having substituent(s),
(10) an aralkyl group optionally having substituent(s),
(11) a cycloalkanedienyl group optionally having substituent(s), or
(12) a heterocyclic group bonded via a carbon atom, which optionally has substituent(s);

provided that 9-chloro-7-(1,1-dimethylethyl)-2,3,4,5-tetrahydro-1,4-benzoxazepine and N-[[(5S)-2-oxo-3-(2,3,4,5-tetrahydro-1,4-benzoxazepin-7-yl)-5-oxazolidinyl]methyl]acetamide are excluded, and provided that when the 2,3,4,5-tetrahydro-1,4-benzoxazepine has $R^7$ or $R^8$ at the 9-position of the 1,4-benzoxazepine ring, then the substituent at the 7-position of the 1,4-benzoxazepine ring is not (i) a group represented by —$B_1$—$SO_2$-$Q_1$
   wherein
   $B_1$ is an amino group optionally having substituent(s), and
   $Q_1$ is a hydrocarbon group optionally having substituent(s) or a heterocyclic group optionally having substituent(s), or $B_1$ combined with $Q_1$ is a nitrogen-containing aromatic heterocyclic group optionally having substituent(s), nor (ii) a group represented by —$SO_2$—$B_2$-$Q_2$
   wherein
   $B_2$ is an amino group optionally having substituent(s), and
   $Q_2$ is a hydrocarbon group optionally having substituent(s) or a heterocyclic group optionally having substituent(s), or —$B_2$-$Q_2$ is a nitrogen-containing aromatic heterocyclic group optionally having substituent(s), or a salt thereof to the mammal.

* * * * *

UNITED STATES PATENT AND TRADEMARK OFFICE
CERTIFICATE OF CORRECTION

PATENT NO. : 8,247,403 B2
APPLICATION NO. : 12/449975
DATED : August 21, 2012
INVENTOR(S) : Junya Shirai It is certified that error appears in the above-identified patent and that said Letters Patent is hereby corrected as shown below:

In the Claims

In claim 1, in column 134, line 11:
"substituents)"
should be:
--substituent(s)--.

In claim 1, in column 134, line 26:
"(6) a cycloalkyenyl"
should be:
--(6) a cycloalkenyl--.

In claim 10, in column 137, line 11:
"substituents)"
should be:
--substituent(s)--.

In claim 11, in column 138, line 63:
"substituents)"
should be:
--substituent(s)--.

Signed and Sealed this
Eighteenth Day of June, 2013

Teresa Stanek Rea
*Acting Director of the United States Patent and Trademark Office*

CERTIFICATE OF CORRECTION (continued)
U.S. Pat. No. 8,247,403 B2

In claim 11, in column 139, line 11:

"(6) a cycloalkyl"

should be:

--(6) a cycloalkenyl--.